United States Patent
Cooper et al.

(10) Patent No.: US 11,370,776 B2
(45) Date of Patent: Jun. 28, 2022

(54) SULFONYLUREAS AND SULFONYLTHIOUREAS AS NLRP3 INHIBITORS

(71) Applicant: Inflazome Limited, Dublin (IE)

(72) Inventors: Matthew Cooper, Cambridge (GB); David Miller, Cambridge (GB); Angus Macleod, Cambridge (GB); Jimmy Van Wiltenburg, Groningen (NL); Stephen Thom, Nottingham (GB); Stephen St-Gallay, Nottingham (GB); Jonathan Shannon, Nottingham (GB)

(73) Assignee: INFLAZOME LIMITED, Dublin (IE)

(*) Notice: Subject to any disclaimer, the term of this patent is extended or adjusted under 35 U.S.C. 154(b) by 0 days.

(21) Appl. No.: 16/629,027

(22) PCT Filed: Jul. 4, 2018

(86) PCT No.: PCT/EP2018/068081
§ 371 (c)(1),
(2) Date: Jan. 6, 2020

(87) PCT Pub. No.: WO2019/008029
PCT Pub. Date: Jan. 10, 2019

(65) Prior Publication Data
US 2020/0270227 A1    Aug. 27, 2020

(30) Foreign Application Priority Data

Jul. 7, 2017   (GB) .................. 1710942
Aug. 15, 2017  (GB) .................. 1713076
Aug. 15, 2017  (GB) .................. 1713082
Nov. 9, 2017   (GB) .................. 1718563
Dec. 22, 2017  (GB) .................. 1721726

(51) Int. Cl.

| | | |
|---|---|---|
| C07D 401/12 | (2006.01) | |
| C07D 213/71 | (2006.01) | |
| C07D 237/18 | (2006.01) | |
| C07D 239/38 | (2006.01) | |
| C07D 239/47 | (2006.01) | |
| C07D 241/18 | (2006.01) | |
| C07D 241/20 | (2006.01) | |
| C07D 241/44 | (2006.01) | |
| C07D 403/04 | (2006.01) | |
| C07D 413/04 | (2006.01) | |
| C07D 471/04 | (2006.01) | |
| G01N 33/50 | (2006.01) | |

(52) U.S. Cl.
CPC ......... *C07D 401/12* (2013.01); *C07D 213/71* (2013.01); *C07D 237/18* (2013.01); *C07D 239/38* (2013.01); *C07D 239/47* (2013.01); *C07D 241/18* (2013.01); *C07D 241/20* (2013.01); *C07D 241/44* (2013.01); *C07D 403/04* (2013.01); *C07D 413/04* (2013.01); *C07D 471/04* (2013.01); *G01N 33/502* (2013.01)

(58) Field of Classification Search
CPC .. C07D 401/12; C07D 213/71; C07D 237/18; C07D 239/38; C07D 239/47; C07D 241/18; C07D 241/20; C07D 241/44; C07D 403/04; C07D 413/04; C07D 471/04; G01N 33/502
See application file for complete search history.

(56) References Cited

U.S. PATENT DOCUMENTS

| 4,244,950 A | 1/1981 | De Ridder et al. |
| 4,681,620 A * | 7/1987 | Bohner ............... C07D 241/18 |
| | | 504/213 |
| 4,723,991 A | 2/1988 | Holyoke, Jr. et al. |
| 4,741,760 A | 5/1988 | Meyer et al. |

(Continued)

FOREIGN PATENT DOCUMENTS

| EP | 0003383 A2 | 8/1979 |
| EP | 0125864 A1 | 11/1984 |

(Continued)

OTHER PUBLICATIONS

Guo; Nature Medicine, 2015, 21(7), 677-687. doi:10.1038/nm.3893 (Year: 2015).*

(Continued)

*Primary Examiner* — Daniel R Carcanague
(74) *Attorney, Agent, or Firm* — Alston & Bird LLP

(57) ABSTRACT

The present invention relates to compounds of formula (I):

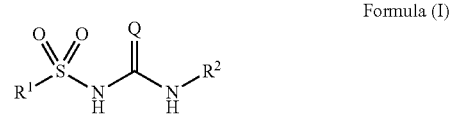

Formula (I)

wherein Q is O or S, $R^1$ is a 6-membered heteroaryl group containing at least one nitrogen atom in the 6-membered ring structure, wherein $R^1$ may optionally be substituted, and $R^2$ is a cyclic group substituted at the α-position, wherein $R^2$ may optionally be further substituted. The present invention further relates to salts, solvates and prodrugs of such compounds, to pharmaceutical compositions comprising such compounds, and to the use of such compounds in the treatment and prevention of medical disorders and diseases, most especially by the inhibition of NLRP3.

19 Claims, No Drawings

(56) References Cited

U.S. PATENT DOCUMENTS

| | | | |
|---|---|---|---|
| 4,795,486 A | 1/1989 | Bohner et al. | |
| 4,802,908 A | 2/1989 | Hillemann | |
| 5,219,856 A | 6/1993 | Olson | |
| 5,298,480 A * | 3/1994 | Watson | A01N 47/36 504/213 |
| 5,486,618 A | 1/1996 | Hagen et al. | |
| 5,529,976 A | 6/1996 | Kehne et al. | |
| 5,814,631 A | 9/1998 | Fukami et al. | |
| 6,316,388 B1 | 11/2001 | Schutze et al. | |
| 2002/0034764 A1 | 3/2002 | Gabel et al. | |
| 2002/0077486 A1 | 6/2002 | Scarborough et al. | |
| 2020/0216389 A1* | 7/2020 | Miller | C07D 213/46 |
| 2020/0237723 A1* | 7/2020 | Miller | A61P 29/00 |
| 2020/0291003 A1* | 9/2020 | Cooper | C07D 405/04 |
| 2020/0317637 A1* | 10/2020 | Cooper | C07D 405/12 |
| 2020/0331850 A1* | 10/2020 | Miller | C07D 211/34 |
| 2020/0331886 A1* | 10/2020 | Miller | C07D 231/18 |
| 2020/0354341 A1* | 11/2020 | Cooper | C07D 417/04 |
| 2020/0361895 A1* | 11/2020 | Cooper | C07D 405/14 |
| 2020/0399242 A1* | 12/2020 | Miller | C07D 409/14 |
| 2020/0399243 A1* | 12/2020 | Miller | A61P 3/00 |
| 2020/0407340 A1* | 12/2020 | Cooper | C07D 207/14 |
| 2021/0002274 A1* | 1/2021 | Cooper | C07D 405/14 |
| 2021/0040065 A1* | 2/2021 | Miller | C07D 231/18 |
| 2021/0047302 A1* | 2/2021 | Cooper | C07D 401/12 |
| 2021/0122716 A1* | 4/2021 | Cooper | A61P 31/00 |
| 2021/0122739 A1* | 4/2021 | Cooper | C07D 403/04 |
| 2021/0130329 A1* | 5/2021 | Cooper | C07D 405/04 |
| 2021/0130359 A1* | 5/2021 | Cooper | C07D 249/12 |

FOREIGN PATENT DOCUMENTS

| | | | |
|---|---|---|---|
| EP | 0262096 A1 | 3/1988 | |
| EP | 0610653 A1 | 8/1994 | |
| EP | 0795548 A1 | 9/1997 | |
| EP | 0885890 A1 | 12/1998 | |
| EP | 1236468 A1 | 9/2002 | |
| GB | 797474 A | 7/1958 | |
| GB | 1146979 A | 3/1969 | |
| GB | 1713079.0 | 8/2017 | |
| GB | 1710943.0 | 7/2018 | |
| IN | 1124MU2013 A | 7/2015 | |
| JP | H06-199053 A | 7/1994 | |
| JP | H06-199054 A | 7/1994 | |
| JP | 2000-053649 A | 2/2000 | |
| PL | 221813 B1 | 5/2016 | |
| WO | WO1992006965 A1 * | 4/1992 | |
| WO | WO 1993/004046 A1 | 3/1993 | |
| WO | WO 1997/011057 A1 | 3/1997 | |
| WO | WO 1998/032733 A1 | 7/1998 | |
| WO | WO 2000/055126 A2 | 9/2000 | |
| WO | WO 2001/019390 A1 | 3/2001 | |
| WO | WO 2001/57037 A1 | 8/2001 | |
| WO | WO 2002/006246 A1 | 1/2002 | |
| WO | WO 2002/094176 A2 | 11/2002 | |
| WO | WO 2003/031194 A1 | 4/2003 | |
| WO | WO 2003/035076 A1 | 5/2003 | |
| WO | WO 2003/099805 A1 | 12/2003 | |
| WO | WO 2004/039376 A1 | 5/2004 | |
| WO | WO 2006/085815 A1 | 8/2006 | |
| WO | WO 2008/090382 A1 | 7/2008 | |
| WO | WO 2009/065096 A1 | 5/2009 | |
| WO | WO 2011/041694 A2 | 4/2011 | |
| WO | WO 2016/131098 A1 | 8/2016 | |
| WO | WO 2016/131098 A8 | 8/2016 | |
| WO | WO 2017/140778 A1 | 8/2017 | |
| WO | WO 2017/184623 A1 | 10/2017 | |
| WO | WO 2017/189652 A1 | 11/2017 | |
| WO | WO 2017/201152 A1 | 11/2017 | |
| WO | WO 2018/215818 A1 | 11/2018 | |
| WO | WO 2019/008025 A1 | 1/2019 | |
| WO | WO 2019/034686 A1 | 2/2019 | |
| WO | WO 2019/034688 A1 | 2/2019 | |
| WO | WO 2019/034690 A1 | 2/2019 | |
| WO | WO 2019/034692 A1 | 2/2019 | |
| WO | WO 2019/034693 A1 | 2/2019 | |
| WO | WO 2019/034696 A1 | 2/2019 | |
| WO | WO 2019/034697 A1 | 2/2019 | |
| WO | WO 2019/068772 A1 | 4/2019 | |
| WO | WO 2019/092170 A1 | 5/2019 | |
| WO | WO 2019/092171 A1 | 5/2019 | |
| WO | WO 2019/092172 A1 | 5/2019 | |
| WO | WO 2019/166619 A1 | 9/2019 | |
| WO | WO 2019/166621 A1 | 9/2019 | |
| WO | WO 2019/166623 A1 | 9/2019 | |
| WO | WO 2019/166624 A1 | 9/2019 | |
| WO | WO 2019/166627 A1 | 9/2019 | |
| WO | WO 2019/166628 A1 | 9/2019 | |
| WO | WO 2019/166629 A1 | 9/2019 | |
| WO | WO 2019/166632 A1 | 9/2019 | |
| WO | WO 2019/166633 A1 | 9/2019 | |
| WO | WO 2019/206871 A1 | 10/2019 | |
| WO | WO 2019/211463 A1 | 11/2019 | |
| WO | WO 2020/010118 A1 | 1/2020 | |
| WO | WO 2020/035464 A1 | 2/2020 | |
| WO | WO 2020/035465 A1 | 2/2020 | |
| WO | WO 2020/035466 A1 | 2/2020 | |
| WO | WO 2020/079207 A1 | 4/2020 | |
| WO | WO 2020/104657 A1 | 5/2020 | |
| WO | WO-2020102096 A1 * | 5/2020 | C07D 221/16 |
| WO | WO-2020102098 A1 * | 5/2020 | C07D 417/12 |
| WO | WO-2020102100 A1 * | 5/2020 | C07D 417/12 |
| WO | WO 2020/208249 A1 | 10/2020 | |
| WO | WO 2021/032588 A1 | 2/2021 | |
| WO | WO 2021/032591 A1 | 2/2021 | |
| WO | WO 2021/043966 A1 | 3/2021 | |
| WO | WO 2021/165245 A1 | 8/2021 | |

OTHER PUBLICATIONS

Youssef; Med. Chem. Res. 2001, 10(6) 404-418. (Year: 2001).*

Booth et al., "A new and efficient approach to the synthesis of 6-amidino-2-oxopurines," Journal of the Chemical Society, Perkin Transactions 1, 1(10):1241-1251, (2001).

CAS RN 1026892-76-1; STN Entry date Jun. 10, 2008; 2,3,4,5,6-pentafluoro-N-[2-[4-[[[[(2,3,4-trifluorophenyl)amino]carbonyl]amino]sulfonyl]phenyl]ethyl]-benzamide.

Database Caplus [Online] : Chemical Abstracts Service, Columbus, Ohio, US; Nam et al., "Database citation of: Acyl derivatives of 3-(p-aminophenyl)-5-aminopyrazole and its N(1)-substituted derivatives," Abstract, XP002785803, Database Accession No. 1999:126025, Compound with the Registry Nos. 223518-59-0, 223518-69-2, and 223518-80-7, (1998).

Database Registry [Online] : Chemical Abstracts Service, Columbus, Ohio, US; Abstract, XP002784778, STN Database Accession No. 959378-14-4, Compound with the Registry Nos. 959378-14-4 and 959378-13-3,(STN Entry Date Dec. 21, 2007).

Database Registry [Online] : Chemical Abstracts Service, Columbus, Ohio, US; Abstract, XP-002784779, STN Database Accession No. 1348169-93-6, Compound with the Registry No. 1348169-93-6, (STN Entry Date Dec. 4, 2011).

Khuntwal, et al., "Credential Role of van der Waal Volumes and Atomic Masses in Modeling Hepatitis C Virus NS5B Polymerase Inhibition by Tetrahydrobenzo-Thiophenes Using SVM and MLR Aided QSAR Studies," Current Bioinformatics, 8(4):465-471, (2013).

Laliberte et al., "Glutathione S-Transferase Omega 1-1 Is a Target of Cytokine Release Inhibitory Drugs and May Be Responsible for Their Effect on Interleukin-1β Posttranslational Processing," Journal of Biological Chemistry, 278(19):16567-16578, (2003).

Li et al., "Discovery of the first SecA inhibitors using structure-based virtual screening," Biochemical and Biophysical Research Communications, 368(4):839-845, (2008).

Pacini et al., "2-(3-Thienyl)-5,6-dihydroxypyrimidine-4-carboxylic acids as inhibitors of HCV NS5B RdRp," Bioorganic & Medicinal Chemistry Letters, 19(21):6245-6249, (2009).

Yamazaki et al., "Design, Synthesis and Biological Activity of Novel Non-Peptidyl Endothelin Converting Enzyme Inhibitors, 1-Phenyl-tetrazole-formazan Analogues," Bioorganic & Medicinal Chemistry Letters, 12(9):1275-1278, (2002).

(56) References Cited

OTHER PUBLICATIONS

Bourgeois et al. "Study of new sulfonylureas by mass spectrometry," Analusis, 23(1): 23-27, (1995).
CAS RN 1332606-77-5; STN Entry date Sep. 16, 2011; 2-(3-(3-Amino-4-(tert-butoxycarbonyl)phenylsulfonyl)ureido)-4-chlorobenzoic acid.
CAS RN 663215-37-0; STN Entry date Mar. 15, 2004; N-(2-chlorophenyl]-5-[[[[(2-chlorophenyl)amino]carbonyl]amino]sulfonyl]-1H-1,2,4-Triazole-1-carboxamide.
Coll et al., "A small-molecule inhibitor of the NLRP3 inflammasome for the treatment of inflammatory diseases," Nature Medicine, 21(3):248-255, (2015).
Database Caplus [Online] : Chemical Abstracts Service, Columbus, Ohio, US; Chiba et al., "Indoaniline dyes for thermal transfer recording," Abstract, XP002784776, STN Database Accession No. 1995:128156, Compound with the Registry No. 159566-61-7 & JP H06 199053 A, Sankyo Kagaku KK, (1994).
Database Caplus [Online] : Chemical Abstracts Service, Columbus, Ohio, US; Dymek et al., "Database citation for: Synthesis of some pyrazolylureas," Abstract, XP002785804, Database Accession No. 1975:57600, Compound with the Registry Nos. 54569-73-2, 54569-74-3, 54569-75-4, 54569-76-5, 54569-77-6, and 54644-70-1, (1975).
Database Caplus [Online] : Chemical Abstracts Service, Columbus, Ohio, US; Eguchi et al., "Thermal transfer sheets using indoaniline cyan dye," Abstract, XP002784775, STN Database Accession No. 1995:128157, Compound with the Registry No. 159566-49-1 & JP H06 199054 A, Dainippon Printing Co Ltd, (1994).
Database Caplus [Online] : Chemical Abstracts Service, Columbus, Ohio, US; Gajjar et al., "Novel organic inhibitors of PTP1B as dual acting antidiabetic agents," Abstract, XP002784777, Database Accession No. 2015:1114845, Compound with the Registry No. 2153519-11-8, (2015).
Database Caplus [Online] : Chemical Abstracts Service, Columbus, Ohio, US; Grandberg et al., "Database citation for: 3-(p-Bromophenyl)-5-aminopyrazole and some derivatives," Abstract, XP002785801, Database Accession No. 2004:153241, Compound with the Registry No. 786688-48-0, (2003).
Database Caplus [Online] : Chemical Abstracts Service, Columbus, Ohio, US; Roychowdhury et al., "Database citation of: Synthesis of some new 1,3,5-triazinylbarbiturates," Abstract, XP002785802, Database Accession No. 2003:321536, Compound with the Registry Nos. 566135-48-6; 566135-49-7; 566135-50-0; and 566135-51-1, (2003).
Deore et al., "NS5B RNA Dependent RNA Polymerase Inhibitors: The Promising Approach to Treat Hepatitis C Virus Infections," Current Medicinal Chemistry, 17(32): 3806-3826, (2010).
Dias et al., "Synthesis of new imidazo[4,5-d][1,3]diazepine derivatives from 5-amino-4-(cyanoformimidoyl)imidazoles," Journal of Heterocyclic Chemistry, 33(3):855-862, (1996).
Fleming et al., "Novel axially chiral bis-arylthiourea-based organocatalysts for asymmetric Friedel-Crafts type reactions," Tetrahedron Letters, 47(39):7037-7042, (2006).
Khelili et al., "Synthesis and vasodilator effects of 3- and 7-sulfonylurea-1,2,4-benzothiadiazin-1,1-dioxides on rat aorta," Bioorganic and Medicinal Chemistry, 3(5):495-503, (1995).
Laporte, et al., "Tetrahydrobenzothiophene inhibitors of hepatitis C Virus NS5B polymerase," Bioorganic & Medicinal Chemistry Letters, 16:100-103, (2006).
Luckhurst et al., "A convenient synthesis of sulfonylureas from carboxylic acids and sulfonamides via an in situ Curtius rearrangement," Tetrahedron Letters, 48(50):8878-8882 (2007).

Masereel, et al., "Synthesis and pharmacology of pyrid-3-yl sulfonylureas and thioureas as astrocytic Na+ 2Cl-K+ cotransporter inhibitors," European Journal of Medicinal Chemistry, 29(7-8):527-535, (1994).
Mokhtar et al., "Synthesis of Nitrogeneous Compounds, Part-III," Pakistan Journal of Scientific and Industrial Research, 34(1):9-15, (1991).
Proks et al., "Sulfonylurea stimulation of insulin secretion," Diabetes, 51(3):S368-S376, (2002).
Sarges et al., "Sulfamylurea hypoglycemic agents. 6. High potency derivatives," Journal of Medicinal Chemistry, 19(5):695-709, (1976).
Wu et al., "Recent advances in discovery and development of promising therapeutcis against hepatitis C virus NS5B RNA-dependent RNA polymerase," Mini Reviews in Medicinal Chemistry, 5(12):1103-1112, (2005).
GB Application No. 1710942.2, Search Report dated Apr. 18, 2018.
GB Application No. 1713082.4, Search Report dated Apr. 30, 2018.
WIPO Application No. PCT/EP2018/068081, PCT International Preliminary Report on Patentability dated Jan. 16, 2020.
WIPO Application No. PCT/EP2018/068081, PCT International Search Report and Written Opinion of the International Searching Authority dated Oct. 9, 2018.
WIPO Application No. PCT/EP2018/072111, PCT International Preliminary Report on Patentability dated Feb. 27, 2020.
WIPO Application No. PCT/EP2018/072111, PCT International Search Report dated Jun. 11, 2018.
WIPO Application No. PCT/EP2018/072111, PCT Written Opinion of the International Searching Authority dated Jun. 11, 2018.
Bundgaard, "Design of Prodrugs: Bioreversible derivatives for various functional groups and chemical entities," Chapter 1, p. 1, 1985.
Silverman, Prodrugs and drug delivery systems, The organic chemistry of drug design and drug action, Chapter 8, pp. 352-400, 1992.
Balant ed in Wolff et al. Burger's Medicinal Chemistry and drug discovery, 5th Ed., vol. 1. Principles and practice, pp. 949-982, 1995.
Stella, "Prodrugs as theraputics" Expert Opinion of theraputic patents, 14(3): 277-280 (2004).
Testa, "Prodrug Research: futile or fertile?" Biochemical Pharmacology, 68 (2004) 2097-2106.
Ettmayer et al., "Lessons learned from marketed and investigational prodrugs" J. Med. Chem., 47(10):2394-2404 (2004).
Banker et al., Prodrugs, Modern Pharmaceutics, 3rd edition, Revised and Expanded, pp. 451 and 596, (1995).
Himiceskij, Chemical Encyclopedia, (1983), p. 130-131, English translation is not available.
Belikov, et al., "The interconnection between chemical structure, properties of substances and their effect on the body", MEDpress-inform, Pharmaceutical Chemistry, Text Book, 4th Edition, Moscow, Chap. 2.6, 27-29, (2007), Brief statement of relevance.
Disease—Wikipedia, retrieved from the internet on Jan. 5, 2022 at: https://en.wikipedia.org/wiki/Disease.
Parajuli, et al., "Prodrug as a novel approach of drug delivery—a review," Journal of Drug Delivery & Therapeutics, 5(3), pp. 5-9, (2015).
Solvation—Wikipedia, retrieved from the internet on Jan. 5, 2022 at: https://en.wikipedia.org/wiki/Solvation.
Zawilska, et al., "Prodrugs: a challenge for the drug development," Pharmacological reports: PR, vol. 65, No. 1, pp. 1-14, (Apr. 2013).
RU Application No. 2020110219/04(017079) Office Action and Search Report dated Feb. 15, 2022, English tranlsation of office action.

\* cited by examiner

SULFONYLUREAS AND SULFONYLTHIOUREAS AS NLRP3 INHIBITORS

CROSS-REFERENCE TO RELATED APPLICATION

This application is the US national stage of PCT/EP2018/068081 filed Jul. 4, 2018, which claims priority to GB 1710942.2 filed Jul. 7, 2017, GB 1713076.6 filed Aug. 15, 2017, GB 1713082.4 filed Aug. 15, 2017, GB 1718563.8 filed Nov. 9, 2017, and GB 1721726.6 filed Dec. 22, 2017.

FIELD OF THE INVENTION

The present invention relates to sulphonylureas and sulphonylthioureas comprising a 6-membered heteroaryl group containing at least one nitrogen atom in the 6-membered ring structure and further comprising a second cyclic group substituted at the α-position, and to associated salts, solvates, prodrugs and pharmaceutical compositions. The present invention further relates to the use of such compounds in the treatment and prevention of medical disorders and diseases, most especially by NLRP3 inhibition.

BACKGROUND

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1β and pro-IL-18 respectively) to thereby activate these cytokines. Caspase-1 also mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1$R_2$ resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NO-MID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using $Nlrp3^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulphoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulphonylurea-containing compounds have been identified as cytokine release inhibitory drugs (CRIDs) (Perregaux et al.; J. Pharmacol. Exp. Ther. 299, 187-197, 2001). CRIDs are a class of diarylsulphonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulphonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1 and WO 2018/015445 A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

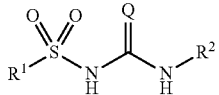

Formula (I)

wherein:
  Q is O or S;
  $R^1$ is a 6-membered heteroaryl group containing at least one nitrogen atom in the 6-membered ring structure, wherein $R^1$ may optionally be substituted; and
  $R^2$ is a cyclic group substituted at the α-position, wherein $R^2$ may optionally be further substituted;
with the proviso that the compound is not:

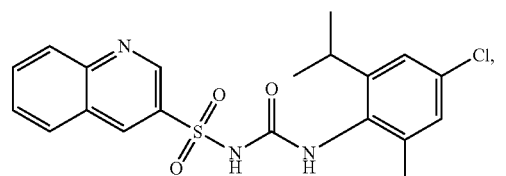

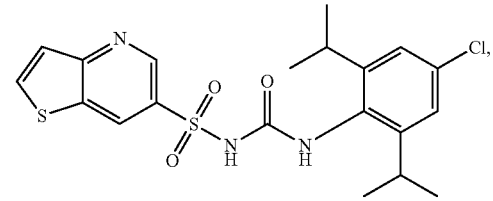

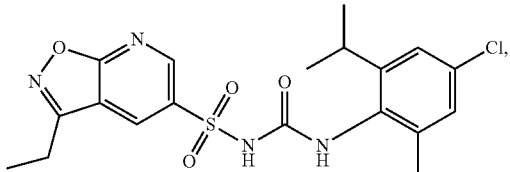

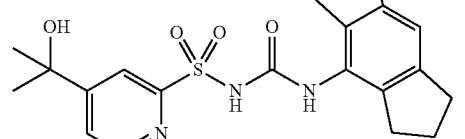

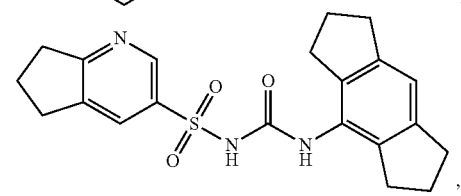

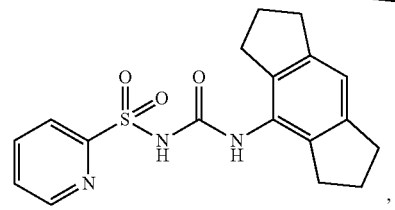

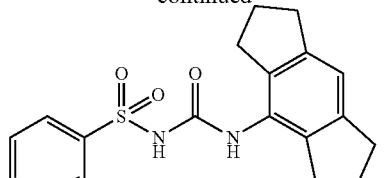

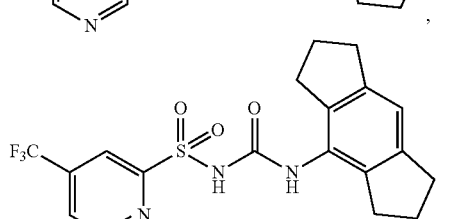

or

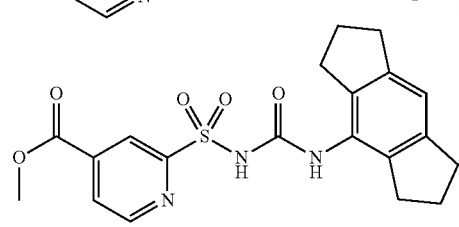

In a preferred embodiment, Q is O.

For the purposes of the present specification, where it is stated that a substituent, group or moiety "is a" specific group, it is to be understood that the specific group is attached directly to the remainder of the molecule, i.e. with no intervening atom(s) or groups being present. Thus, in the first aspect of the invention, where it is stated that "$R^1$ is a 6-membered heteroaryl group" it is to be understood that a ring atom of the 6-membered ring of the 6-membered heteroaryl group is directly attached to the sulphur atom of the sulphonyl group, with no intervening atom(s) or groups being present. Similarly, where it is stated that "$R^2$ is a cyclic group", it is to be understood that a ring atom of the cyclic group is directly attached to the nitrogen atom of the (thio)urea group, with no intervening atom(s) or groups being present.

For the purposes of the present specification, in an optionally substituted group or moiety:
  (i) each hydrogen atom may optionally be replaced by a group independently selected from halo; —CN; —NO$_2$; —N$_3$; —$R^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$RP; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^\alpha$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^\alpha$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO;

—R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$NH$_2$; —N$^+$(R$^\beta$)$_2$—R$^\alpha$—NHR$^\alpha$; —N$^+$(R$^\beta$)$_2$—R$^\alpha$—N(R$^\beta$)$_2$; or —N$^+$(R$^\beta$)$_2$R$^\alpha$—N(O)(R$^\beta$)$_2$; and/or (ii) any two hydrogen atoms attached to the same atom may optionally be replaced by a π-bonded substituent independently selected from oxo (=O), =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —N=N—, —N(R$^\beta$)—, —N(O)(R$^\beta$)—, —N$^+$(R$^\beta$)$_2$— or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (=O), or 4- to 6-membered heterocyclic group.

Typically, the compounds of the present invention comprise at most one quaternary ammonium group such as —N$^+$(R$^\beta$)$_3$ or —N$^+$(R$^\beta$)$_2$—.

Where reference is made to a —R$^\alpha$—C(N$_2$)R$^\beta$ group, what is intended is:

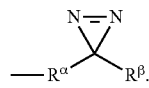

Typically, in an optionally substituted group or moiety:
(i) each hydrogen atom may optionally be replaced by a group independently selected from a halo, —CN, —NO$_2$, —R$^\beta$, —OH, —OR$^\beta$, —SH, —SR$^\beta$, —NH$_2$, —NHR$^\beta$, —N(R$^\beta$)$_2$, —R$^\alpha$—OH, —R$^\alpha$—OR$^\beta$, —R$^\alpha$—NH$_2$, —R$^\alpha$—NHR$^\beta$, —R$^\alpha$—N(R$^\beta$)$_2$, —CHO, —COR$^\beta$, —COOH, —COOR$^\beta$, —OCOR$^\beta$, —NH—CHO, —NR$^\beta$—CHO, —NH—COR$^\beta$, —NR$^\beta$—COR$^\beta$, —CONH$_2$, —CONHR$^\beta$, —CON(R$^\beta$)$_2$, —O—R$^\alpha$—OH, —O—R$^\alpha$—OR$^\beta$, —O—R$^\alpha$—NH$_2$, —O—R$^\alpha$—NHR$^\beta$, —O—R$^\alpha$—N(R$^\beta$)$_2$, —NH—R$^\alpha$—OH, —NH—R$^\alpha$—OR$^\beta$, —NH—R$^\alpha$—NH$_2$, —NH—R$^\alpha$—NHR$^\beta$, —NH—R$^\alpha$—N(R$^\beta$)$_2$, —NR$^\beta$—R$^\alpha$—OH, —NR$^\beta$—R$^\alpha$—OR$^\beta$, —NR$^\beta$—R$^\alpha$—NH$_2$, —NR$^\beta$—R$^\alpha$—NHR$^\beta$, —NR$^\beta$—R$^\alpha$—N(R$^\beta$)$_2$,

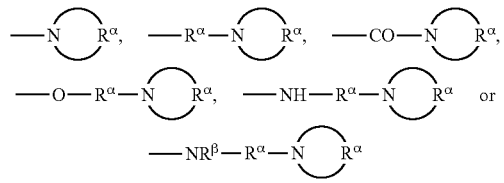

group; and/or
(ii) any two hydrogen atoms attached to the same carbon atom may optionally be replaced by a π-bonded substituent independently selected from =O, =S, =NH or =NR$^\beta$; and/or (iii) any two hydrogen atoms attached to the same or different atoms, within the same optionally substituted group or moiety, may optionally be replaced by a bridging substituent independently selected from —O—, —S—, —NH—, —NR$^\beta$— or —R$^\alpha$—;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups;

wherein each R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any RP may optionally be substituted with one or more halo groups.

Alternately, in an optionally substituted group or moiety:
(i) each hydrogen atom may optionally be replaced by a group independently selected from a halo, —CN, —NO$_2$, —R$^\beta$, —OH, —OR$^\beta$, —SH, —SR$^\beta$, —NH$_2$, —NHR$^\beta$, —N(R$^\beta$)$_2$, —CHO, —COR$^\beta$, —COOH, —COOR$^\beta$, —OCOR$^\beta$, —NH—CHO, —NR$^\beta$—CHO, —NH—COR$^\beta$, —NR$^\beta$—COR$^\beta$, —CONH$_2$, —CONHR$^\beta$, —CON(R$^\beta$)$_2$, —O—R$^\alpha$—OH, —O—R$^\alpha$—OR$^\beta$, —O—R$^\alpha$—NH$_2$, —O—R$^\alpha$—NHR$^\beta$, —O—R$^\alpha$—N(R$^\beta$)$_2$, —NH—R$^\alpha$—OH, —NH—R$^\alpha$—OR$^\beta$, —NH—R$^\alpha$—NH$_2$, —NH—R$^\alpha$—NHR$^\beta$, —NH—R$^\alpha$—N(R$^\beta$)$_2$, —NR$^\beta$—R$^\alpha$—OH, —NR$^\beta$—R$^\alpha$—OR$^\beta$, —NR$^\beta$—R$^\alpha$—NH$_2$, —NR$^\beta$—R$^\alpha$—NHR$^\beta$, —NR$^\beta$—R$^\alpha$—N(R$^\beta$)$_2$,

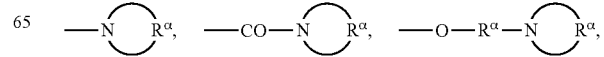

-continued

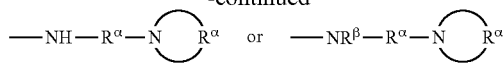

group; and/or
(ii) any two hydrogen atoms attached to the same carbon atom may optionally be replaced by a π-bonded substituent independently selected from =O, =S, =NH or =NR$^β$; and/or
(iii) any two hydrogen atoms attached to the same or different atoms, within the same optionally substituted group or moiety, may optionally be replaced by a bridging substituent independently selected from —O—, —S—, —NH—, —NR$^β$— or —R$^α$—;
  wherein each —R$^α$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —RP groups;
  wherein each R$^β$ is independently selected from a $C_1$-$C_6$ alkyl, $C_2$-$C_6$ alkenyl, $C_2$-$C_6$ alkynyl or $C_2$-$C_6$ cyclic group, and wherein any R$^β$ may optionally be substituted with one or more halo groups.

More typically, in an optionally substituted group or moiety:
(i) each hydrogen atom may optionally be replaced by a group independently selected from a fluoro, chloro, —CN, —NO$_2$, —R$^β$, —OH, —OR$^β$, —NH$_2$, —NHR$^β$, —N(R$^β$)$_2$, —R$^α$—OH, —R$^α$—OR$^β$, —R$^α$—NH$_2$, —R$^α$—NHR$^β$, —R$^α$—N(R$^β$)$_2$, —COR$^β$, —COOH, —COOR$^β$, —OCOR$^β$, —NH—COR$^β$, —CONH$_2$, —CONHR$^β$, —CON(R$^β$)$_2$, —O—R$^α$—OH, —O—R$^α$—OR$^β$, —O—R$^α$—NH$_2$, —O—R$^α$—NHR$^β$, —O—R$^α$—N(R$^β$)$_2$, —NH—R$^α$—OH, —NH—R$^α$—OR$^β$, —NH—R$^α$—NH$_2$, —NH—R$^α$—NHR$^β$, —NH—R$^α$—N(R$^β$)$_2$,

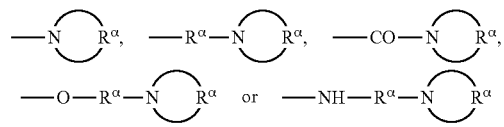

group; and/or
(ii) any two hydrogen atoms attached to the same carbon atom may optionally be replaced by an oxo (=O) group; and/or
(iii) any two hydrogen atoms attached to the same or different atoms, within the same optionally substituted group or moiety, may optionally be replaced by a bridging substituent —R$^α$—;
  wherein each —R$^α$— is independently selected from an alkylene or alkenylene group, wherein the alkylene or alkenylene group contains from 1 to 5 atoms in its backbone, wherein one or more carbon atoms in the backbone of the alkylene or alkenylene group may optionally be replaced by one or more heteroatoms N or O, and wherein the alkylene or alkenylene group may optionally be substituted with one or more fluoro, chloro and/or —RP groups;
  wherein each RP is independently selected from a $C_1$-$C_6$ alkyl, $C_2$-$C_6$ alkenyl or $C_2$-$C_6$ cyclic group, and wherein any R$^β$ may optionally be substituted with one or more fluoro and/or chloro groups.

Alternately, in an optionally substituted group or moiety:
(i) each hydrogen atom may optionally be replaced by a group independently selected from a fluoro, chloro, —CN, —NO$_2$, —R$^β$, —OH, —OR$^β$, —NH$_2$, —NHR$^β$, —N(R$^β$)$_2$, —COR$^β$, —COOH, —COOR$^β$, —OCOR$^β$, —NH—COR$^β$, —CONH$_2$, —CONHR$^β$, —CON(R$^β$)$_2$, —O—R$^α$—OH, —O—R$^α$—OR$^β$, —O—R$^α$—NH$_2$, —O—R$^α$—NHR$^β$, —O—R$^α$—N(R$^β$)$_2$, —NH—R$^α$—OH, —NH—R$^α$—OR$^β$, —NH—R$^α$—NH$_2$, —NH—R$^α$—NHR$^β$, —NH—R$^α$—N(R$^β$)$_2$,

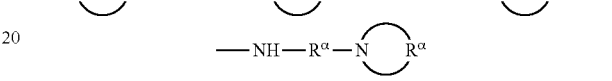

group; and/or
(ii) any two hydrogen atoms attached to the same carbon atom may optionally be replaced by an oxo (=O) group; and/or
(iii) any two hydrogen atoms attached to the same or different atoms, within the same optionally substituted group or moiety, may optionally be replaced by a bridging substituent —R$^α$—;
  wherein each —R$^α$— is independently selected from an alkylene or alkenylene group, wherein the alkylene or alkenylene group contains from 1 to 4 atoms in its backbone, wherein one or more carbon atoms in the backbone of the alkylene or alkenylene group may optionally be replaced by one or more heteroatoms N or O, and wherein the alkylene or alkenylene group may optionally be substituted with one or more fluoro, chloro and/or —RP groups;
  wherein each RP is independently selected from a $C_1$-$C_6$ alkyl, $C_2$-$C_6$ alkenyl or $C_2$-$C_6$ cyclic group, and wherein any RP may optionally be substituted with one or more fluoro and/or chloro groups.

More typically still, in an optionally substituted group or moiety each hydrogen atom may optionally be replaced by a group independently selected from a fluoro, chloro, —CN, —R$^β$, —OR$^β$, —NH$_2$, —NHR$^β$, —N(R$^β$)$_2$, —R$^α$—OR$^β$, —R$^α$—NH$_2$, —R$^α$—NHR$^β$, —R$^α$—N(R$^β$)$_2$, —O—R$^α$—OR$^β$, —O—R$^α$—NH$_2$, —O—R$^α$—NHR$^β$, —O—R$^α$—N(R$^β$)$_2$, —NH—R$^α$—OR$^β$, —NH—R$^α$—NH$_2$, —NH—R$^α$—NHR$^β$, —NH—R$^α$—N(R$^β$)$_2$,

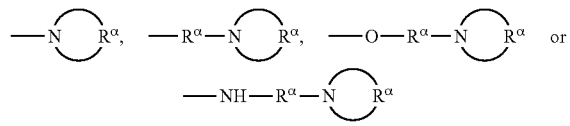

group;
  wherein each —R$^α$— is independently selected from an alkylene group, wherein the alkylene group contains from 1 to 5 atoms in its backbone, wherein one carbon atom in the backbone of the alkylene group may optionally be replaced by a single heteroatom N or O, and wherein the alkylene group may optionally be substituted with one or more fluoro, chloro and/or —R$^\beta$ groups;

wherein each RP is independently selected from a C$_1$-C$_4$ alkyl group, and wherein any R$^\beta$ may optionally be substituted with one or more fluoro and/or chloro groups.

The term "halo" includes fluoro, chloro, bromo and iodo.

Typically a substituted group comprises 1, 2, 3 or 4 substituents, more typically 1, 2 or 3 substituents, more typically 1 or 2 substituents, and even more typically 1 substituent.

Unless stated otherwise, any divalent bridging substituent (e.g. —O—, —S—, —NH—, —NR$^\beta$—, —N(O)(R$^\beta$)—, —N$^+$(R$^\beta$)$_2$— or —R$^\alpha$—) of an optionally substituted group or moiety (e.g. R$^1$) must only be attached to the specified group or moiety and may not be attached to a second group or moiety (e.g. R$^2$), even if the second group or moiety can itself be optionally substituted.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Where reference is made to a carbon atom of a hydrocarbyl or other group being replaced by a N, O or S atom, what is intended is that:

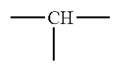

is replaced by

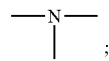

—CH$_2$— is replaced by —NH—, —O— or —S—;
—CH$_3$ is replaced by —NH$_2$, —OH, or —SH;
—CH= is replaced by —N=;
CH$_2$= is replaced by NH=, O= or S=; or
CH≡ is replaced by N≡;

provided that the resultant group comprises at least one carbon atom. For example, methoxy, dimethylamino and aminoethyl groups are considered to be hydrocarbyl groups including one or more heteroatoms N, O or S in their carbon skeleton.

Where reference is made to a —CH$_2$— group in the backbone of a hydrocarbyl or other group being replaced by a —N(O)(R$^\beta$)— or —N$^+$(R$^\beta$)$_2$— group, what is intended is that:

—CH$_2$— is replaced by or

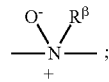

—CH$_2$— is replaced by

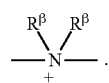

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a C$_1$-C$_{20}$ hydrocarbyl group. More typically a hydrocarbyl group is a C$_1$-C$_{15}$ hydrocarbyl group. More typically a hydrocarbyl group is a C$_1$-C$_{10}$ hydrocarbyl group. A "hydrocarbylene" group is similarly defined as a divalent hydrocarbyl group.

Unless otherwise stated, an "alkyl" substituent group or an alkyl moiety in a substituent group may be linear or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a C$_1$-C$_{12}$ alkyl group. More typically an alkyl group is a C$_1$-C$_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a C$_2$-C$_{12}$ alkenyl group. More typically an alkenyl group is a C$_2$-C$_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl groups/moieties. Typically an alkynyl group is a C$_2$-C$_{12}$ alkynyl group. More typically an alkynyl group is a C$_2$-C$_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. fused, bridged or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

As used herein, where it is stated that a cyclic group such as a 6-membered heteroaryl group is monocyclic, it is to be understood that the cyclic group is not substituted with a divalent bridging substituent (e.g. —O—, —S—, —NH—, —NR$^\beta$—, —N(O)(R$^\beta$)—, —N$^+$(R$^\beta$)$_2$— or —R$^\alpha$—) so as to form a fused, bridged or spiro substituent. However, unless stated otherwise, a substituted monocyclic group may be substituted with one or more monovalent cyclic groups. Similarly, where it is stated that a group is bicyclic, it is to be understood that the cyclic group including any fused, bridged or spiro divalent bridging substituents attached to the cyclic group, but excluding any monovalent cyclic substituents, is bicyclic.

A "heterocyclic" substituent group or a heterocyclic moiety in a substituent group refers to a cyclic group or moiety including one or more carbon atoms and one or more heteroatoms, e.g. N, O or S, in the ring structure. Examples of heterocyclic groups include heteroaryl groups as discussed below and non-aromatic heterocyclic groups such as azetinyl, azetidinyl, oxetanyl, thietanyl, tetrahydrofuranyl, pyrrolidinyl, tetrahydrothiophenyl, pyrazolidinyl, imidazolidinyl, dioxolanyl, oxathiolanyl, tetrahydropyranyl, piperidinyl, thianyl, piperazinyl, dioxanyl, morpholinyl and thiomorpholinyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/ moieties include the following:

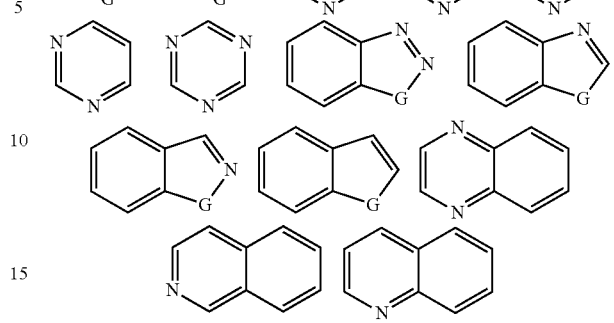

wherein G=O, S or NH

As used herein, the term "heteroaryl" includes heterocyclic groups or moieties which possess aromatic tautomers and thus have significant aromatic character. For example, the term includes unsaturated δ-lactam, unsaturated cyclic urea and uracil groups such as those illustrated below by virtue of the tautomerism shown:

For the avoidance of doubt, the term "heteroaryl" does not include heterocyclic groups or moieties which may possess aromatic character only by virtue of mesomeric charge separation or formation, since such groups or moieties have very low or no aromatic character. For example, the term "heteroaryl" does not include N-alkylated uracil groups which may have the tautomeric and mesomeric forms shown below:

As is apparent from the above, in certain circumstances the nature of any optional substitution may affect whether or not a group is considered aromatic. Unless stated otherwise, where a cyclic group or moiety is stated to be aromatic, such as an aryl or a heteroaryl group, it is to be understood that the group or moiety when considered after any optional substitution is aromatic. Similarly, where a cyclic group or moiety is stated to be non-aromatic, such as a cycloalkyl, cycloalkenyl or non-aromatic heterocyclic group, it is to be understood that the group or moiety when considered after any optional substitution is non-aromatic. In other words, it is the final structure of the compound as a whole that should be considered. For example, consider the compounds (A), (B) and (C) below:

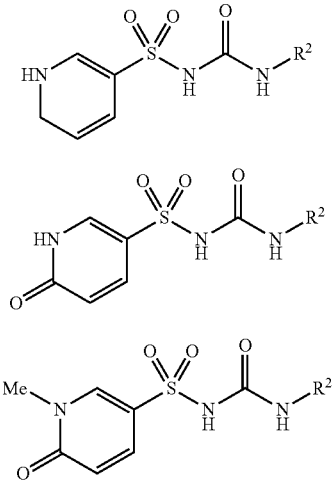

In the compound (A), no optional substitution is present and so $R^1$ is non-aromatic, i.e. $R^1$ is not a 6-membered heteroaryl group. In the compound (B), the $R^1$ group includes an optional oxo (=O) substituent; the resultant cyclic group when considered after this optional substitution is aromatic and so $R^1$ is a 6-membered heteroaryl group. In the compound (C), the $R^1$ group includes optional oxo (=O) and methyl substituents; the resultant cyclic group when considered after this optional substitution is non-aromatic and so $R^1$ is not a 6-membered heteroaryl group.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

In the context of the present specification, unless otherwise stated, a $C_x$-$C_y$ group is defined as a group containing from x to y carbon atoms. For example, a $C_1$-$C_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, such as nitrogen, oxygen and sulphur are not to be counted as carbon atoms when calculating the number of carbon atoms in a $C_x$-$C_y$ group. For example, a morpholinyl group is to be considered a $C_4$ heterocyclic group, not a $C_6$ heterocyclic group.

As stated above, $R^1$ is a 6-membered heteroaryl group containing at least one nitrogen atom in the 6-membered ring structure. Thus, the heteroaryl group of $R^1$ comprises a 6-membered ring structure (i.e. a ring formed of 6 atoms) which includes at least one nitrogen atom, and the 6-membered ring structure is directly attached to the —$SO_2$— group of formula (I). The 6-membered heteroaryl group may optionally be substituted, for example with any optional substituent as defined above.

For the purposes of the present specification, where it is stated that a first atom or group is "directly attached" to a second atom or group it is to be understood that the first atom or group is covalently bonded to the second atom or group with no intervening atom(s) or groups being present. So, for example, for the group —(C=O)N($CH_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

In one embodiment, the 6-membered heteroaryl group of $R^1$ is monocyclic. Where the 6-membered heteroaryl group of $R^1$ is monocyclic, the 6-membered heteroaryl group may optionally be substituted with any monovalent substituent and/or divalent π-bonded substituent, such as those defined above, but may not be substituted with a divalent bridging substituent (e.g. —O—, —S—, —NH—, —$NR^β$—, —N(O)($R^β$)—, —$N^+(R^β)_2$— or —$R^α$—) so as to form a fused, bridged or spiro substituent. Examples of monocyclic 6-membered heteroaryl groups include pyridinyl, pyridazinyl, pyrimidinyl, pyrazinyl and triazinyl groups, as well as aromatic 6-lactam, aromatic cyclic urea and uracil groups such as:

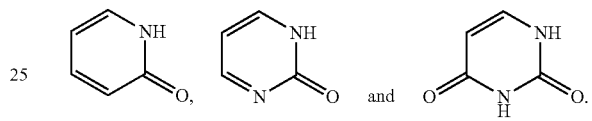

In another embodiment, the 6-membered heteroaryl group of $R^1$ may be substituted with one or more fused cycloalkyl, cycloalkenyl, non-aromatic heterocyclic, aryl or heteroaryl rings such that the resultant group is bicyclic, tricyclic or polycyclic. For example, the 6-membered heteroaryl group may optionally be substituted with —$R^α$— as defined above. The resultant group may optionally be substituted with any monovalent substituent and/or divalent π-bonded substituent, such as those defined above. Typically in such an embodiment, the resultant group is bicyclic or tricyclic, most typically bicyclic. Examples of such resultant bicyclic groups include:

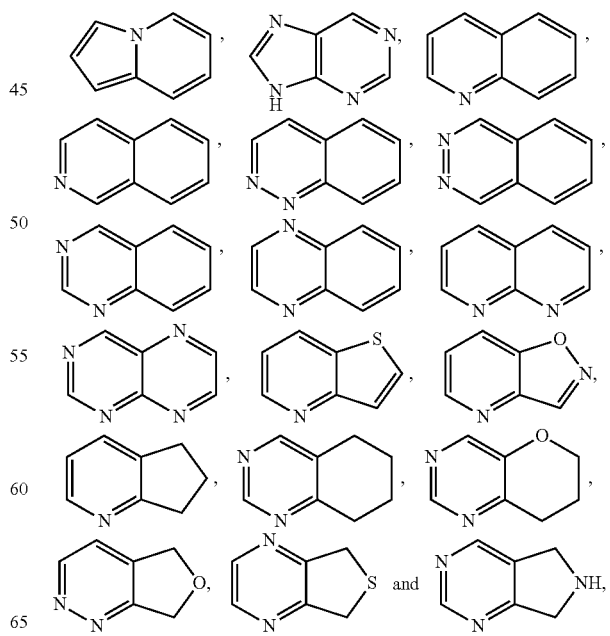

wherein a 6-membered heteroaryl ring structure in the above bicyclic groups is directly attached to the —SO₂— group of formula (I).

In another embodiment, the 6-membered heteroaryl group of R¹ does not possess a tautomer wherein the 6-membered ring structure is substituted with an oxo (=O) group. Optionally, the 6-membered heteroaryl group of R¹ does not possess a non-aromatic tautomer. In such an embodiment, the 6-membered heteroaryl group of R¹ is not an unsaturated δ-lactam, an unsaturated cyclic urea or a uracil group such as:

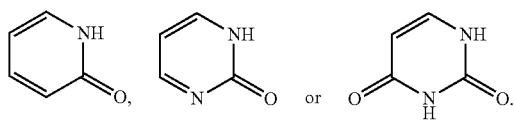

In one embodiment of the first aspect of the invention, R¹ is a 6-membered heteroaryl group containing at least two nitrogen atoms in the 6-membered ring structure, wherein R¹ may optionally be substituted. Typically, such a 6-membered heteroaryl group contains two or three nitrogen atoms in the 6-membered ring structure, with the remainder of the atoms in the 6-membered ring structure being carbon atoms. More typically, such a 6-membered heteroaryl group contains two nitrogen atoms and four carbon atoms in the 6-membered ring structure. Examples of such 6-membered heteroaryl groups containing at least two nitrogen atoms in the 6-membered ring structure include monocyclic groups such as pyridazinyl, pyrimidinyl, pyrazinyl and triazinyl groups, as well as aromatic cyclic urea and uracil groups such as:

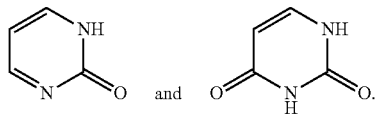 [SMILES: O=c1nccc[nH]1 ; O=c1cc[nH]c(=O)[nH]1]

Typically, such 6-membered heteroaryl groups containing at least two nitrogen atoms in the 6-membered ring structure are not groups that possess a tautomer wherein the 6-membered ring structure is substituted with an oxo (=O) group. More typically, such groups are not groups that possess a non-aromatic tautomer, i.e. not the aromatic cyclic urea and uracil groups shown above.

Further examples of suitable 6-membered heteroaryl groups containing at least two nitrogen atoms in the 6-membered ring structure include bicyclic groups such as:

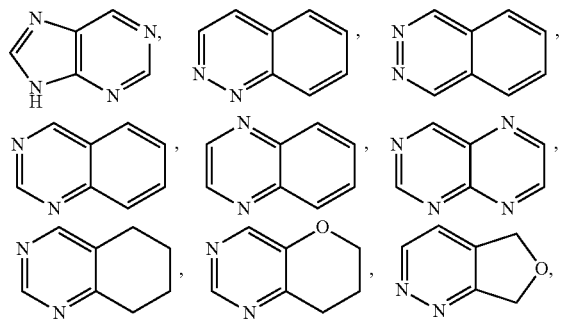

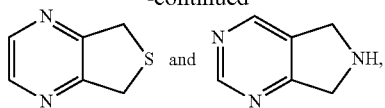

wherein a 6-membered heteroaryl ring structure in the above bicyclic groups is directly attached to the —SO₂— group of formula (I).

Typically, where R¹ is a 6-membered heteroaryl group containing at least two nitrogen atoms in the 6-membered ring structure, R² is a cyclic group substituted at the α and α' positions, wherein R² may optionally be further substituted. For example, R² may be an aryl or a heteroaryl group, wherein the aryl or the heteroaryl group is substituted at the α and α' positions, and wherein R² may optionally be further substituted.

Typically, where R¹ is a 6-membered heteroaryl group containing at least two nitrogen atoms in the 6-membered ring structure, R² is a phenyl or a 6-membered heteroaryl group, wherein the phenyl or the heteroaryl group is substituted at the α-position, and wherein R² may optionally be further substituted. For example, R² may be a phenyl or a 6-membered heteroaryl group, wherein the phenyl or the heteroaryl group is substituted at the α and α' positions, and wherein R² may optionally be further substituted.

As used herein, the nomenclature α,β, α',β' refers to the position of the atoms of a cyclic group, such as —R², relative to the point of attachment of the cyclic group to the remainder of the molecule. For example, where —R² is a 1,2,3,5,6,7-hexahydro-s-indacen-4-yl moiety, the α,β, α' and β' positions are as follows:

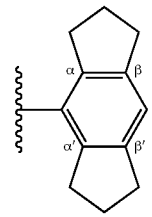 [SMILES: *c1c2c(cc3c1CCC3)CCC2]

Examples of compounds of the invention where R¹ is a 6-membered heteroaryl group containing at least two nitrogen atoms in the 6-membered ring structure include:

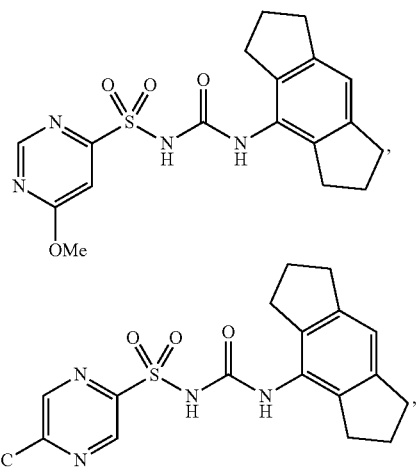

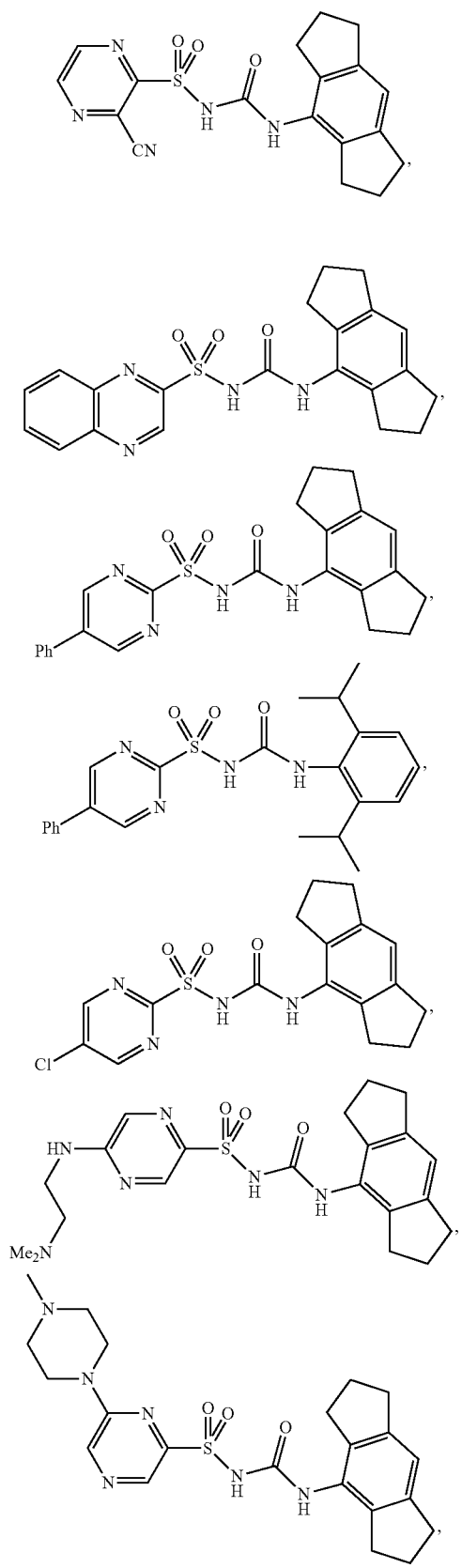
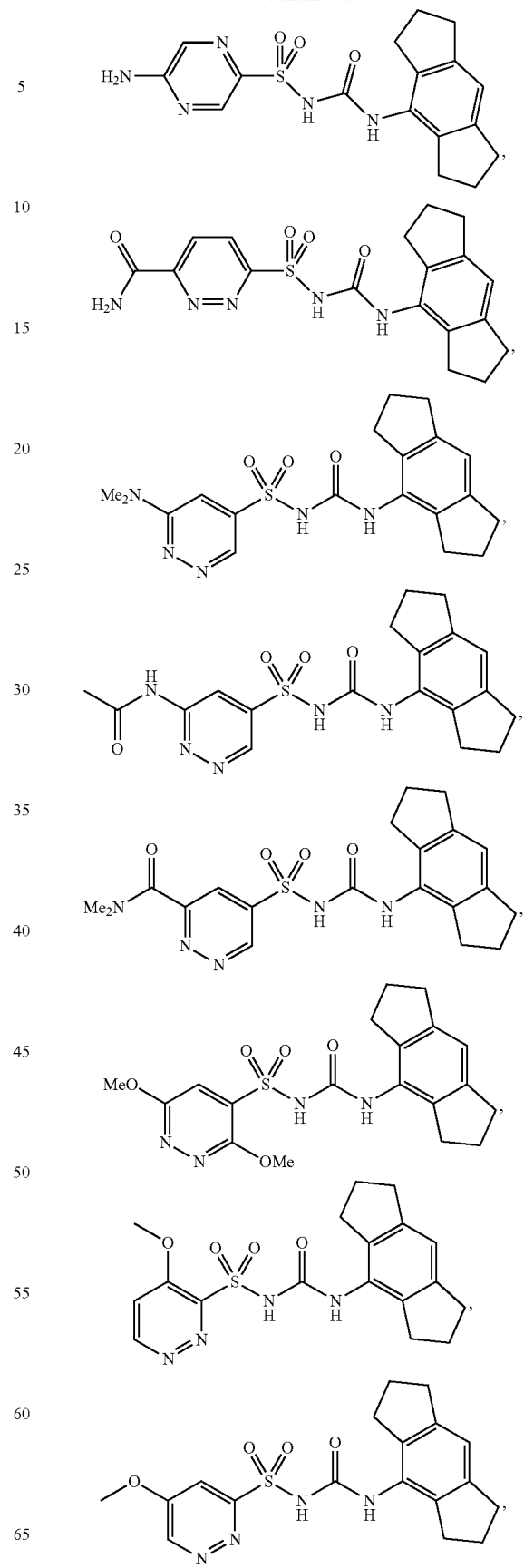

-continued
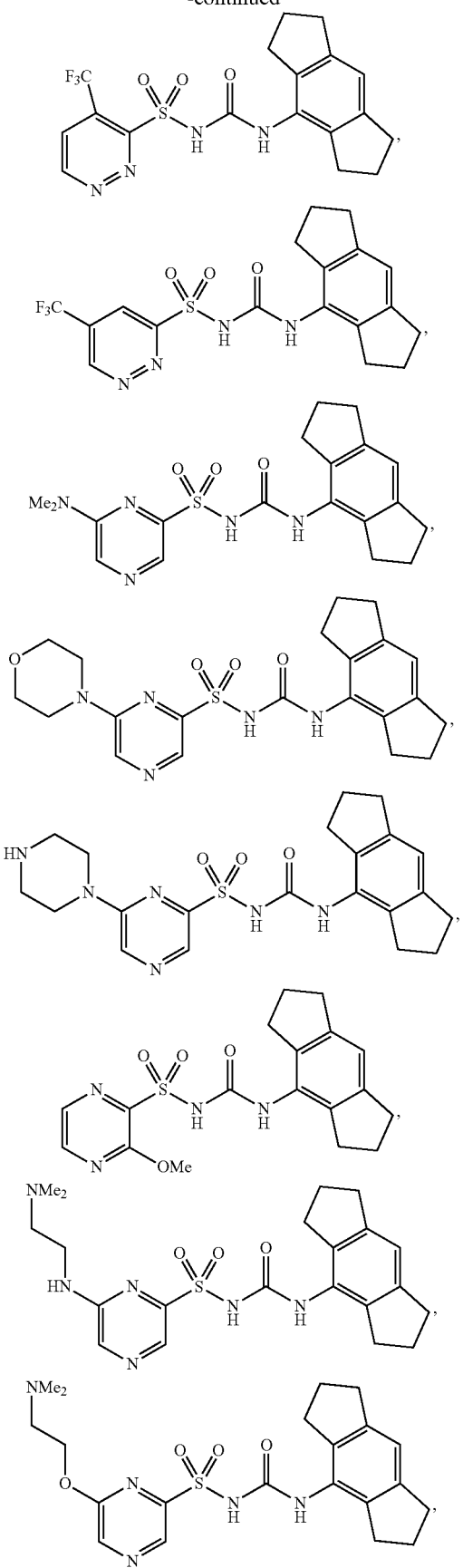
-continued
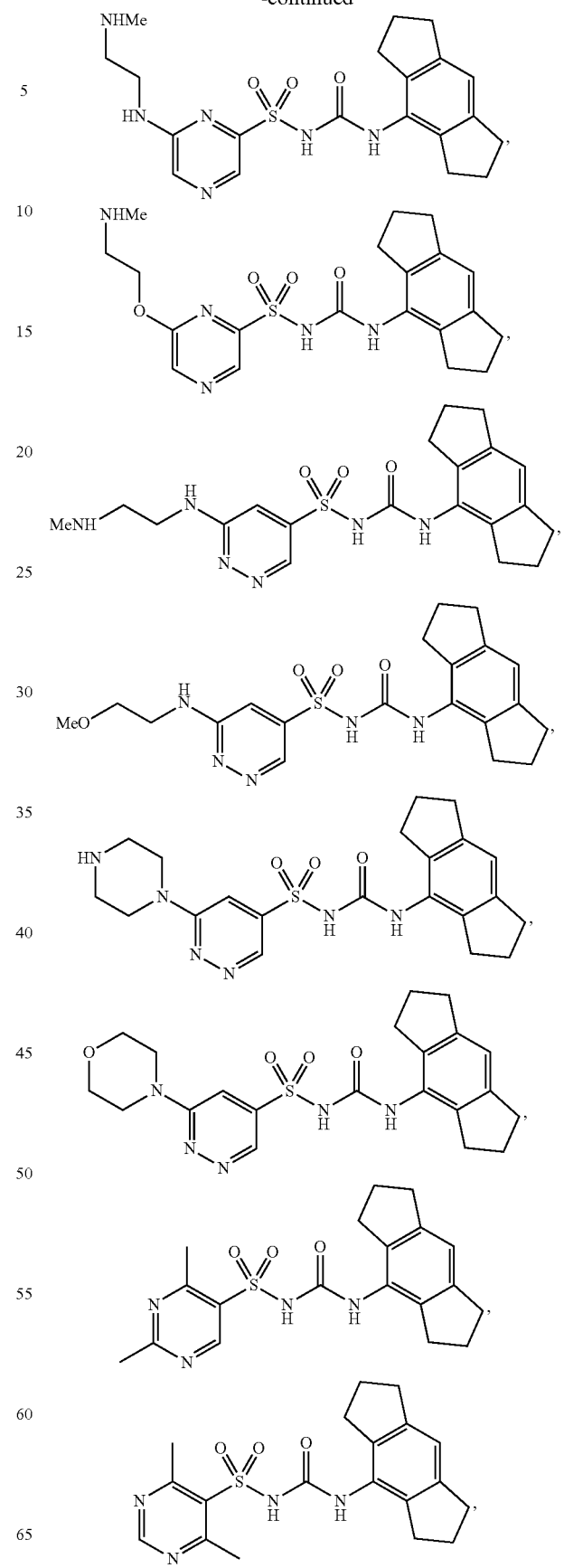

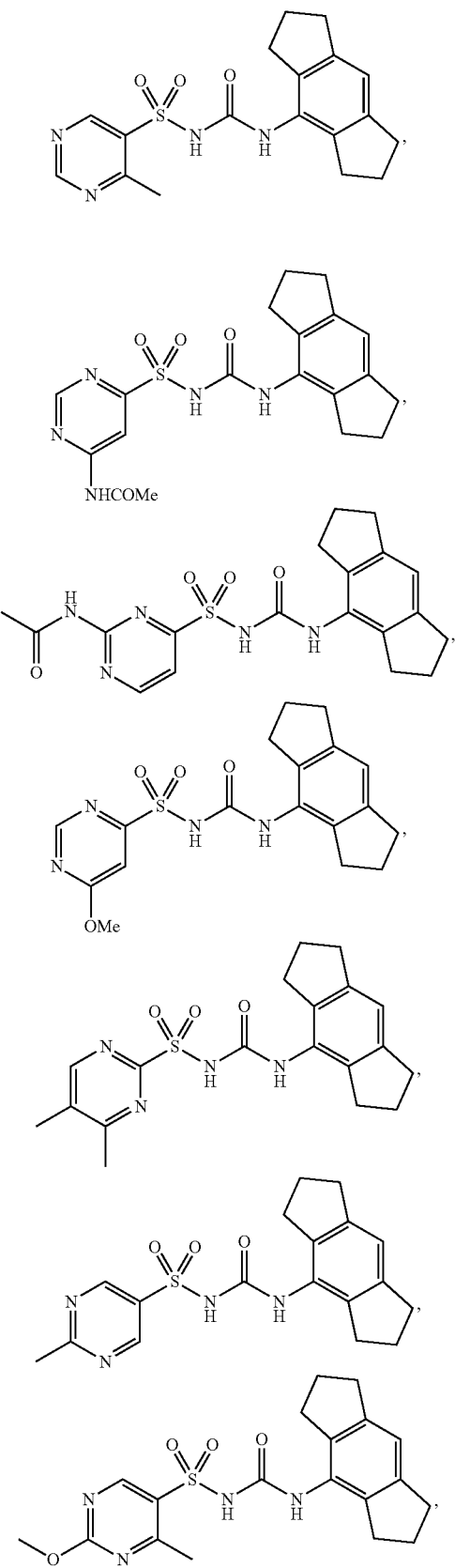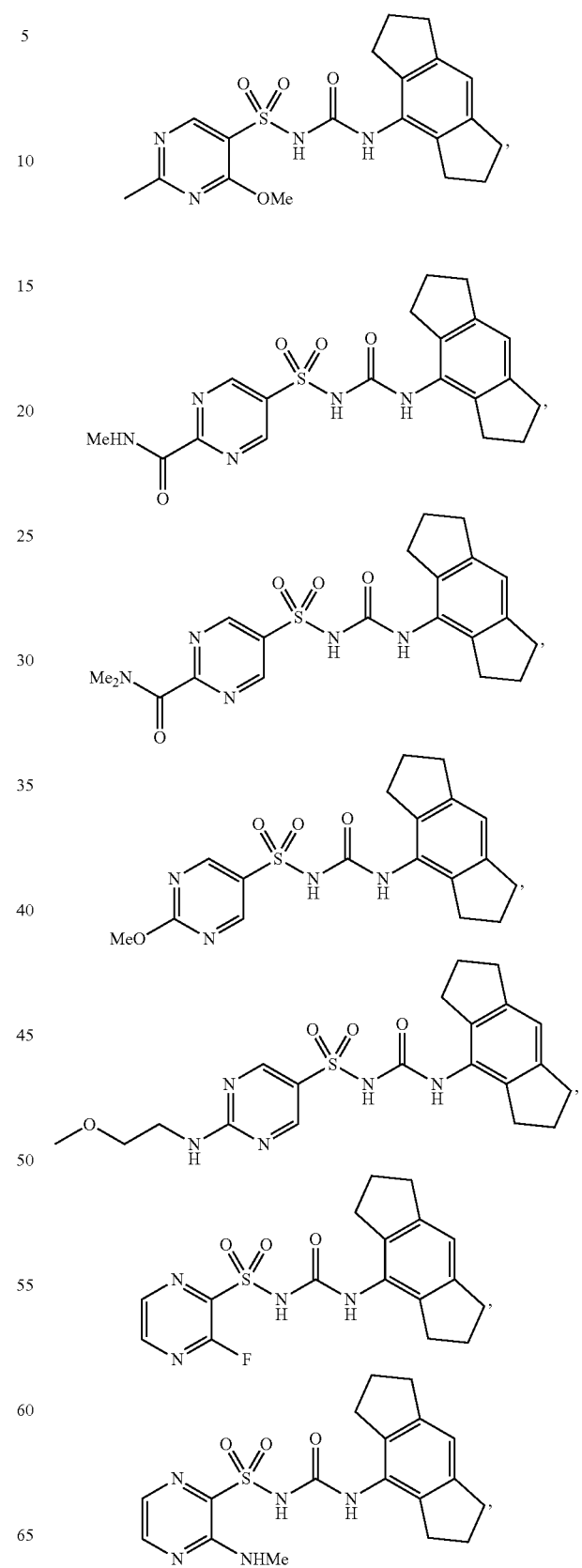

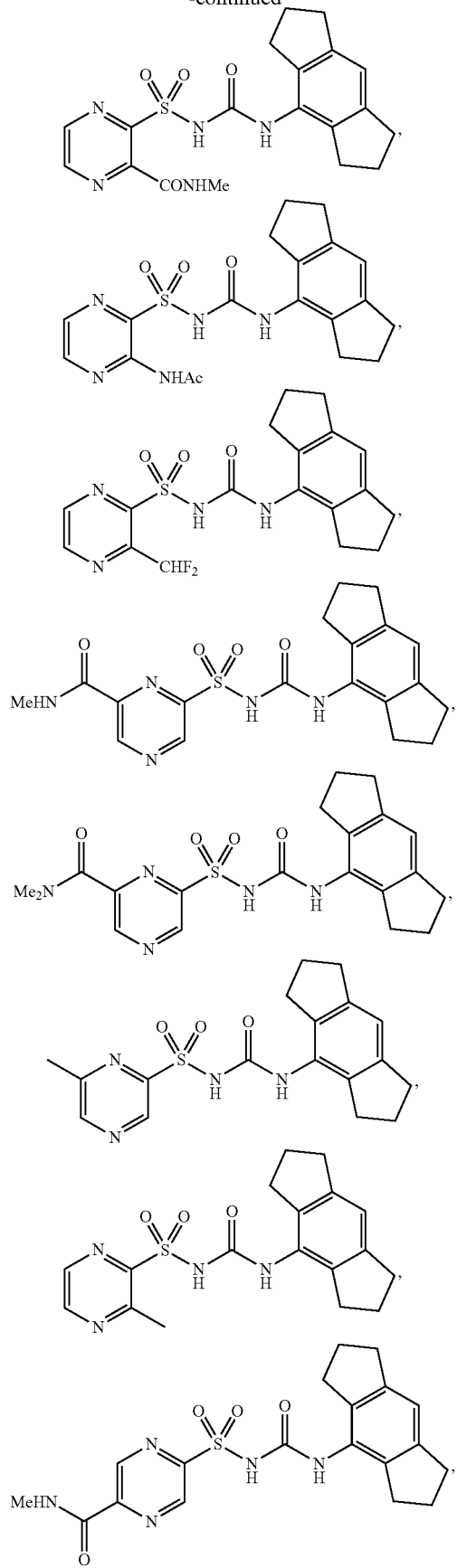
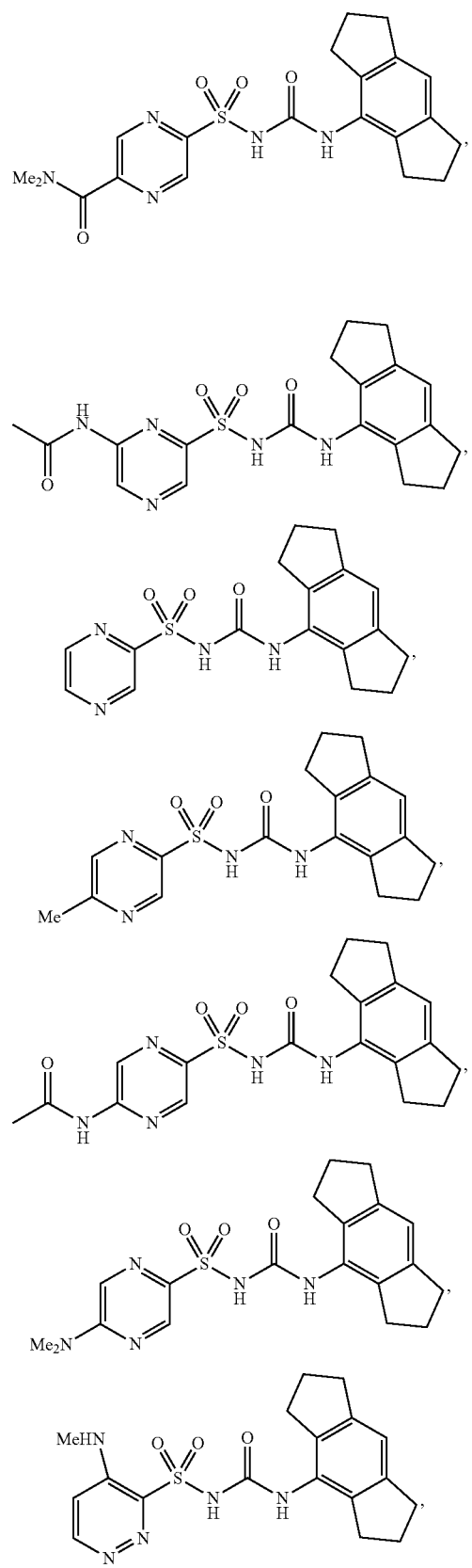

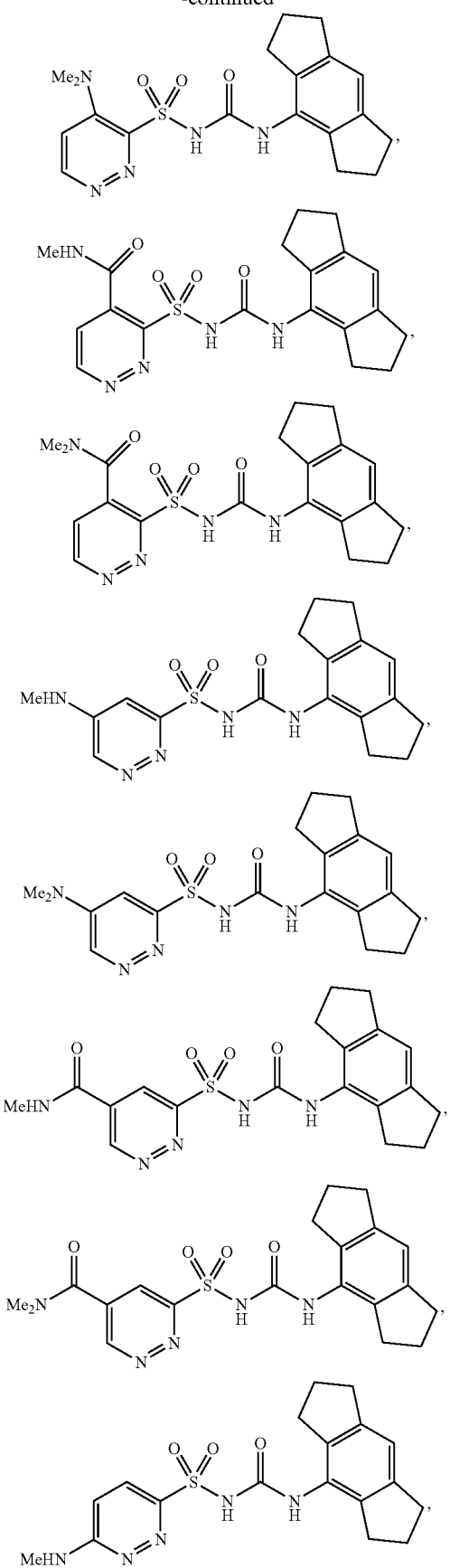
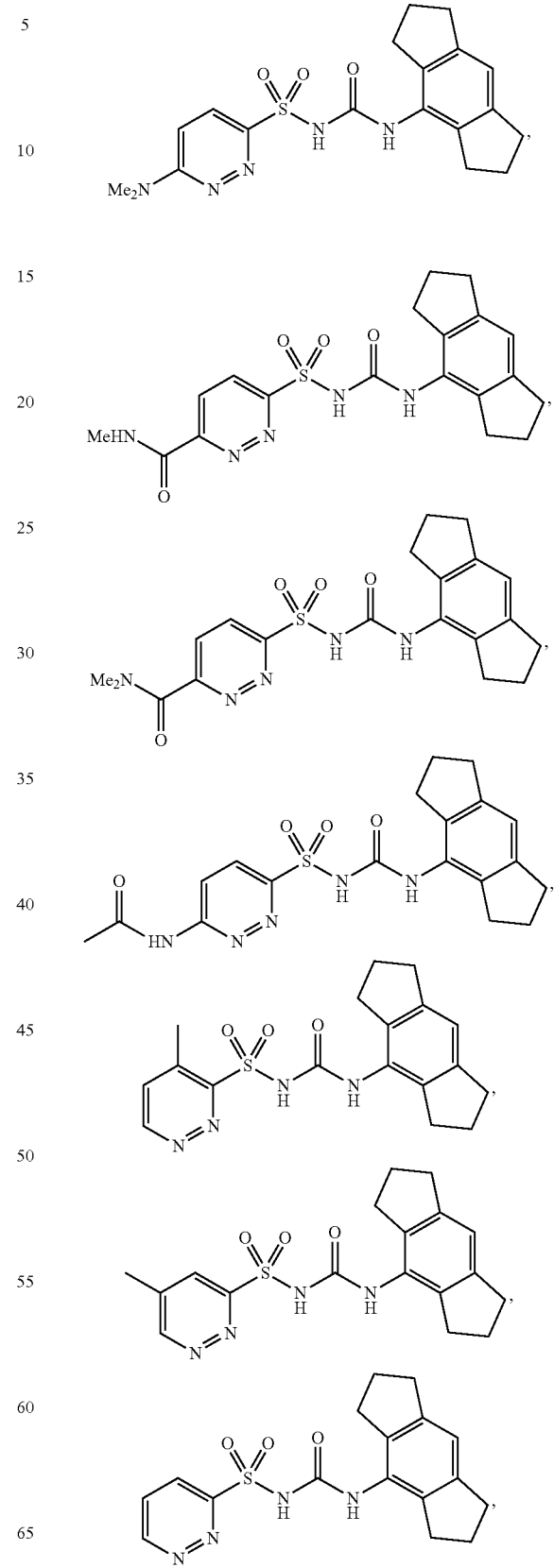

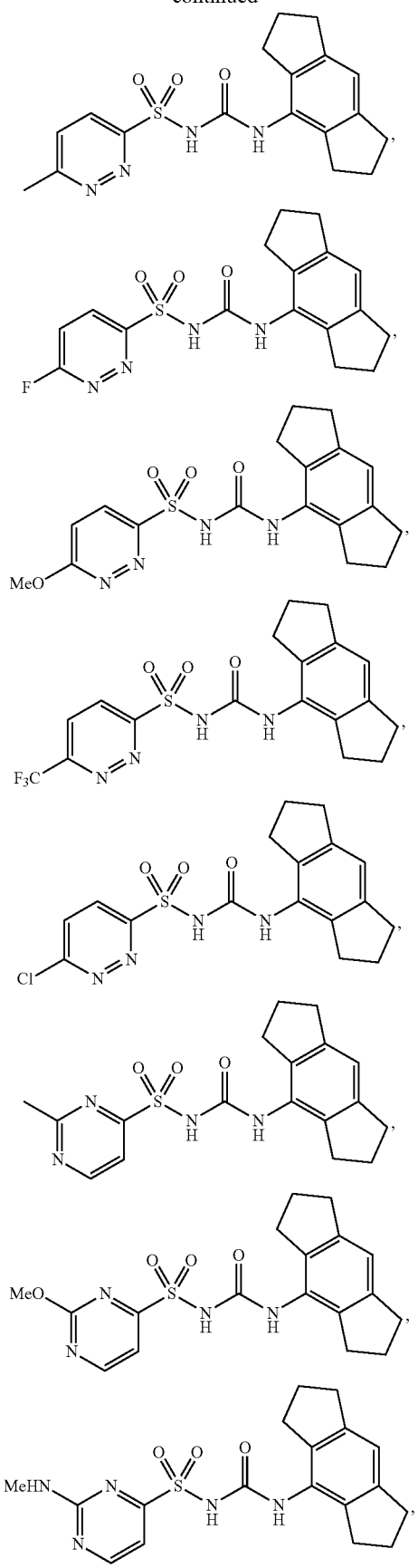
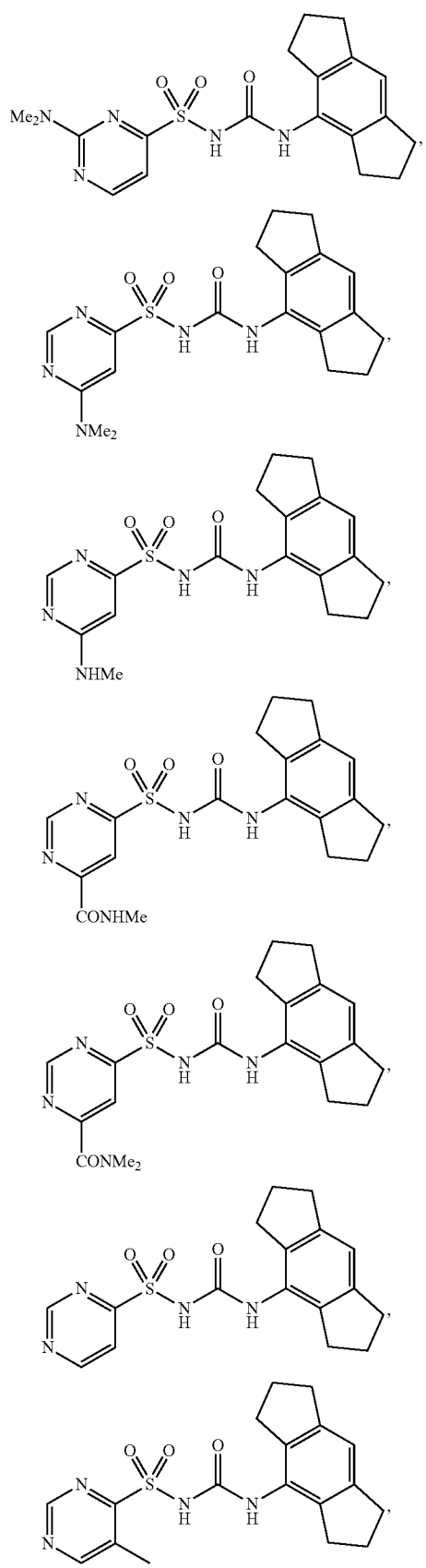

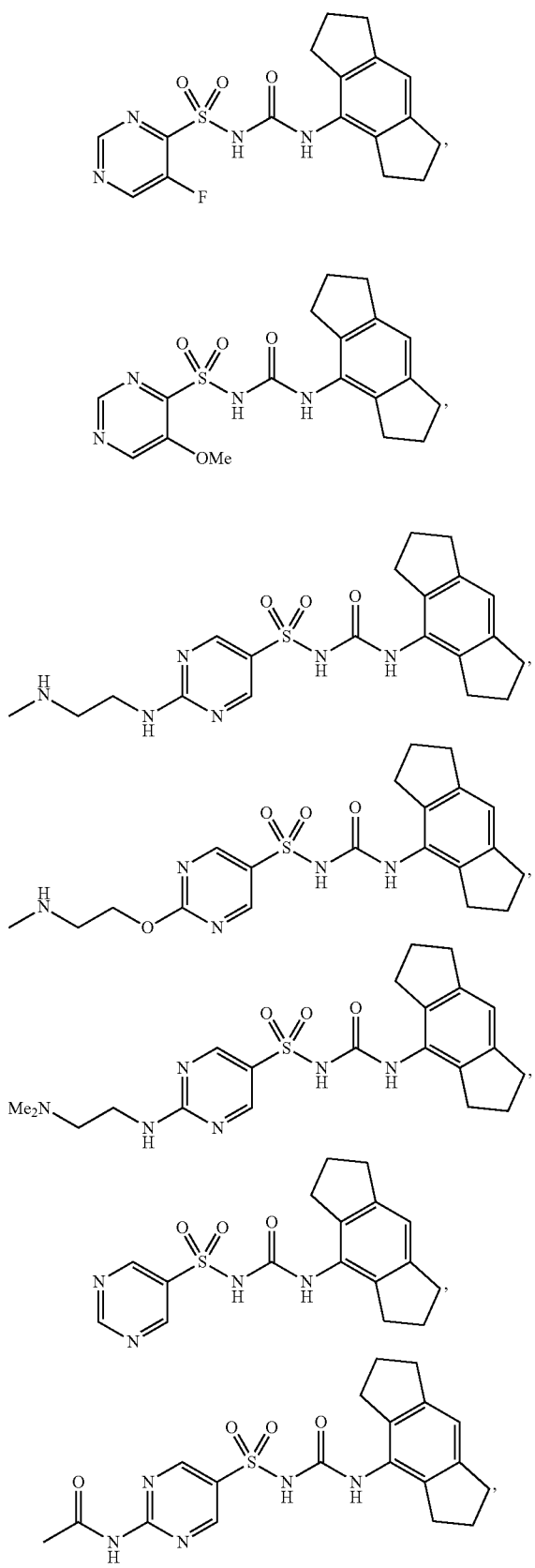
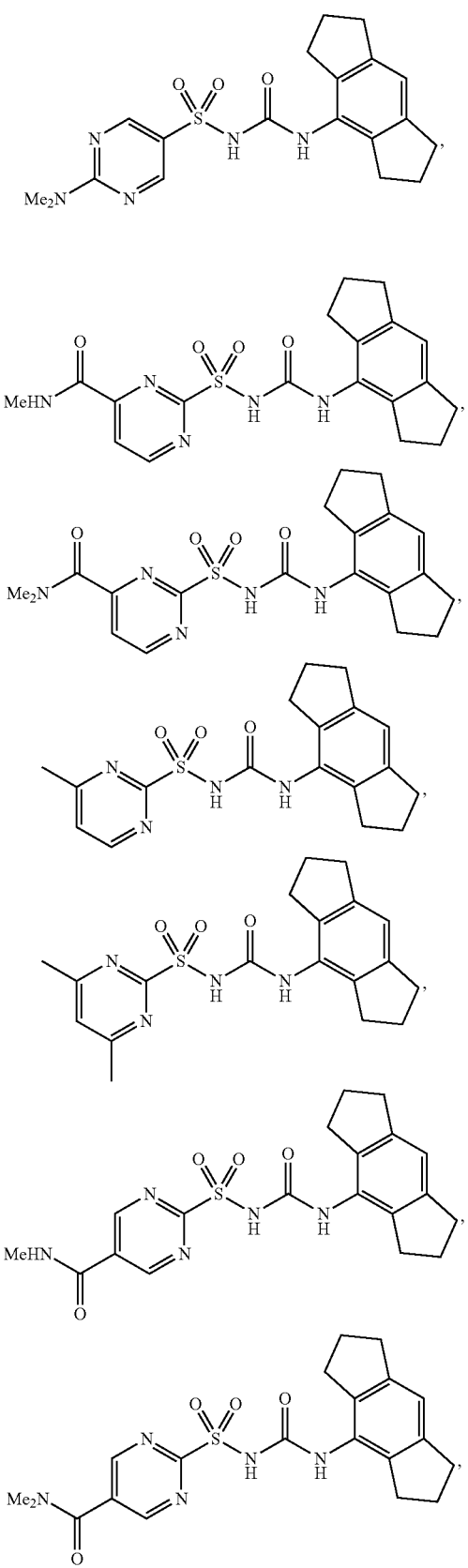

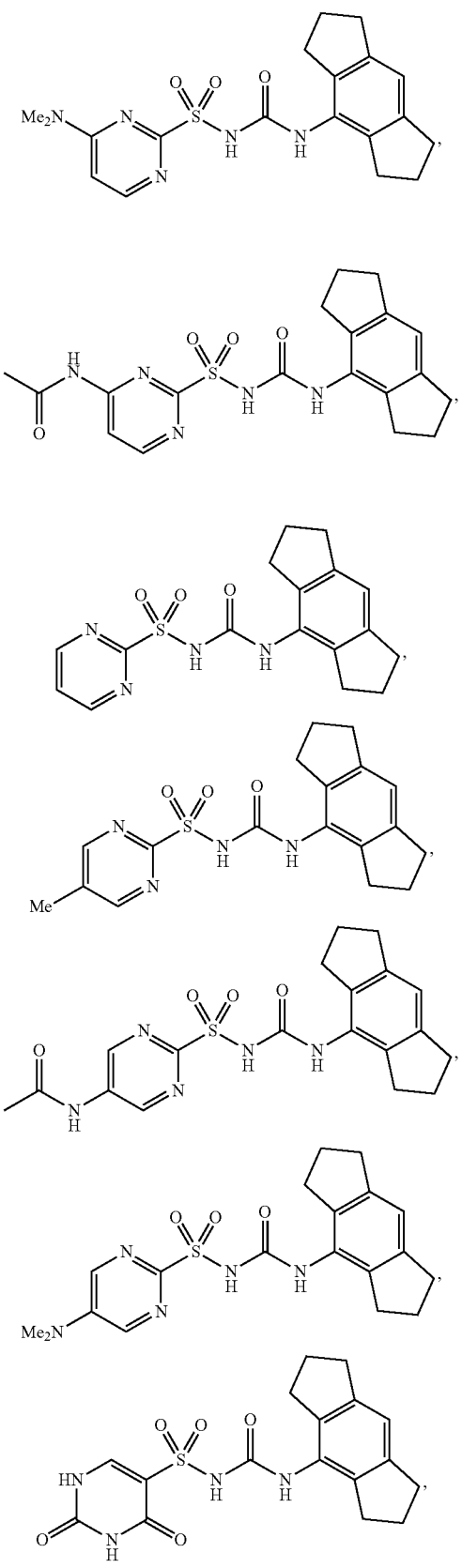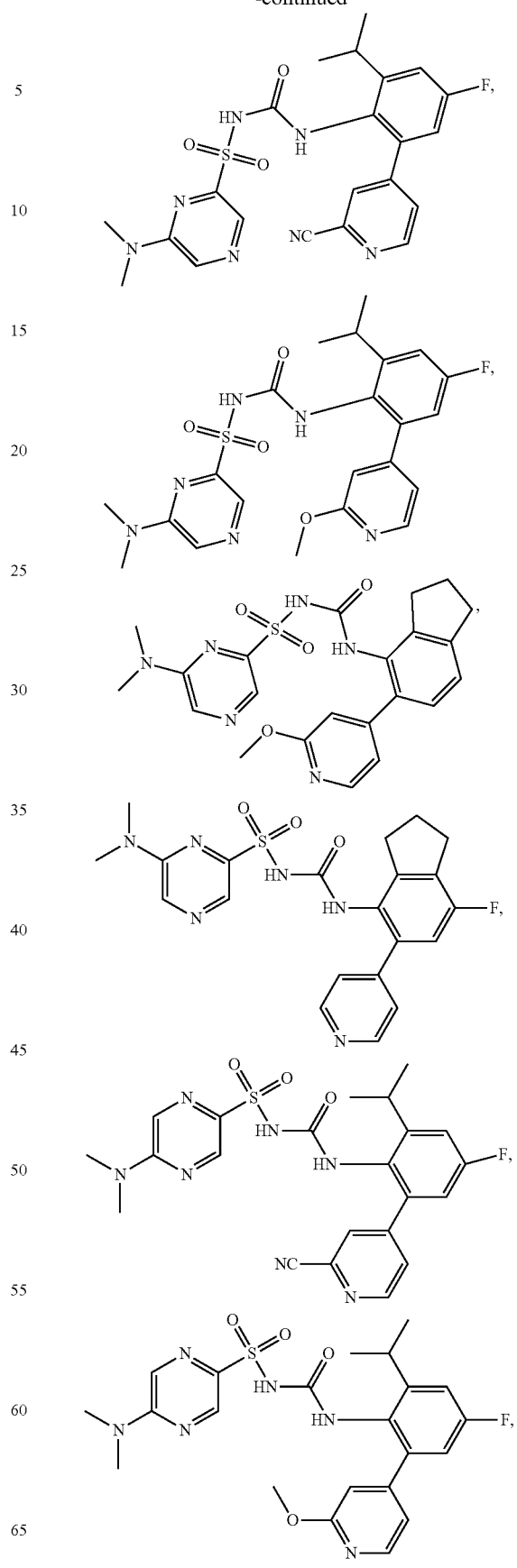

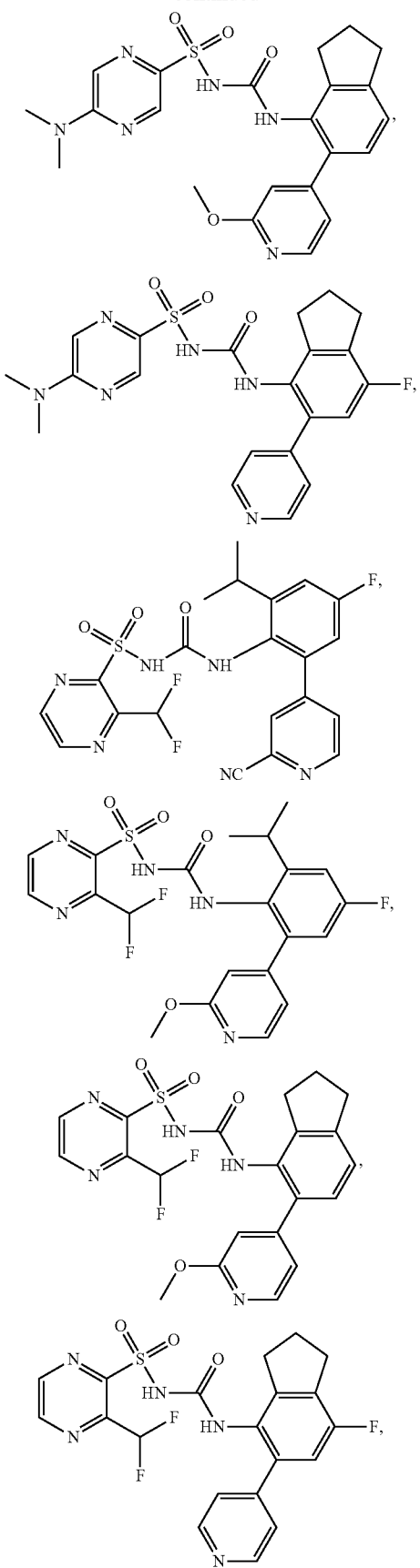
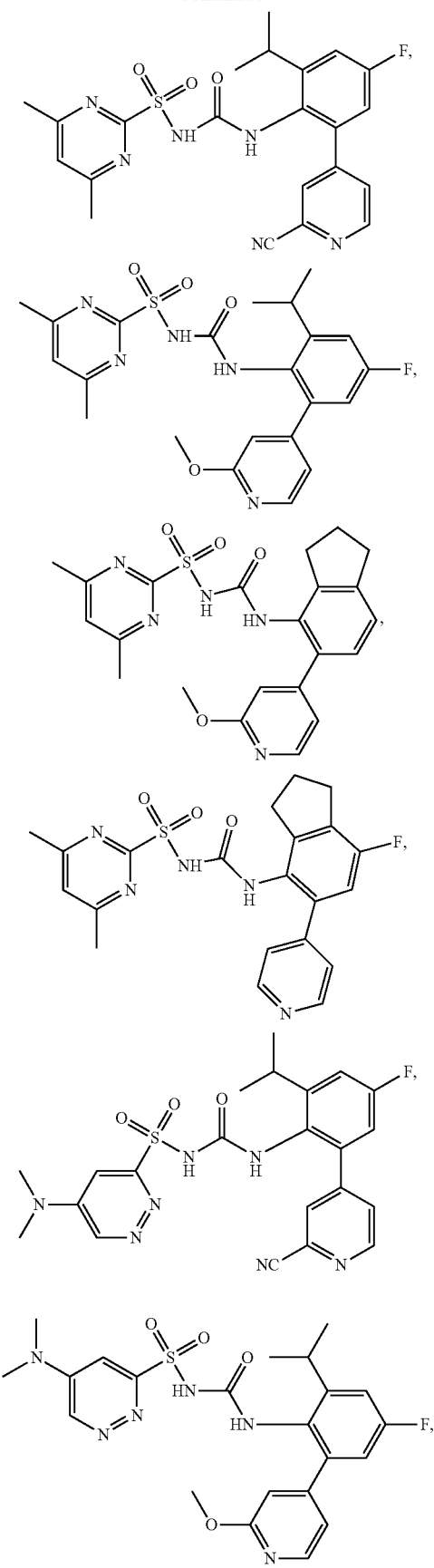

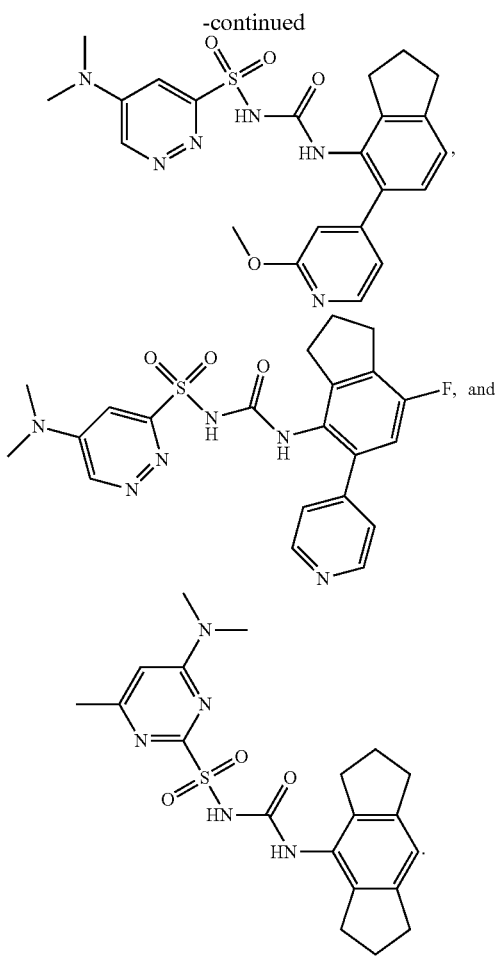

The at least one nitrogen atom in the 6-membered ring structure may be located at the 2, 3, 4, 5 or 6-position of the 6-membered ring structure. The atom at the 1-position of the 6-membered ring structure is a carbon atom.

As used herein, reference to substitution at the n-position in relation to a group, where n is an integer, refers to the position of substitution relative to the point of attachment of the group to the remainder of the molecule. For example, where $R^1$ is a 6-membered heteroaryl group the positions of the group may be numbered as follows:

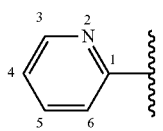 [SMILES: *c1ccccn1]

As is evident in the above example, the nitrogen atom is located at the 2-position.

In one embodiment of the first aspect of the invention, where $R^1$ is a 6-membered heteroaryl group containing at least two nitrogen atoms in the 6-membered ring structure, at least one of the two nitrogen atoms is located at the 3, 4 or 5-position of the 6-membered ring structure. A second nitrogen atom is typically located at any of the 2, 3, 4, 5 or 6-positions. The atom at the 1-position of the 6-membered ring structure is a carbon atom. For example, $R^1$ may be a 6-membered heteroaryl group containing two nitrogen atoms and four carbon atoms in the 6-membered ring structure, wherein the nitrogen atoms are located at the 2- and 3-, 2- and 4-, 2- and 5-, 3- and 4-, or 3- and 5-positions.

In another embodiment of the first aspect of the invention, where $R^1$ is a 6-membered heteroaryl group containing at least two nitrogen atoms in the 6-membered ring structure, a first nitrogen atom is located at the 2-position and a second nitrogen atom is located at the 6-position of the 6-membered ring structure. Typically the 6-membered heteroaryl group is monocyclic and the remainder of the atoms in the 6-membered ring structure are carbon atoms. In such an embodiment, where $R^1$ is optionally substituted, typically the 6-membered heteroaryl group is substituted with one or more monovalent groups at the 3- and/or 5-positions of the 6-membered ring structure. More typically, the 6-membered heteroaryl group is substituted with two monovalent groups at the 3- and 5-positions of the 6-membered ring structure. Typically, such monovalent groups are each independently selected from $C_1$-$C_4$ alkyl, $C_2$-$C_4$ alkenyl, $C_1$-$C_4$ haloalkyl, $C_2$-$C_4$ haloalkenyl and X' groups, wherein X' is as defined below. More typically such monovalent groups are each independently selected $C_1$-$C_3$ alkyl groups, most typically methyl.

In another embodiment of the first aspect of the invention, the 6-membered heteroaryl group of $R^1$ is substituted with at least one monovalent group X, wherein X is at each occurrence any group that can mesomerically donate a lone pair of electrons from a nitrogen, oxygen or sulphur atom onto at least one nitrogen atom in the 6-membered ring structure, and wherein the 6-membered heteroaryl group may optionally be further substituted. For example, $R^1$ may have the structure $R^1$(a) as shown below, wherein X is a —OMe group. As illustrated, a lone pair of electrons may be mesomerically donated from the oxygen atom of the —OMe group onto the ring nitrogen atom, to give the mesomer $R^1$(b):

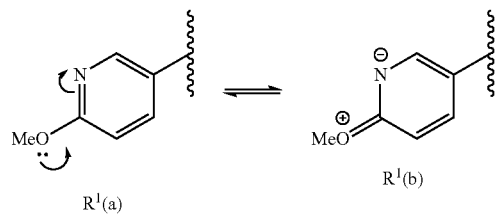

Typically in such an embodiment, the 6-membered heteroaryl group of $R^1$ is monocyclic. Typically, X is at each occurrence any group that can mesomerically donate a lone pair of electrons from a nitrogen or oxygen atom onto at least one nitrogen atom in the 6-membered ring structure. Optionally, X at each occurrence is X' as defined below, wherein each X' is attached at a position ortho- or para- to at least one nitrogen atom in the 6-membered ring structure. Typically, the 6-membered heteroaryl group of $R^1$ is substituted with one or two monovalent groups X, where the 6-membered heteroaryl group may optionally be further substituted. More typically, the 6-membered heteroaryl group of $R^1$ is substituted with a single group X, where the 6-membered heteroaryl group may optionally be further substituted with one or more groups Y, wherein Y is as defined below. Most typically, the 6-membered heteroaryl group of $R^1$ is substituted with a single group X, where the 6-membered heteroaryl group is not further substituted.

Typically, where X is at each occurrence any group that can mesomerically donate a lone pair of electrons from a nitrogen, oxygen or sulphur atom onto at least one nitrogen atom in the 6-membered ring structure, $R^2$ is a cyclic group substituted at the α and α' positions, wherein $R^2$ may optionally be further substituted. Typically, where X is at each occurrence any group that can mesomerically donate a lone pair of electrons from a nitrogen, oxygen or sulphur atom onto at least one nitrogen atom in the 6-membered ring structure, $R^2$ is an aryl or a heteroaryl group, wherein the aryl or the heteroaryl group is substituted at the α-position, and wherein $R^2$ may optionally be further substituted. For example, $R^2$ may be an aryl or a heteroaryl group, wherein the aryl or the heteroaryl group is substituted at the α and α' positions, and wherein $R^2$ may optionally be further substituted.

Examples of compounds where X is at each occurrence any group that can mesomerically donate a lone pair of electrons from a nitrogen, oxygen or sulphur atom onto at least one nitrogen atom in the 6-membered ring structure include:

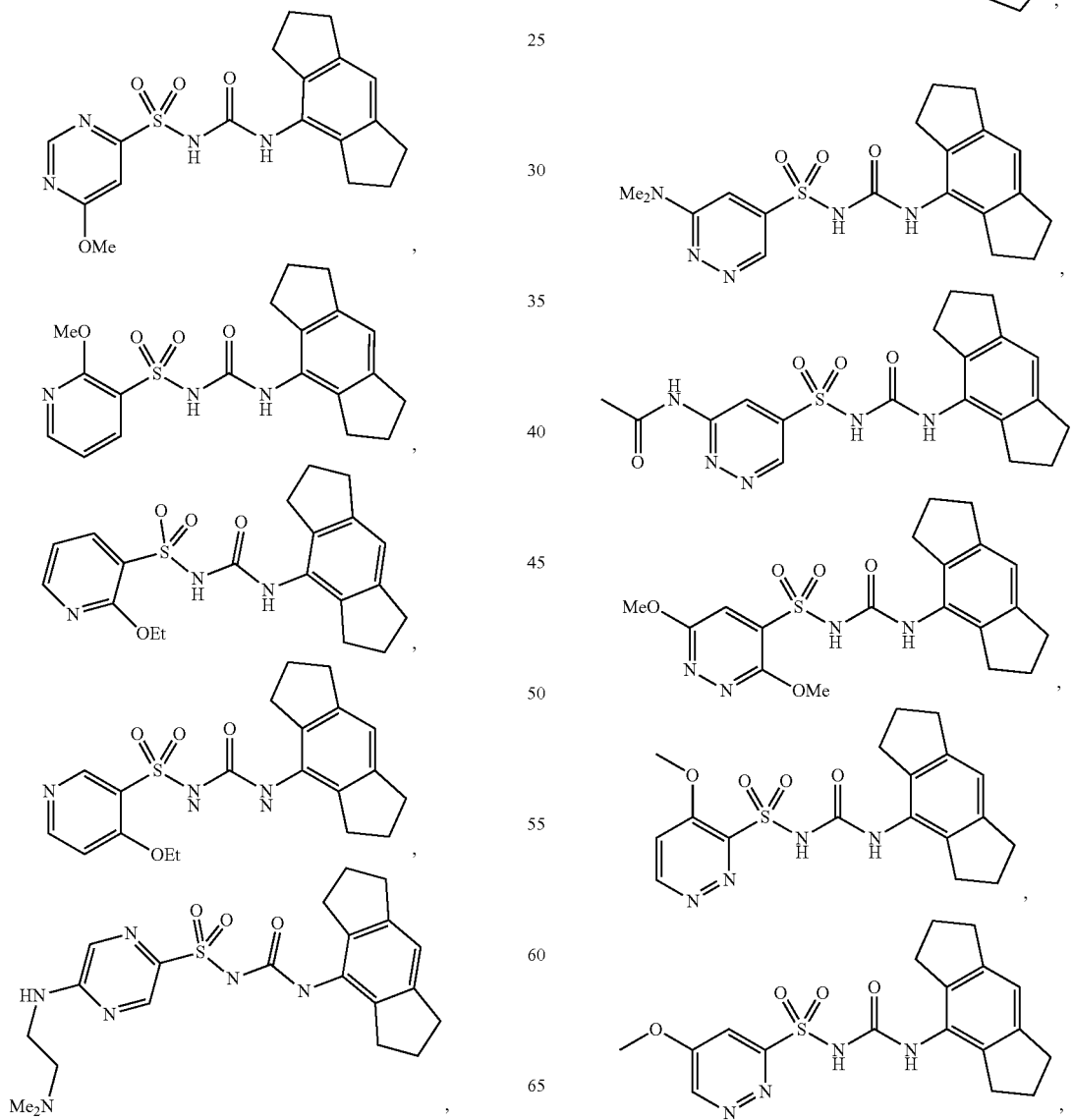
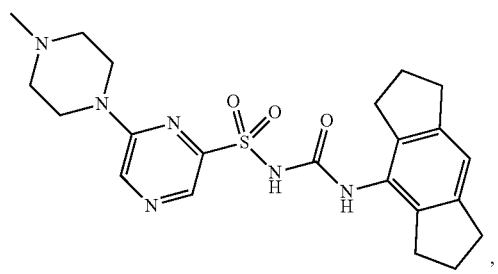
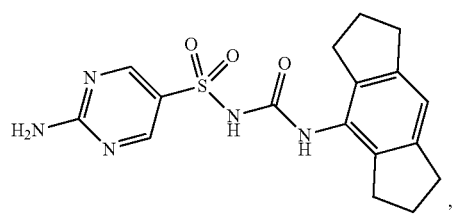

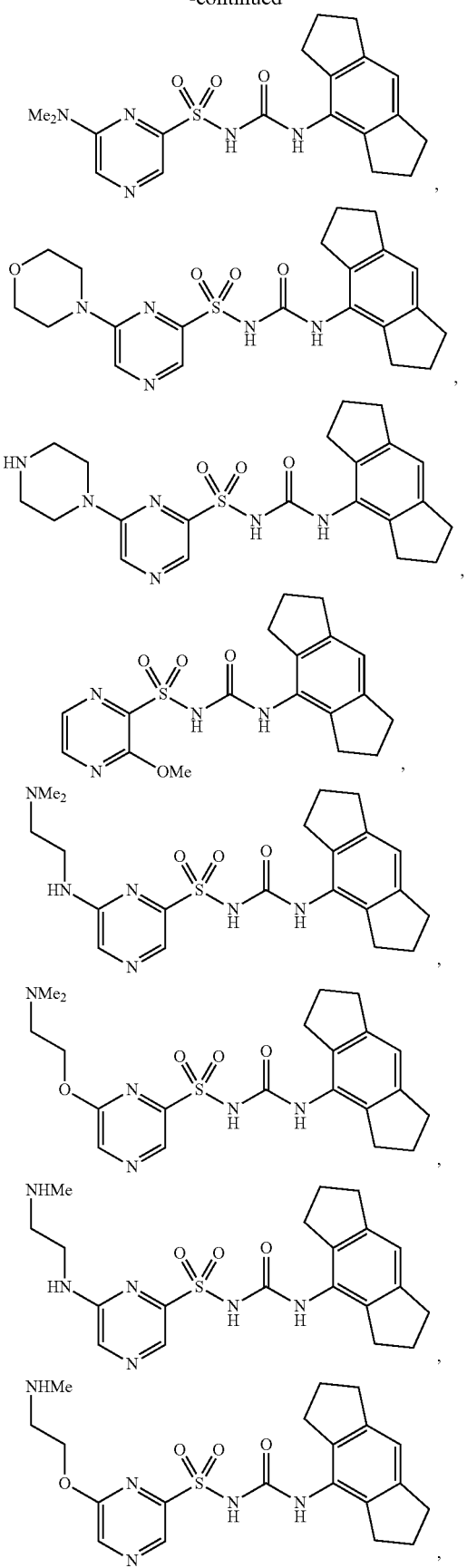
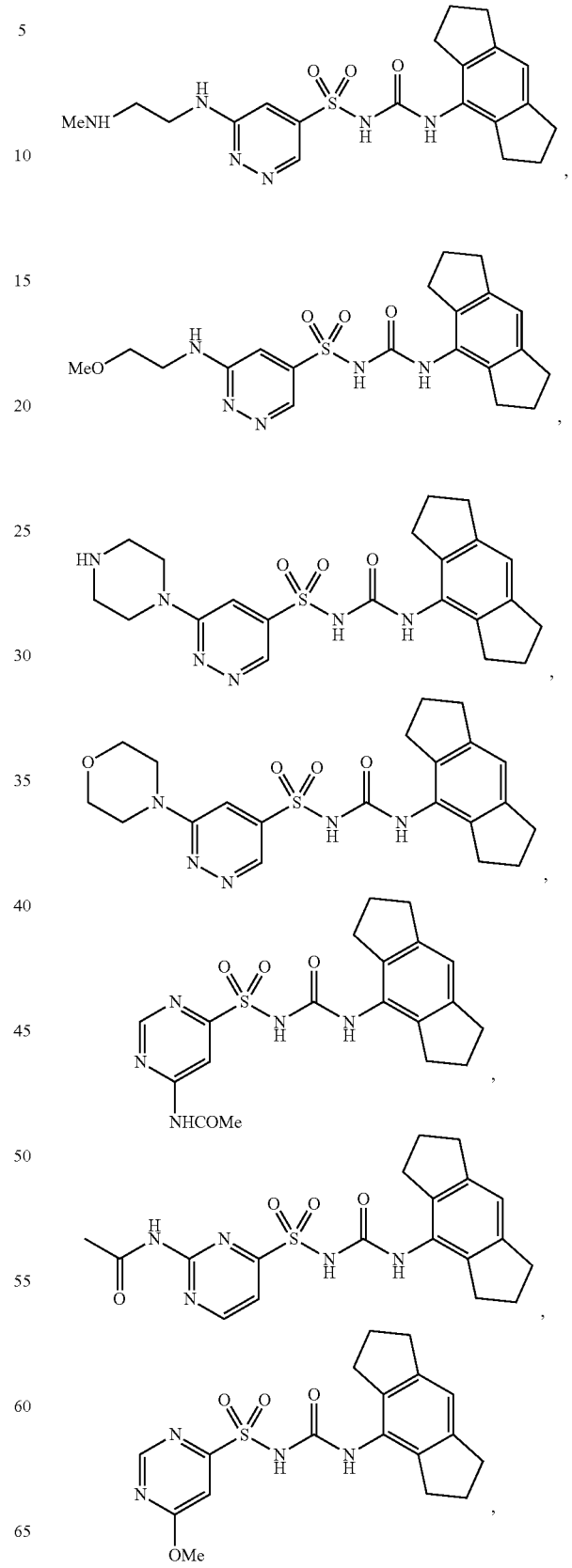

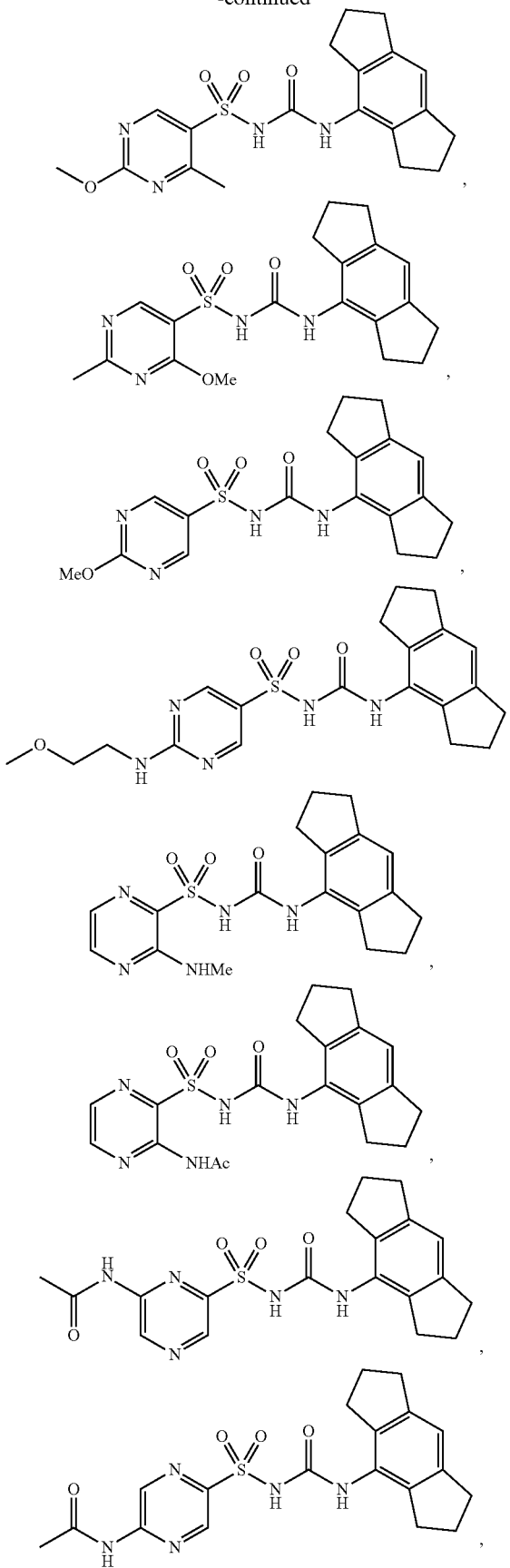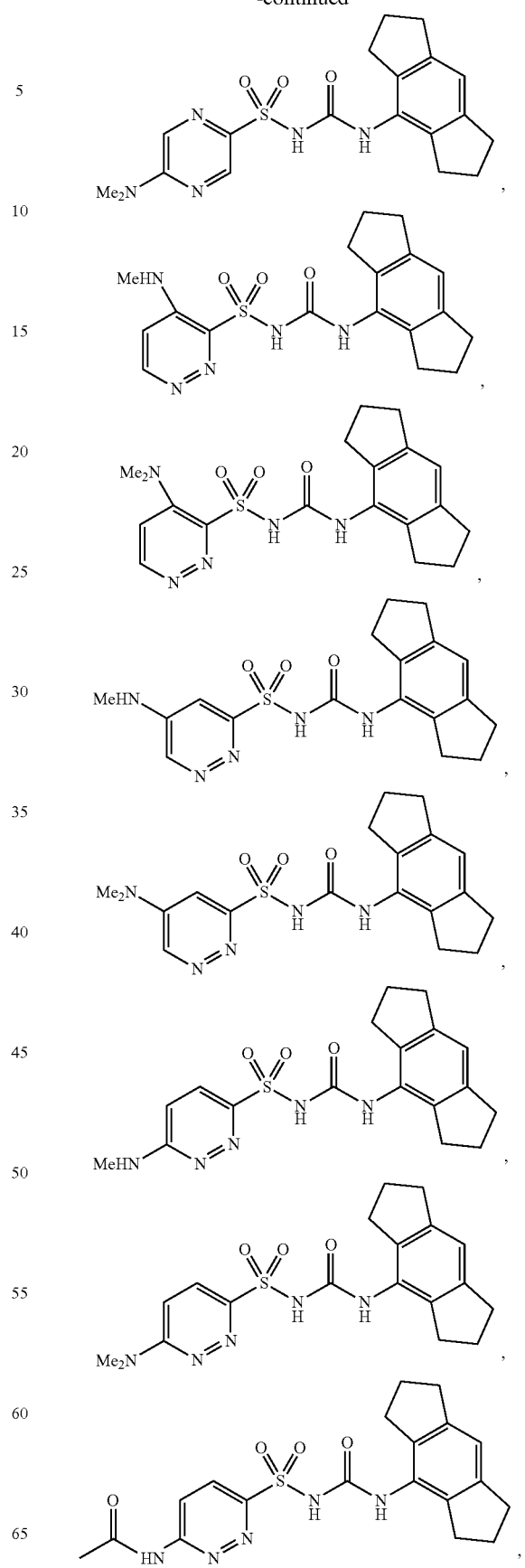

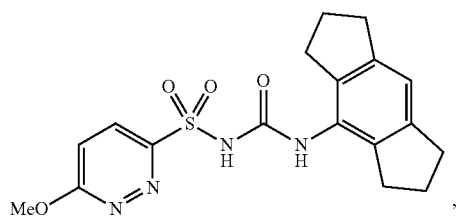,
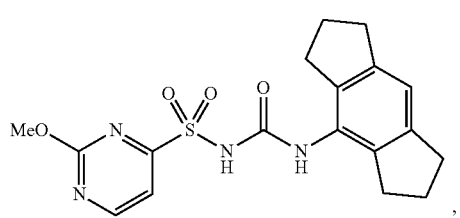,
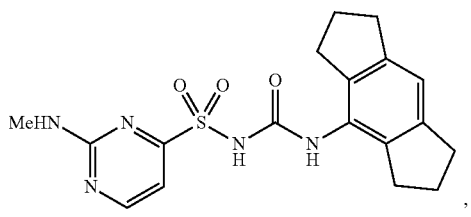,
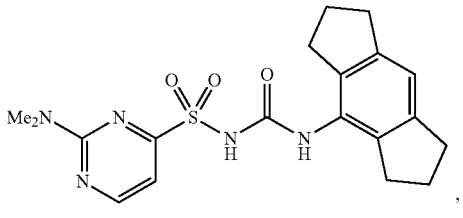,
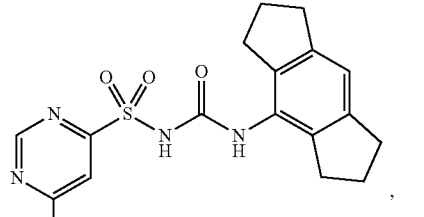,
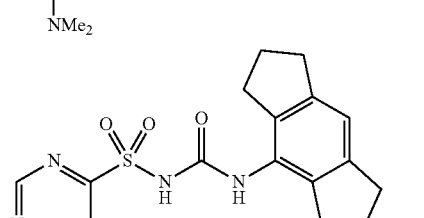,
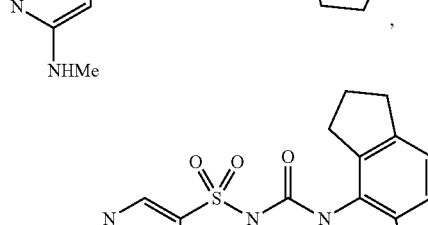,
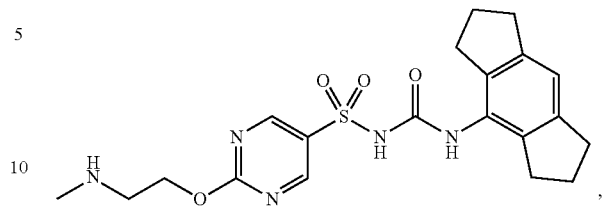,
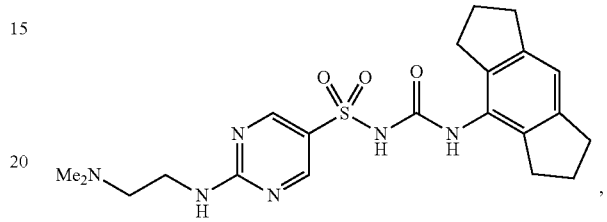,
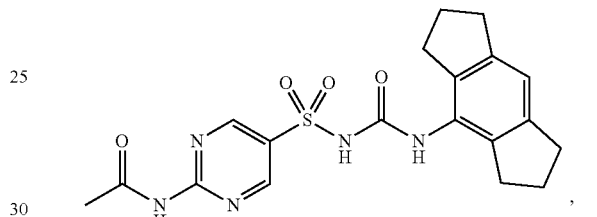,
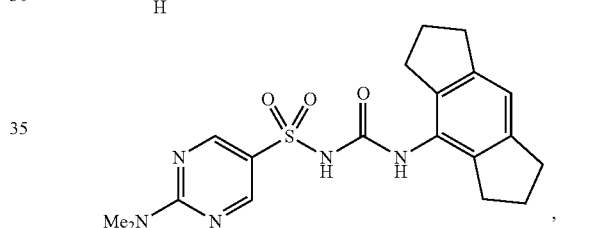,
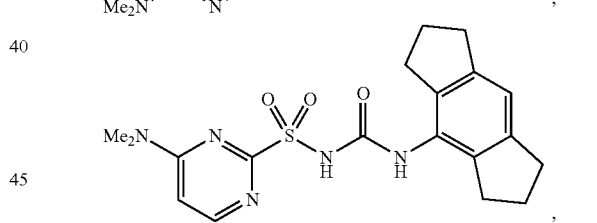,
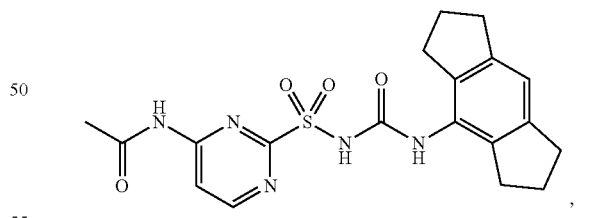,
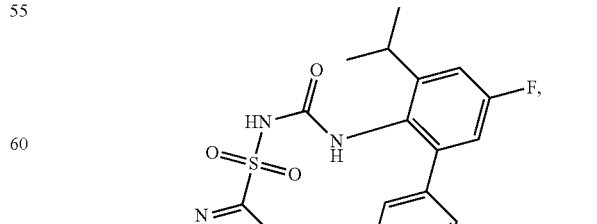

-continued
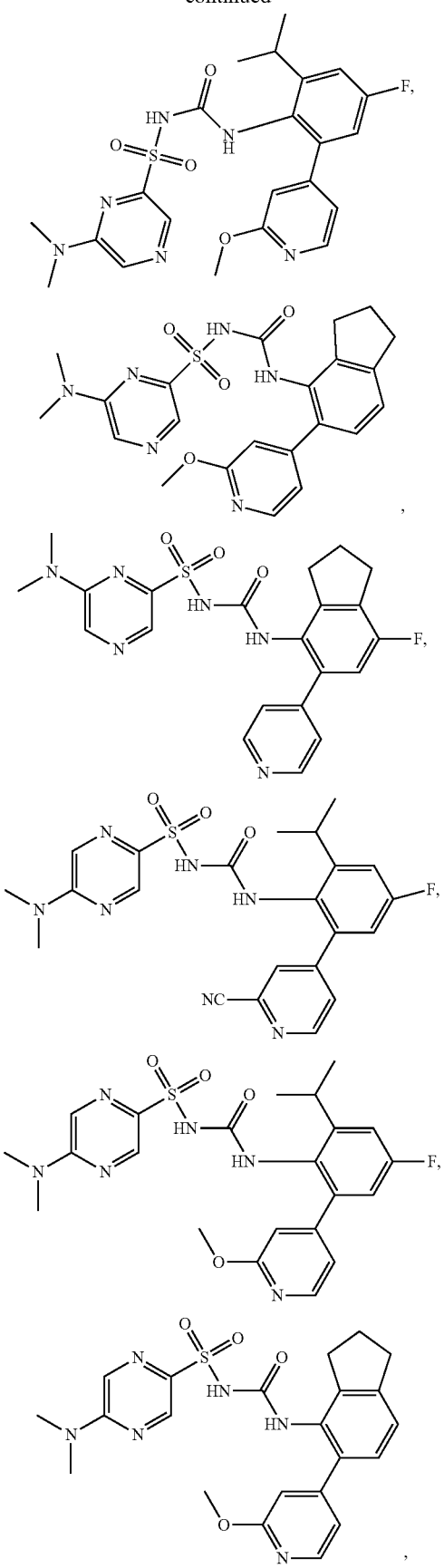
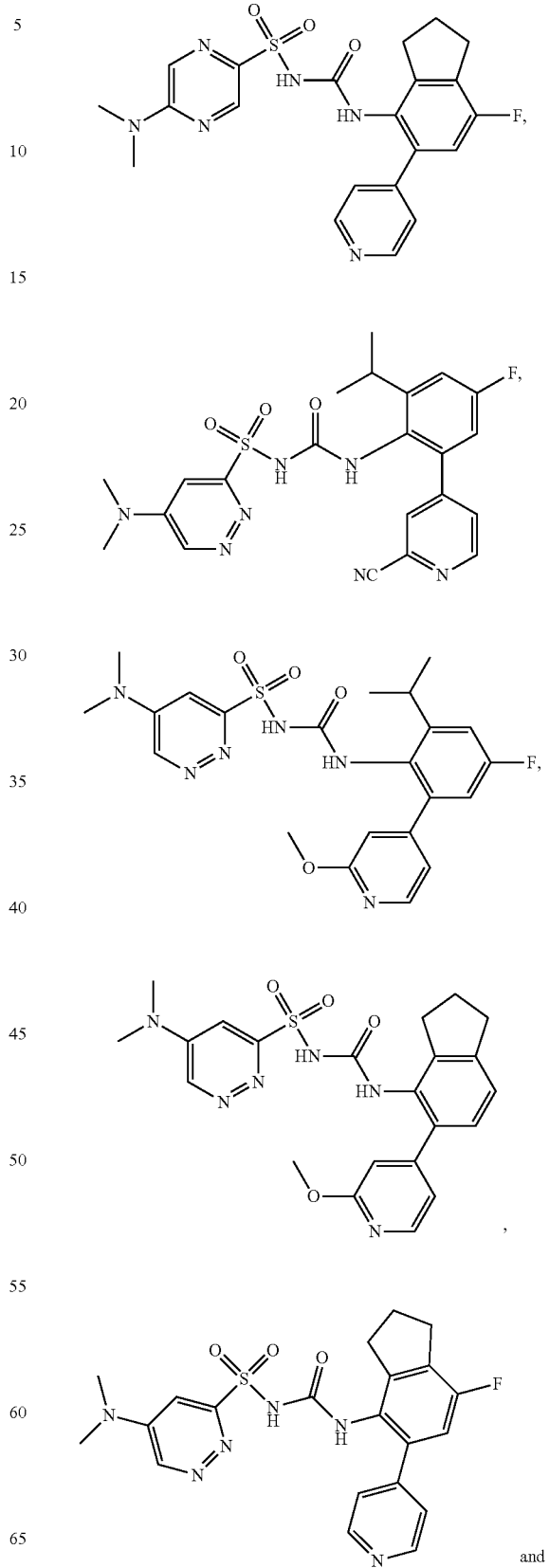
and

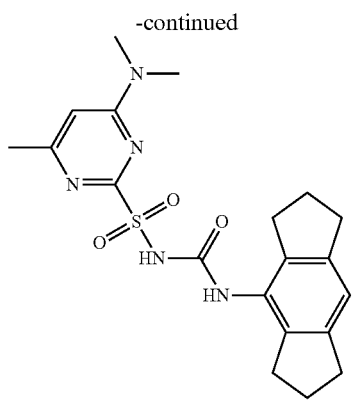

In a further embodiment of the first aspect of the invention:
the 6-membered heteroaryl group of $R^1$ is substituted with at least one monovalent group X' at a position ortho- or para- to at least one nitrogen atom in the 6-membered ring structure;
the 6-membered heteroaryl group of $R^1$ may optionally be further substituted;
X' is at each occurrence independently selected from a —$OR^3$, —$SR^3$, —$N(R^3)_2$, —O-L-$OR^3$, —O-L-$SR^3$, —O-L-$N(R^3)_2$, —S-L-$OR^3$, —S-L-$SR^3$, —S-L-$N(R^3)_2$, —$NR^3$-L-$OR^3$, —$NR^3$-L-$SR^3$ or —$NR^3$-L-N$(R^3)_2$ group;
each $R^3$ is independently selected from hydrogen or an alkyl, alkenyl, alkynyl or cyclic group, or any two $R^3$ in the same group X' may together with the atom or atoms to which they are attached form a heterocyclic group;
each L is independently selected from an alkylene, alkenylene or alkynylene group; and
any L or $R^3$ may optionally be substituted.

Typically in such an embodiment, the 6-membered heteroaryl group of $R^1$ is monocyclic. Typically, the 6-membered heteroaryl group of $R^1$ is substituted with one or two monovalent groups X', each at a position ortho- or para- to at least one nitrogen atom in the 6-membered ring structure, where the 6-membered heteroaryl group may optionally be further substituted. More typically, the 6-membered heteroaryl group of $R^1$ is substituted with a single monovalent group X', where the 6-membered heteroaryl group may optionally be further substituted with one or more groups Y, wherein Y is as defined below. Most typically, the 6-membered heteroaryl group of $R^1$ is substituted with a single monovalent group X', wherein the 6-membered heteroaryl group is not further substituted.

Typically, X' is at each occurrence independently selected from a —$OR^3$, —$N(R^3)_2$, —O-L-$OR^3$, —O-L-$N(R^3)_2$, —$NR^3$-L-$OR^3$ or —$NR^3$-L-$N(R^3)_2$ group. More typically, X' is at each occurrence independently selected from a —$OR^3$ or —$N(R^3)_2$ group.

Typically, each $R^3$ is independently selected from hydrogen or a $C_1$-$C_{12}$ alkyl, $C_2$-$C_{12}$ alkenyl, $C_2$-$C_{12}$ alkynyl or $C_2$-$C_{12}$ cyclic group, or any two $R^3$ in the same group X' may together with the atom or atoms to which they are attached form a $C_2$-$C_{12}$ heterocyclic group. More typically, each $R^3$ is independently selected from hydrogen or a $C_1$-$C_6$ alkyl, $C_2$-$C_6$ alkenyl, $C_2$-$C_6$ alkynyl or $C_3$-$C_{10}$ cyclic group, or any two $R^3$ in the same group X' may together with the atom or atoms to which they are attached form a $C_3$-$C_{10}$ heterocyclic group. More typically still, each $R^3$ is independently selected from hydrogen or a $C_1$-$C_4$ alkyl, $C_2$-$C_4$ alkenyl or $C_3$-$C_7$ monocyclic group, or any two $R^3$ in the same group X' may together with the atom or atoms to which they are attached form a non-aromatic monocyclic $C_3$-$C_6$ heterocyclic group. Most typically, each $R^3$ is independently selected from hydrogen or a $C_1$-$C_4$ alkyl or cyclopropyl group, or any two $R^3$ in the same group X' may together with the atom or atoms to which they are attached form a saturated 4, 5 or 6 membered monocyclic heterocyclic group.

Typically, each L is independently selected from a $C_1$-$C_6$ alkylene, $C_2$-$C_6$ alkenylene or $C_2$-$C_6$ alkynylene group. More typically, each L is independently selected from a $C_1$-$C_4$ alkylene or $C_2$-$C_4$ alkenylene group, such as —$(CH_2)_x$— wherein x is 1, 2, 3 or 4. Most typically, x is 2.

As stated above, any L or $R^3$ may optionally be substituted. Typically, each L or $R^3$ is unsubstituted or substituted with one or more monovalent substituents and/or oxo (=O) groups. More typically, each L or $R^3$ is unsubstituted or substituted with one or more monovalent substituents such as halo, —CN, —OH, $C_1$-$C_4$ alkyl, $C_1$-$C_4$ haloalkyl, —O—($C_1$-$C_4$ alkyl) and/or —O—($C_1$-$C_4$ haloalkyl) groups. More typically, each L or $R^3$ is unsubstituted or substituted with one or more halo, methyl, methoxy, halomethyl and/or halomethoxy groups. Most typically, each L or $R^3$ is unsubstituted or substituted with one or more chloro and/or fluoro groups.

Typically, where the 6-membered heteroaryl group of $R^1$ is substituted with at least one monovalent group X' at a position ortho- or para- to at least one nitrogen atom in the 6-membered ring structure, $R^2$ is a cyclic group substituted at the α and α' positions, wherein $R^2$ may optionally be further substituted. Typically, where the 6-membered heteroaryl group of $R^1$ is substituted with at least one monovalent group X' at a position ortho- or para- to at least one nitrogen atom in the 6-membered ring structure, $R^2$ is an aryl or a heteroaryl group, wherein the aryl or the heteroaryl group is substituted at the α-position, and wherein $R^2$ may optionally be further substituted. For example, $R^2$ may be an aryl or a heteroaryl group, wherein the aryl or the heteroaryl group is substituted at the α and α' positions, and wherein $R^2$ may optionally be further substituted.

In any embodiment where the 6-membered heteroaryl group of $R^1$ is substituted with at least one monovalent group X or X', the 6-membered heteroaryl group of $R^1$ typically contains one, two or three nitrogen atoms in the 6-membered ring structure, with the remainder of the atoms in the 6-membered ring structure being carbon atoms. More typically, such a 6-membered heteroaryl group contains two nitrogen atoms and four carbon atoms in the 6-membered ring structure. More typically still, such a 6-membered heteroaryl group is a pyrazinyl or a pyridazinyl group. Where the 6-membered heteroaryl group of $R^1$ contains more than one nitrogen atom in the 6-membered ring structure, any group X may be able to mesomerically donate a lone pair of electrons onto a single nitrogen atom in the 6-membered ring structure, or alternatively onto more than one nitrogen atom in the 6-membered ring structure. Similarly, any group X' may be at a position ortho- or para- to a single nitrogen atom in the 6-membered ring structure, or ortho- or para- to more than one nitrogen atom in the 6-membered ring structure. Where the 6-membered heteroaryl group of $R^1$ contains more than one nitrogen atom in the 6-membered ring structure and is substituted with more than one monovalent group X, each group X may be able to mesomerically donate a lone pair of electrons onto the same nitrogen atom in the 6-membered ring structure, or onto different nitrogen atoms in the 6-membered ring structure.

Similarly, where the 6-membered heteroaryl group of $R^1$ contains more than one nitrogen atom in the 6-membered ring structure and is substituted with more than one monovalent group X', each group X' may be at a position ortho- or para- to the same nitrogen atom in the 6-membered ring structure, or ortho- or para- to different nitrogen atoms in the 6-membered ring structure.

In any embodiment where the 6-membered heteroaryl group of $R^1$ is substituted with at least one monovalent group X or X', typically each group X or X' contains from 1 to 6 atoms other than hydrogen or halogen.

In any embodiment where the 6-membered heteroaryl group of $R^1$ is substituted with at least one monovalent group X or X', unless stated otherwise the 6-membered heteroaryl group of $R^1$ may optionally be further substituted. Typically, where the 6-membered heteroaryl group of $R^1$ is further substituted, it is further substituted with one or more groups Y, wherein Y is at each occurrence independently selected from a halo, oxo, $C_1$-$C_4$ alkyl, $C_3$-$C_6$ cycloalkyl or $C_2$-$C_4$ alkenyl group, wherein any of the $C_1$-$C_4$ alkyl, $C_3$-$C_6$ cycloalkyl and $C_2$-$C_4$ alkenyl groups may be optionally substituted with one or more halo and/or oxo groups. More typically, where the 6-membered heteroaryl group of $R^1$ is further substituted, it is further substituted with one or two groups Y, wherein Y is at each occurrence independently selected from a fluoro, chloro, methyl or ethyl group, wherein each methyl or ethyl group may optionally be substituted with one or more chloro and/or fluoro groups.

In another embodiment of the first aspect of the invention, at least one nitrogen atom is located at the 4-position of the 6-membered ring structure of $R^1$. Typically in such an embodiment, the 6-membered heteroaryl group of $R^1$ is monocyclic. Typically in such an embodiment, the 6-membered heteroaryl group of $R^1$ contains one, two or three nitrogen atoms in the 6-membered ring structure, with the remainder of the atoms in the 6-membered ring structure being carbon atoms. Typically, where the 6-membered heteroaryl group of $R^1$ contains two or three nitrogen atoms in the 6-membered ring structure, the second and, if present, third nitrogen atoms are located at any of the 2, 3, 5 or 6-positions. The 6-membered heteroaryl group of $R^1$ may be unsubstituted or substituted with any optional substituent or X, X' or Y group as defined above.

Typically, where at least one nitrogen atom is located at the 4-position of the 6-membered ring structure of $R^1$, $R^1$ is unsubstituted or substituted with one or more groups independently selected from a halo, oxo, $C_1$-$C_{12}$ alkyl, $C_2$-$C_{12}$ alkenyl, $C_2$-$C_{12}$ alkynyl, $C_2$-$C_{12}$ cyclic, —$OR^3$, —$N(R^3)_2$, -L-$OR^3$, -L-$N(R^3)_2$, —O-L-$OR^3$, —O-L-$N(R^3)_2$, —$NR^3$-L-$OR^3$ or —$NR^3$-L-$N(R^3)_2$ group, wherein each $R^3$ is independently selected from hydrogen or a $C_1$-$C_{12}$ alkyl, $C_2$-$C_{12}$ alkenyl, $C_2$-$C_{12}$ alkynyl or $C_2$-$C_{12}$ cyclic group, or any two $R^3$ in the same group may together with the atom or atoms to which they are attached form a $C_2$-$C_{12}$ heterocyclic group, wherein each L is independently selected from a $C_1$-$C_6$ alkylene, $C_2$-$C_6$ alkenylene or $C_2$-$C_6$ alkynylene group, and wherein any alkyl, alkenyl, alkynyl, cyclic, alkylene, alkenylene or alkynylene group may be optionally substituted with one or more halo and/or oxo groups. Alternately, where at least one nitrogen atom is located at the 4-position of the 6-membered ring structure of $R^1$, $R^1$ is unsubstituted or substituted with one or more groups independently selected from a halo, oxo, $C_1$-$C_{12}$ alkyl, $C_2$-$C_{12}$ alkenyl, $C_2$-$C_{12}$ alkynyl, $C_2$-$C_{12}$ cyclic, —$OR^3$, —$N(R^3)_2$, —O-L-$OR^3$, —O-L-$N(R^3)_2$, —$NR^3$-L-$OR^3$ or —$NR^3$-L-$N(R^3)_2$ group, wherein each $R^3$ is independently selected from hydrogen or a $C_1$-$C_{12}$ alkyl, $C_2$-$C_{12}$ alkenyl, $C_2$-$C_{12}$ alkynyl or $C_2$-$C_{12}$ cyclic group, or any two $R^3$ in the same group may together with the atom or atoms to which they are attached form a $C_2$-$C_{12}$ heterocyclic group, wherein each L is independently selected from a $C_1$-$C_6$ alkylene, $C_2$-$C_6$ alkenylene or $C_2$-$C_6$ alkynylene group, and wherein any alkyl, alkenyl, alkynyl, cyclic, alkylene, alkenylene or alkynylene group may be optionally substituted with one or more halo and/or oxo groups. More typically, $R^1$ is unsubstituted or substituted with one or more groups independently selected from a fluoro, chloro, oxo, $C_1$-$C_4$ alkyl, $C_2$-$C_4$ alkenyl, $C_3$-$C_7$ monocyclic, —$OR^3$, —$N(R^3)_2$, -L-$OR^3$, -L-$N(R^3)_2$, —O-L-$OR^3$, —O-L-$N(R^3)_2$, —$NR^3$-L-$OR^3$ or —$NR^3$-L-$N(R^3)_2$ group, wherein each $R^3$ is independently selected from hydrogen or a $C_1$-$C_4$ alkyl, $C_2$-$C_4$ alkenyl, or $C_3$-$C_7$ monocyclic group, or any two $R^3$ in the same group may together with the atom or atoms to which they are attached form a non-aromatic monocyclic $C_3$-$C_6$ heterocyclic group, wherein each L is independently selected from a $C_1$-$C_4$ alkylene or $C_2$-$C_4$ alkenylene group, and wherein any alkyl, alkenyl, cyclic, alkylene or alkenylene group may be optionally substituted with one or more fluoro, chloro and/or oxo groups. Alternately, $R^1$ is unsubstituted or substituted with one or more groups independently selected from a fluoro, chloro, oxo, $C_1$-$C_4$ alkyl, $C_2$-$C_4$ alkenyl, $C_3$-$C_7$ monocyclic, —$OR^3$, —$N(R^3)_2$, —O-L-$OR^3$, —O-L-$N(R^3)_2$, —$NR^3$-L-$OR^3$ or —$NR^3$-L-$N(R^3)_2$ group, wherein each $R^3$ is independently selected from hydrogen or a $C_1$-$C_4$ alkyl, $C_2$-$C_4$ alkenyl, or $C_3$-$C_7$ monocyclic group, or any two $R^3$ in the same group may together with the atom or atoms to which they are attached form a non-aromatic monocyclic $C_3$-$C_6$ heterocyclic group, wherein each L is independently selected from a $C_1$-$C_4$ alkylene or $C_2$-$C_4$ alkenylene group, and wherein any alkyl, alkenyl, cyclic, alkylene or alkenylene group may be optionally substituted with one or more fluoro, chloro and/or oxo groups.

Typically, where at least one nitrogen atom is located at the 4-position of the 6-membered ring structure of $R^1$, $R^2$ is a cyclic group substituted at the α and α' positions, wherein $R^2$ may optionally be further substituted. For example, $R^2$ may be an aryl or a heteroaryl group, wherein the aryl or the heteroaryl group is substituted at the α and α' positions, and wherein $R^2$ may optionally be further substituted.

In one embodiment, where at least one nitrogen atom is located at the 4-position of the 6-membered ring structure of $R^1$, $R^2$ is a phenyl or a 6-membered heteroaryl group, wherein the phenyl or the heteroaryl group is substituted at the α and α' positions, and wherein $R^2$ may optionally be further substituted.

Examples of compounds of the invention where at least one nitrogen atom is located at the 4-position of the 6-membered ring structure of $R^1$ include:

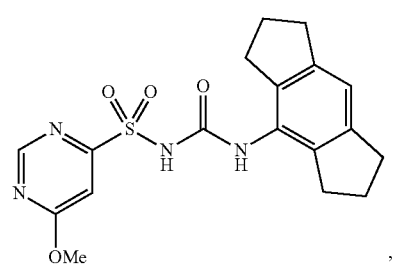

,

51
-continued
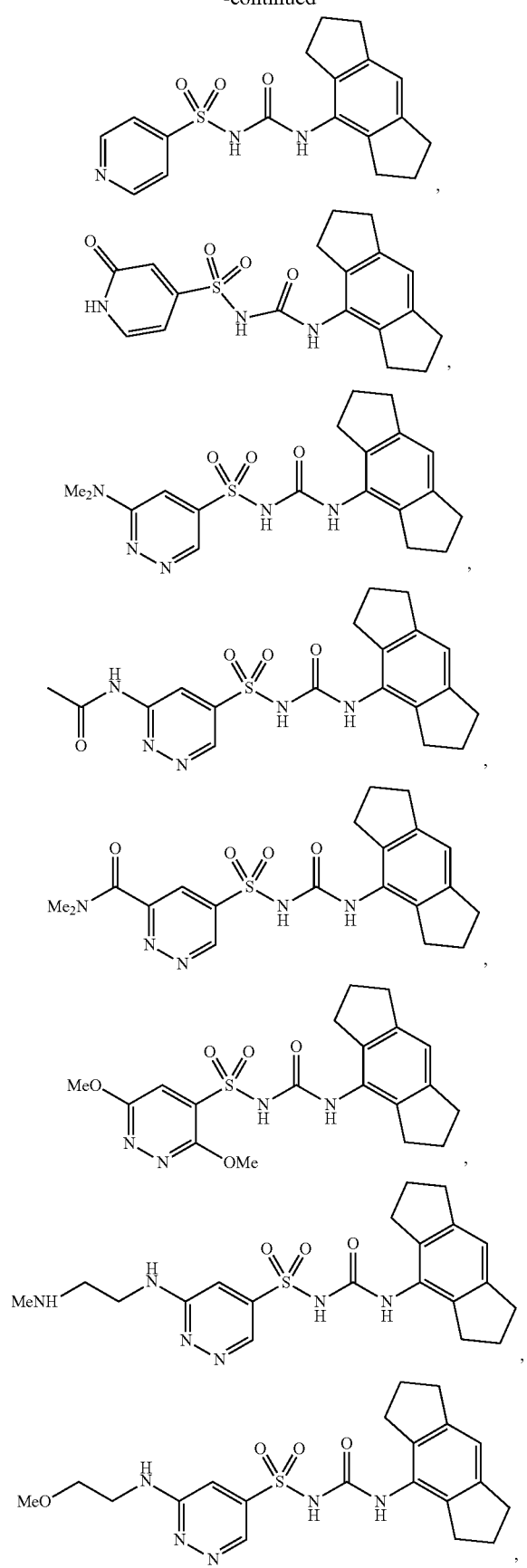
52
-continued
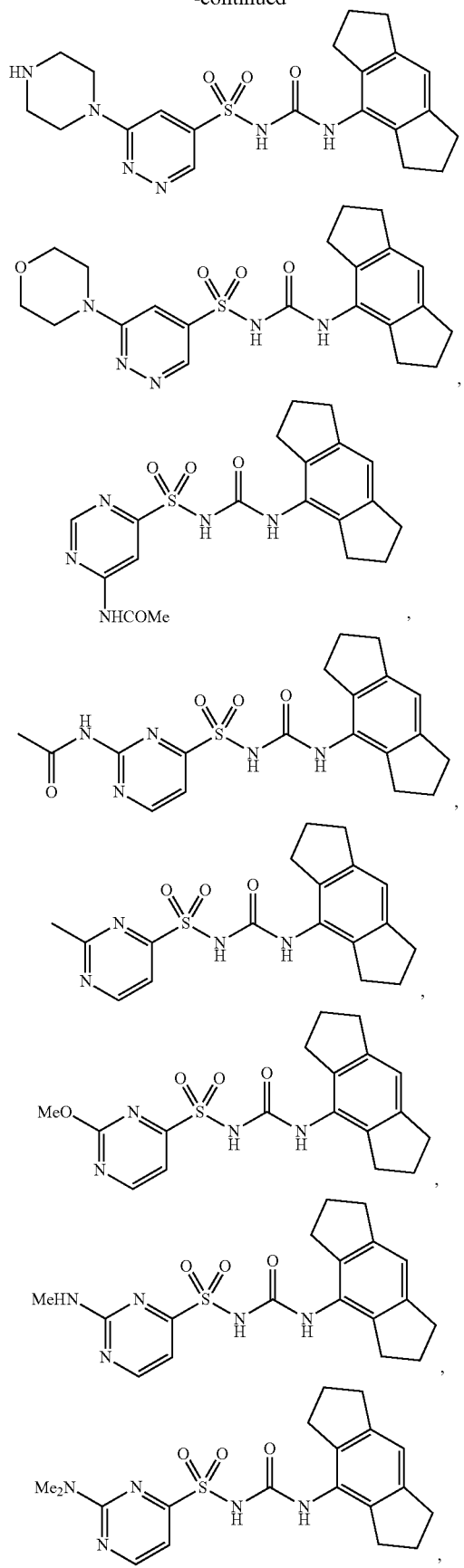

-continued

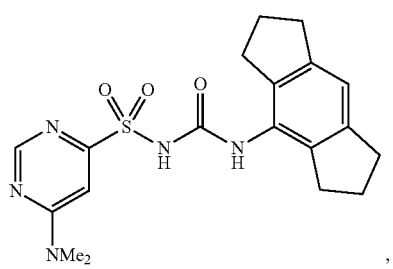,

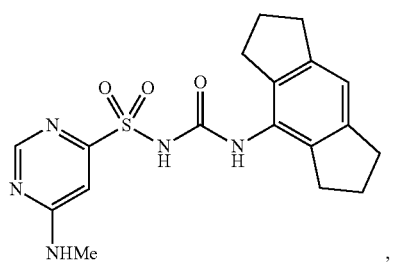,

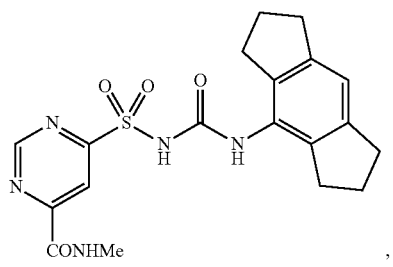,

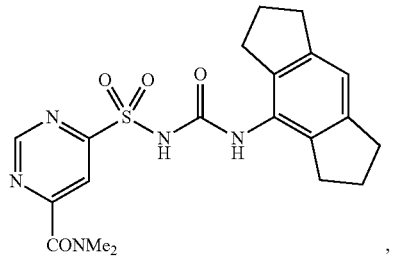,

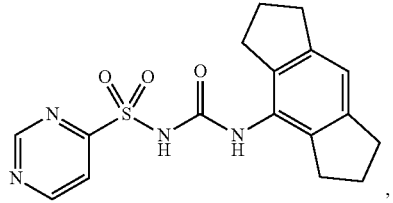,

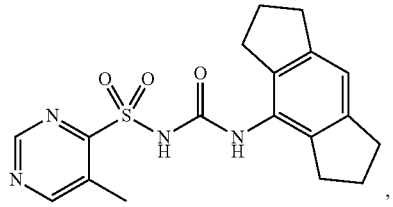,

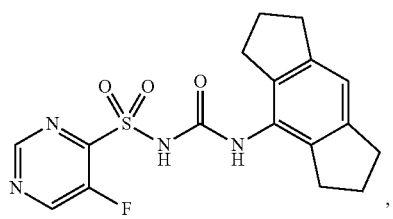,

-continued

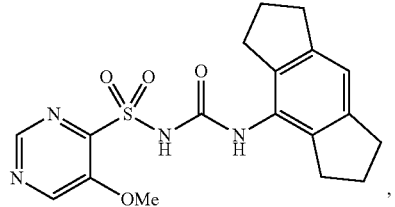,

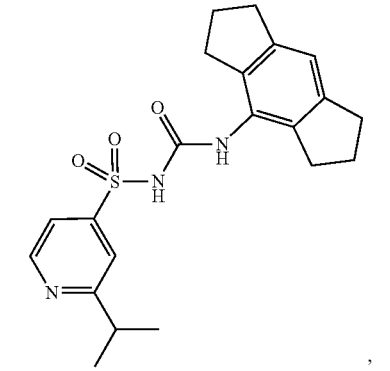,

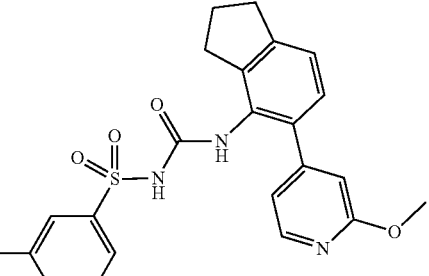,

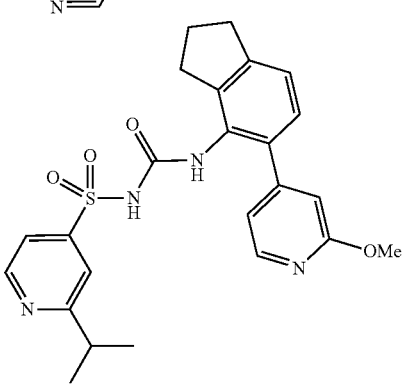 and

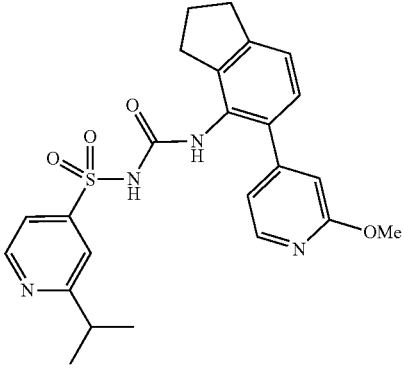.

In one aspect of any of the above embodiments, $R^1$ contains from 8 to 30 atoms. More typically, $R^1$ contains from 9 to 25 atoms.

In one embodiment of the first aspect of the invention, $R^2$ is an aryl or a heteroaryl group, wherein the aryl or the heteroaryl group is substituted at the α-position, and wherein $R^2$ may optionally be further substituted. Typically, $R^2$ is a phenyl or a 5- or 6-membered heteroaryl group, wherein the phenyl or the heteroaryl group is substituted at the α-position, and wherein $R^2$ may optionally be further substituted. More typically, $R^2$ is a phenyl or a 6-membered heteroaryl group, wherein the phenyl or the heteroaryl group is substituted at the α-position, and wherein $R^2$ may optionally be further substituted.

Typically, $R^2$ is an aryl or a heteroaryl group, wherein the aryl or the heteroaryl group is substituted at the α and α' positions, and wherein $R^2$ may optionally be further substituted. Typically, $R^2$ is a phenyl or a 5- or 6-membered heteroaryl group, wherein the phenyl or the heteroaryl group is substituted at the α and α' positions, and wherein $R^2$ may optionally be further substituted. More typically, $R^2$ is a phenyl or a 6-membered heteroaryl group, wherein the phenyl or the heteroaryl group is substituted at the α and α' positions, and wherein $R^2$ may optionally be further substituted. For example, $R^2$ may be a phenyl group substituted at the 2- and 6-positions or a phenyl group substituted at the 2-, 4- and 6-positions.

In another embodiment, $R^2$ is a cyclic group substituted at the α and α' positions, wherein $R^2$ may optionally be further substituted. For example, $R^2$ may be a cycloalkyl, cycloalkenyl or non-aromatic heterocyclic group substituted at the α and α' positions.

In any of the above embodiments, typical substituents at the α and/or α' positions of the parent cyclic group of $R^2$ comprise a carbon atom. For example, typical substituents at the α and/or α' positions may be independently selected from $—R^4$, $—OR^4$ and $—COR^4$ groups, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. More typically, the substituents at the α and/or α' positions are independently selected from alkyl and cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, each substituent at the α and α' positions comprises a carbon atom.

In one embodiment, $—R^2$ has a formula selected from:

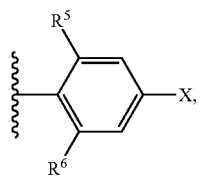

wherein $R^5$ and $R^6$ are independently selected from $C_1$-$C_4$ alkyl, and X is hydrogen or halo.

Typically, $—R^2$ has a formula selected from:

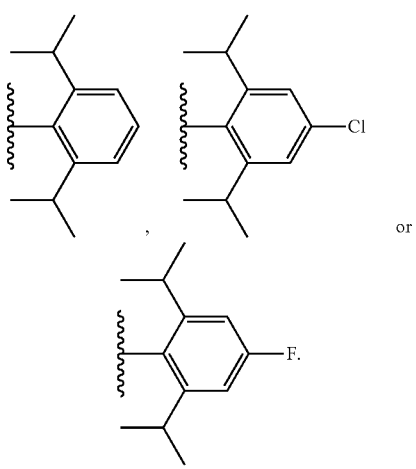

Other typical substituents at the α and/or α' positions of the parent cyclic group of $R^2$ may include cycloalkyl, cycloalkenyl, non-aromatic heterocyclic, aryl or heteroaryl rings which are fused to the parent cyclic group across the α,β and/or α',β' positions respectively. Such fused cyclic groups are described in greater detail below.

In one embodiment, $R^2$ is a fused aryl or a fused heteroaryl group, wherein the aryl or heteroaryl group is fused to one or more cycloalkyl, cycloalkenyl, non-aromatic heterocyclic, aryl or heteroaryl rings, wherein $R^2$ may optionally be further substituted.

In another embodiment, $R^2$ is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein $R^2$ may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically, $R^2$ is tricyclic.

In yet another embodiment, $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein $R^2$ may optionally be further substituted.

Typically in any embodiment where $R^2$ is a fused aryl or a fused heteroaryl group, Q is O.

In one embodiment, $—R^2$ has a formula selected from:

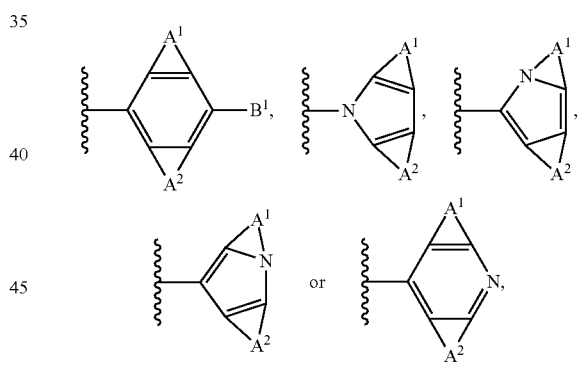

wherein $A^1$ and $A^2$ are each independently selected from an optionally substituted alkylene or alkenylene group, wherein one or more carbon atoms in the backbone of the alkylene or alkenylene group may optionally be replaced by one or more heteroatoms N, O or S, and wherein $B^1$ is hydrogen or any optional substituent. $B^1$ and any optional substituent attached to $A^1$ or $A^2$ may together with the atoms to which they are attached form a further fused cycloalkyl, cycloalkenyl, non-aromatic heterocyclic, aryl or heteroaryl ring which may itself be optionally substituted. Similarly, any optional substituent attached to $A^1$ and any optional substituent attached to $A^2$ may also together with the atoms to which they are attached form a further fused cycloalkyl, cycloalkenyl, non-aromatic heterocyclic, aryl or heteroaryl ring which may itself be optionally substituted.

Typically, $B^1$ is hydrogen or a halo, hydroxyl, —CN, —$NO_2$, —$B^2$ or —$OB^2$ group, wherein $B^2$ is a $C_1$-$C_4$ alkyl group which may optionally be halo-substituted.

Typically, any ring containing $A^1$ or $A^2$ is a five or a six membered ring. Typically, $A^1$ and $A^2$ are unsubstituted or substituted with one or more halo, hydroxyl, —CN, —NO$_2$, —B$^3$ or —OB$^3$ groups, wherein B$^3$ is any C$_1$-C$_4$ alkyl group which may optionally be halo-substituted.

In a further embodiment, —R$^2$ has a formula selected from:

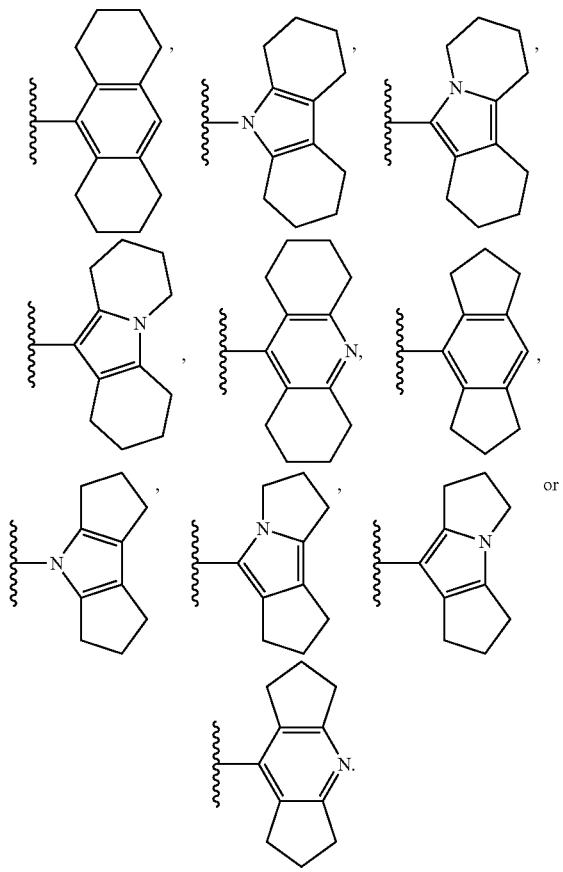

Typically, —R$^2$ has the formula:

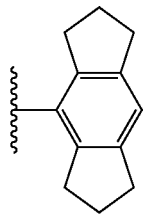

Yet other typical substituents at the α-position of the parent cyclic group of R$^2$ may include monovalent heterocyclic groups and monovalent aromatic groups, wherein a ring atom of the heterocyclic or aromatic group is directly attached via a single bond to the α-ring atom of the parent cyclic group, wherein the heterocyclic or aromatic group may optionally be substituted, and wherein the parent cyclic group may optionally be further substituted. Such R$^2$ groups are described in greater detail below.

In one embodiment, the α-substituted parent cyclic group of R$^2$ is a 5- or 6-membered cyclic group, wherein the cyclic group may optionally be further substituted. In one embodiment, the α-substituted parent cyclic group of R$^2$ is an aryl or a heteroaryl group, all of which may optionally be further substituted. In one embodiment, the α-substituted parent cyclic group of R$^2$ is a phenyl or a 5- or 6-membered heteroaryl group, all of which may optionally be further substituted. In one embodiment, the α-substituted parent cyclic group of R$^2$ is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl group, all of which may optionally be further substituted. In one embodiment, the α-substituted parent cyclic group of R$^2$ is a phenyl group, which may optionally be further substituted.

In one embodiment, the α-substituted parent cyclic group of R$^2$ is substituted at the α and α' positions, and may optionally be further substituted. For example, the α-substituted parent cyclic group of R$^2$ may be a phenyl group substituted at the 2- and 6-positions or a phenyl group substituted at the 2-, 4- and 6-positions.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, the monovalent heterocyclic or aromatic group at the α-position is phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, piperidinyl or tetrahydropyranyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl or tetrahydropyranyl group, all of which may optionally be substituted. In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH$_2$, —CN, —NO$_2$, —B$^4$, —OB$^4$, —NHB$^4$ or —N(B$^4$)$_2$, wherein B$^4$ is independently selected from a C$_1$-C$_4$ alkyl, C$_2$-C$_4$ alkenyl or C$_2$-C$_4$ alkynyl group, any of which may optionally be halo-substituted. In one embodiment, the monovalent heterocyclic or aromatic group at the α-position is an unsubstituted phenyl, pyridinyl, pyrimidinyl or pyrazolyl group. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH$_2$, —CN, —NO$_2$, —B$^4$, —OB$^4$, —NHB$^4$ or —N(B$^4$)$_2$, wherein B$^4$ is independently selected from a C$_1$-C$_4$ alkyl, C$_2$-C$_4$ alkenyl or C$_2$-C$_4$ alkynyl group, any of which may optionally be halo-substituted. In one embodiment, the monovalent heterocyclic group at the α-position is an unsubstituted pyridin-3-yl group or a pyridin-4-yl group optionally substituted with one or two substituents independently selected from halo, —OH, —NH$_2$, —CN, —NO$_2$, —B$^4$, —OB$^4$, —NHB$^4$ or —N(B$^4$)$_2$, wherein B$^4$ is independently selected from a C$_1$-C$_4$ alkyl, C$_2$-C$_4$ alkenyl or C$_2$-C$_4$ alkynyl group, any of which may optionally be halo-substituted.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, such further substituents are in the α' position of the α-substituted parent cyclic group of R$^2$. Such further substituents may be independently selected from halo, —R$^6$, —OR$^6$ or —COR$^6$ groups, wherein each R$^6$ is independently selected from a C$_1$-C$_6$ alkyl, C$_2$-C$_6$ alkenyl, C$_2$-C$_6$ alkynyl or C$_2$-C$_6$ cyclic group and wherein each R$^6$ is optionally further substituted with one or more halo groups. Typically, such further substituents on the α-substituted parent cyclic group of R$^2$ are independently selected from halo, C$_1$-C$_6$ alkyl (in particular C$_3$-C$_6$ branched alkyl) or C$_3$-C$_6$ cycloalkyl groups, e.g. fluoro, chloro, isopropyl, cyclopropyl, cyclohexyl or t-butyl groups, wherein the alkyl and cycloalkyl groups are optionally further substituted with one or more fluoro and/or chloro groups.

In one embodiment, —R$^2$ has a formula selected from:

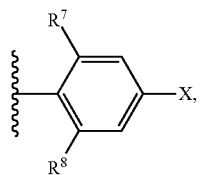

wherein R$^7$ is C$_1$-C$_4$ alkyl, R$^8$ is a 5- or 6-membered, optionally substituted heterocyclic or aromatic group, and X is hydrogen or halo. In one embodiment, the optional substituents on the heterocyclic or aromatic group are selected from halo, —OH, —NH$_2$, —CN, —NO$_2$, —B$^5$, —OB$^5$, —NHB$^5$ or —N(B$^5$)$_2$, wherein B$^5$ is independently selected from a C$_1$-C$_4$ alkyl, C$_2$-C$_4$ alkenyl or C$_2$-C$_4$ alkynyl group, any of which may optionally be halo-substituted.

Typically, —R$^2$ has a formula selected from:

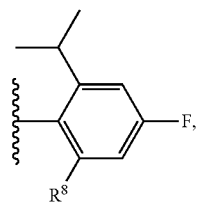

wherein R$^8$ is a 5- or 6-membered, optionally substituted heterocyclic or aromatic group. In one embodiment, the optional substituents on the heterocyclic or aromatic group are selected from halo, —OH, —NH$_2$, —CN, —NO$_2$, —B$^6$, —OB$^6$, —NHB$^6$ or —N(B$^6$)$_2$, wherein B$^6$ is independently selected from a C$_1$-C$_4$ alkyl, C$_2$-C$_4$ alkenyl or C$_2$-C$_4$ alkynyl group, any of which may optionally be halo-substituted.

In one embodiment, R$^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. The further substituents on the α-substituted parent cyclic group of R$^2$ also include cycloalkyl, cycloalkenyl, non-aromatic heterocyclic, aryl or heteroaryl rings which are fused to the α-substituted parent cyclic group of R$^2$. Typically, the cycloalkyl, cycloalkenyl, non-aromatic heterocyclic, aryl or heteroaryl rings are ortho-fused to the α-substituted parent cyclic group of R$^2$, i.e. each fused cycloalkyl, cycloalkenyl, non-aromatic heterocyclic, aryl or heteroaryl ring has only two atoms and one bond in common with the α-substituted parent cyclic group of R$^2$. Typically, the cycloalkyl, cycloalkenyl, non-aromatic heterocyclic, aryl or heteroaryl rings are ortho-fused to the α-substituted parent cyclic group of R$^2$ across the α',β' positions.

In one embodiment, —R$^2$ has a formula selected from:

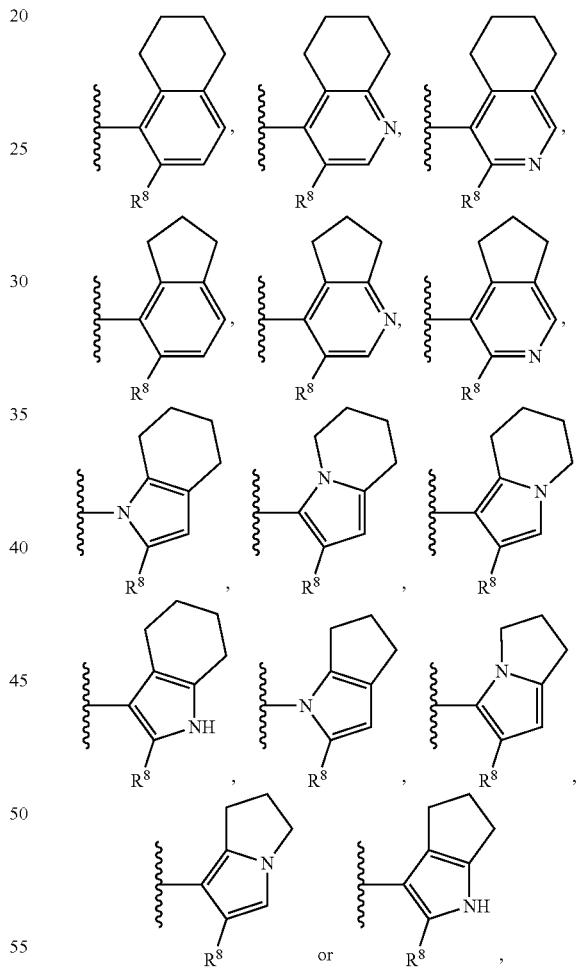

wherein R$^8$ is a 5- or 6-membered, optionally substituted heterocyclic or aromatic group. In one embodiment, the optional substituents on the heterocyclic or aromatic group are selected from halo, —OH, —NH$_2$, —CN, —NO$_2$, —B$^7$, —OB$^7$, —NHB$^7$ or —N(B$^7$)$_2$, wherein B$^7$ is independently selected from a C$_1$-C$_4$ alkyl, C$_2$-C$_4$ alkenyl or C$_2$-C$_4$ alkynyl group, any of which may optionally be halo-substituted.

In one embodiment, R$^2$ is phenyl or a 5- or 6-membered heteroaryl group (such as phenyl, pyridinyl, pyridazinyl, pyrimidinyl or pyrazinyl); wherein (i) the phenyl or 5- or 6-membered heteroaryl group is substituted at the α position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted at the α' position with a substituent selected from —$R^{14}$, —$OR^{14}$ and —$COR^{14}$, wherein $R^{14}$ is selected from a $C_1$-$C_6$ alkyl, $C_2$-$C_6$ alkenyl, $C_2$-$C_6$ alkynyl or $C_2$-$C_6$ cyclic group and wherein $R^{14}$ is optionally substituted with one or more halo groups; and optionally the phenyl or 5- or 6-membered heteroaryl group is further substituted (typically with one, two or three substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted (typically with one or two substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{12}$—$OR^{13}$, —$R^{12}$—$N(R^{13})_2$, —$R^{12}$—CN or —$R^{12}$—C≡$CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted (typically with one, two or three substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{12}$—$OR^{13}$, —$R^{12}$—$N(R^{13})_2$, —$R^{12}$—CN or —$R^{12}$—C≡$CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —$NO_2$, —CN, —$COOR^{15}$, —$CONH_2$, —$CONHR^{15}$ or —$CON(R^{15})_2$, wherein each —$R^{15}$ is independently selected from a $C_1$-$C_4$ alkyl or $C_1$-$C_4$ haloalkyl group).

In the embodiment directly above, where a group or moiety is optionally substituted with one or more halo groups, it may be substituted for example with one, two, three, four, five or six halo groups.

In one aspect of any of the above embodiments, $R^2$ contains from 15 to 50 atoms. More typically, $R^2$ contains from 20 to 40 atoms. Most typically, $R^2$ contains from 25 to 35 atoms.

In one aspect of any of the above embodiments, $R^2$ contains from 10 to 50 atoms other than hydrogen. More typically, $R^2$ contains from 10 to 40 atoms other than hydrogen. More typically, $R^2$ contains from 10 to 35 atoms other than hydrogen. Most typically, $R^2$ contains from 12 to 30 atoms other than hydrogen.

In one aspect of any of the above embodiments, the compound of formula (I) has a molecular weight of from 250 to 2000 Da. Typically, the compound of formula (I) has a molecular weight of from 300 to 750 Da. More typically, the compound of formula (I) has a molecular weight of from 350 to 500 Da.
A second aspect of the invention provides a compound selected from the group consisting of:
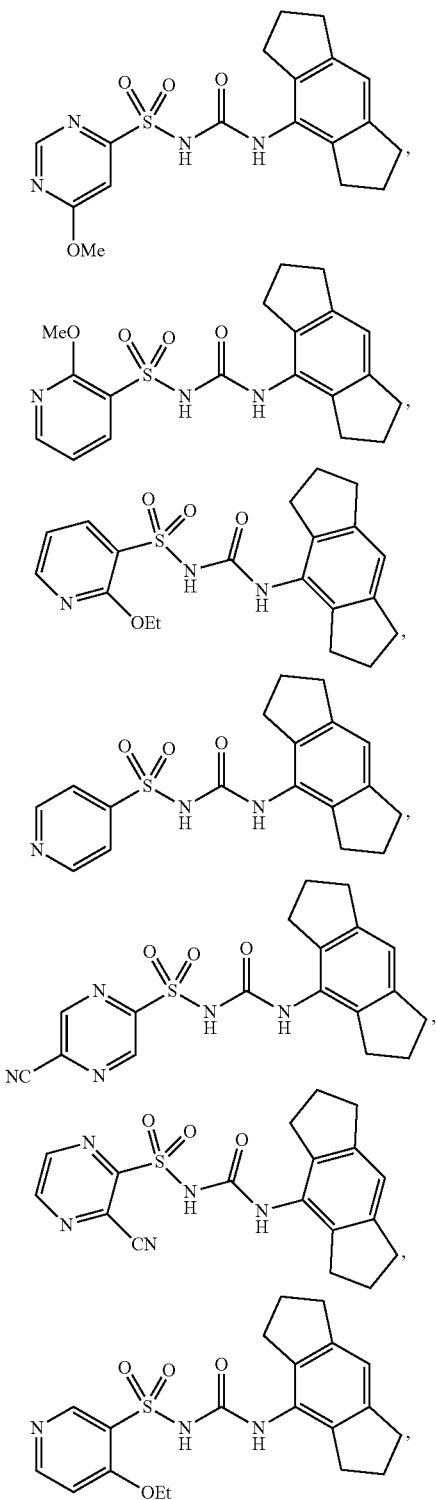
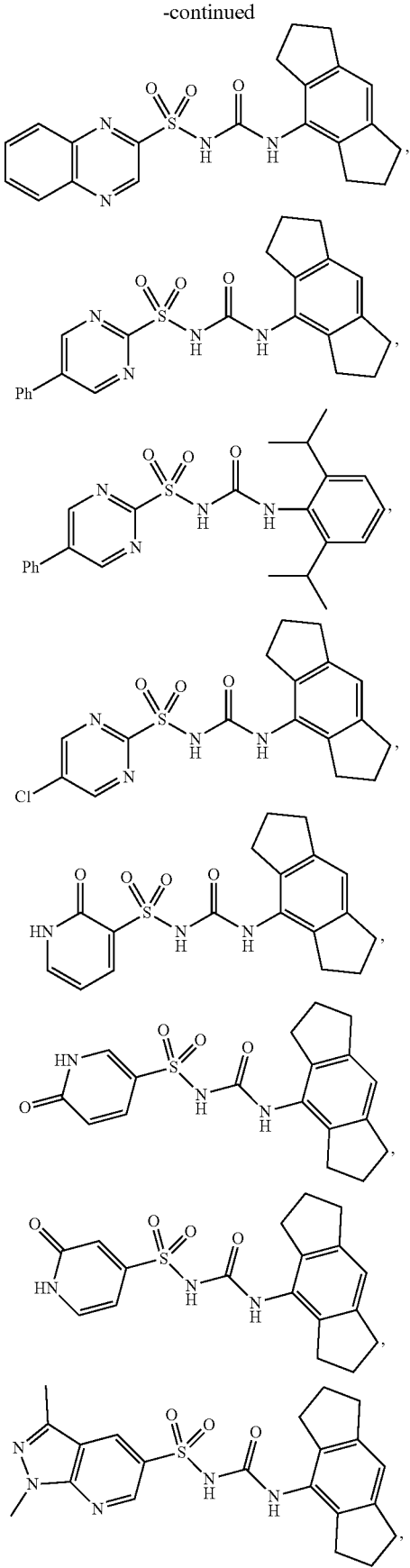

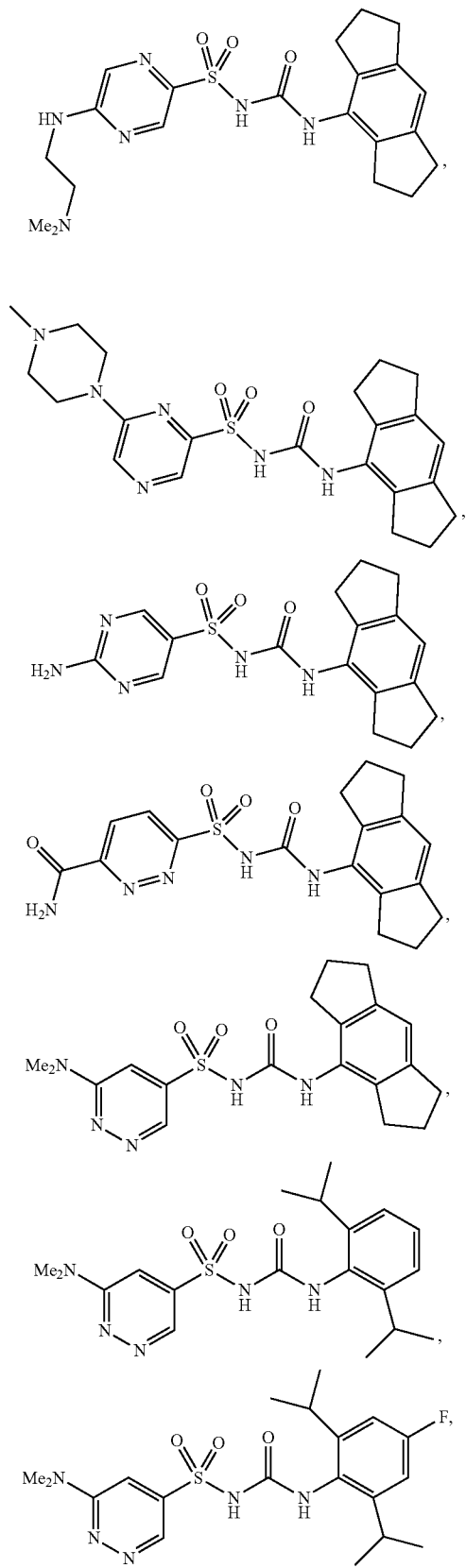
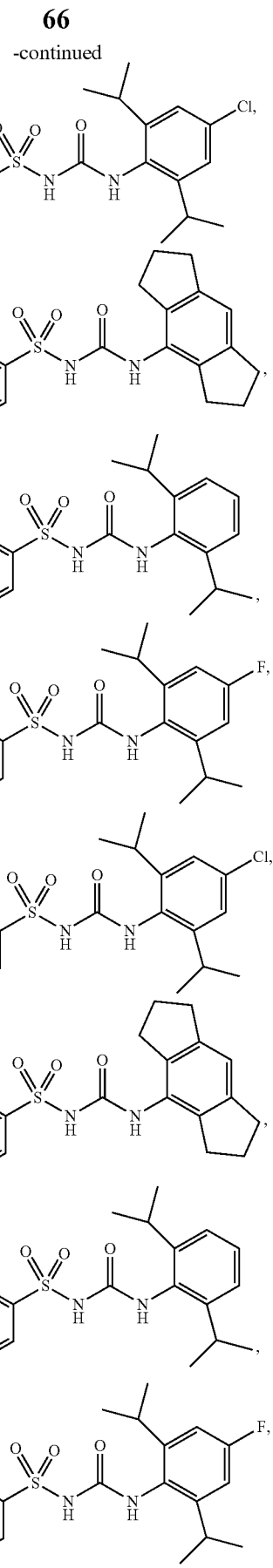

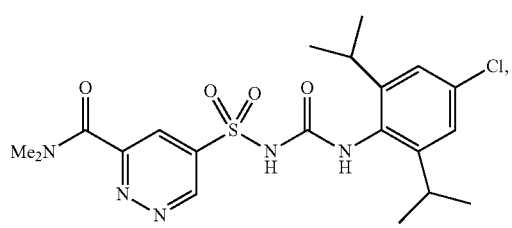
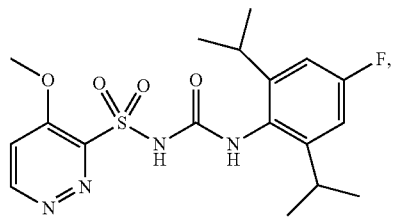
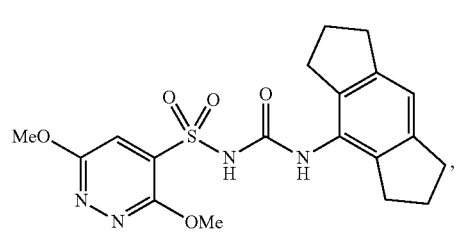
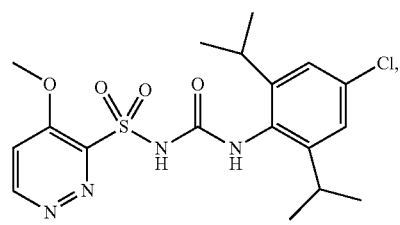
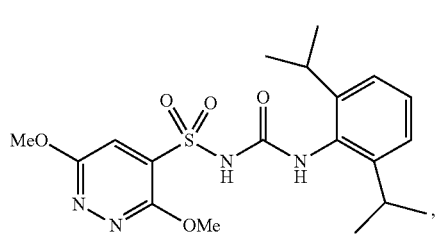
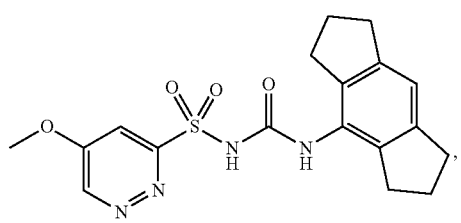
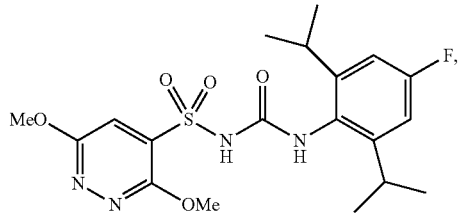
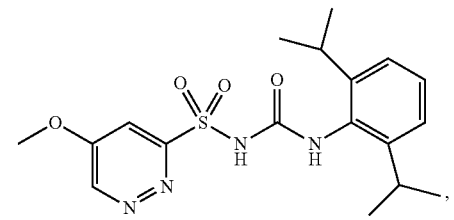
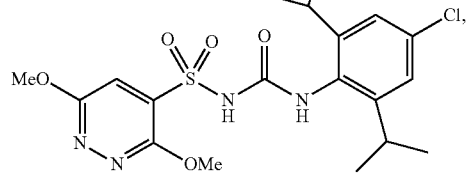
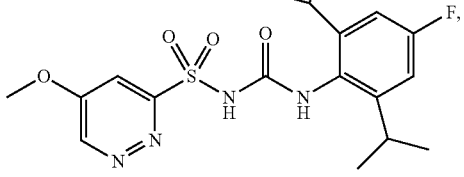
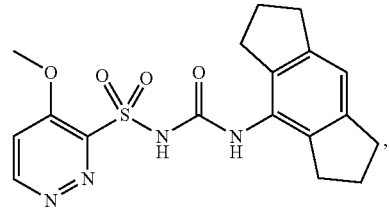
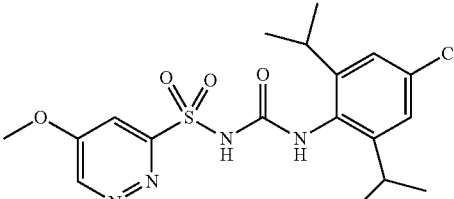
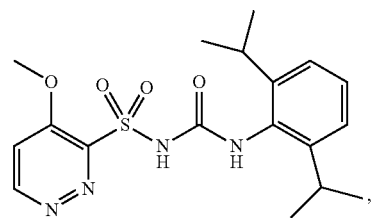
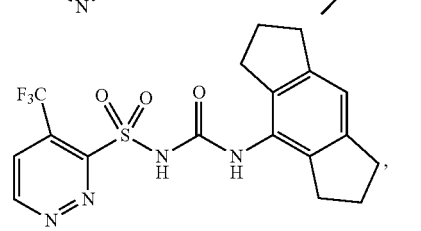

-continued
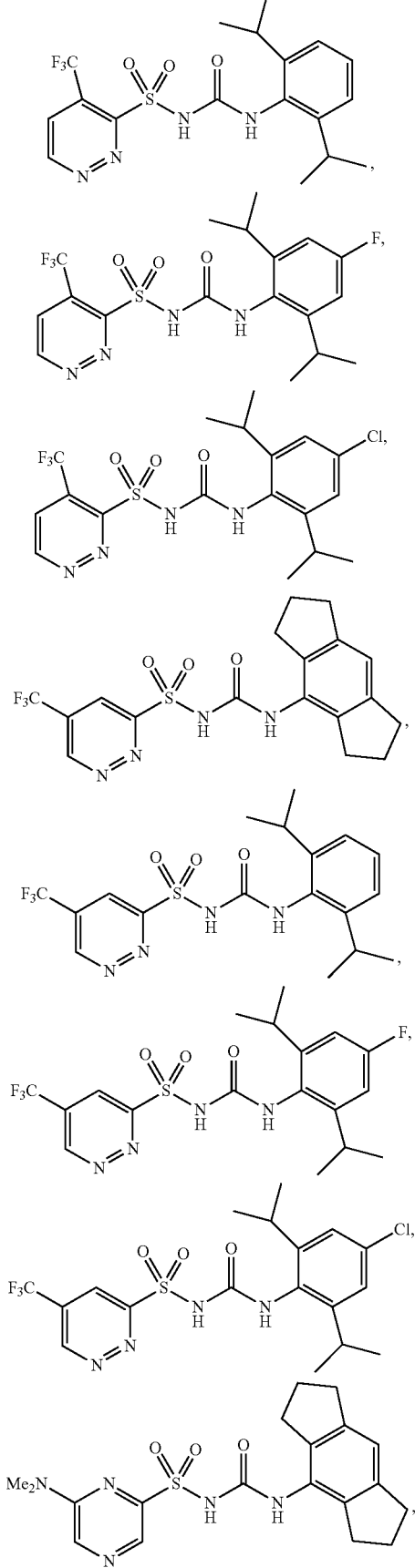
-continued
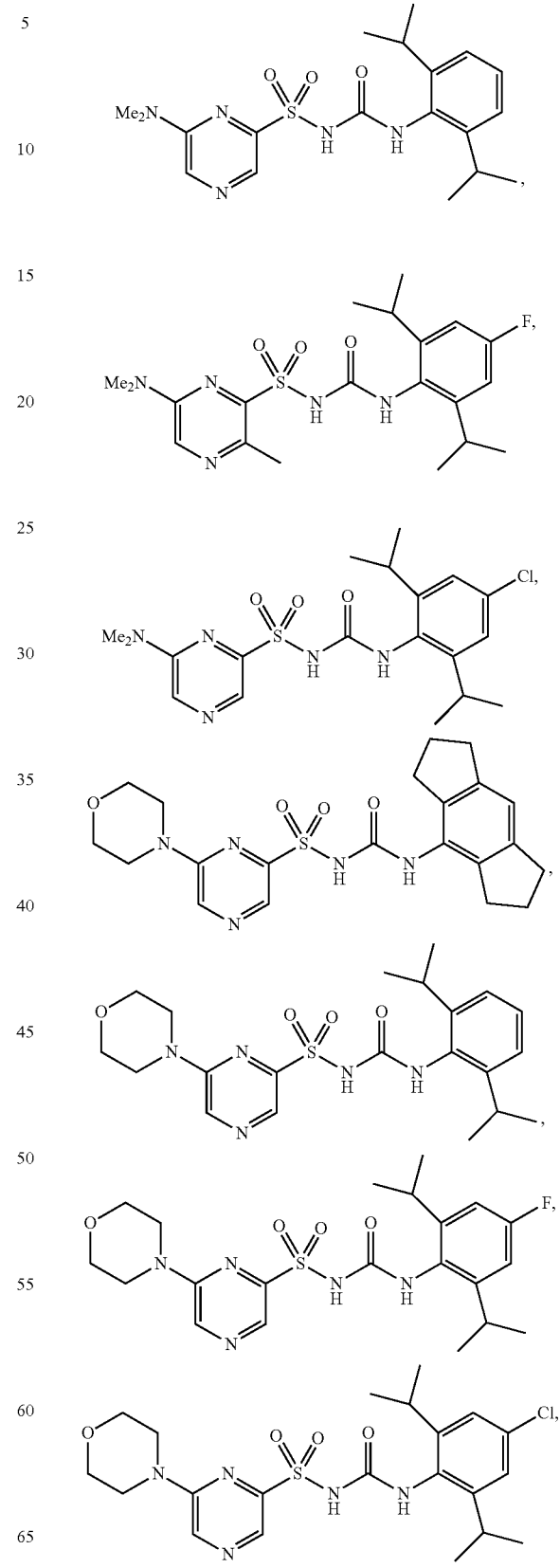

-continued
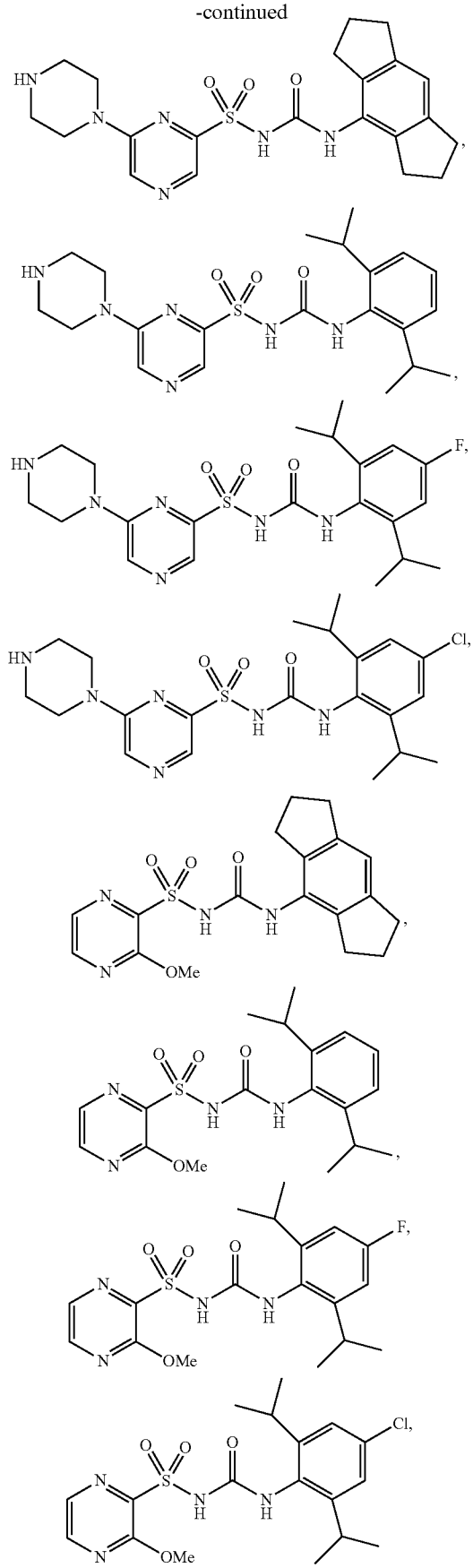
-continued
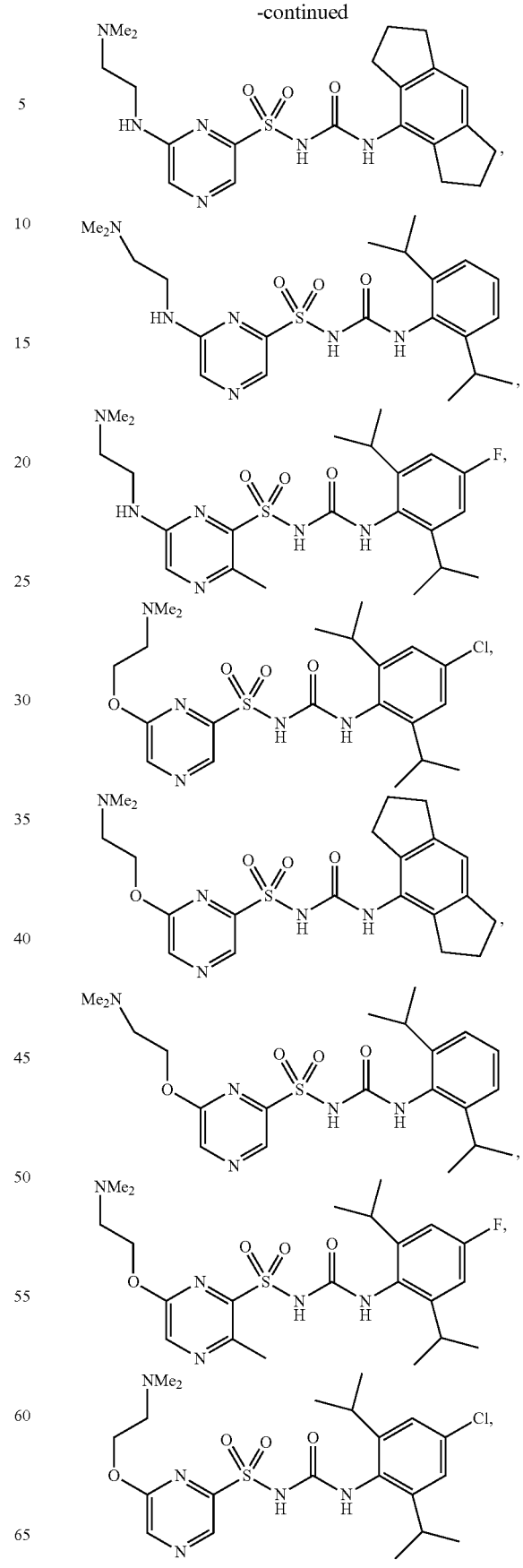

73
-continued
74
-continued
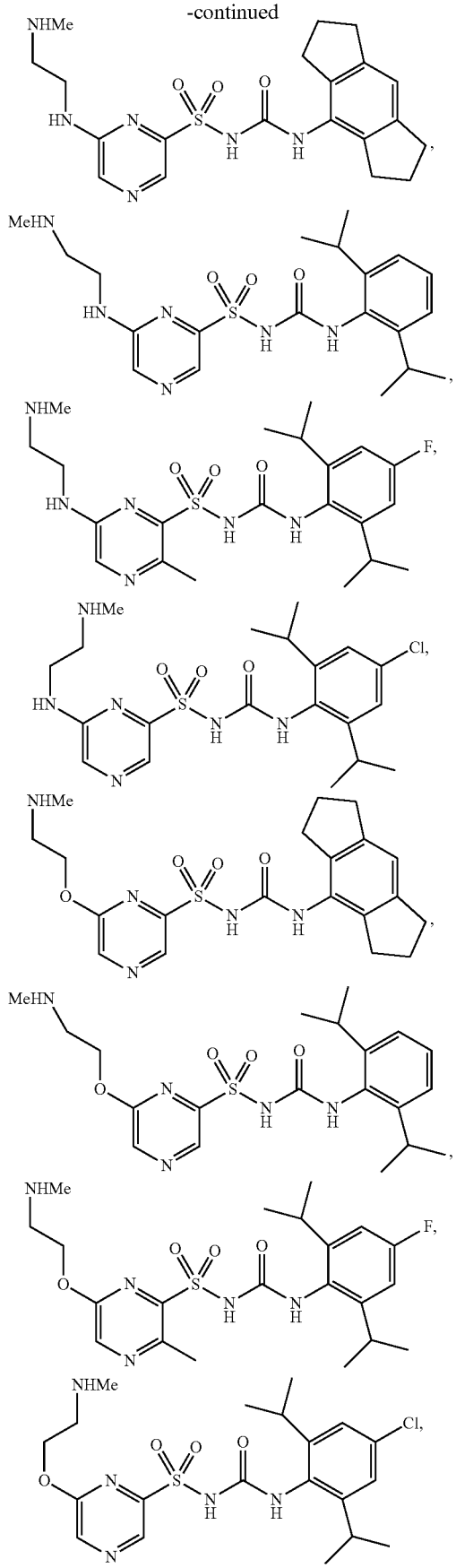
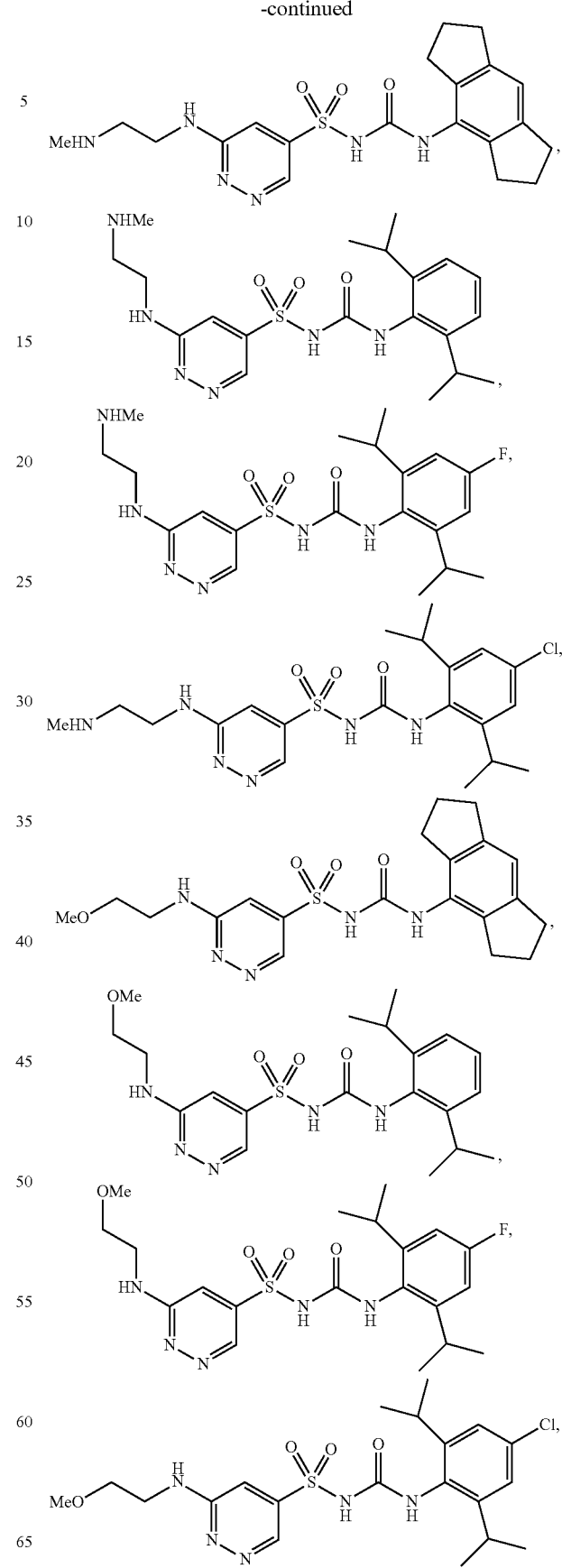

75
-continued
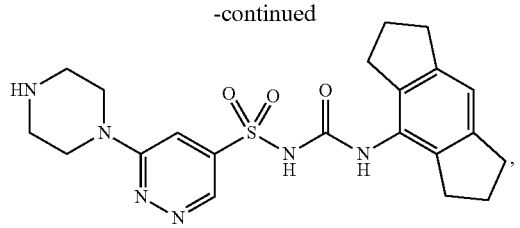
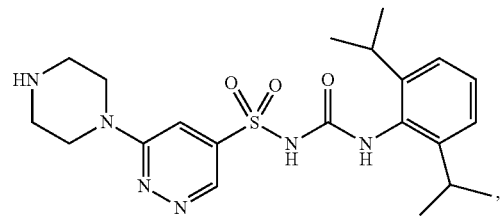
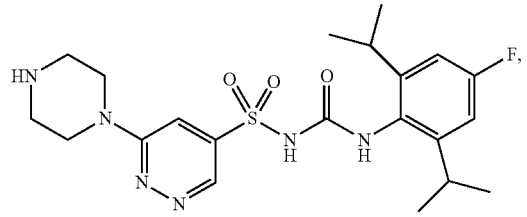
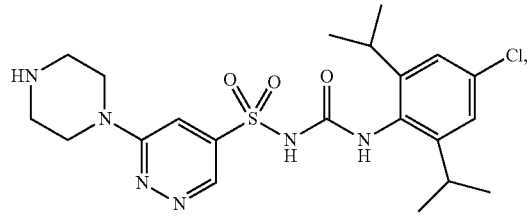
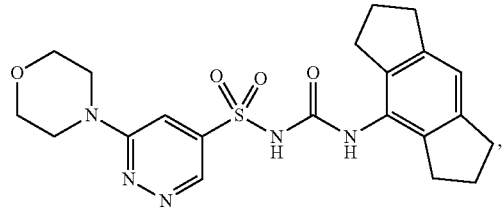
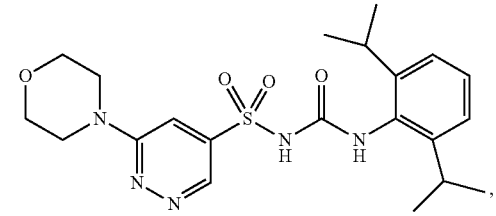
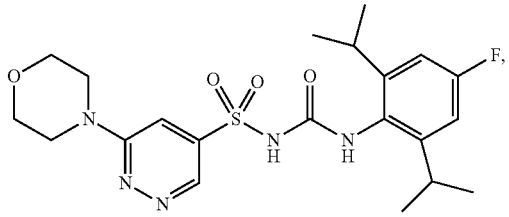
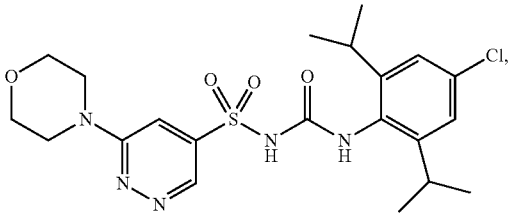
76
-continued
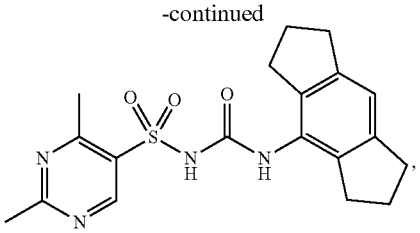
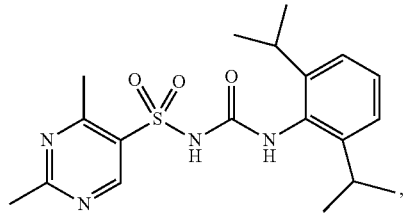
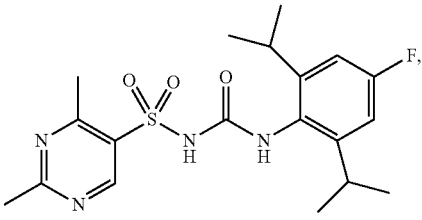
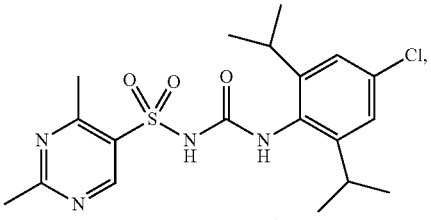
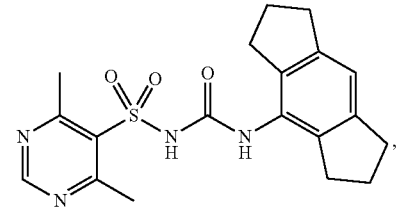
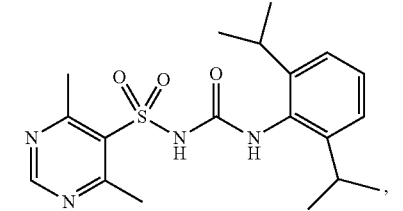
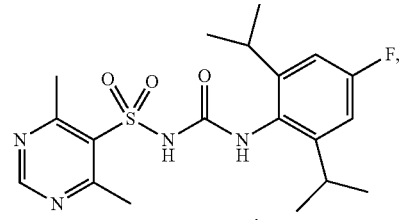
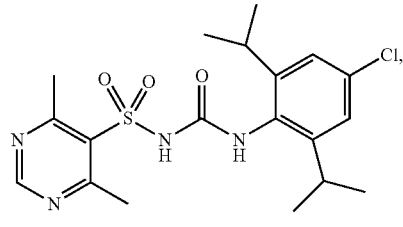

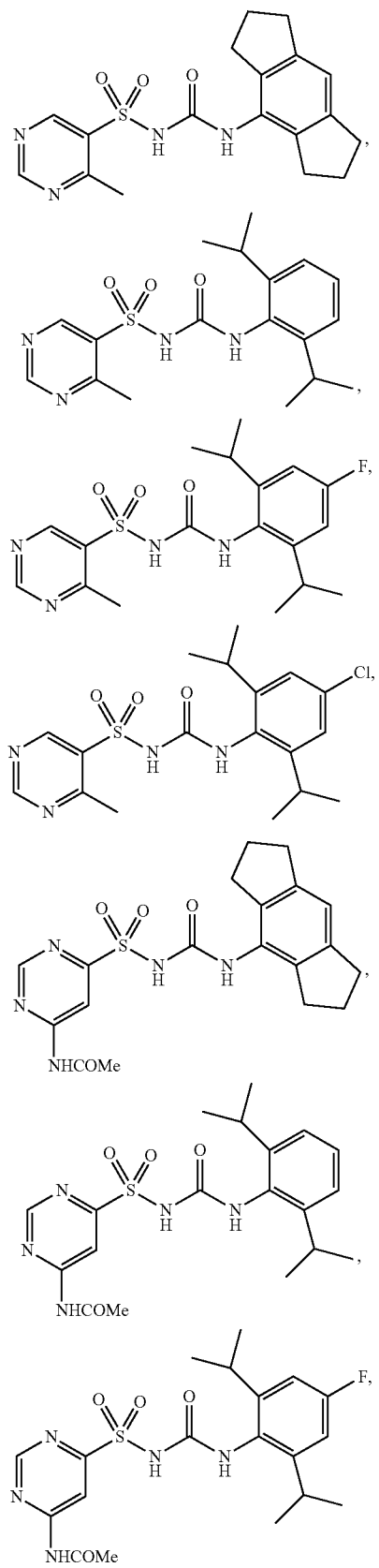
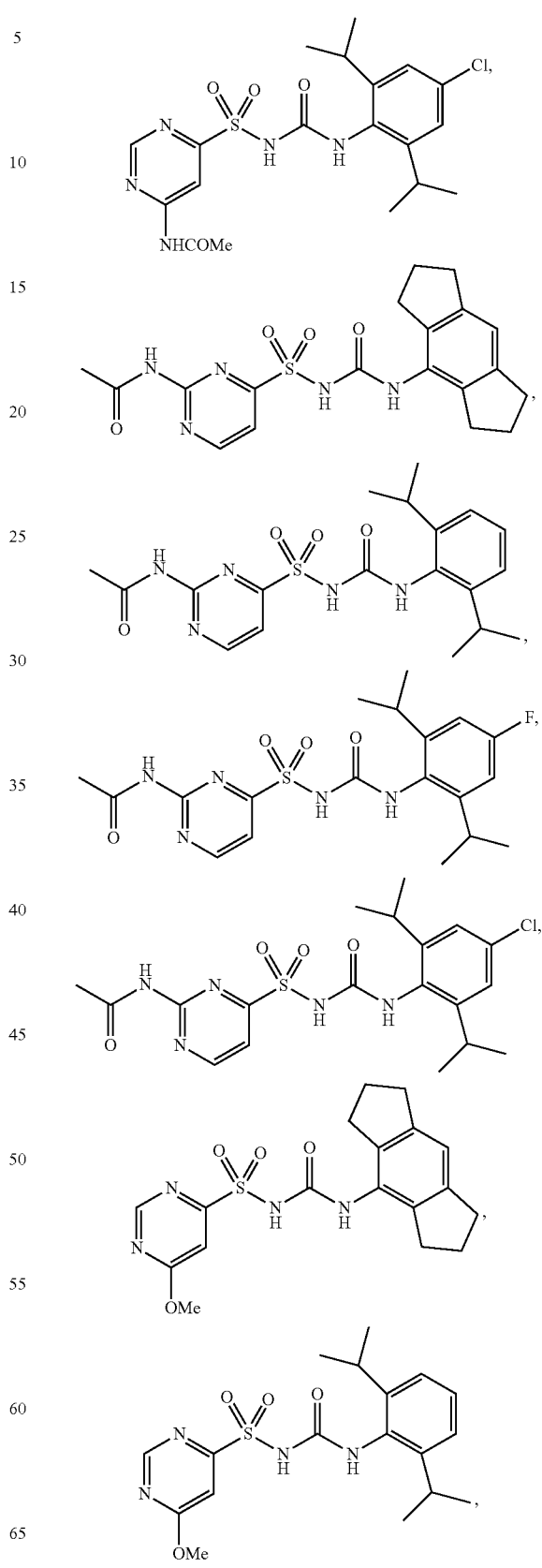

79
-continued
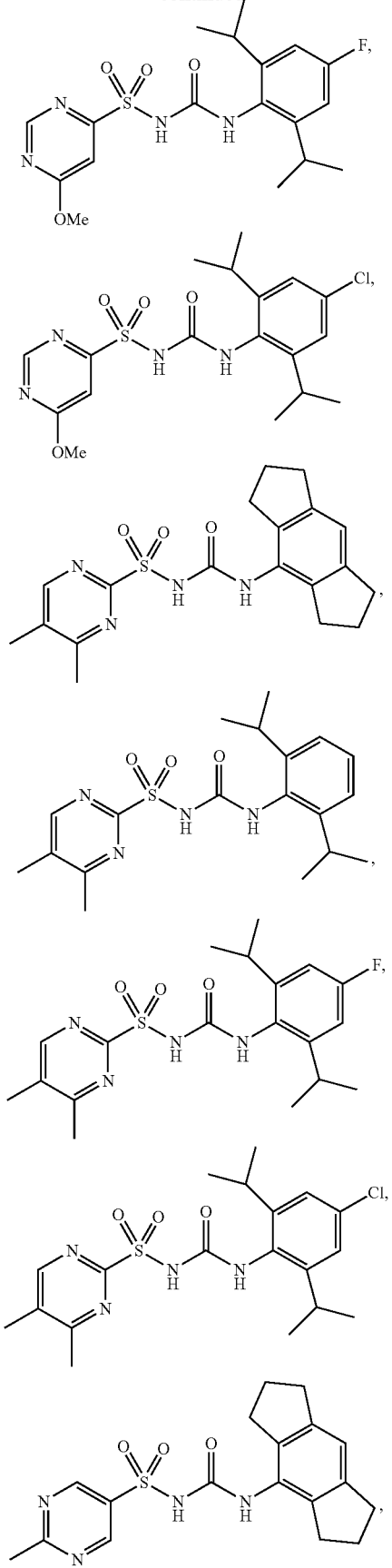
80
-continued
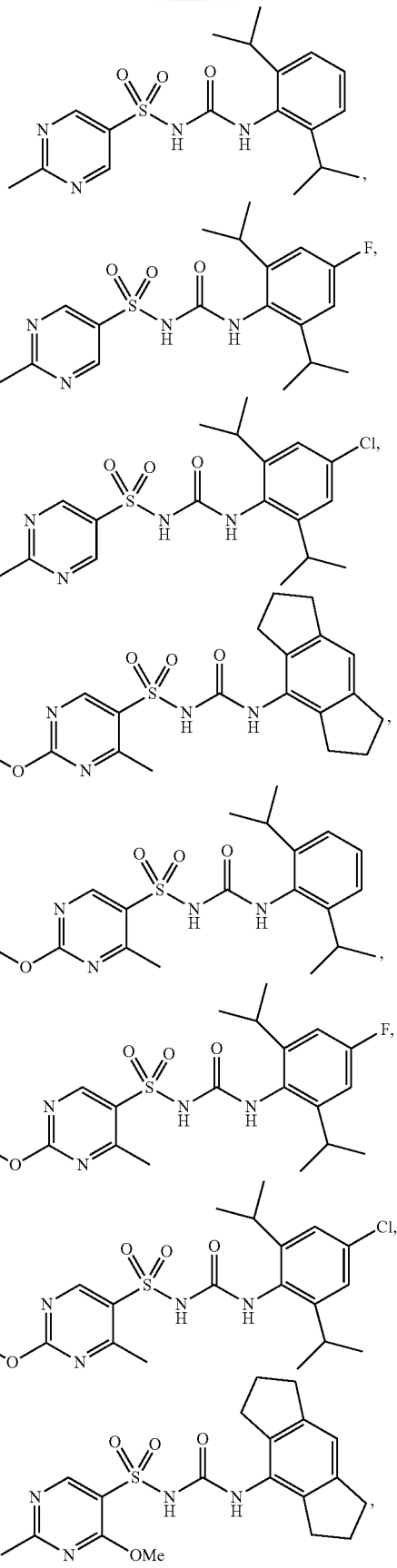

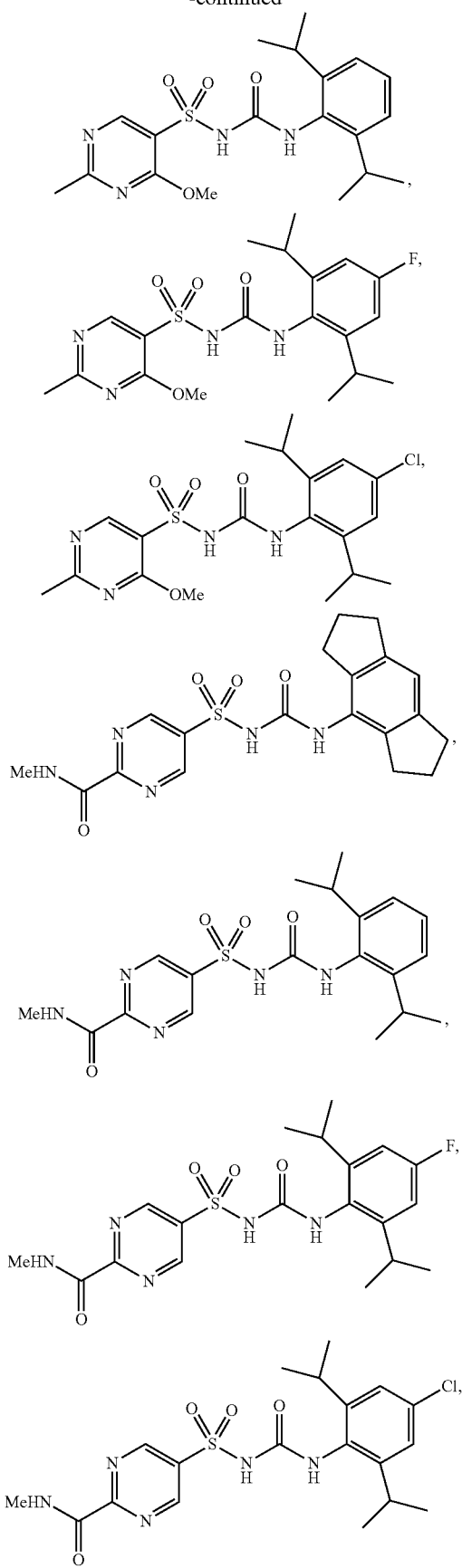
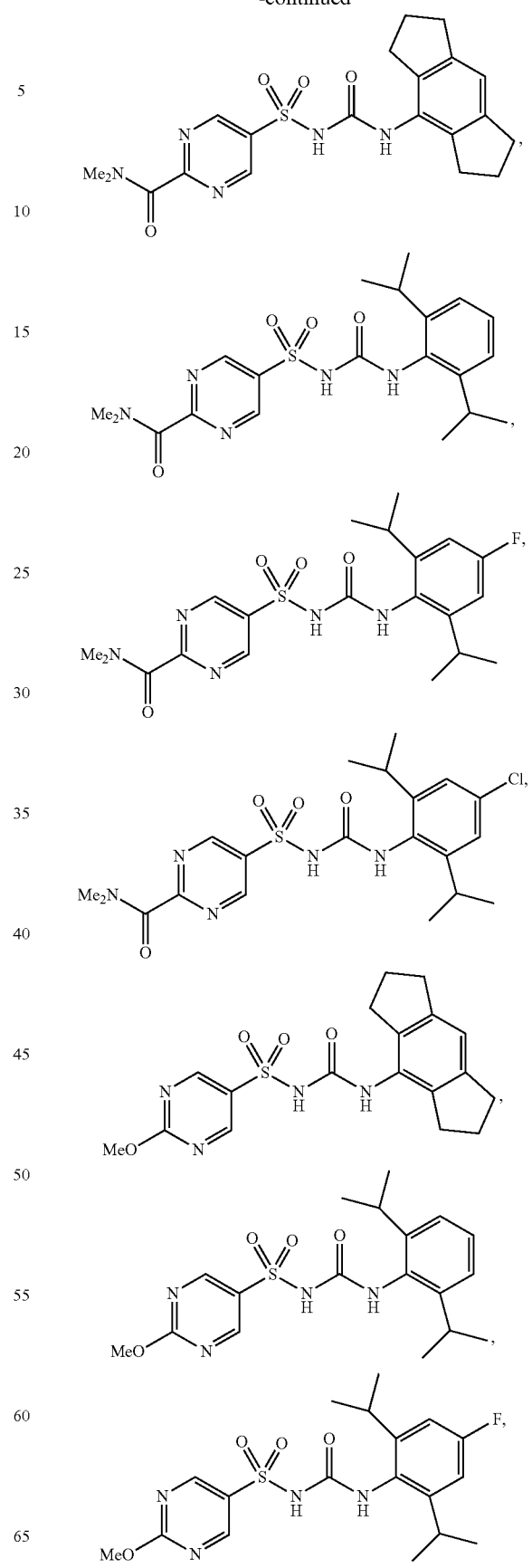

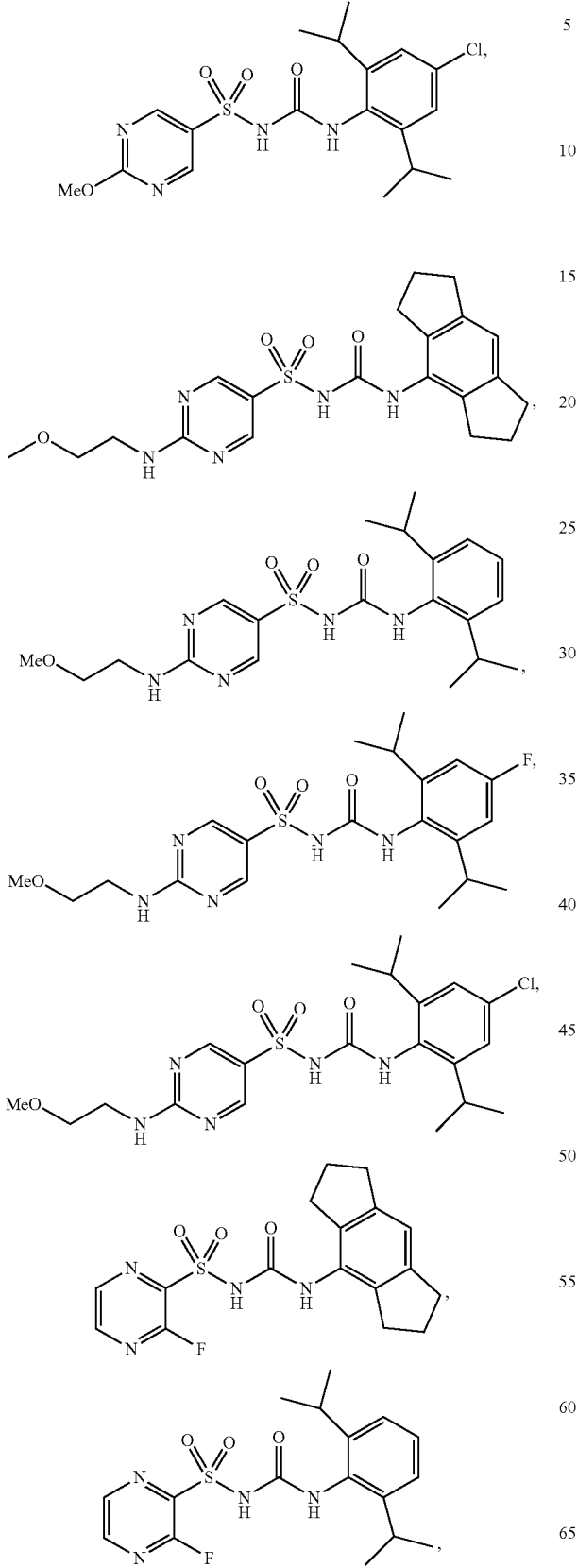
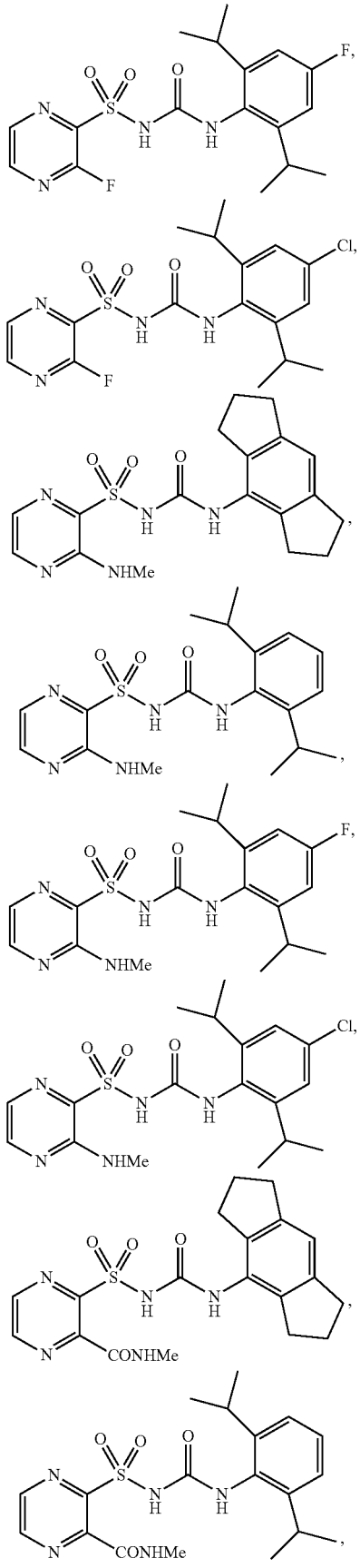

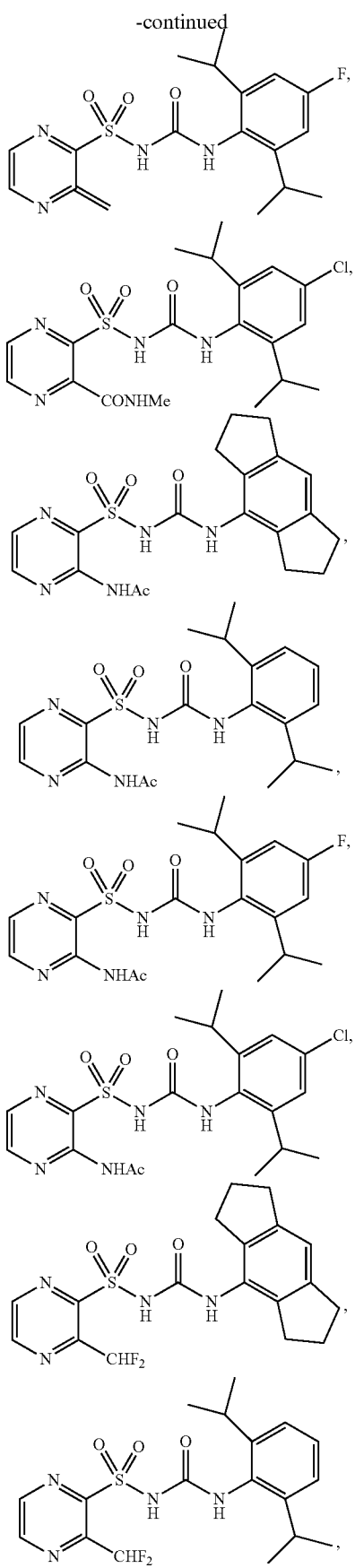
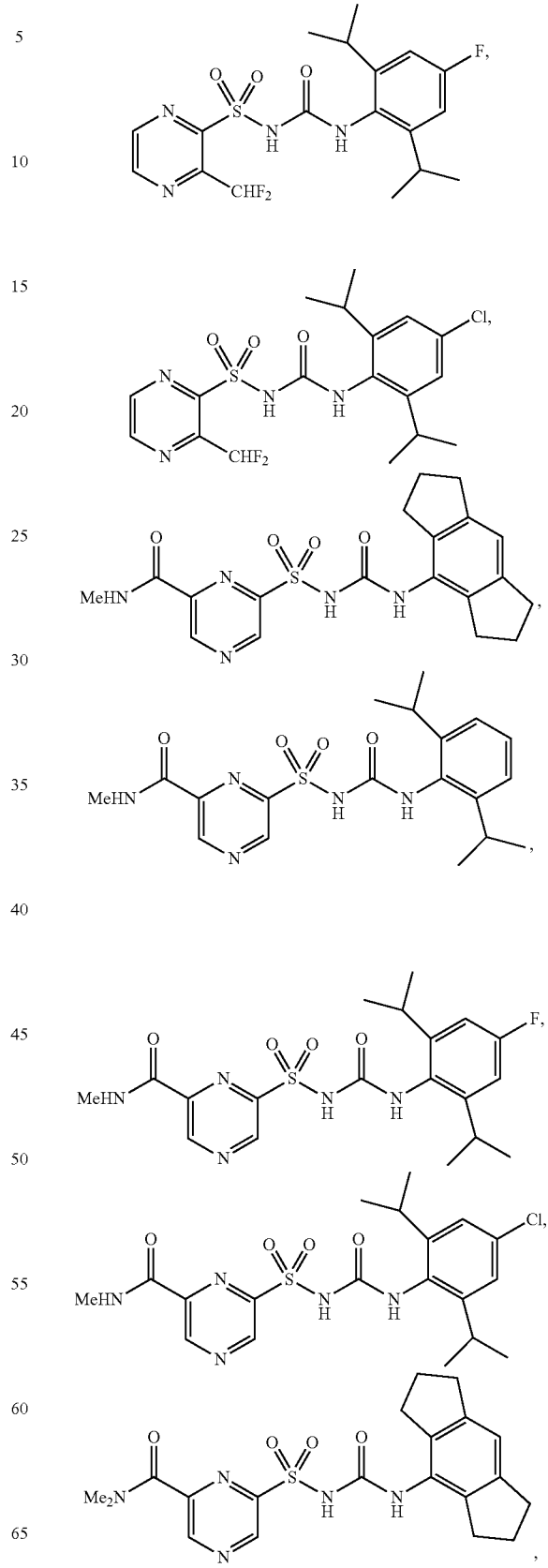

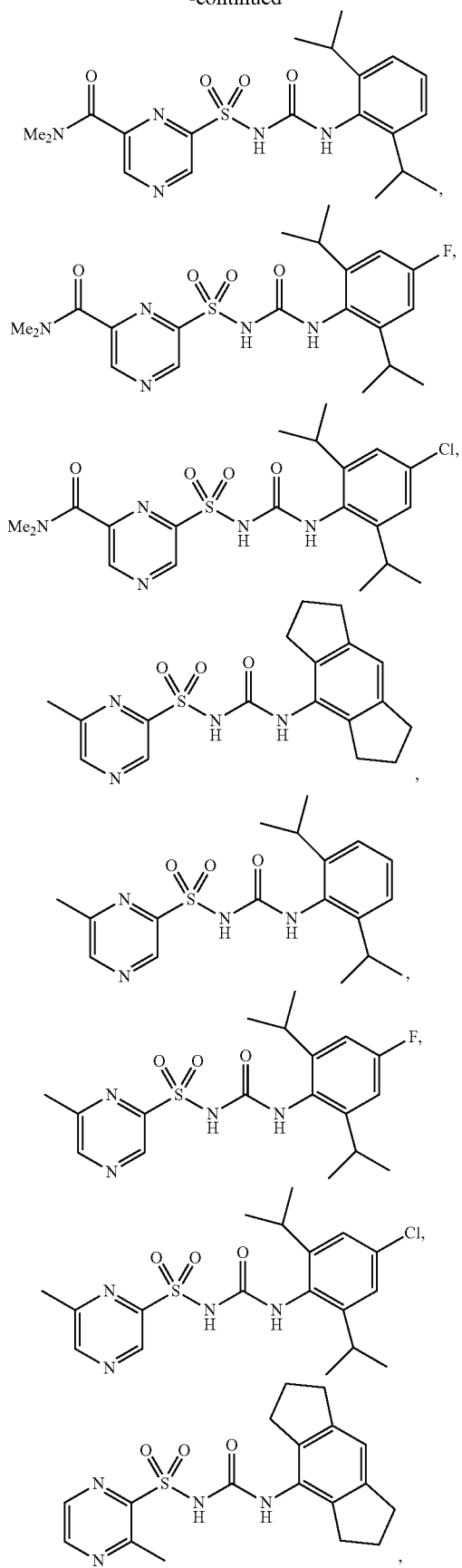
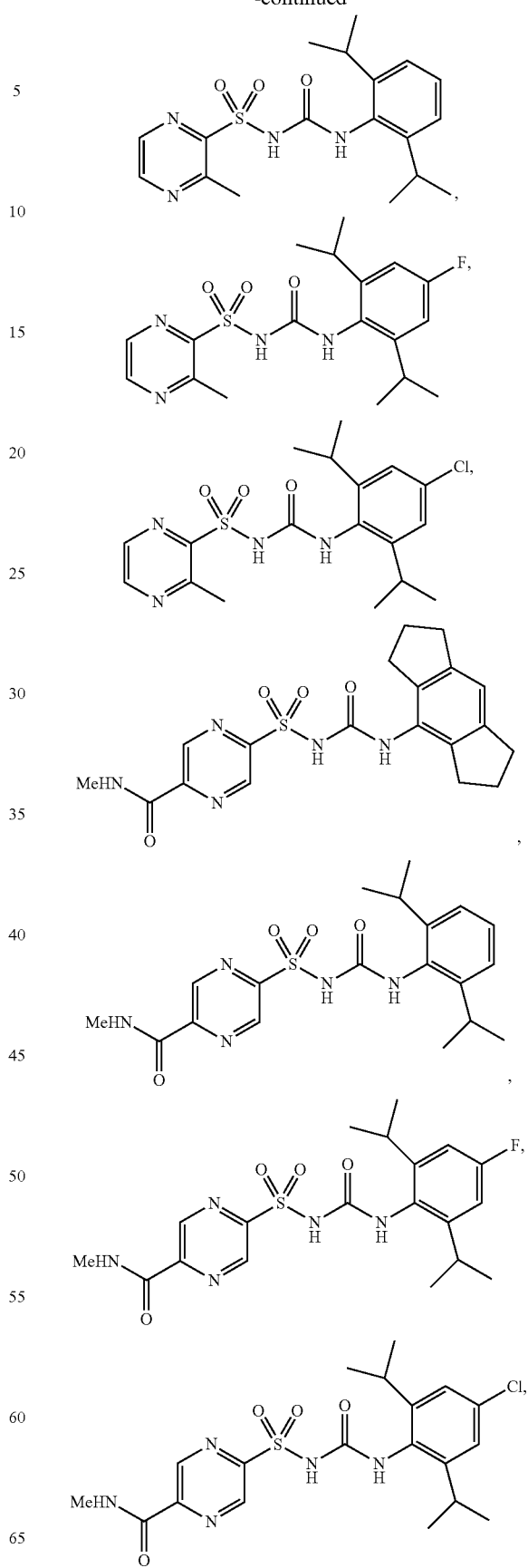

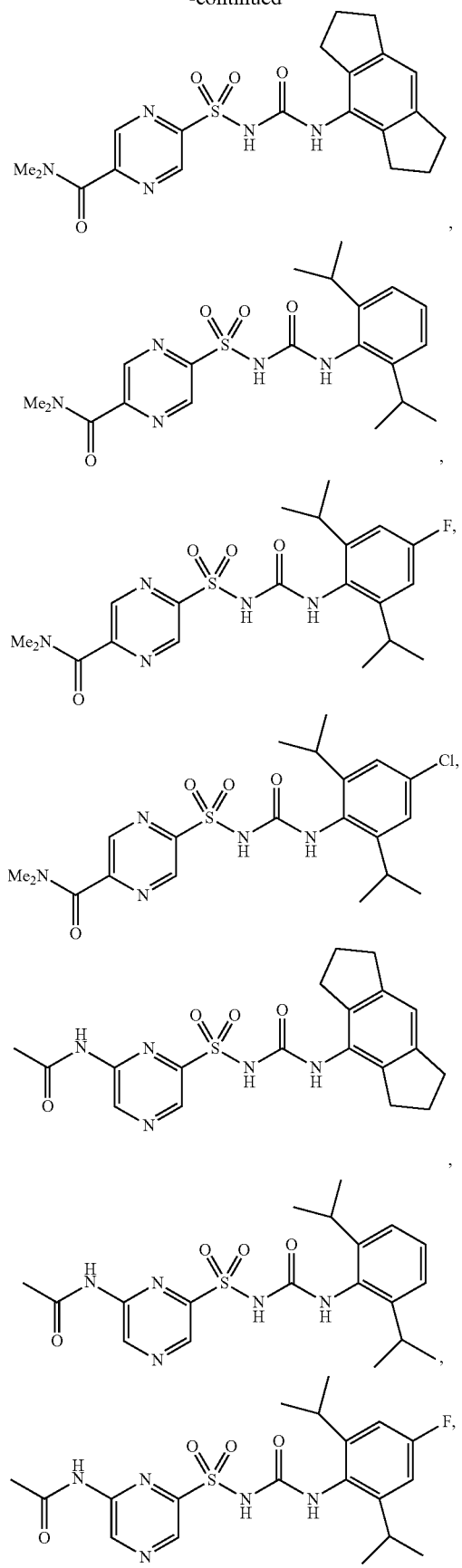

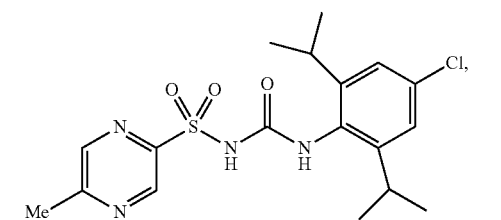
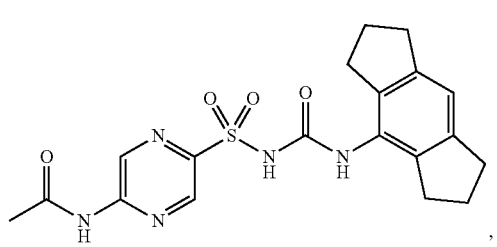
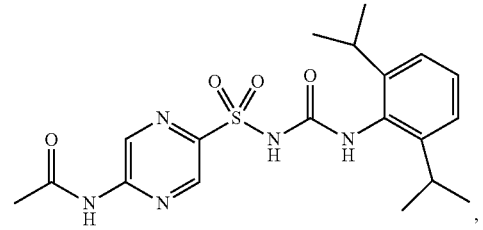
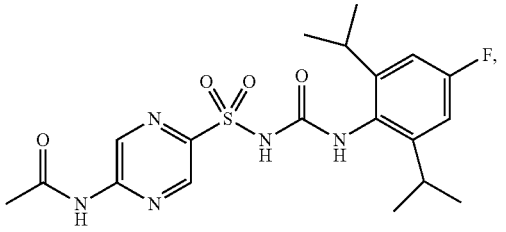
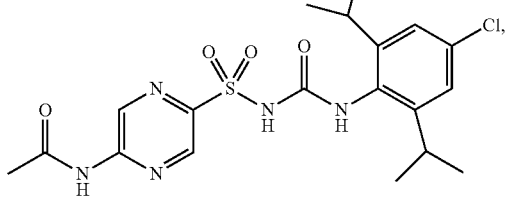
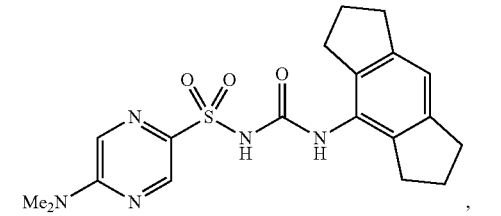
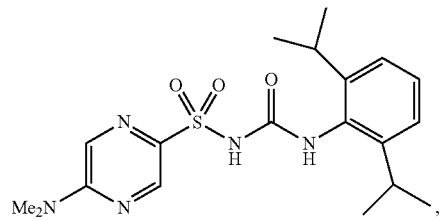
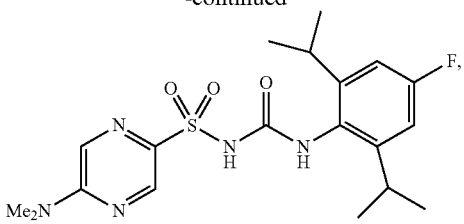
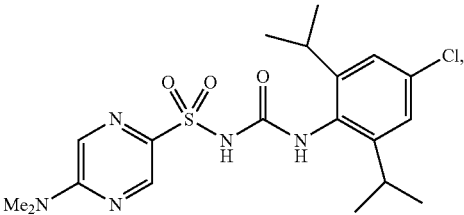
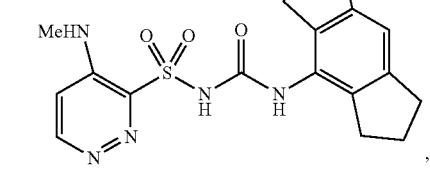
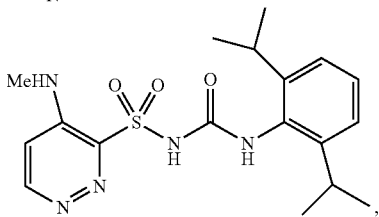
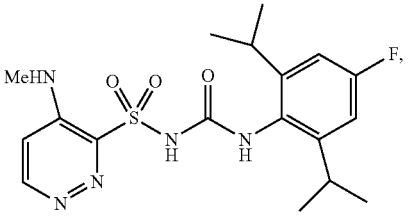
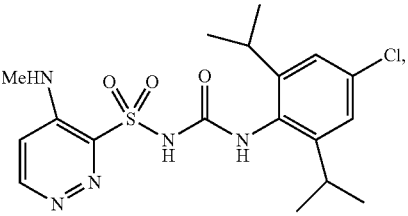
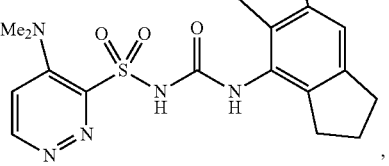
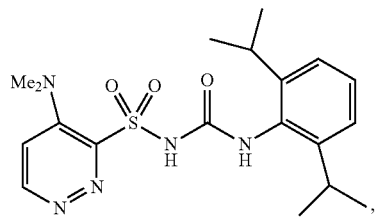

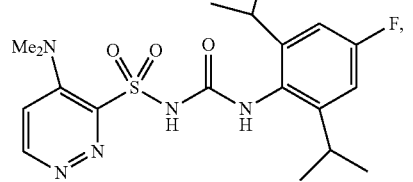
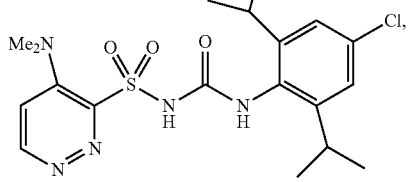
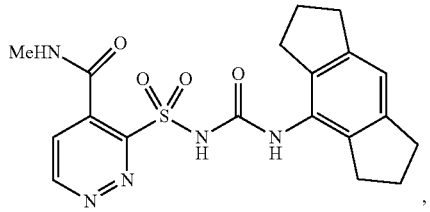
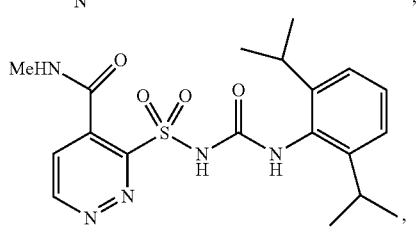
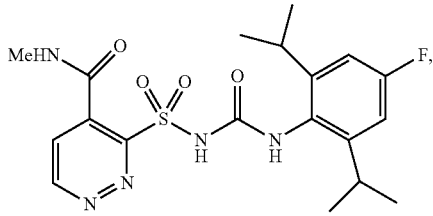
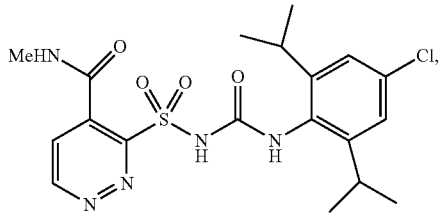
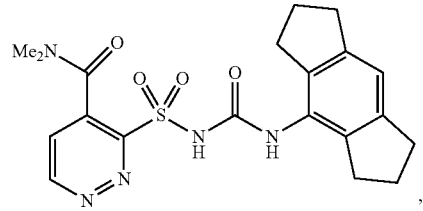
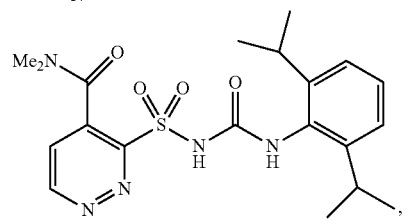
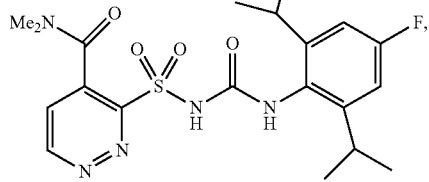
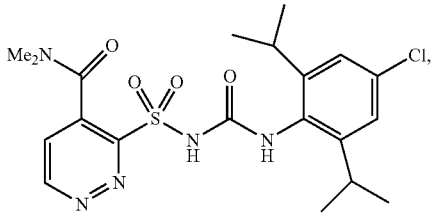
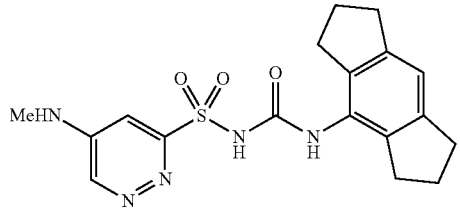
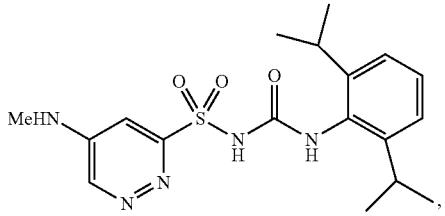
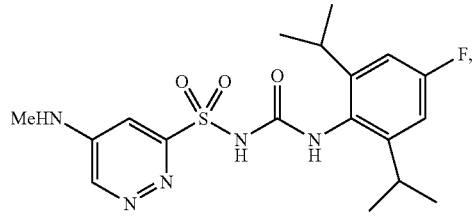
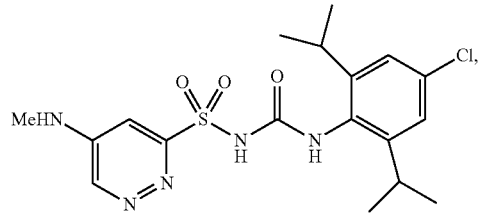
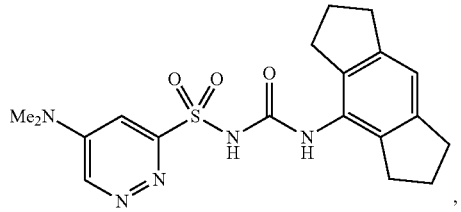
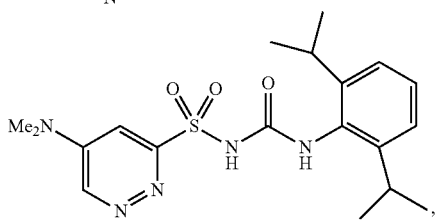

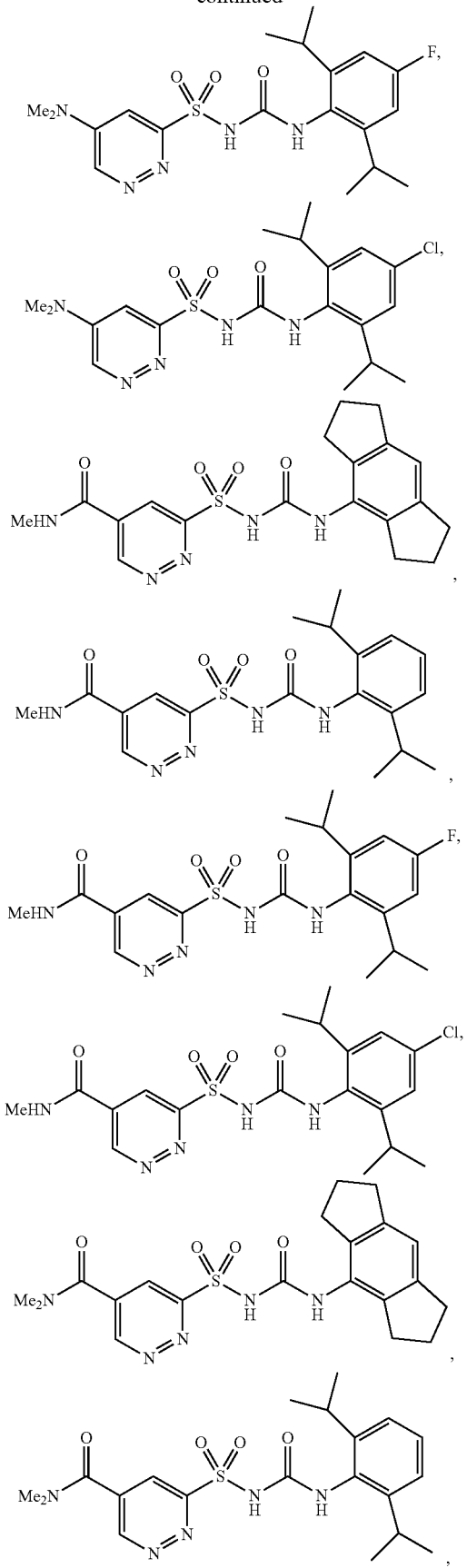
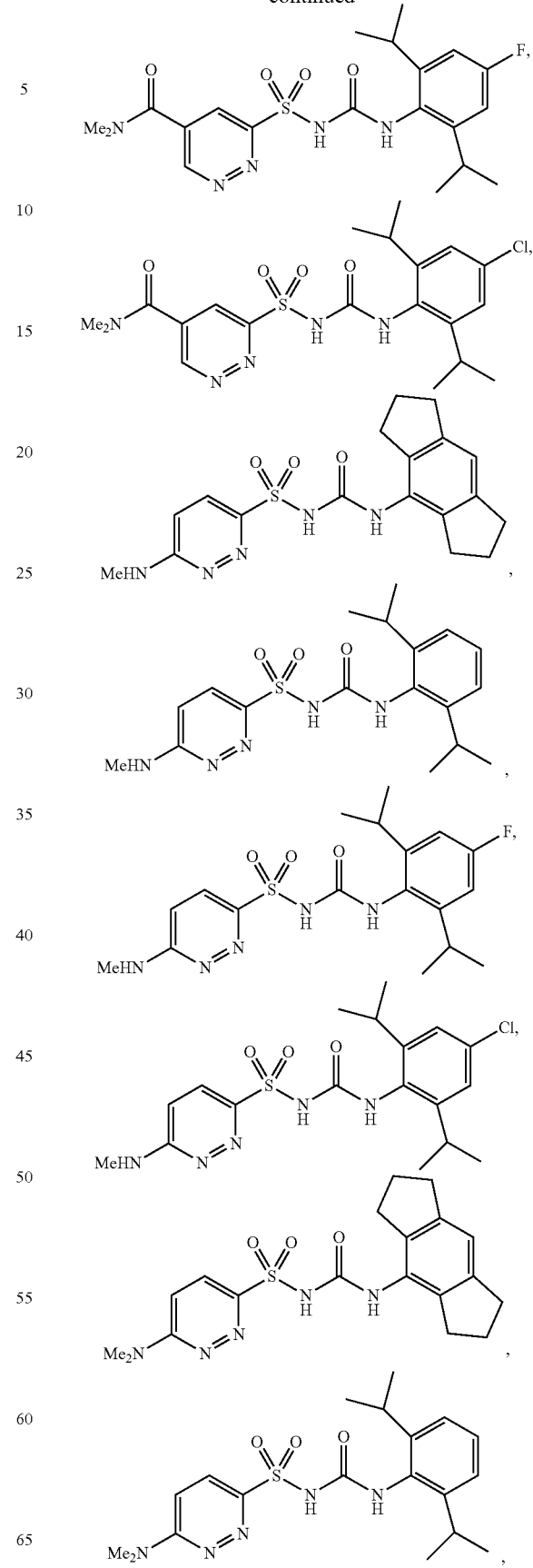

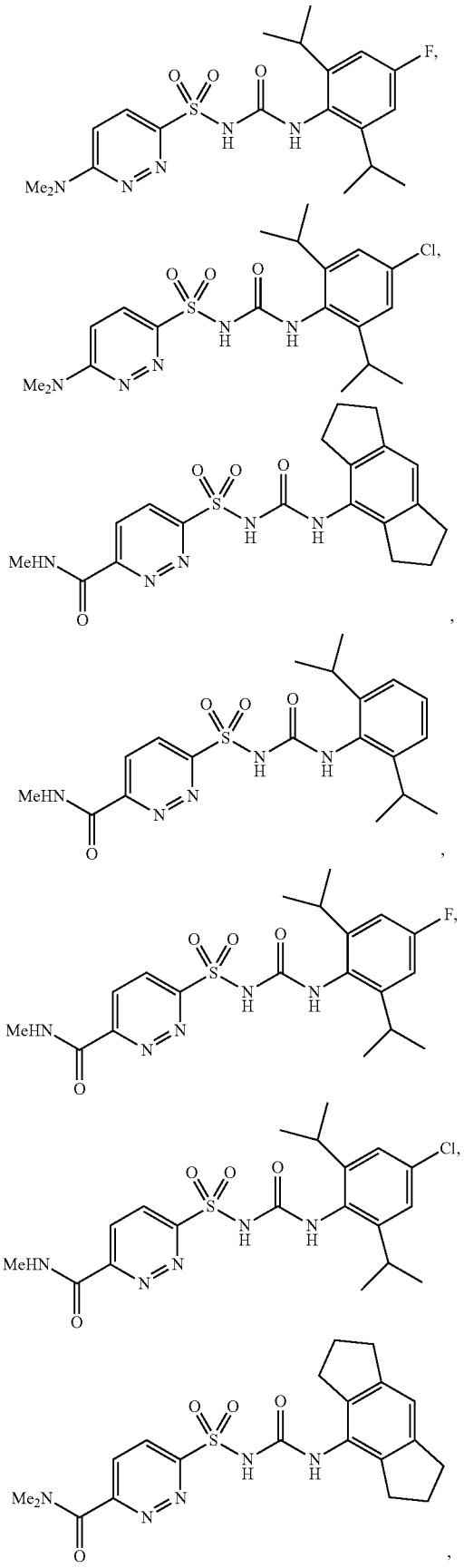
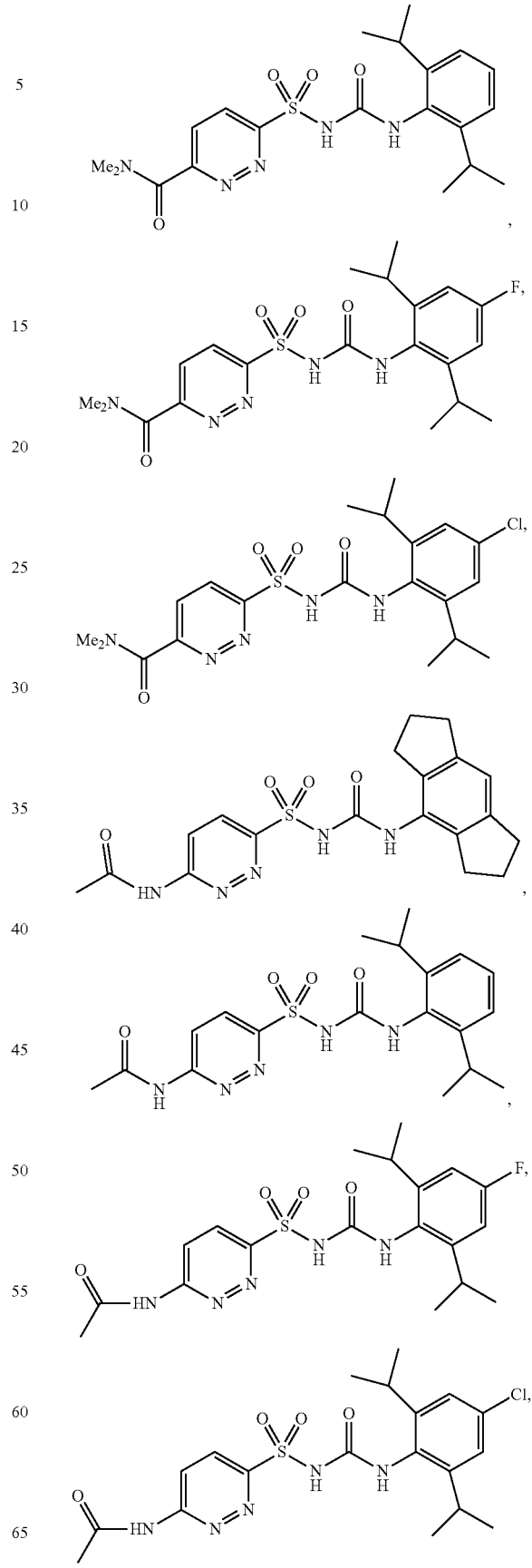

-continued

101
-continued
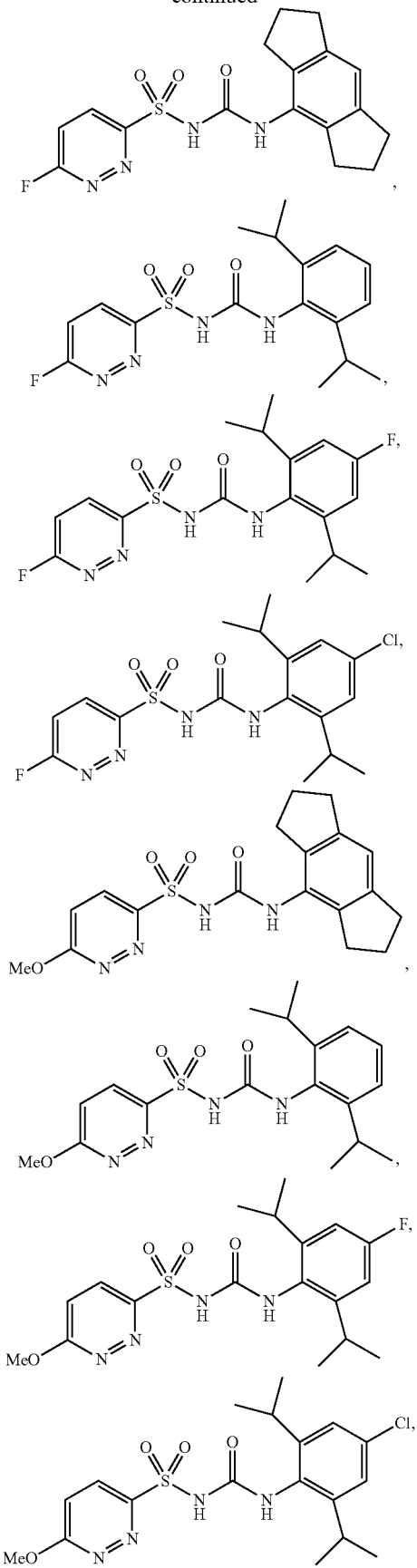
102
-continued
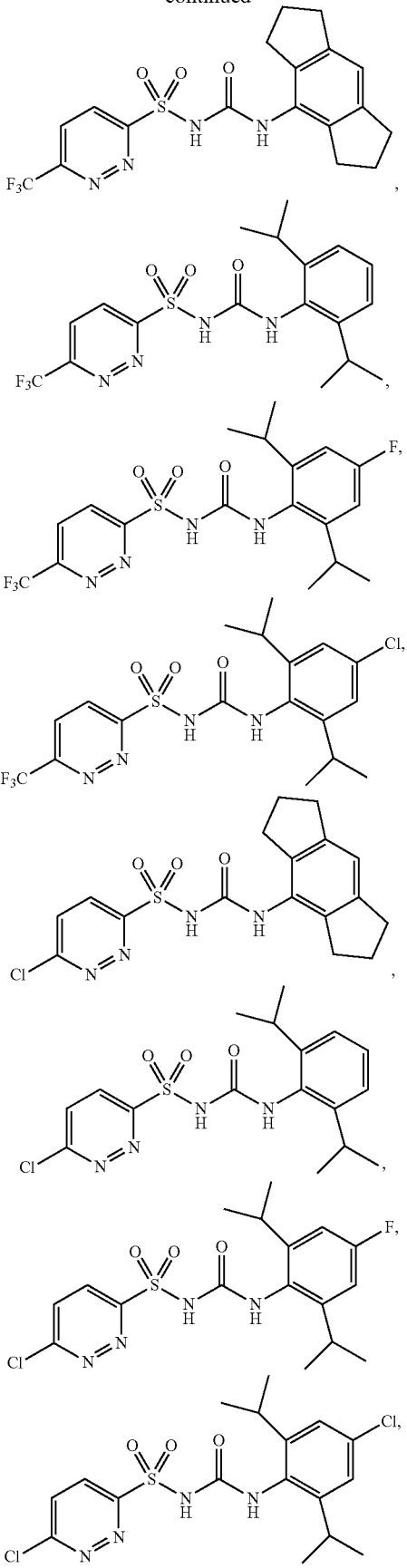

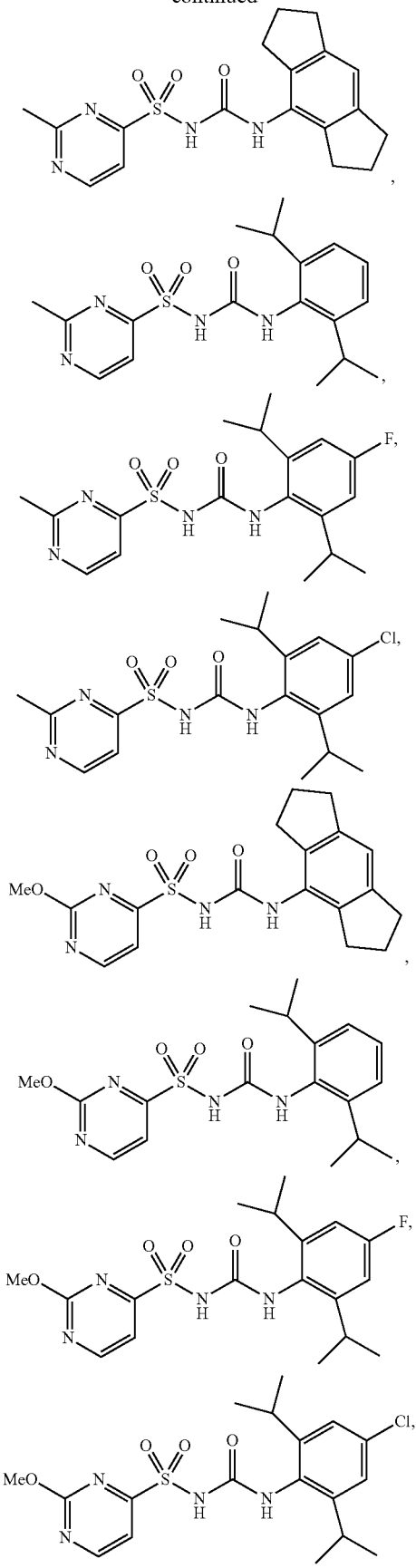
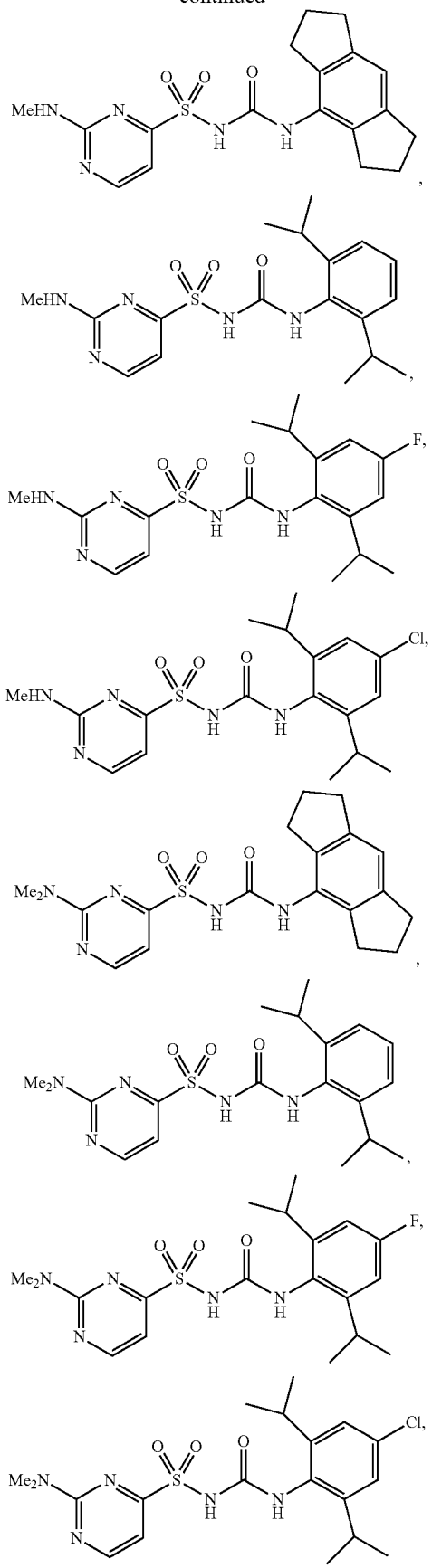

-continued
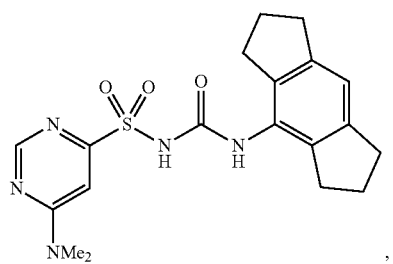
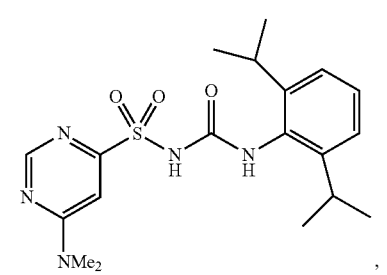
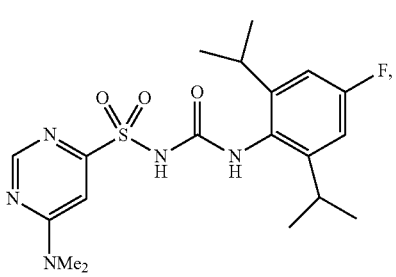
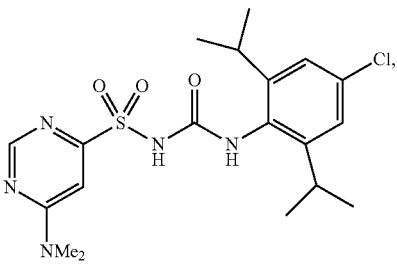
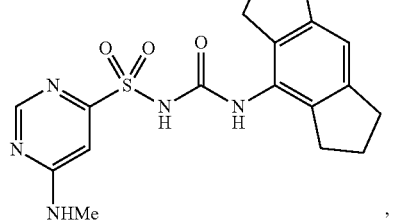
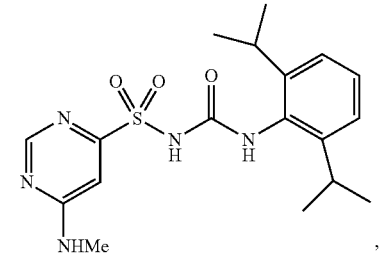
-continued
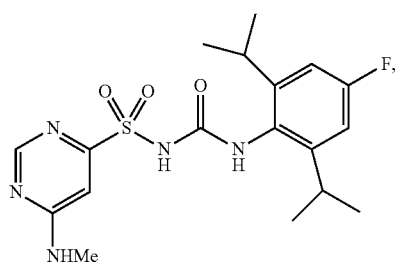
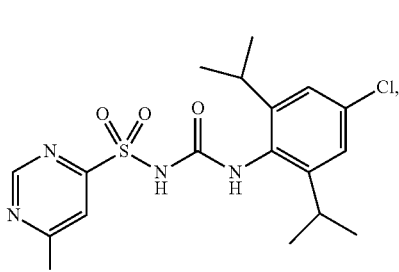
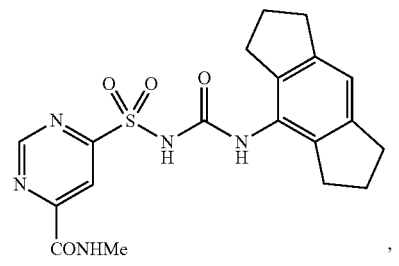
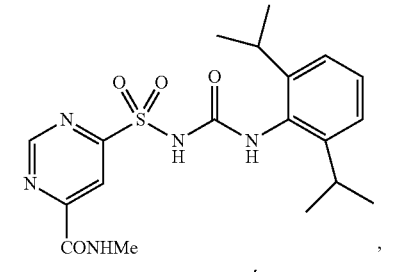
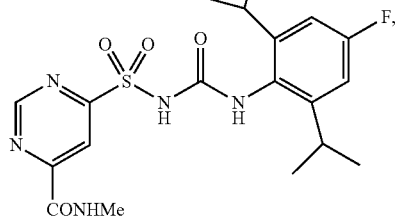
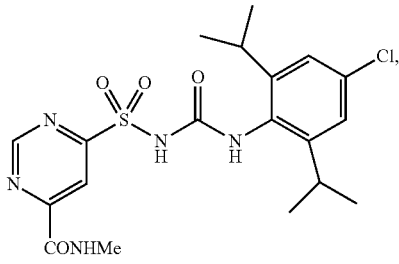

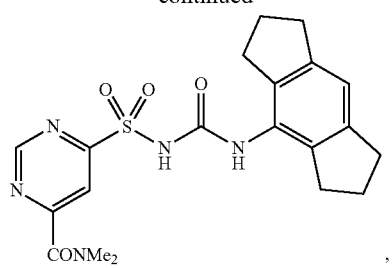
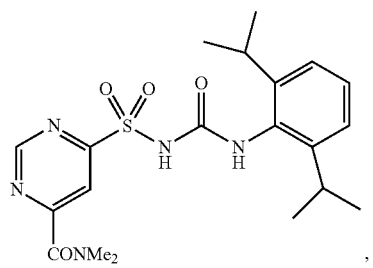
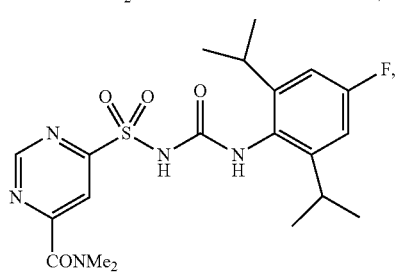
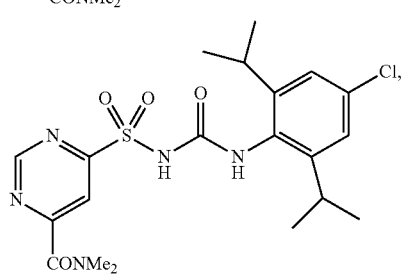
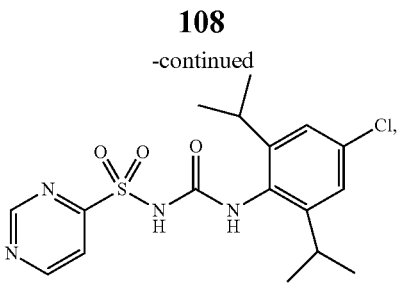
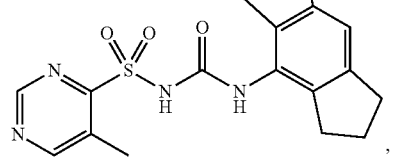
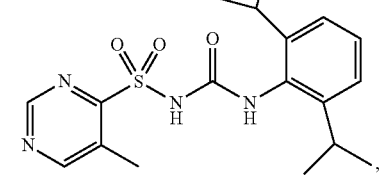
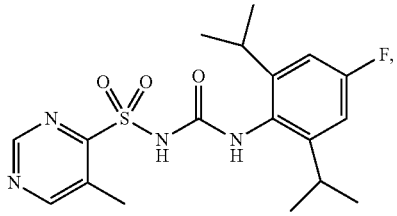
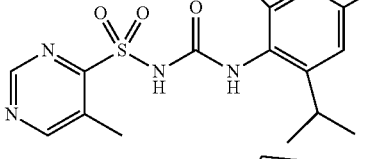
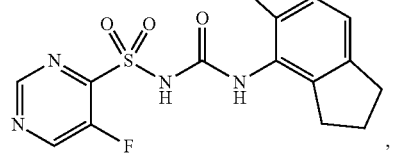
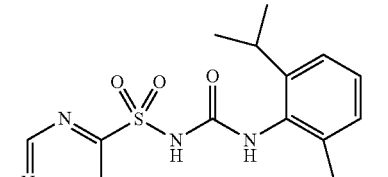
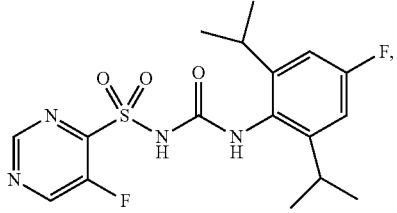

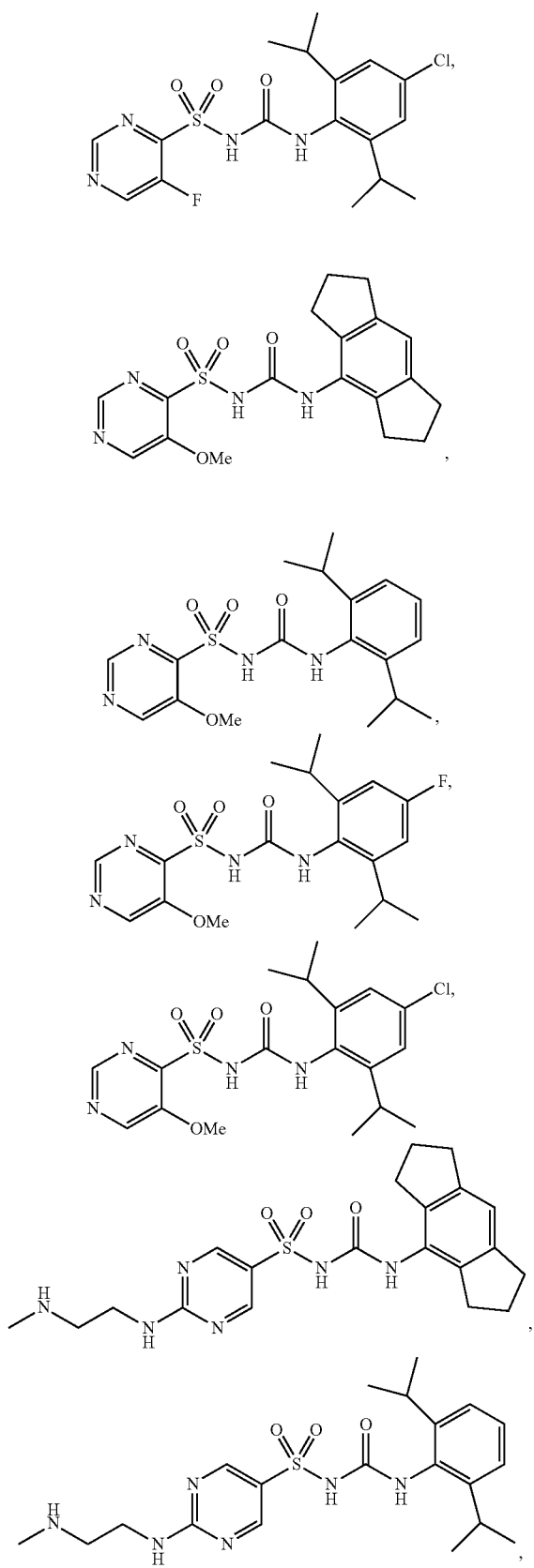
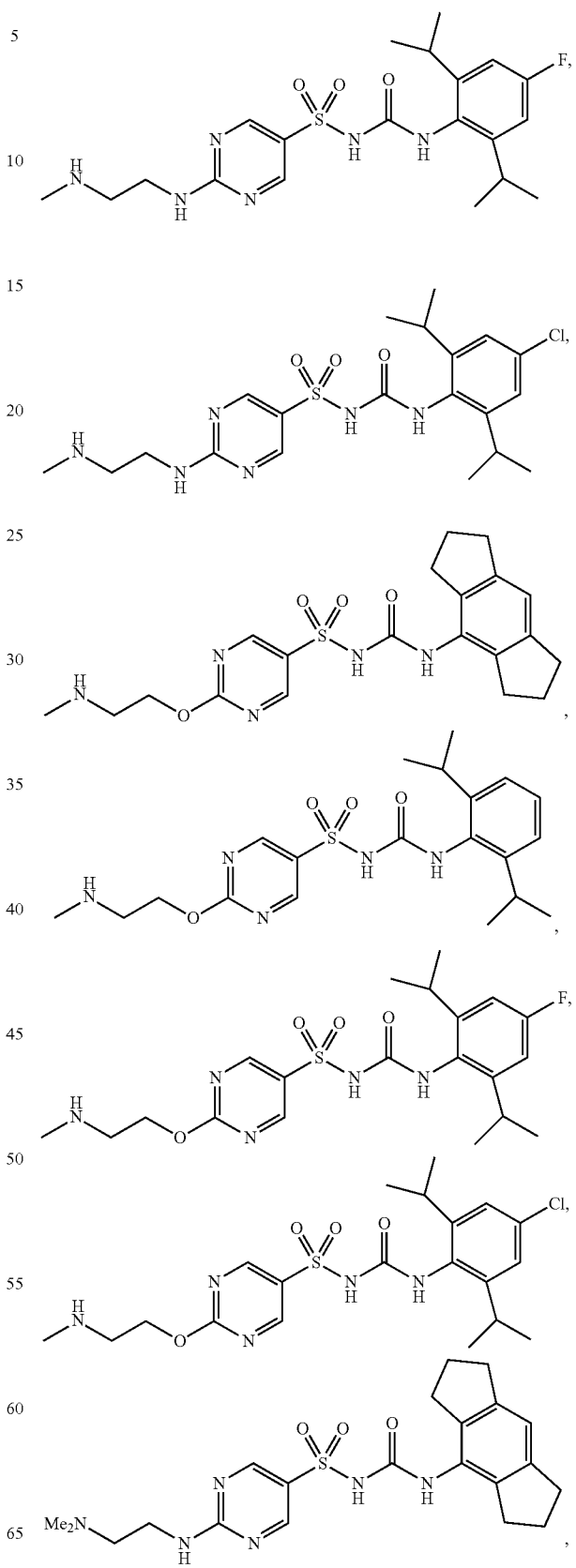

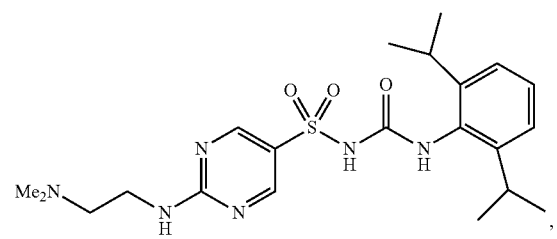
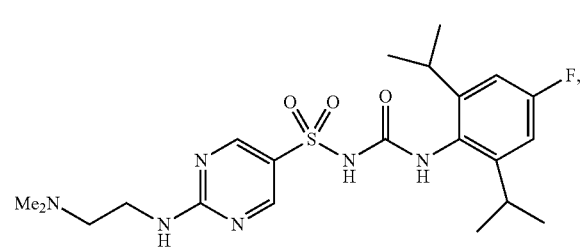
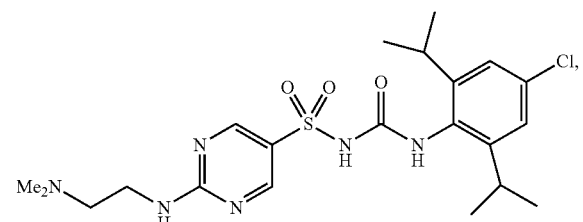
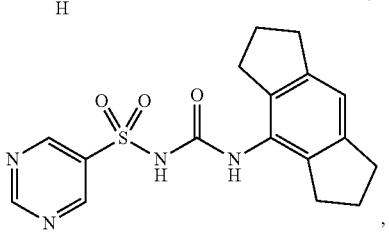
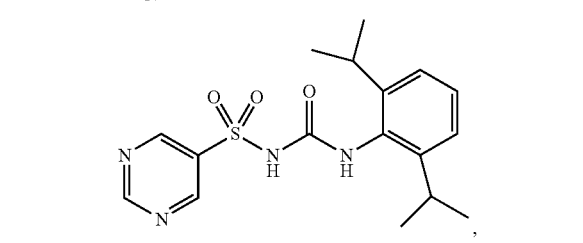
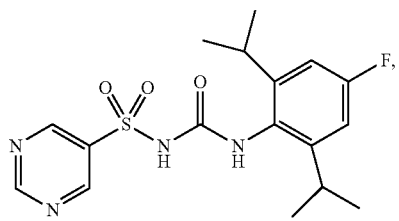
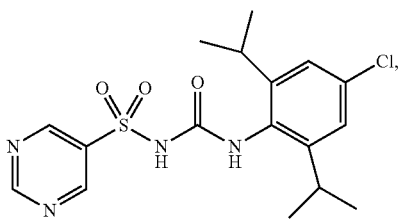
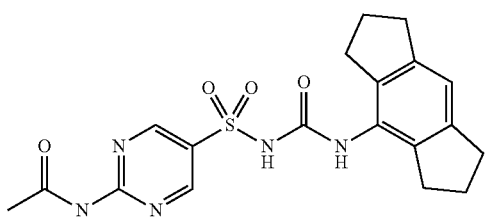
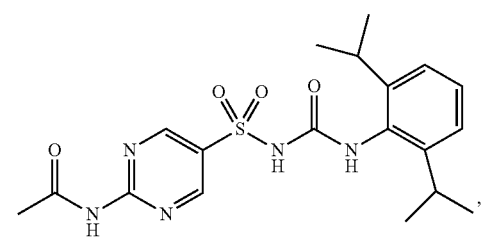
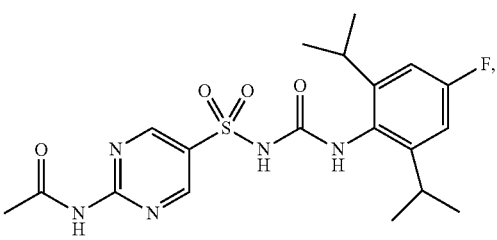
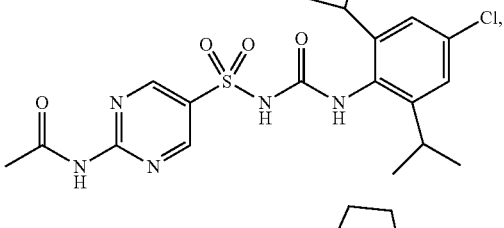
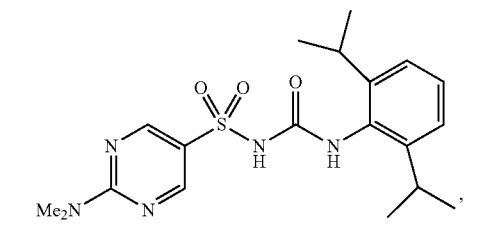
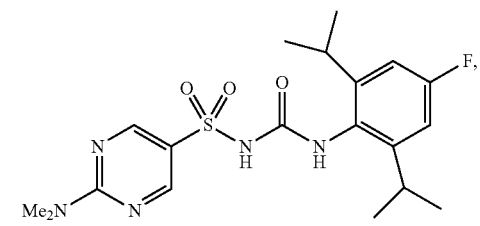

-continued
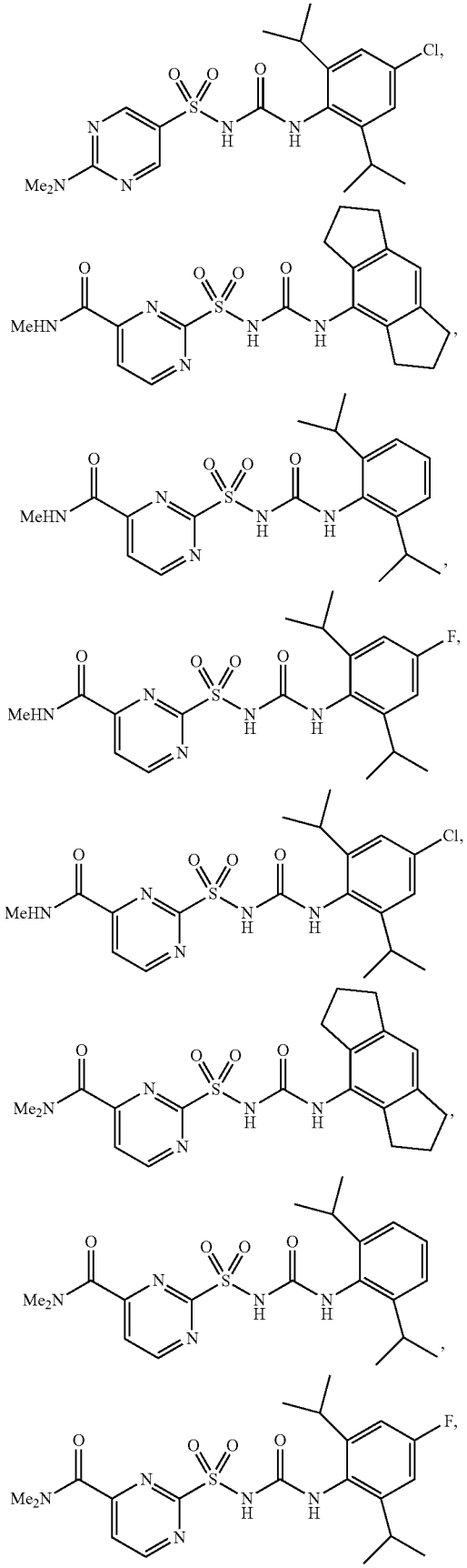
-continued
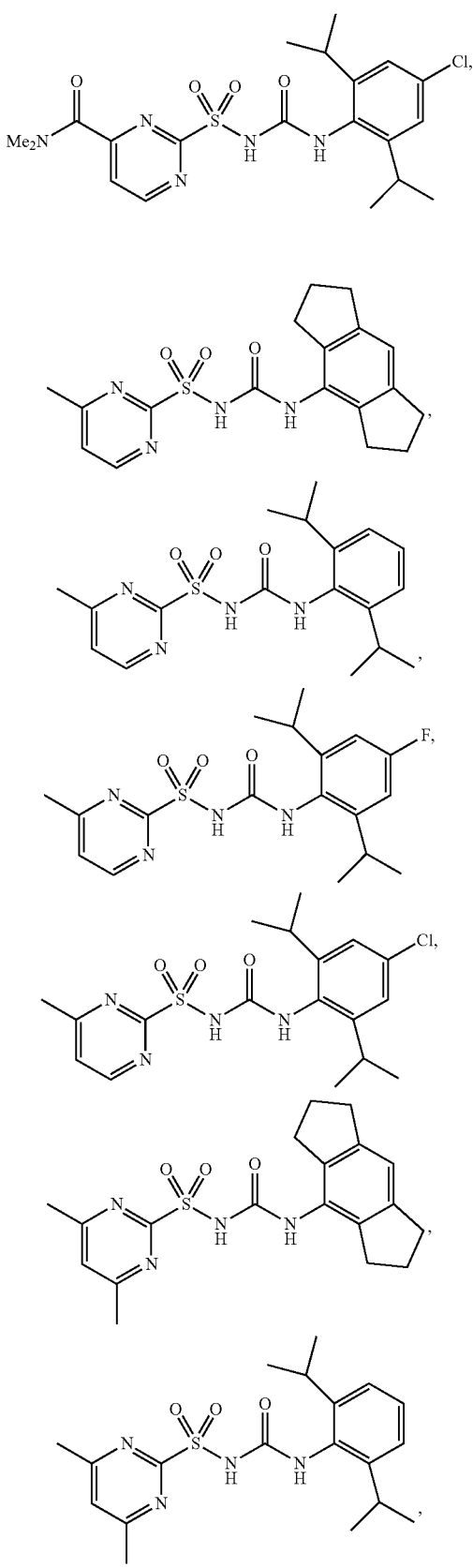

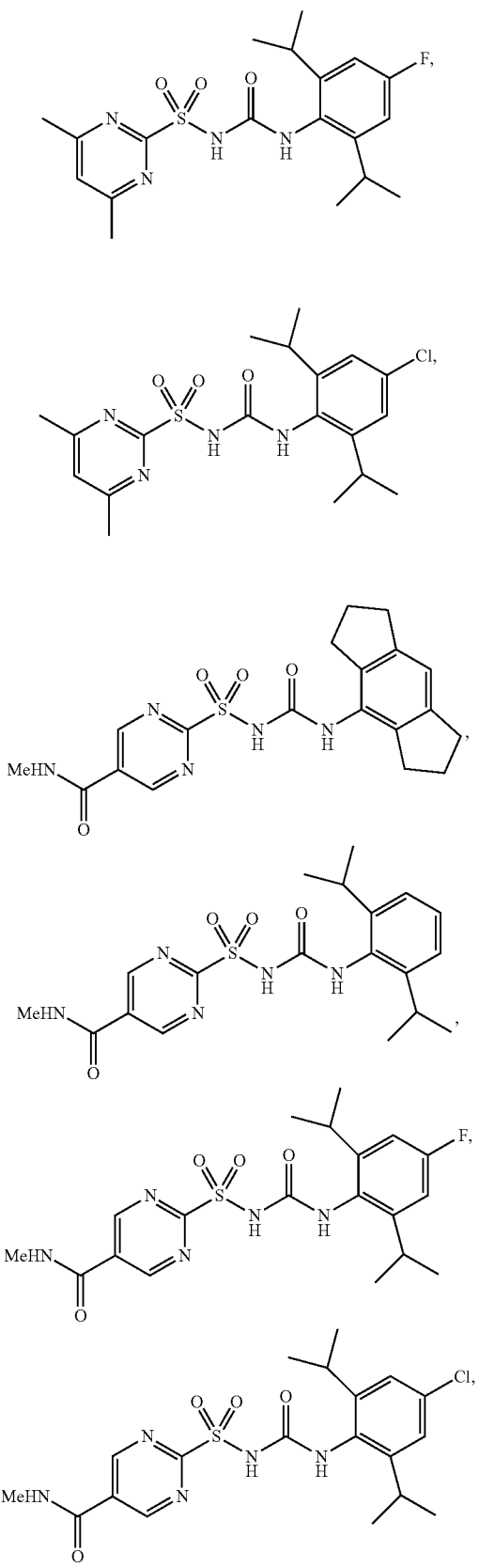
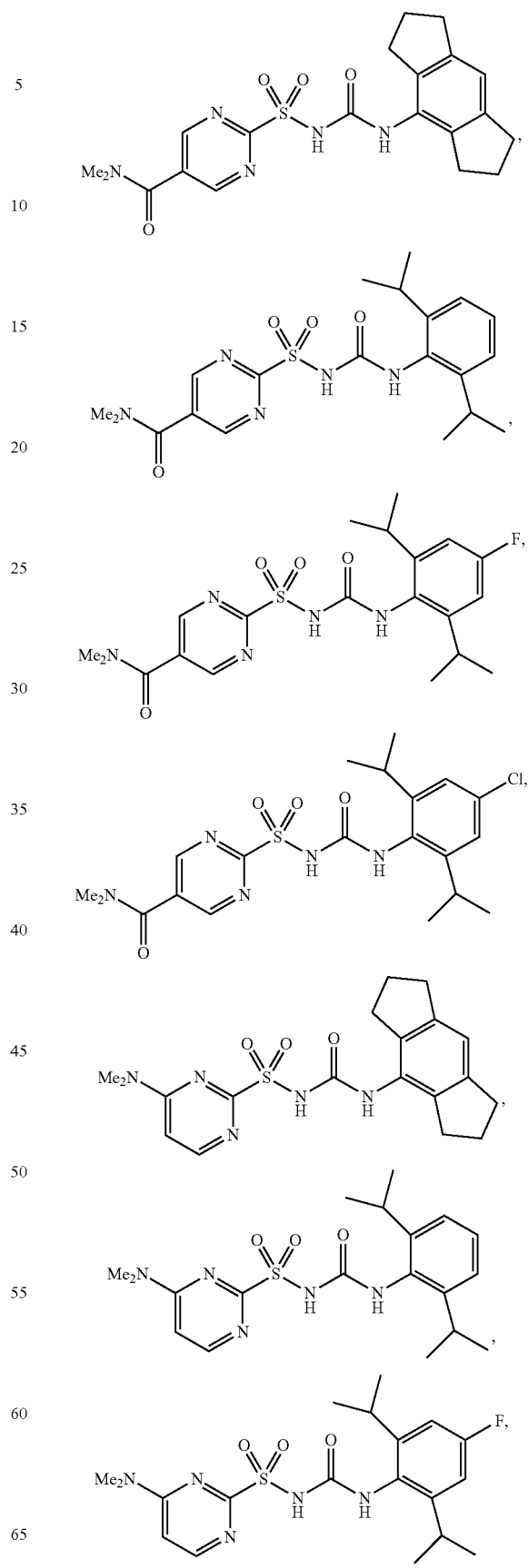

-continued
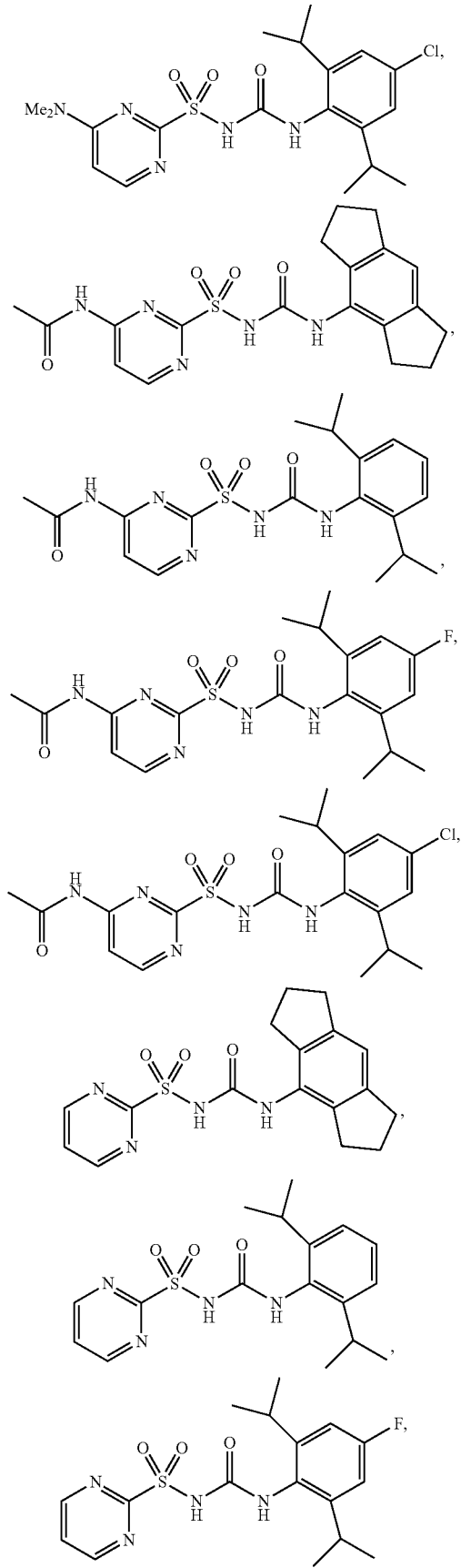
-continued
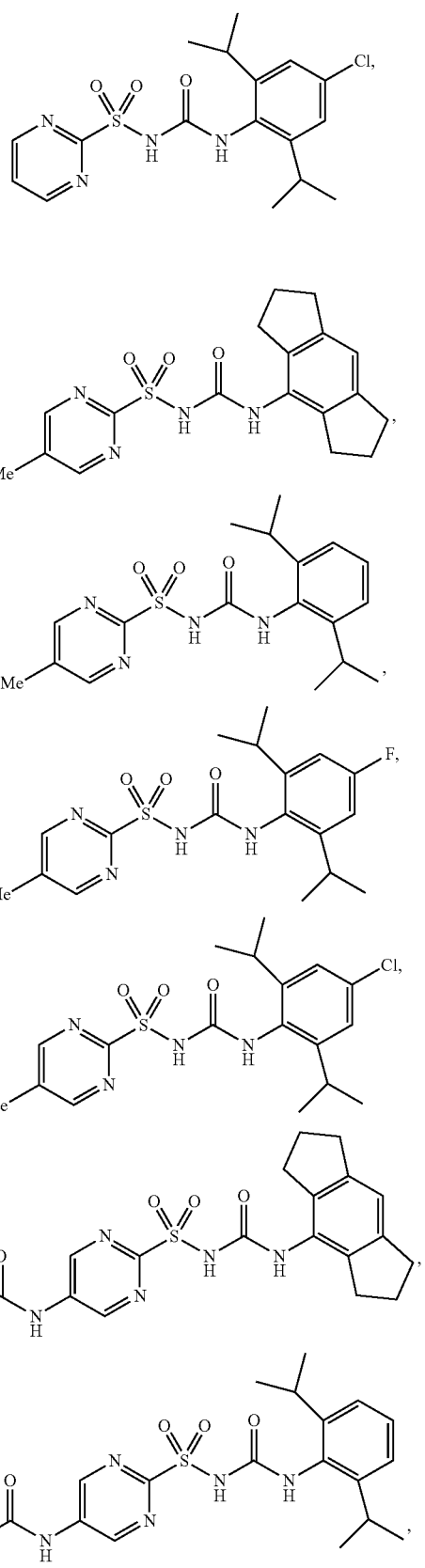

-continued
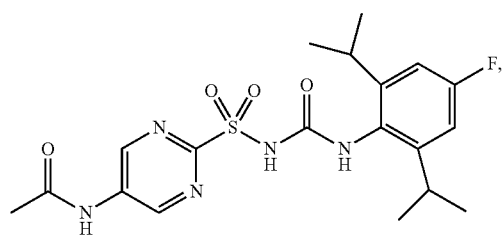
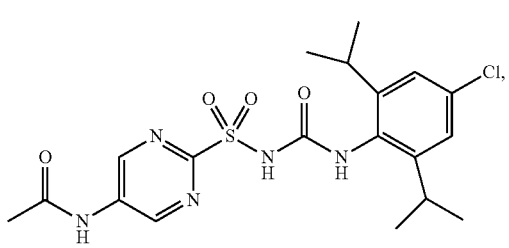
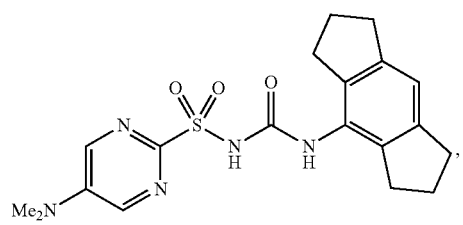
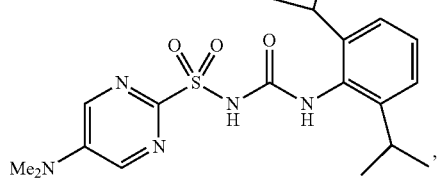
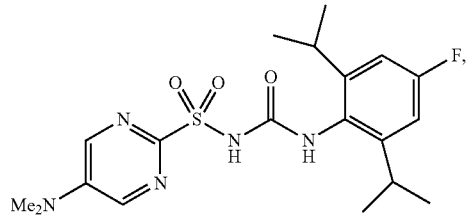
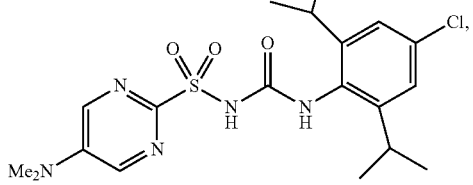
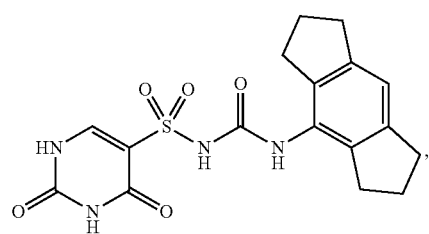
-continued
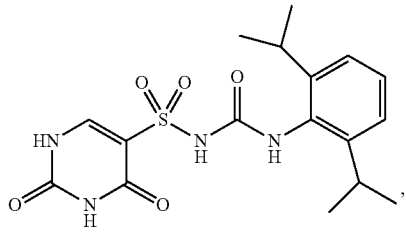
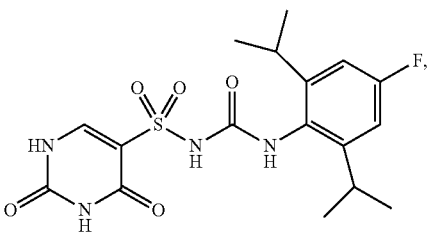
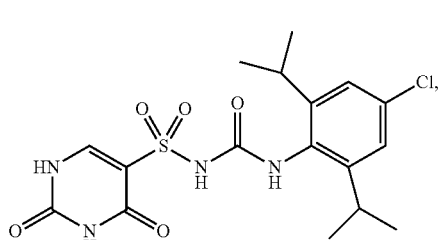
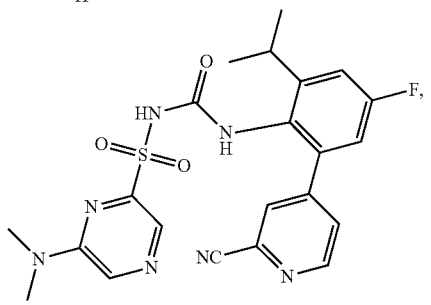
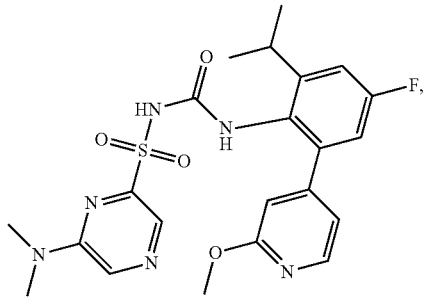
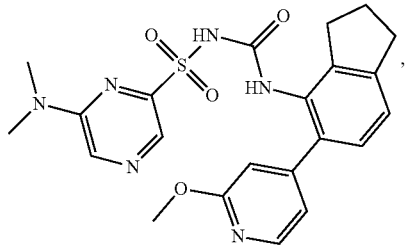

121
-continued
122
-continued
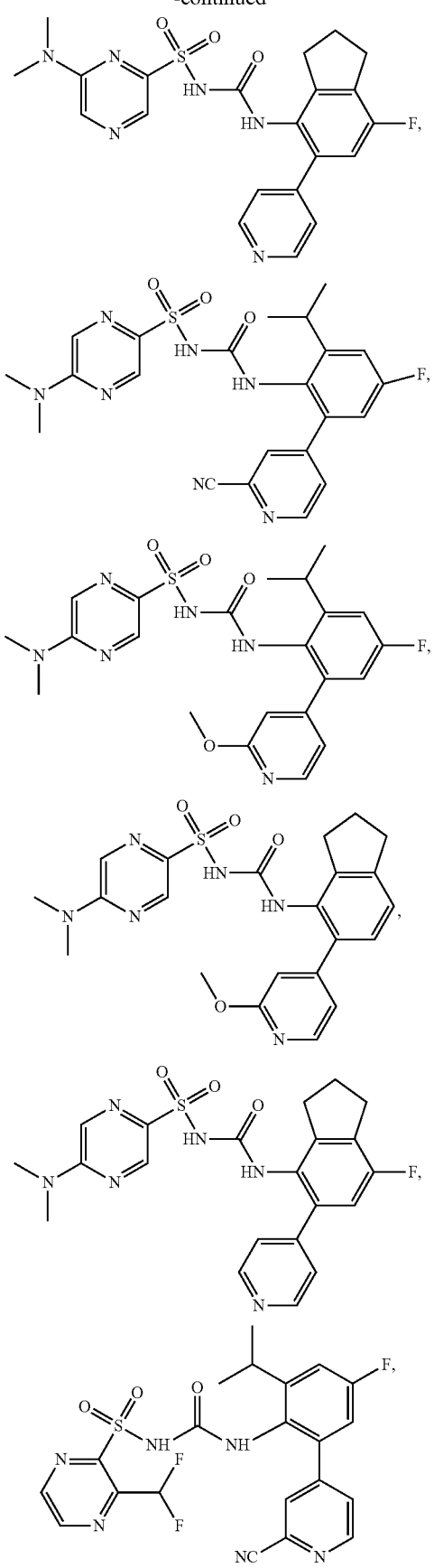
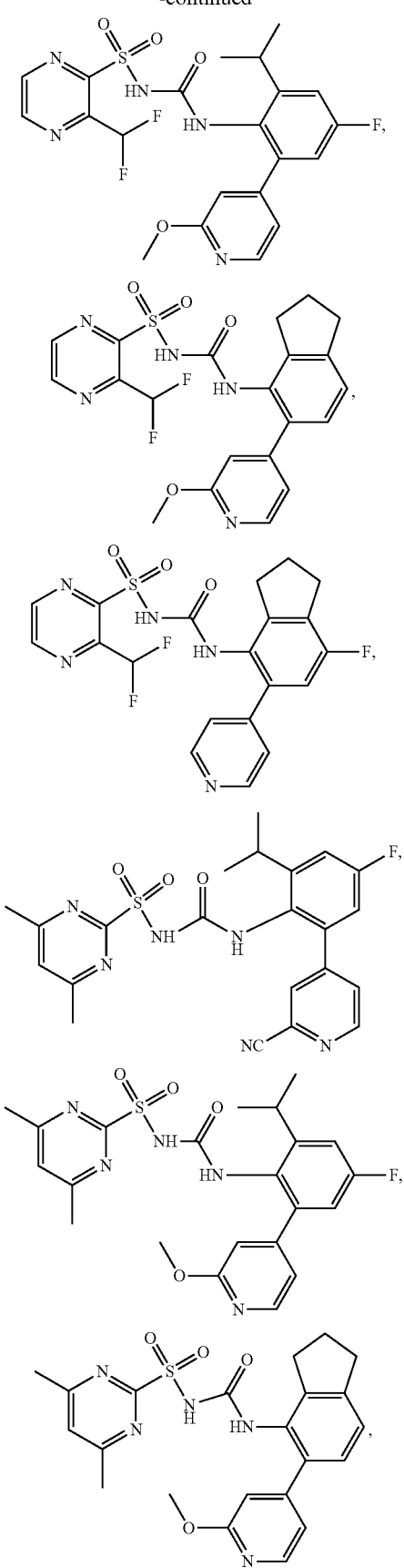

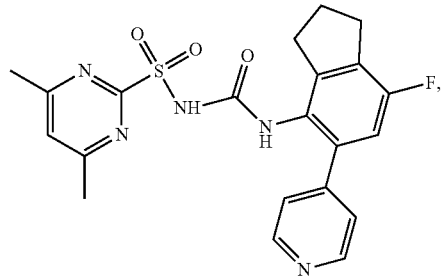

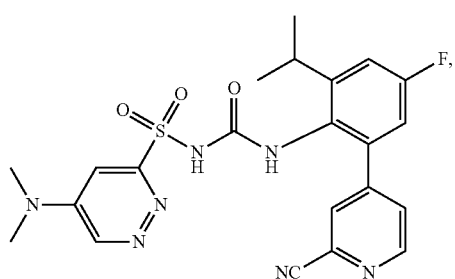

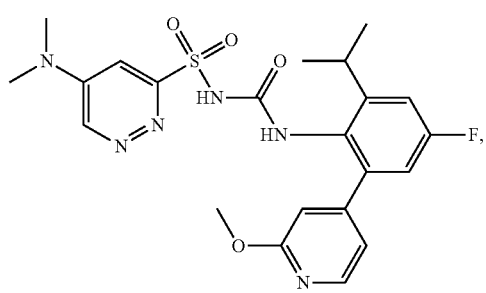

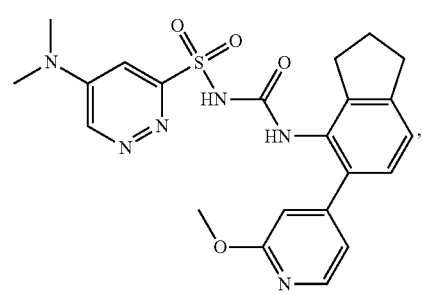

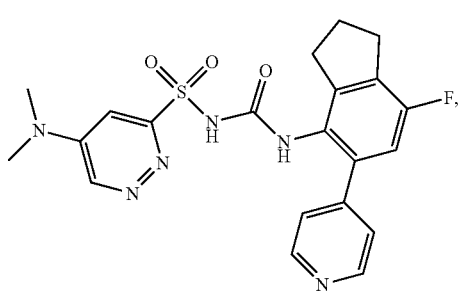

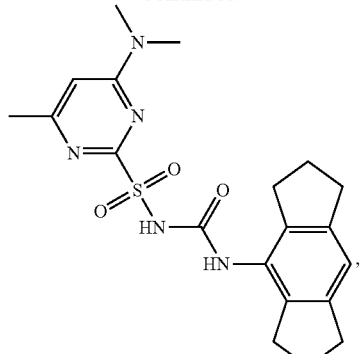

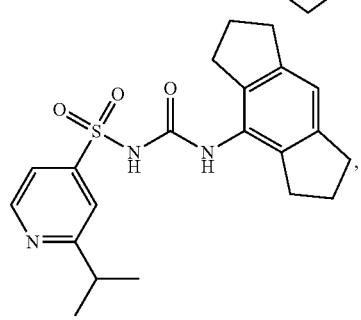

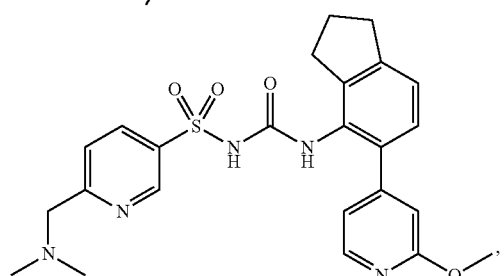

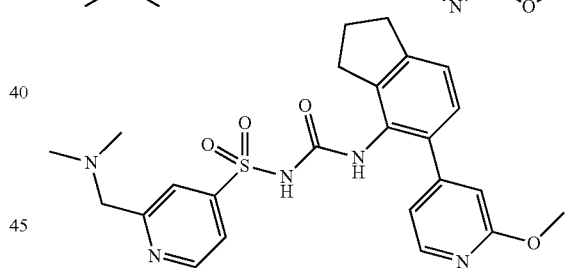

and

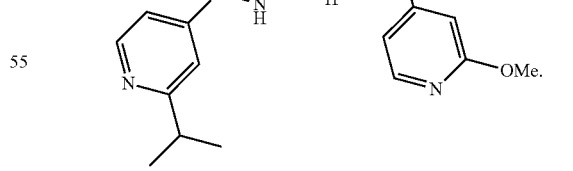

A third aspect of the invention provides a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulphuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulphonic acids (for example, methanesulphonic, trifluoromethanesulphonic, ethanesulphonic, 2-hydroxyethanesulphonic, benzenesulphonic, toluene-p-sulphonic, naphthalene-2-sulphonic or camphorsulphonic acid) or amino acids (for example, ornithinic, glutamic or aspartic acid). The acid addition salt may be a mono-, di-, tri- or multi-acid addition salt. A preferred salt is a hydrohalogenic, sulphuric, phosphoric or organic acid addition salt. A more preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter ion. Examples of suitable counter ions include the conjugate bases of the protic acids discussed above in relation to acid-addition salts.

The compounds of the present invention can also be used both, in their free acid form and their salt form. For the purposes of this invention, a "salt" of a compound of the present invention includes one formed between a protic acid functionality (such as a carboxylic acid group or a urea group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulphate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant ($p \geq 0.05$) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481:278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8:15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3: 1-10; Inoue et al., Immunology 139: 11-18, Coll et al. Nat. Med. 2015 21(3):248-55; and Scott et al. Clin. Exp. Rheumatol 2016 34(1): 88-93), systemic lupus erythematosus (Lu et al. J Immunol. 2017 198(3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017 196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (Mridha et al. J Hepatol. 2017 66(5): 1037-46). A role for NLRP3 via IL-1β has also been suggested in atherosclerosis, myocardial infarction (van Hout et al. Eur. Heart J. 2017 38(11): 828-36), heart failure (Sano et al. JAM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al., N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012 149 (4): 847-59), diabetic retinopathy (Loukovaara et al. Acta Ophthalmol. 2017; 95(8): 803-808) and optic nerve damage (Puyang et al. Sci Rep. 2016 Feb. 19; 6:20998); liver diseases including non-alcoholic steatohepatitis (NASH) (Henao-Meija et al., Nature, 482: 179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 134(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014); chronic kidney disease (Granata et al. PLoS One 2015 10(3): e0122272); and inflammatory bowel diseases including ulcerative colitis and Crohn's disease (Braddock et al., Nat. Rev. Drug Disc., 3: 1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166: 1-15, 2011; and Masters Clin. Immunol. 2013). For example, several previous studies have suggested a role for IL-1β in cancer invasiveness, growth and metastasis, and inhibition of IL-1β with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1β has also been shown to inhibit the proliferation and migration of lung cancer cells in vitro (Wang et al. Oncol Rep. 2016; 35(4): 2053-64). A role for the NLRP3 inflammasome has been suggested in myelodysplastic syndromes (Basiorka et al. Blood. 2016 Dec. 22; 128(25):2960-2975) and also in the carcinogenesis of various other cancers including glioma (Li et al. Am J Cancer Res. 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3):

144-51), and squamous cell carcinoma of the head and neck (Huang et al. J Exp Clin Cancer Res. 2017 2; 36(1): 116). Activation of the NLRP3 inflammasome has also been shown to mediate chemoresistance of tumour cells to 5-Fluorouracil (Feng et al. J Exp Clin Cancer Res. 2017 21; 36(1): 81), and activation of NLRP3 inflammasome in peripheral nerve contributes to chemotherapy-induced neuropathic pain (Jia et al. Mol Pain. 2017; 13: 1-11).

NLRP3 has also been shown to be required for the efficient control of viral, bacterial, fungal, and helminth pathogen infections (Strowig et al., Nature, 481:278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:

(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;

(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behçet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia;

(iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;

(iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicellazoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or *Trypanosomes*), helminth infections (e.g. from *schistosoma*, roundworms, tapeworms or flukes) and prion infections;

(v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;

(vi) metabolic diseases such as type 2 diabetes (T2D), atherosclerosis, obesity, gout, and pseudo-gout;

(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;

(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;

(ix) liver diseases including non-alcoholic fatty liver disease (NAFLD) and non-alcoholic steatohepatitis (NASH) including advanced fibrosis stages F3 and F4, alcoholic fatty liver disease (AFLD), and alcoholic steatohepatitis (ASH);

(x) renal diseases including chronic kidney disease, oxalate nephropathy, nephrocalcinosis, glomerulonephritis, and diabetic nephropathy;

(xi) ocular diseases including those of the ocular epithelium, age-related macular degeneration (AMD) (dry and wet), uveitis, corneal infection, diabetic retinopathy, optic nerve damage, dry eye, and glaucoma;

(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;

(xiii) lymphatic conditions such as lymphangitis and Castleman's disease; (xiv) psychological disorders such as depression and psychological stress;

(xv) graft versus host disease;

(xvi) allodynia including mechanical allodynia; and (xvii) any disease where an individual has been determined to carry a germline or somatic non-silent mutation in NLRP3.

In one embodiment, the disease, disorder or condition is selected from:
(i) cancer;
(ii) an infection;
(iii) a central nervous system disease;
(iv) a cardiovascular disease;
(v) a liver disease;
(vi) an ocular diseases; or
(vii) a skin disease.

More typically, the disease, disorder or condition is selected from:
(i) cancer;
(ii) an infection;
(iii) a central nervous system disease; or
(iv) a cardiovascular disease.

In another embodiment, the disease, disorder or condition is selected from:
(i) an auto-immune disease;
(ii) a central nervous system disease;
(iii) a cardiovascular disease;
(iv) a respiratory disease;
(v) a renal disease;
(vi) an ocular disease;
(vii) a skin disease;
(viii) a lymphatic condition;
(ix) a psychological disorder;
(x) graft versus host disease;
(xi) allodynia; and
(xii) any disease where an individual has been determined to carry a germline or somatic non-silent mutation in NLRP3.

Typically in the embodiment immediately above, $R^1$ is a 6-membered heteroaryl group containing at least two nitrogen atoms in the 6-membered ring structure, wherein $R^1$ may optionally be substituted.

In a further embodiment, the disease, disorder or condition is selected from:
(i) an auto-immune disease;
(ii) cancer;
(iii) a central nervous system disease;
(iv) a respiratory disease;
(v) an ocular disease;
(vi) a lymphatic condition;
(vii) a psychological disorder;
(viii) graft versus host disease;
(ix) allodynia; and
(x) any disease where an individual has been determined to carry a germline or somatic non-silent mutation in NLRP3.

Typically in the embodiment immediately above, the 6-membered heteroaryl group of $R^1$ is substituted with at least one monovalent group X, wherein X is at each occurrence any group that can mesomerically donate a lone pair of electrons from a nitrogen, oxygen or sulphur atom onto at least one nitrogen atom in the 6-membered ring structure, and wherein the 6-membered heteroaryl group may optionally be further substituted.

More typically in the embodiment immediately above:
the 6-membered heteroaryl group of $R^1$ is substituted with at least one monovalent group X' at a position ortho- or para- to at least one nitrogen atom in the 6-membered ring structure;
the 6-membered heteroaryl group of $R^1$ may optionally be further substituted;
X' is at each occurrence independently selected from a $-OR^3$, $-SR^3$, $-N(R^3)_2$, $-O-L-OR^3$, $-O-L-SR^3$, $-O-L-N(R^3)_2$, $-S-L-OR^3$, $-S-L-SR^3$, $-S-L-N(R^3)_2$, $-NR^3-L-OR^3$, $-NR^3-L-SR^3$ or $-NR^3-L-N(R^3)_2$ group;
each $R^3$ is independently selected from hydrogen or an alkyl, alkenyl, alkynyl or cyclic group, or any two $R^3$ in the same group X' may together with the atom or atoms to which they are attached form a heterocyclic group;
each L is independently selected from an alkylene, alkenylene or alkynylene group; and
any L or $R^3$ may optionally be substituted.

In yet another embodiment, the disease, disorder or condition is selected from:
(i) a liver disease;
(ii) graft versus host disease; and
(iii) any disease where an individual has been determined to carry a germline or somatic non-silent mutation in NLRP3.

Typically in the embodiment immediately above, at least one nitrogen atom is located at the 4-position of the 6-membered ring structure of $R^1$.

In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);
(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;
(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;

(xxix) systemic juvenile idiopathic arthritis;
(xxx) systemic lupus erythematosus;
(xxxi) traumatic brain injury;
(xxxii) transient ischemic attack; and
(xxxiii) ulcerative colitis.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:

(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(ii) a joint condition such as osteoarthritis, systemic juvenile idiopathic arthritis, adult-onset Still's disease, relapsing polychondritis, rheumatoid arthritis, osteoarthritis, juvenile chronic arthritis, gout, or a seronegative spondyloarthropathy (e.g. ankylosing spondylitis, psoriatic arthritis or Reiter's disease);

(iii) a muscular condition such as polymyositis or myasthenia gravis;

(iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(vi) a vascular condition such as atherosclerosis, Behcet's disease, vasculitides, or wegener's granulomatosis;

(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;

(viii) an ocular condition such as uveitis, allergic conjunctivitis, or vernal conjunctivitis;

(ix) a nervous condition such as multiple sclerosis or encephalomyelitis;

(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *legionella*, Lyme disease, influenza A, epstein-barr virus, viral encephalitis/aseptic meningitis, or pelvic inflammatory disease;

(xi) a renal condition such as mesangial proliferative glomerulonephritis, nephrotic syndrome, nephritis, glomerular nephritis, acute renal failure, uremia, or nephritic syndrome;

(xii) a lymphatic condition such as Castleman's disease;

(xiii) a condition of, or involving, the immune system, such as hyper IgE syndrome, lepromatous leprosy, familial hemophagocytic lymphohistiocytosis, or graft versus host disease;

(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(xv) a cancer, including those cancers listed above;

(xvi) a burn, wound, trauma, haemorrhage or stroke;

(xvii) radiation exposure;

(xviii) obesity; and/or (xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3.

In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically, the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically, such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically, the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
 (i) chemotherapeutic agents;
 (ii) antibodies;
 (iii) alkylating agents;
 (iv) anti-metabolites;
 (v) anti-angiogenic agents;
 (vi) plant alkaloids and/or terpenoids;
 (vii) topoisomerase inhibitors;
 (viii) mTOR inhibitors;
 (ix) stilbenoids;
 (x) STING agonists;
 (xi) cancer vaccines;
 (xii) immunomodulatory agents;
 (xiii) antibiotics;
 (xiv) anti-fungal agents;
 (xv) anti-helminthic agents; and/or
 (xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPR109881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulphonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulphate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositumomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulphydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a vinca alkaloid, a podophyllotoxin and/or a taxane. In some embodiments, the one or more vinca alkaloids may be derived from the Madagascar periwinkle, *Catharanthus roseus* (formerly known as *Vinca rosea*), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'—O linkage, phosphorothioate linkage, adenine and/or guanine analogue, and/or 2'-OH modification (e.g. protection of the 2'-OH with a methyl group or replacement of the 2'-OH by —F or —$N_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAGS), MHC class I, MHC class II, 4-1BB, 4-1BBL, OX40, OX40L, GITR, GITRL, CD27, CD70, TNFRSF25, TLIA, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30, CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDR001 (PD1), BMS-986016, MGA271, lirilumab, IPH2201, emactuzumab, INCB024360, galunisertib, ulocuplumab, BKT140, bavituximab, CC-90002, bevacizumab, and/or MNR131685 A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal or topical (including transdermal, buccal, mucosal and sublingual) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For transdermal and other topical administration, the compounds, salts, solvates or prodrugs of the invention will generally be provided in the form of ointments, cataplasms (poultices), pastes, powders, dressings, creams, plasters or patches.

Suitable suspensions and solutions can be used in inhalers for airway (aerosol) administration.

The dose of the compounds, salts, solvates or prodrugs of the present invention will, of course, vary with the disorder, disease or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

EXAMPLES-COMPOUND SYNTHESIS

All solvents, reagents and compounds were purchased and used without further purification unless stated otherwise.

Abbreviations

2-MeTHF 2-methyltetrahydrofuran
$Ac_2O$ acetic anhydride
AcOH acetic acid
aq aqueous
Boc tert-butyloxycarbonyl
br broad
Cbz carboxybenzyl
CDI 1,1-carbonyl-diimidazole
conc concentrated
d doublet
DABCO 1,4-diazabicyclo[2.2.2]octane
DCE 1,2-dichloroethane, also called ethylene dichloride
DCM dichloromethane
DIPEA N,N-diisopropylethylamine, also called Hünig's base
DMAP 4-dimethylaminopyridine, also called N,N-dimethylpyridin-4-amine
DME dimethoxyethane
DMF N,N-dimethylformamide
DMSO dimethyl sulfoxide
(ES+) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)+ protonated molecular ion
MHz megahertz
min minute(s)
MS mass spectrometry
Ms mesyl, also called methanesulfonyl
MSCl mesyl chloride, also called methanesulfonyl chloride
MTBE methyl tert-butyl ether, also called tert-butyl methyl ether
m/z mass-to-charge ratio
NaOtBu sodium tert-butoxide
NBS 1-bromopyrrolidine-2,5-dione, also called N-bromosuccinimide
NCS 1-chloropyrrolidine-2,5-dione, also called N-chlorosuccinimide
$Ni(dppp)Cl_2$ [1,3-bis(diphenylphosphino)propane]nickel(II) chloride
NMP N-methylpyrrolidine
NMR nuclear magnetic resonance (spectroscopy)
$Pd(dba)_3$ tris(dibenzylideneacetone) dipalladium(o)
$Pd(dppf)Cl_2$ [1,1'-bis(diphenylphosphino)ferrocene]dichloropalladium(II)
PE petroleum ether
Ph phenyl
PMB p-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
Sept septuplet
sat saturated
SCX solid supported cation exchange (resin)
t triplet
T3P propylphosphonic anhydride
TBME tert-butyl methyl ether, also called methyl tert-butyl ether
TEA triethylamine
TFA 2,2,2-trifluoroacetic acid
THF tetrahydrofuran
TLC thin layer chromatography
wt % weight percent or percent by weight
Xantphos 4,5-bis(diphenylphosphino)-9,9-dimethylxanthene Analytical Methods NMR spectra were recorded at 300 MHz (unless stated otherwise) with chemical shifts reported in parts per million. Spectra were collected using one of the three machines below:
- an Agilent VNMRS 300 instrument fitted with a 7.05 Tesla magnet from Oxford instruments, indirect detection probe and direct drive console including PFG module.
- An Agilent MercuryPlus 300 instrument fitted with a 7.05 Tesla magnet from Oxford instruments, 4 nuclei auto-switchable probe and Mercury plus console.
- A Bruker 400 MHz spectrometer using ICON-NMR, under TopSpin program control.

Spectra were measured at 298K, unless indicated otherwise, and were referenced relative to the solvent resonance.

HPLC and LC-MS were recorded on an Agilent 1290 series with UV detector and HP 6130 MSD mass detector. Mobile phase A: ammonium acetate (10 mM); water/MeOH/acetonitrile (900:60:40); mobile phase B: ammonium acetate (10 mM); water/MeOH/acetonitrile (100:540:360); column, Waters XBridge BEH C18 XP (2.1×50 mm, 2.5 µM)

| | |
|---|---|
| Pump flow: 0.6 mL/min | UV detection: 215, 238 nm |
| Injection volume: 0.2 µL | Run time: 4.0 min |
| Column temperature: 35° C. | Mass detection: API-ES +ve and −ve |

Pump Program:

| Gradient Time (min) | % A | % B |
|---|---|---|
| 0.0 | 80 | 20 |
| 0.5 | 80 | 20 |
| 2.0 | 0 | 100 |

Preparative Reversed Phase HPLC General Methods
Purification Method 1

Automated reversed phase column chromatography was carried out using a Buchi Sepracore® X50 system driven by a C-605 pump module, C-620 Sepracore control package, C-640 UV photometer detection unit and C-660 fraction collector.

Revelis C18 Reversed-Phase 12 g Cartridge

| | |
|---|---|
| Carbon loading | 18% |
| Surface area | 568 m²/g |
| Pore diameter | 65 Angstrom |
| pH (5% slurry) | 5.1 |
| Average particle size | 40 µm |

Column was conditioned before use with MeOH (5 min) then brought to H$_2$O (in 5 min) and kept 5 min at H$_2$O. Flow rate=30 mL/min.
Separation Runs:

| Time (min) | A: water (%) | B: MeOH (%) |
|---|---|---|
| 0 | 100 | 0 |
| 5 | 100 | 0 |
| 30 | 30 | 70 |
| 30.1 | 0 | 100 |
| 35 | 0 | 100 |

Detection wavelength: 215, 235, 254 and 280 nm. Before each new run, the cartridge was cleaned using the conditioning method.

Acidic prep: Waters X-Select CSH column C18, 5 µm (19×50 mm), flow rate 28 mL min$^{-1}$ eluting with a H$_2$O—MeCN gradient containing 0.1% v/v formic acid over 6.5 min using UV detection at 254 nm. Gradient information: 0.0-0.2 min, 20% MeCN; 0.2-5.5 min, ramped from 20% MeCN to 40% MeCN; 5.5-5.6 min, ramped from 40% MeCN to 95% MeCN; 5.6-6.5 min, held at 95% MeCN.

Basic prep: Waters X-Bridge Prep column C18, 5 µm (19×50 mm), flow rate 28 mL min$^{-1}$ eluting with a 10 mM NH$_4$HCO$_3$-MeCN gradient over 6.5 min using UV detection at 254 nm. Gradient information: 0.0-0.2 min, 10% MeCN; 0.2-5.5 min, ramped from 10% MeCN to 40% MeCN; 5.5-5.6 min, ramped from 40% MeCN to 95% MeCN; 5.6-6.5 min, held at 95% MeCN.

SYNTHESIS OF INTERMEDIATES

Intermediate A1:
4-Isocyanato-1,2,3,5,6,7-hexahydro-s-indacene

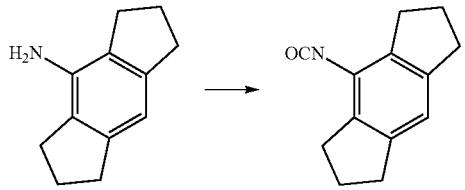

To a solution of phosgene (4.45 mL, 20% weight in toluene, 8.4 mmol) in ethyl acetate (90 mL) was added drop-wise a solution of 1,2,3,5,6,7-hexahydro-s-indacen-4-amine (589 mg, 3.4 mmol) in ethyl acetate (45 mL) at ambient temperature. The resulting reaction mixture was then heated to reflux for 3 hours and upon cooling was filtered and concentrated in vacua to afford the title compound as a brown oil (756 mg, 100% yield). The crude product was used directly in the next step without further purification.

$^1$H NMR (CDCl$_3$): δ 6.8 (s, 1H), 2.89 (m, 8H) and 2.09 (m, 4H).

Intermediate A2:
2-Isocyanato-1,3-diisopropylbenzene

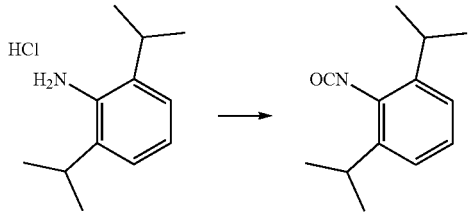

To a suspension of 2,6-diisopropylaniline hydrochloride (1 g, 4.7 mmol) in toluene (50 mL) was added 1 drop of pyridine and the resulting mixture was heated to near reflux whilst a solution of phosgene (7.3 mL, 20% wt in toluene, 13.8 mmol) was added drop-wise over a period of 10 minutes. The mixture was stirred for an additional 45 minutes at 105° C. and then allowed to partially cool before being concentrated in vacua to afford the title compound as a mobile yellow oil (1.5 g, >100% yield). The crude product was used directly in the next step without further purification.

¹H NMR (CDCl₃): δ 7.2 (m, 3H), 3.12 (m, 2H) and 1.25 (d, 12H).

Intermediate A3: 4-(5-Fluoro-2-isocyanato-3-isopropylphenyl)picolinonitrile

Step A: 4-Fluoro-2-(prop-1-en-2-yl)aniline

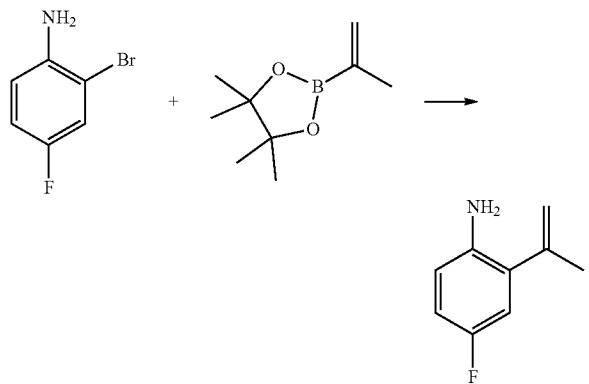

To a mixture of 2-bromo-4-fluoroaniline (39 g, 205.25 mmol, 1 eq), 4,4,5,5-tetramethyl-2-(prop-1-en-2-yl)-1,3,2-dioxaborolane (36.21 g, 215.51 mmol, 1.05 eq) and K₂CO₃ (70.92 g, 513.12 mmol, 2.5 eq) in dioxane (200 mL) and H₂O (40 mL) was added Pd(dppf)Cl₂ (7.51 g, 10.26 mmol, 0.05 eq) under N₂ atmosphere. Then the reaction mixture was stirred at 80° C. for 5 hours. The reaction mixture was quenched by addition of H₂O (boo mL) and extracted with EtOAc (2×500 mL). The combined organic layers were washed with brine (2×600 mL), dried over anhydrous Na₂SO₄, filtered and concentrated under reduced pressure. The residue was purified by silica gel column chromatography (SiO₂, petroleum ether: ethyl acetate, 1:0 to 100:1) to give the title compound (27 g, 77% yield, 89% purity on LCMS) as a yellow oil.

¹H NMR (CDCl₃): δ 6.81-6.76 (m, 2H), 6.66-6.62 (m, 1H), 5.38 (s, 1H), 5.08 (s, 1H), 3.69 (br s, 2H) and 1.25 (s, 3H).

LCMS: m/z 152.2 (M+H)⁺(ES⁺).

Step B: 4-Fluoro-2-isopropylaniline

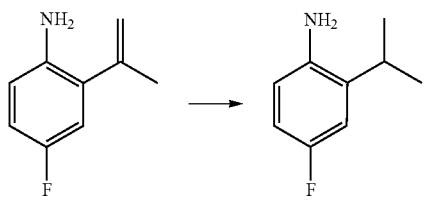

To a solution of 4-fluoro-2-(prop-1-en-2-yl)aniline (21 g, 138.91 mmol, 1 eq) in MeOH (300 mL) was added Pd/C (2.1 g, 178.59 mmol, 10 wt % loading on activated carbon) under N₂ atmosphere. The reaction mixture was degassed in vacua and purged with H2 several times. The reaction mixture was stirred at 25° C. for 12 hours under H2 (so psi). The reaction mixture was filtered and the filtrate was concentrated in vacua to give the title compound (20 g, crude) as a yellow oil.

¹H NMR (CDCl₃): δ 6.86 (dd, 1H), 6.75-6.72 (m, 1H), 6.63-6.61 (m, 1H), 3.50 (br s, 2H), 2.95-2.84 (m, 1H) and 1.25 (d, 6H).

LCMS: m/z 154.2 (M+H)⁺(ES⁺).

Step C: 2-Bromo-4-fluoro-6-isopropylaniline

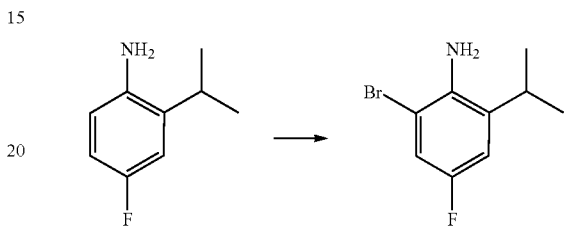

To a solution of 4-fluoro-2-isopropylaniline (20 g, 130.55 mmol, 1 eq) in toluene (250 mL) was added NBS (23.24 g, 130.55 mmol, 1 eq) at 25° C. The reaction mixture was stirred at 25° C. for 10 minutes. The reaction mixture was poured into H₂O (300 mL) and extracted with EtOAc (2×250 mL). The combined organic phases were washed with brine (2×400 mL), dried over anhydrous Na₂SO₄, filtered and concentrated in vacua. The residue was purified by silica gel column chromatography (SiO₂, eluting only by using petroleum ether) to give the title compound (30 g, 99%) as a black brown oil.

¹H NMR (CDCl₃): δ 6.99 (dd, 1H), 6.78 (dd, 1H), 3.91 (br s, 2H), 2.88-2.71 (m, 1H) and 1.17 (d, 6H).

LCMS: m/z 232.1 (M+H)⁺(ES⁺).

Step D: 4-(2-Amino-5-fluoro-3-isopropylphenyl)picolinonitrile

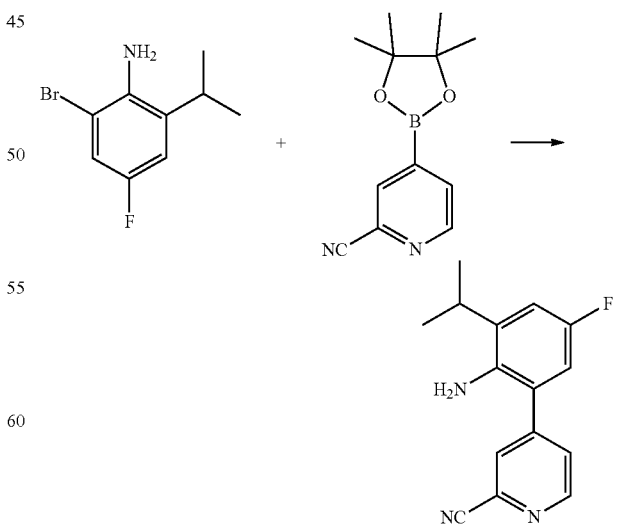

To a solution of 2-bromo-4-fluoro-6-isopropylaniline (3.6 g, 15.51 mmol, 1 eq) and 4-(4,4,5,5-tetramethyl-1,3,2-dioxaborolan-2-yl)picolinonitrile (3.60 g, 15.67 mmol, 1.01 eq) in dioxane (90 mL) and H₂O (9 mL) was added Na₂CO₃ (4.11 g, 38.78 mmol, 2.5 eq). Then Pd(dppf)Cl₂ (1.13 g, 1.55 mmol, 0.1 eq) was added to the mixture under N₂ atmosphere. The resulting mixture was stirred at 80° C. for 2 hours under N₂ atmosphere. The mixture was concentrated in vacua. The residue was purified by silica gel column chromatography (SiO₂, petroleum ether:ethyl acetate, 20:1 to 5:1) and then triturated with petroleum ether (10 mL) to give the title compound (2.65 g, 65% yield, 97% purity on LCMS) as a yellow solid.

¹H NMR (CDCl₃): δ 8.79 (d, 1H), 7.86 (d, 1H), 7.65 (dd, 1H), 6.99 (dd, 1H), 6.70 (dd, 1H), 3.63 (br s, 2H), 2.98-2.87 (m, 1H) and 1.30 (d, 6H).

LCMS: m/z 256.2 (M+H)⁺(ES⁺).

Step E: 4-(5-Fluoro-2-isocyanato-3-isopropylphenyl)picolinonitrile

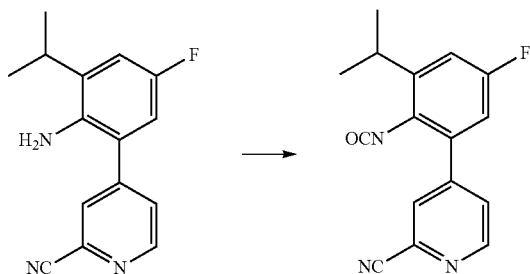

To a solution of 4-(2-amino-5-fluoro-3-isopropylphenyl)picolinonitrile (1 g, 3.92 mmol, 1 eq) in THF (40 mL) was added TEA (793 mg, 7.83 mmol, 2 eq). Then triphosgene (465 mg, 1.57 mmol, 0.4 eq) was added in portions at 5° C. The mixture was stirred at 70° C. for 1 hour. The mixture was diluted with EtOAc (200 mL) and then filtered through silica gel. The filtrate was concentrated in vacuo to give the title compound (1.2 g, crude) as a yellow solid, which was used directly in the next step.

Intermediate A4: 4-(5-Fluoro-2-isocyanato-3-isopropylphenyl)-2-methoxypyridine

Step A: 4-Fluoro-2-isopropyl-6-(2-methoxypyridin-4-yl)aniline

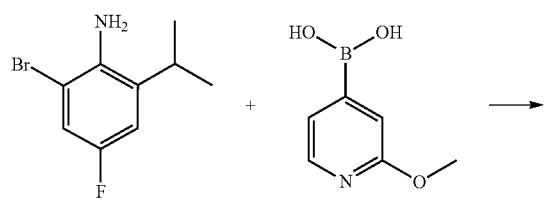

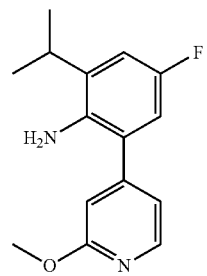

To a solution of 2-bromo-4-fluoro-6-isopropylaniline (12 g, 51.70 mmol, 1 eq) in dioxane (240 mL) and H₂O (48 mL) was added (2-methoxypyridin-4-yl)boronic acid (9.49 g, 62.04 mmol, 1.2 eq) and Na₂CO₃ (13.70 g, 129.26 mmol, 2.5 eq). The reaction mixture was purged with N₂ three times. Then Pd(dppf)C12 (3.78 g, 5.17 mmol, 0.1 eq) was added to the mixture under N₂ atmosphere. The resulting mixture was heated at 80° C. for 2 hours. The reaction mixture was quenched with H₂O (800 mL) and extracted with EtOAc (2×600 mL). The combined organic layers were washed with brine (2×800 mL), dried over anhydrous Na₂SO₄, filtered and concentrated under reduced pressure. The residue was purified by silica gel column chromatography (SiO₂, petroleum ether:ethyl acetate, 70:1 to 10:1) and then triturated with hexane (100 mL) to give the title compound (10.05 g, 72% yield, 96% purity on LCMS).

¹H NMR (CDCl₃): δ 8.24 (d, 1H), 6.97 (d, 1H), 6.93 (d, 1H), 6.83 (s, 1H), 6.73-6.70 (m, 1H), 3.99 (s, 3H), 3.66 (br s, 2H), 2.97-2.89 (m, 1H), 1.29 (dd, 6H).

LCMS: m/z 261.1 (M+H)⁺(ES⁺).

Step B: 4-(5-Fluoro-2-isocyanato-3-isopropylphenyl)-2-methoxypyridine

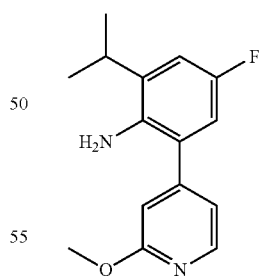

To a solution of 4-fluoro-2-isopropyl-6-(2-methoxypyridin-4-yl)aniline (1 g, 3.84 mmol, 1 eq) in THF (40 mL) was added TEA (777 mg, 7.68 mmol, 2 eq). Then triphosgene (456 mg, 1.54 mmol, 0.4 eq) was added in portions at 5° C. The mixture was stirred at 70° C. for 1 hour. The mixture was diluted with EtOAc (200 mL) and filtered through silica gel. The filtrate was concentrated in vacua to give the title compound (1.1 g, crude) as yellow oil, which was used directly in the next step.

Intermediate A5: 4-(4-Isocyanato-2,3-dihydro-1H-inden-5-yl)-2-methoxypyridine

Step A: 4-Nitro-2,3-dihydro-1H-indene

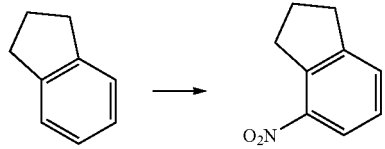 [SMILES: c1ccc2c(c1)CCC2 ; O=[N+]([O-])c1cccc2c1CCC2]

To a mixture of 2,3-dihydro-1H-indene (60 g, 57.72 mmol, 62.50 mL, 1 eq) in concentrated $H_2SO_4$ (30 mL) was added a mixture of $HNO_3$ (50 mL, 69 wt % in water) and concentrated $H_2SO_4$ (50 mL) dropwise at 0° C. over a period of 3.5 hours. The reaction mixture was stirred at 0° C. for 0.5 hour. Then the reaction mixture was poured into ice water (600 mL) and extracted with ethyl acetate (2×400 mL). The combined organic layers were washed with water (500 mL), saturated aqueous $NaHCO_3$ solution (500 mL) and brine (2×500 mL). The organic layer was dried over anhydrous $Na_2SO_4$, filtered and concentrated in vacua. The residue was purified by silica gel column chromatography ($SiO_2$, petroleum ether:ethyl acetate, 1:0 to 100:1) to give the title compound (55 g, 66%) as a colourless oil.

$^1$H NMR ($CDCl_3$): δ 7.98 (d, 1H), 7.51 (d, 1H), 7.30 (t, 1H), 3.41 (t, 2H), 302 (t, 2H) and 2.22-2.20 (m, 2H).

Step B: 2,3-Dihydro-1H-inden-4-amine

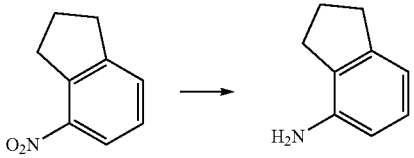 [SMILES: O=[N+]([O-])c1cccc2c1CCC2 ; Nc1cccc2c1CCC2]

To a solution of 4-nitro-2,3-dihydro-1H-indene (55 g, contained another regio-isomer) in MeOH (500 mL) was added Pd/C (5 g, 10 wt % loading on activated carbon) under $N_2$ atmosphere. The suspension was degassed under vacuum and purged with $H_2$ several times. The reaction mixture was stirred under $H_2$ (50 psi) at 20° C. for 12 hours. The reaction mixture was filtered and the filtrate was concentrated in vacua. The residue was purified by silica gel column chromatography ($SiO_2$, petroleum ether:ethyl acetate, 1:0 to 100:4) to give the title compound (19.82 g, 43% yield, 96.39% purity on LCMS) as a brown oil.

$^1$H NMR ($CDCl_3$): δ 7.01 (t, 1H), 6.71 (d, 1H), 6.51 (d, 1H), 3.57 (br s, 2H), 2.93 (t, 2H), 2.75 (t, 2H) and 2.16-2.08 (m, 2H).

LCMS: m/z 134.2 $(M+H)^+(ES^+)$.

Step C: N-(2,3-Dihydro-1H-inden-4-yl)acetamide

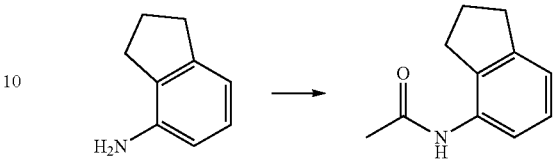

To a solution of 2,3-dihydro-1H-inden-4-amine (19.8 g, 148.66 mmol, 1 eq) and TEA (19.56 g, 193.26 mmol, 1.3 eq) in DCM (300 mL) was added dropwise $Ac_2O$ (17.45 g, 170.96 mmol, 1.15 eq) over 6 minutes at 0° C. Then the reaction mixture was warmed to 16° C. and stirred for 1.4 hours. The mixture was poured into water (500 mL) and extracted with DCM (2×300 mL). The combined organic phases were washed with brine (2×500 mL), dried over anhydrous $Na_2SO_4$, filtered and concentrated in vacua to give the title compound (25.74 g, 96% yield, 96.69% purity on LCMS) as a white solid.

$^1$H NMR ($CDCl_3$): δ 7.70 (d, 1H), 7.15 (t, 1H), 7.02 (d, 1H), 2.95 (t, 2H), 2.81 (t, 2H), 2.18 (s, 3H) and 2.15-2.08 (m, 2H).

LCMS: m/z 176.2 $(M+H)^+(ES^+)$

Step D: N-(5-Bromo-2,3-dihydro-1H-inden-4-yl)acetamide

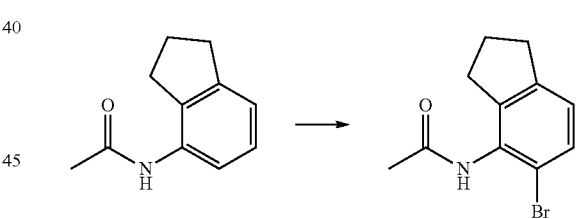

N-(2,3-dihydro-1H-inden-4-yl)acetamide (34.6 g, 197.46 mmol, 1 eq), p-toluenesulfonic acid (18.70 g, 108.60 mmol, 0.55 eq) and $Pd(OAc)_2$ (2.22 g, 9.87 mmol, 0.05 eq) were suspended in toluene (400 mL) and stirred at 20° C. for 0.5 hour under air atmosphere. NBS (38.66 g, 217.20 mmol, 1.1 eq) was added. Then the reaction mixture was stirred at 20° C. for 2 hours. The reaction mixture was poured into water (500 mL) and extracted with ethyl acetate (2×500 mL). The combined organic phases were washed with brine (2×500 mL), dried over anhydrous $Na_2SO_4$, filtered and concentrated in vacua. The residue was purified by silica gel column chromatography ($SiO_2$, petroleum ether:ethyl acetate, 10:1 to 2:1) to give the title compound (13.9 g, 27% yield, 98.1% purity on LCMS) as a white solid.

$^1$H NMR ($CDCl_3$): δ 7.33 (d, 1H), 7.16 (s, 1H), 6.98 (d, 1H), 2.92-2.83 (m, 4H), 2.21 (s, 3H) and 2.10-2.02 (m, 2H).

LCMS: m/z 254.1 $(M+H)^+(ES^+)$.

Step E: 5-Bromo-2,3-dihydro-1H-inden-4-amine

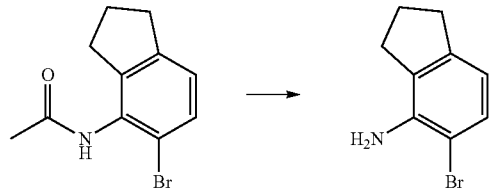

A mixture of N-(5-bromo-2,3-dihydro-1H-inden-4-yl)acetamide (45.68 g, 179.76 mmol, 1 eq) in EtOH (200 mL) and concentrated HCl (300 mL, 36 wt % in water) was stirred at 80° C. for 36 hours. The reaction mixture was cooled to 0° C. in an ice bath and some solid precipitated. The suspension was filtered. The filter cake was washed with ice water (50 mL) and dried in vacua to give the title compound (34.1 g, 72% yield, 94.08% purity on LCMS, HCl salt) as a grey solid.

$^1$H NMR (DMSO-$d_6$): δ 7.67 (br s, 2H), 7.24 (d, 1H), 6.69 (d, 1H), 2.85 (t, 2H), 2.79 (t, 2H) and 2.04-1.96 (m, 2H).

LCMS: m/z 212.0 (M+H)$^+$(ES$^+$).

Step F: 5-(2-Methoxypyridin-4-yl)-2,3-dihydro-1H-inden-4-amine

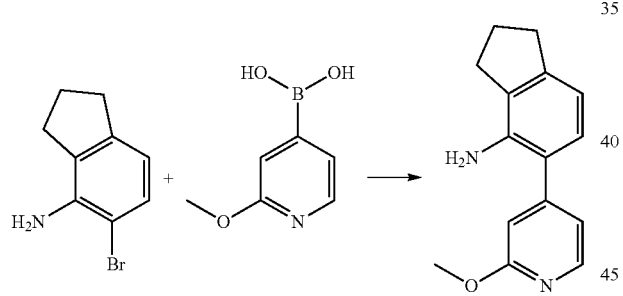

A solution of (2-methoxypyridin-4-yl)boronic acid (25.11 g, 164.15 mmol, 1.2 eq), 5-bromo-2,3-dihydro-1H-inden-4-amine (34 g, 136.80 mmol, 1 eq, HCl salt) and $K_2CO_3$ (60.50 g, 437.74 mmol, 3.2 eq) in dioxane (500 mL) and $H_2O$ (100 mL) was degassed with nitrogen for 15 minutes before Pd(dppf)$Cl_2$·$CH_2Cl_2$ (6 g, 7.35 mmol, 0.053 eq) was added. The reaction mixture was heated to 80° C. for 12 hours. The mixture was poured into water (500 mL) and extracted with ethyl acetate (2×500 mL). The combined organic phases were washed with brine (2×700 mL), dried over anhydrous $Na_2SO_4$, filtered and concentrated in vacua. The residue was purified by silica gel column chromatography (SiO$_2$, petroleum ether:ethyl acetate, 1:0 to 10:1) to give the title compound (27.4 g, 79% yield, 95% purity on LCMS) as a white solid.

$^1$H NMR (CDCl$_3$): δ 8.22 (d, 1H), 7.03-7.00 (m, 1H), 6.99 (d, 1H), 6.87 (s, 1H), 6.77 (d, 1H), 3.99 (s, 3H), 3.77 (br s, 2H), 2.97 (t, 2H), 2.77 (t, 2H) and 2.21-2.13 (m, 2H).

LCMS: m/z 241.2 (M+H)$^+$(ES$^+$).

Step G: 4-(4-Isocyanato-2,3-dihydro-1H-inden-5-yl)-2-methoxypyridine

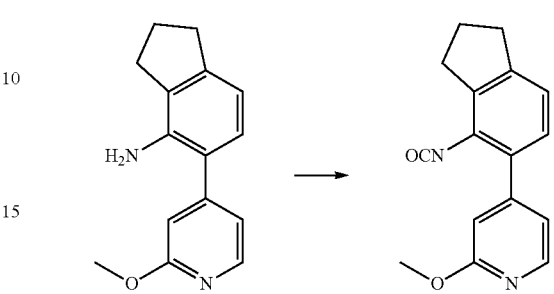

To a solution of 5-(2-methoxypyridin-4-yl)-2,3-dihydro-1H-inden-4-amine (ii g, 45.78 mmol, 1 eq) and TEA (5.10 g, 50.35 mmol, 1.1 eq) in THF (275 mL) was added bis(trichloromethyl) carbonate (4.93 g, 16.61 mmol, 0.36 eq) in portions at 0° C. Then the reaction mixture was stirred at 16° C. for 0.5 hour. The reaction mixture was filtered and the filter cake was washed with THF (2 L). The filtrate was concentrated in vacuo to give the title compound (9.04 g, 74%) as a light yellow solid.

$^1$H NMR (CDCl$_3$): δ 8.28 (d, 1H), 7.20-7.16 (m, 3H), 7.02 (s, 1H), 4.16 (s, 3H), 3.04-2.99 (m, 4H) and 2.23-2.15 (m, 2H).

Intermediate A6: 4-(7-Fluoro-4-isocyanato-2,3-dihydro-1H-inden-5-yl)pyridine

Step A: 7-Fluoro-4-nitro-2,3-dihydro-1H-inden-1-one

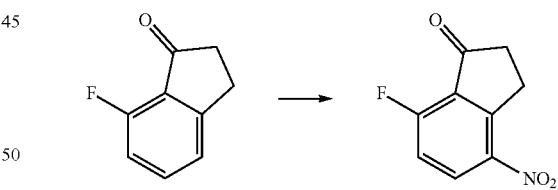

To a mixture of 7-fluoro-2,3-dihydro-1H-inden-1-one (9.5 g, 63.27 mmol, 1 eq) in concentrated $H_2SO_4$ (100 mL) was added dropwise a solution of HNO$_3$ (5.37 mL, 82.25 mmol, 69 wt % in water, 1.3 eq) in concentrated $H_2SO_4$ (20 mL) at −15° C. Then the reaction mixture was stirred at 0° C. for 0.5 hour. The mixture was quenched with water (500 mL) at 0° C., and then extracted with EtOAc (3×300 mL). The combined organic phases were dried over anhydrous Na$_2$SO$_4$, filtered and concentrated in vacuo. The residue was purified by silica gel column chromatography (SiO$_2$, petroleum ether:ethyl acetate, 10:1 to 3:1) to give the title compound (11.4 g, 92%) as a yellow solid.

$^1$H NMR (CDCl$_3$): δ 8.51 (dd, 1H), 7.22 (t, 1H), 3.69-3.65 (m, 2H) and 2.88-2.82 (m, 2H).

Step B: 7-Fluoro-4-nitro-2,3-dihydro-1H-inden-1-ol

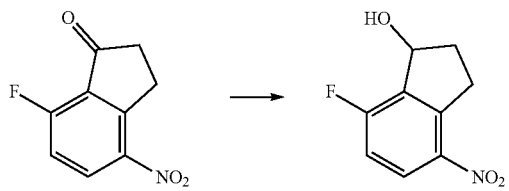 [SMILES: O=C1CCc2c([N+](=O)[O-])ccc(F)c21 ; O=[N+]([O-])c1ccc(F)c2c1CCC2O]

To a mixture of 7-fluoro-4-nitro-2,3-dihydro-1H-inden-1-one (30 g, 153.73 mmol, 1 eq) in EtOH (450 mL) was added NaBH$_4$ (11.63 g, 307.46 mmol, 2 eq) in portions. Then the reaction mixture was stirred at 15° C. for 1 hour. The mixture was poured into the water (500 mL) and extracted with DCM (2×200 mL). The combined organic phases were washed with brine (200 mL), dried over anhydrous Na$_2$SO$_4$, filtered and concentrated in vacua to give the title compound (30 g, crude) as brown oil.

$^1$H NMR (CDCl$_3$): δ 8.21 (dd, 1H), 7.08 (t, 1H), 5.59-5.56 (m, 1H), 3.66-3.59 (m, 1H), 3.44-3.39 (m, 1H), 2.56-2.51 (m, 1H) and 2.22-2.17 (m, 2H).

Step C: 4-Fluoro-7-nitro-2,3-dihydro-1H-indene

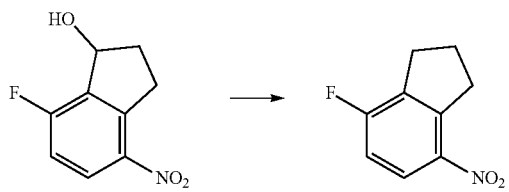 [SMILES: O=[N+]([O-])c1ccc(F)c2c1CCC2O ; O=[N+]([O-])c1ccc(F)c2c1CCC2]

To a mixture of 7-fluoro-4-nitro-2,3-dihydro-1H-inden-1-ol (4.5 g, 22.82 mmol, 1 eq) in TFA (20 mL) was added Et$_3$SiH (7.96 g, 68.47 mmol, 3 eq) in one portion. Then the reaction mixture was stirred at 2$_5$° C. for 12 hours. The mixture was quenched with water (100 mL) and extracted with EtOAc (3×100 mL). The combined organic layers were washed with saturated aqueous NaHCO$_3$ solution (2×100 mL), dried over anhydrous Na$_2$SO$_4$, filtered and concentrated in vacua to give the title compound (5 g, crude) as brown oil.

$^1$H NMR (CDCl$_3$): δ 8.06 (dd, 1H), 7.01 (t, 1H), 3.46 (t, 2H), 3.04 (t, 2H) and 2.25-2.20 (m, 2H).

Step D: 7-Fluoro-2,3-dihydro-1H-inden-4-amine

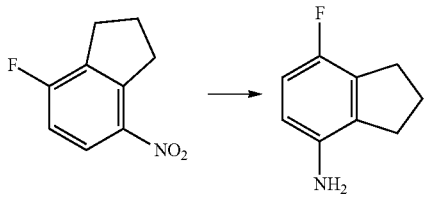 [SMILES: O=[N+]([O-])c1ccc(F)c2c1CCC2 ; Nc1ccc(F)c2c1CCC2]

To a mixture of 4-fluoro-7-nitro-2,3-dihydro-1H-indene (5 g, 27.60 mmol, 1 eq) in MeOH (50 mL) was added Pd/C (0.5 g, 10 wt % loading on activated carbon) at 25° C. under N$_2$ atmosphere. Then the reaction mixture was stirred at 25° C. for 12 hours under H$_2$ (15 psi). The mixture was filtered and the filtrate was concentrated in vacua. The residue was purified by silica gel column chromatography (SiO$_2$, petroleum ether:ethyl acetate, 5:1 to 10:1) to give the title compound (1.8 g, 43%) as a brown solid.

$^1$H NMR (CDCl$_3$): δ 6.69 (t, 1H), 6.44 (dd, 1H), 3.47 (br s, 2H), 2.95 (t, 2H), 2.75 (t, 2H) and 2.19-2.11 (m, 2H).

Step E: 5-Bromo-7-fluoro-2,3-dihydro-1H-inden-4-amine

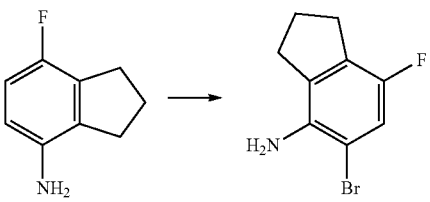 [SMILES: Nc1ccc(F)c2c1CCC2 ; Nc1c(Br)cc(F)c2c1CCC2]

To a solution of 7-fluoro-2,3-dihydro-1H-inden-4-amine (8.3 g, 54.90 mmol, 1 eq) in toluene (100 mL) was added NBS (10.26 g, 57.65 mmol, 1.05 eq) in one portion at 25° C. The reaction mixture turned dark brown immediately and then the mixture was stirred at 25° C. for 30 minutes. The reaction mixture was quenched with saturated aqueous Na$_2$SO$_3$ solution (200 mL) and extracted with EtOAc (2×100 mL). The combined organic phases were washed with brine (100 mL), dried over anhydrous Na$_2$SO$_4$, filtered and concentrated in vacuo. The residue was purified by silica gel column chromatography (SiO$_2$, petroleum ether:ethyl acetate, 1:0 to 20:1) to give the title compound (8.51 g, 67%) as a brown solid.

$^1$H NMR (CDCl$_3$): δ 6.99 (d, 1H), 3.81 (br s, 2H), 2.92 (t, 2H), 2.78 (t, 2H) and 2.21-2.13 (m, 2H).

Step F: 7-Fluoro-5-(pyridin-4-yl)-2,3-dihydro-1H-inden-4-amine

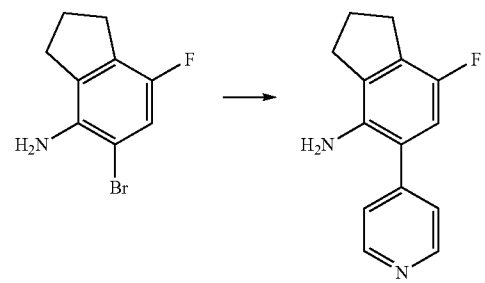 [SMILES: Nc1c(Br)cc(F)c2c1CCC2 ; Nc1c(-c2ccncc2)cc(F)c2c1CCC2]

To a mixture of 5-bromo-7-fluoro-2,3-dihydro-1H-inden-4-amine (3.5 g, 15.21 mmol, 1 eq) and pyridin-4-ylboronic acid (1.96 g, 15.97 mmol, 1.05 eq) in dioxane (50 mL) and H$_2$O (5 mL) was added K$_2$CO$_3$ (6.31 g, 45.64 mmol, 3 eq) and Pd(dppf)Cl$_2$ (1.11 g, 1.52 mmol, 0.1 eq) in one portion under N$_2$ atmosphere. Then the reaction mixture was heated to 80° C. for 12 hours. The reaction mixture was filtered. The filtrate was diluted with water (50 mL) and extracted with EtOAc (3×100 mL). The combined organic phases were washed with brine (100 mL), dried over anhydrous Na$_2$SO$_4$, filtered and concentrated in vacua. The residue was purified by silica gel column chromatography (SiO$_2$, petroleum ether:ethyl acetate, 10:1 to 2:1) to give the title compound (1.7 g, 45% yield, 90.98% purity on HPLC) as a brown solid.

$^1$H NMR (CDCl$_3$): δ 8.68 (dd, 2H), 7.40 (dd, 2H), 6.72 (d, 1H), 3.76 (br s, 2H), 3.01 (t, 2H), 2.80 (t, 2H) and 2.26-2.18 (m, 2H).

Step G: 4-(7-Fluoro-4-isocyanato-2,3-dihydro-1H-inden-5-yl)pyridine

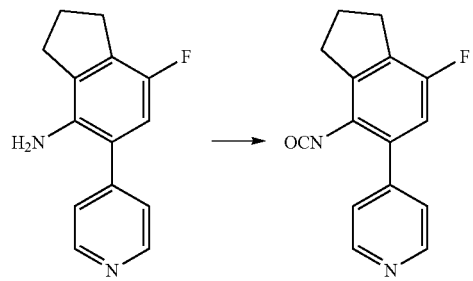

To a solution of 7-fluoro-5-(pyridin-4-yl)-2,3-dihydro-1H-inden-4-amine (400 mg, 1.75 mmol, 1 eq) and TEA (355 mg, 3.50 mmol, 487.82 µL, 2 eq) in THF (30 mL) was added bis(trichloromethyl) carbonate (208 mg, 700.94 µmol, 0.4 eq) at 0° C. The reaction mixture was stirred at 70° C. for 30 minutes. The reaction mixture was filtered through a pad of silica gel and the filter cake was washed with THF (20 mL). The filtrate was concentrated in vacua to reduce to 10 mL, which was used directly in the next step.

Intermediate P3: 6-Chloropyridazine-3-sulfonamide

Step A: 6-Chloropyridazine-3(2H)-thione

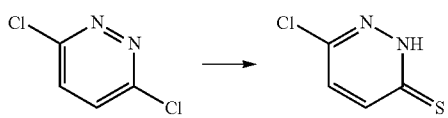 [SMILES: Clc1ccc(Cl)nn1 ; S=c1ccc(Cl)n[nH]1]

To a suspension of thiourea (3.8 g, 49.9 mmol) in acetone (150 mL) was added 3,6-dichloropyridazine (7.5 g, 5.3 mmol) at ambient temperature. The resulting reaction mixture was heated to reflux for 2 hours and upon cooling the mixture was filtered and the precipitate washed with acetone (2×20 mL). The solid was dissolved in aqueous sodium hydroxide solution (4 g in 80 mL water) and acidified with 37% hydrochloric acid to pH5. The resulting precipitate was filtered and washed with water (10 mL), then dried in vacuo to afford the title compound as a yellow solid (4.3 g, 58% yield). The crude product was used directly in the next step without further purification.

$^1$H NMR (DMSO-d$_6$): δ 7.6 (d, 1H), 7.37 (d, 1H) and 7.35 (s, 1H).

Step B: 6-Chloropyridazine-3-sulfonamide

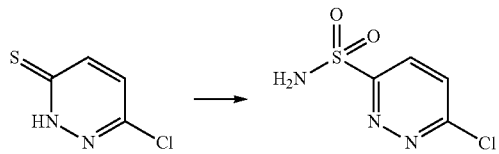 [SMILES: S=c1ccc(Cl)n[nH]1 ; NS(=O)(=O)c1ccc(Cl)nn1]

To a solution of 6-chloropyridazine-3(2H)-thione (250 mg, 1.7 mmol) in dichloromethane (10 mL) was added hydrochloric acid (10 mL 1 M). The mixture was cooled to −10° C. before a solution of sodium hypochlorite (3.5 mL, 10-15%) was added drop-wise. After 10 minutes stirring at −10° C., the dichloromethane layer was separated and poured into aqueous ammonium hydroxide (200 mL 25%). The aqueous layer was evaporated and the residue was triturated with methanol before the suspension was isolated by filtration and the mother liquors evaporated. The residue was purified over silica using ethyl acetate-methanol as the solvent. The product containing fractions were combined and evaporated. The product was triturated with TBME-heptane to afford the title compound (120 mg; 33%) as a pale brown solid.

$^1$H NMR (300 MHz, CD$_3$OD): δ 8.2 (d, J=Hz, 1H), 8.0 (d, J=Hz, 1H).

Intermediate P4:
3,6-Dimethoxypyridazine-4-sulfonamide

Step A: 4-Iodo-3,6-dimethoxypyridazine

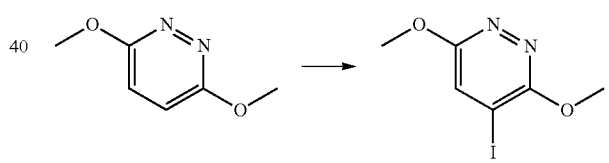

To a cold (−50° C.) solution of n-BuLi (2.5 M in hexanes, 12 mL, 30 mmol) in anhydrous THF (110 mL) under nitrogen was added 2,2,6,6-tetramethylpiperidine (5.1 mL, 30 mmol) drop-wise and the mixture was stirred towards −20° C. for 50 min, then recooled to −78° C. A solution of 3,6-dimethoxypyridazine (2 g, 14.3 mmol) in THF (30 mL) was added drop-wise and the resulting mixture was stirred at −78° C. for 60 min. Iodine (8 g, 31.4 mmol) was added and the reaction was stirred for a further 90 min and quenched at −50° C. with saturated aqueous sodium thiosulphate (30 mL). The mixture was allowed to warm to room temperature and partitioned between dichloromethane (200 mL) and water (50 mL). The organic layer was separated, washed with brine (20 mL), dried (Na$_2$SO$_4$), filtered and concentrated in vacua to give a crude yellow semi-solid (4.5 g). The material was subjected to column chromatography (silica, eluting with heptane/EtOAc gradient, 0 to 20%) to give 4-iodo-3,6-dimethoxypyridazine as a white solid (1.7 g, 45% yield).

$^1$H NMR (CDCl$_3$): δ 7.48 (s, 1H), 4.04 (s, 3H) and 4.02 (s, 3H).

Step B: 4-(Benzylthio)-3,6-dimethoxypyridazine

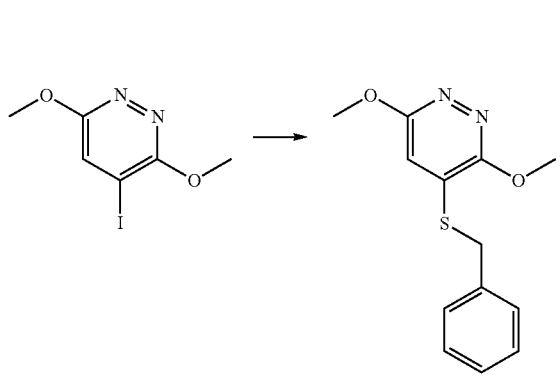

To a solution of 4-iodo-3,6-dimethoxypyridazine (1 g, 3.76 mmol) in 1,4-dioxane (20 mL) was added diisopropylethylamine (1.24 mL, 7.52 mmol) and Xantphos (218 mg, 0.38 mmol) and the resulting mixture was degassed with nitrogen for 10 minutes. Subsequently, tris(dibenzylideneacetone)dipalladium (172 mg, 0.19 mmol) was added, followed by benzyl mercaptan (0.44 mL, 3.76 mmol). The solution was heated with stirring under microwave irradiation for 2 hours at to 0° C. The resulting mixture was allowed to cool to room temperature and diluted with water and ethyl acetate. The aqueous phase was extracted with further ethyl acetate. The combined organic phase was dried ($Na_2SO_4$), filtered and concentrated to afford a bright orange oil (3.23 g). The material was subjected to column chromatography (silica, eluting with heptane/ethyl acetate gradient, 0 to 40%) to afford the title compound as a white solid (0.7 g, 71% yield).

$^1$H NMR ($CDCl_3$): δ 7.4 (s, 1H), 6.63 (s, 5H), 4.11 (s, 2H), 4.09 (s, 3H) and 4.0 (s, 3H).

Step C: 3,6-Dimethoxypyridazine-4-sulfonamide

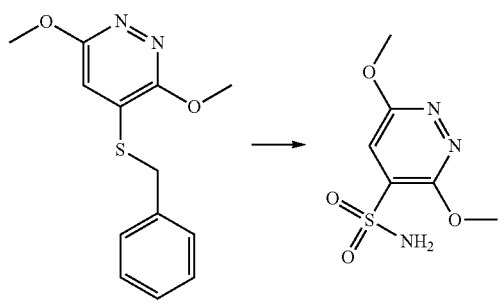

Prepared as described for 6-chloropyridazine-3-sulfonamide (intermediate P3, step B) to afford the title compound as a pale brown solid (52 mg, 36%).

$^1$H NMR ($CD_3OD$): δ 7.46 (s, 1H), 4.17 (s, 3H) and 4.07 (s, 3H).

Intermediate 6-(Dimethylamino)pyridazine-sulfonamide

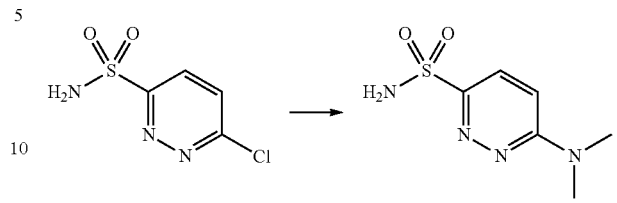

To 6-chloropyridazine-3-sulfonamide (19 mg, 0.13 mmol) was added a solution of dimethylamine in methanol (2 mL, 2 M) and the mixture was heated for to minutes at 120° C. in a microwave. The solvents were evaporated and triethylamine (too mg, 1 mmol) and THF (1 mL) were added to the residue. After stirring for 1 hour at room temperature the mixture was filtered and the THF was evaporated to afford the title compound as a solid (20 mg, 77%).

$^1$H NMR ($CD_3OD$): δ=7.82 (d, 1H), 7.18 (d, 1H) and 3.25 (s, 6H).

Intermediate P6: 5-(Dimethylamino)pyridazine-3-sulfonamide

Step A: 6-Chloro-N,N-dimethylpyridazin-4-amine

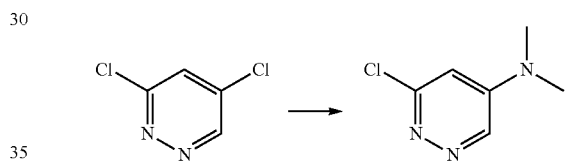

To 3,5-dichloropyridazine (500 mg, 3.36 mmol) was added a solution of dimethylamine in tetrahydrofuran (10 mL 2 M). The mixture was stirred for 18 hours at room temperature before the solvents were evaporated and to the residue was added triethylamine (720 mg, 1 mmol) and tetrahydrofuran (10 mL). After stirring for 1 hour, the mixture was filtered and the solvent was evaporated to afford the title compound as a solid (510 mg, 96%).

$^1$H NMR ($CDCl_3$): δ=8.64 (d, 1H), 6.53 (d 1H) and 3.09 (s, 6H).

Step B: 6-(Benzylthio)-N,N-dimethylpyridazin-4-amine

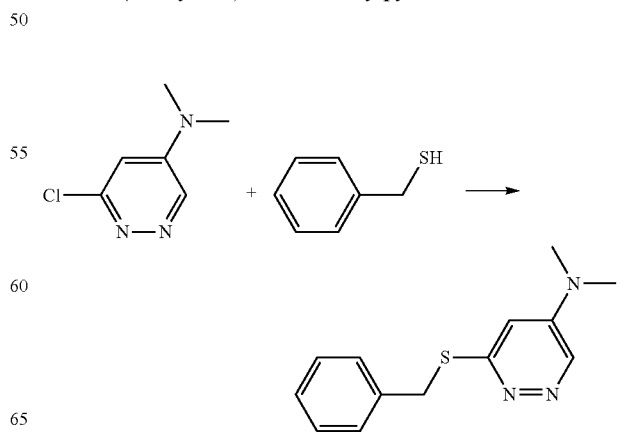

To a solution of 6-chloro-N,N-dimethylpyridazin-4-amine (500 mg, 3.2 mmol) in 1,4-dioxane (10 mL) was added diisopropylethylamine (833 mg, 6.4 mmol) and Xantphos [4,5-Bis(diphenylphosphino)-9,9-dimethylxanthene, 184 mg, 0.3 mmol]. The resulting mixture was degassed with nitrogen for 10 minutes. Subsequently, tris(dibenzylidene acetone)dipalladium (145 mg, 0.16 mmol) was added, followed by benzyl mercaptan (433 mg, 3.5 mmol) and the solution was heated to reflux overnight under a nitrogen atmosphere and upon cooling the solution was concentrated in vacua. The residue was purified via chromatography over neutral aluminium oxide using dichloromethane as the eluent to afford the title compound (220 mg, 26%) as a pale brown solid.

$^1$H NMR (CDCl$_3$): δ=8.50 (d, 1H), 7.42 (d, 2H), 7.26 (m, 3H), 6.32 (d, 1H), 4.56 (s, 2H) and 2.99 (s, 6H).

Step C: 5-(dimethylamino)pyridazine-3-sulfonamide

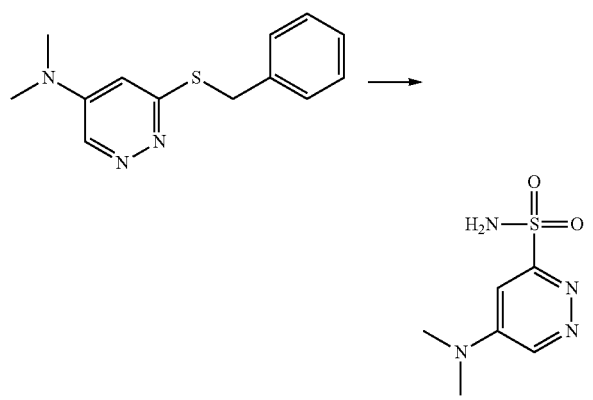

Prepared as described for 6-chloropyridazine-3-sulfonamide (intermediate P3, step B). This afforded the title compound as a pale brown solid (100 mg, 30%).

$^1$H NMR (CD$_3$OD): δ 8.81 (d, 1H), 7.24 (d, 1H) and 3.22 (s, 6H).

Intermediate P7: 5-((2-(Dimethylamino)ethyl)amino)pyrazine-2-sulfonamide

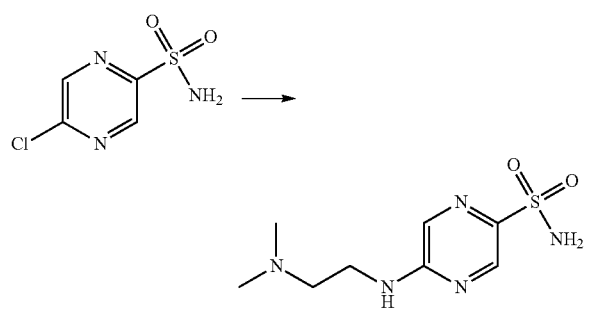

To a solution of 5-chloropyrazine-2-sulfonamide (150 mg, 775 μmol) in tetrahydrofuran (20 mL) was added N,N-dimethylethane-1,2-diamine (341 mg, 3.9 mmol) and triethylamine (235.19 mg, 2.32 mmol). The mixture was stirred at 50° C. for 5 hours before being allowed to cool and concentrated in vacua. The crude material was purified by preparative HPLC (column: Gemini 150*25 5u; mobile phase: [water (0.04% ammonia)-acetonitrile]; 1-30%, 10 minutes) to give the pure title compound (103 mg, 54%) as a white solid.

$^1$H NMR (DMSO): δ 8.37 (d, 1H), 7.99 (d, 1H), 7.78 (br s, 1H), 7.19 (br s, 2H), 3.41 (q, 2H), 2.42 (t, 2H) and 2.17 (s, 6H).

LCMS: m/z 246 (M+H)+(ES+); 513 (M*2+Na)+(ES+).

Intermediate P8:
5-(Dimethylamino)pyrazine-2-sulfonamide

Step A: 2-(Benzylthio)-5-chloropyrazine

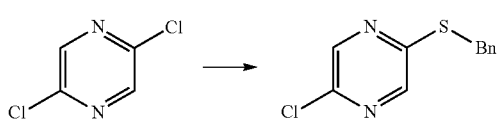 [SMILES: Clc1cnc(Cl)cn1 ; Clc1cnc(SCc2ccccc2)cn1]

To a mixture of 2,5-dichloropyrazine (2 g, 13.42 mmol) and phenylmethanethiol (1.63 g, 13.12 mmol, 1.54 mL) in N,N-dimethylformamide (20 mL) was added potassium carbonate (3.71 g, 26.85 mmol) in one portion at 20° C. The mixture was stirred at 20° C. for 2 hours and then diluted with water (80 mL) and extracted into ethyl acetate (30 mL×3). The organic layers were combined, washed with water (40 mL) and brine (40 mL), dried (anhydrous sodium sulfate), filtered and concentrated in vacuo to afford a crude product. This was purified by column chromatography (petroleum ether) to give the title compound (2.9 g, 12.25 mmol, 91% yield) as a yellow oil.

$^1$H NMR (CDCl$_3$): δ 8.45-8.40 (m, 1H), 8.23 (d, 1H), 7.43-7.38 (m, 2H), 7.36-7.29 (m, 3H) and 4.42 (s, 2H).

Step B: 5-Chloropyrazine-2-sulfonamide

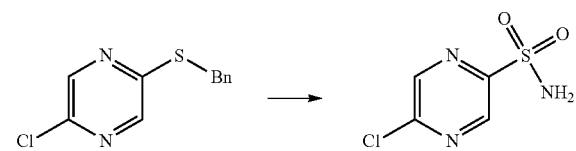 [SMILES: Clc1cnc(SCc2ccccc2)cn1 ; NS(=O)(=O)c1cnc(Cl)cn1]

Chlorine gas was bubbled into the solution of 2-(benzylthio)-5-chloropyrazine (800 mg, 3.38 mmol) in carbon tetrachloride (20 mL) and water (5 mL) at 0° C. for 30 minutes and the resulting mixture was stirred at 20° C. for 1 hour. The phases were separated and into the organic phase was bubbled ammonia gas at 0° C. for 30 minutes. The mixture was stirred at 20° C. for another 1 hour and the mixture was concentrated in vacua and then purified by column chromatography (petroleum ether:ethyl acetate=3:1-2:1) to give the pure product (300 mg, 47% yield) as a white solid.

$^1$H NMR (DMSO): δ 9.01 (d, 1H), 8.97 (d, 1H) and 7.89 (s, 2H).

Step C: 5-(Dimethylamino)pyrazine-2-sulfonamide

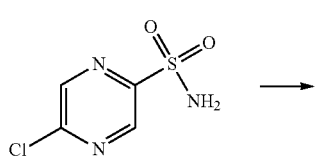

-continued

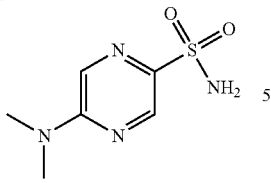

To a solution of 5-chloropyrazine-2-sulfonamide (200 mg, 1.03 mmol) in tetrahydrofuran (5 mL) was added N,N-dimethylamine (2 M, 1.03 mL). The mixture was stirred at 20° C. for 0.5 hours and then concentrated in vacua to afford a crude product. This was purified by preparative TLC (petroleum ether:ethyl acetate=0-100%) to give the title compound (16 mg, yield: 8%) as a white solid.

$^1$H NMR (DMSO): δ 8.45 (d, 1H), 8.18 (d, 1H), 7.26 (s, 2H) and 3.16 (s, 6H).

LCMS: m/z 225 (M+Na)+(ES+); 427 (M*2+Na)+(ES+).

Intermediate P9:
6-(Dimethylamino)pyrazine-2-sulfonamide

Step A: 2-(Benzylthio)-6-chloropyrazine

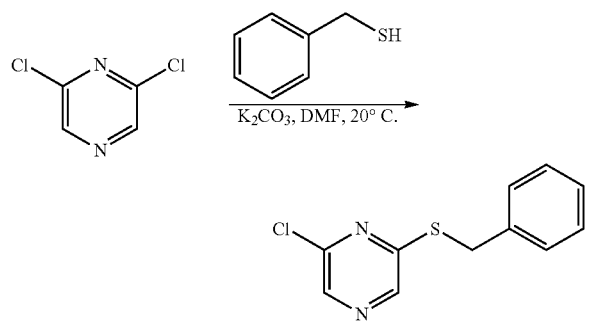

To a solution of phenylmethanethiol (3.8 g, 30.4 mmol) and 2,6-dichloropyrazine (50.0 g, 33.5 mmol) in N,N-dimethylformamide (50 mL) was added potassium carbonate (4.2 g, 30.4 mmol). The reaction was stirred at 20° C. for 15 hours and the resulting mixture was diluted with water (200 mL) and then extracted into ethyl acetate (200 mL×3). The combined organic layers were washed with brine (100 mL×2), dried (anhydrous sodium sulfate), filtered and concentrated in vacua to afford the title compound (6.8 g, 94% yield) as a yellow oil. The crude product was used in next step without further purification.

LCMS: m/z 237 (M+H)$^+$(ES$^+$).

Step B: 6-Chloropyrazine-2-sulfonyl chloride

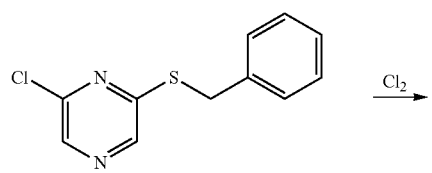

-continued

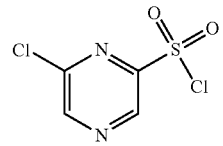

Chlorine gas was bubbled into a solution of 2-(benzylthio)-6-chloropyrazine (0.5 g, 2.11 mmol) in carbon tetrachloride (20 mL) and water (5 mL) at 0° C. for 30 minutes. The resulting mixture was concentrated in vacua and the residue was taken up into dichloromethane (30 mL) and washed with brine (10 mL×3). The organic layer was dried (anhydrous sodium sulfate), filtered and concentrated in vacuo to afford the title compound (0.3 g, 1.41 mmol, 67% yield) as yellow oil. The crude product was used in next step without further purification.

Step C: 6-Chloropyrazine-2-sulfonamide

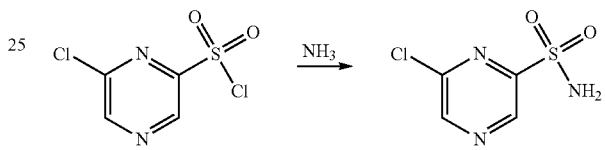

Ammonia gas was bubbled into a solution of 6-chloropyrazine-2-sulfonyl chloride (0.3 g, 1.41 mmol) in tetrahydrofuran (20 mL) at 0° C. for 20 minutes and then the mixture was stirred at 0-20° C. for 2 hours. The reaction was then concentrated in vacua and the residue was diluted with ethyl acetate (30 mL), washed with brine (10 mL×2), dried (anhydrous sodium sulfate), filtered and concentrated in vacuo. The residue was purified by silica gel column chromatography (petroleum ether:ethyl acetate=10:1 to 1:1) to give the title compound (0.26 g, 95% yield) as a yellow solid.

$^1$H NMR (400 MHz, DMSO-d$_6$) δ 9.09 (d, 2H) and 7.94 (s, 2H).

Step D: 6-(Dimethylamino)pyrazine-2-sulfonamide

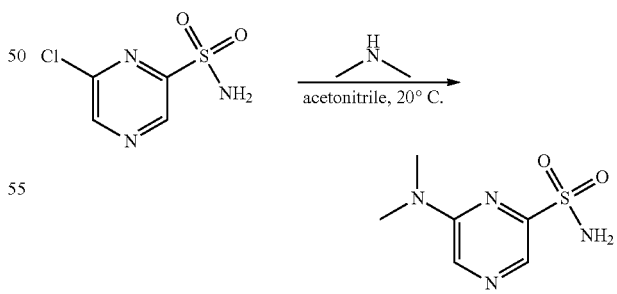

To a solution of 6-chloropyrazine-2-sulfonamide (170 mg, 0.88 mmol) in acetonitrile (2 mL) was added N-methylmethanamine (47.5 mg, 1.1 mmol). The resulting mixture was stirred at 20° C. for 2 hours and then concentrated in vacua. The residue was purified by preparative TLC (silica gel, petroleum ether:ethyl acetate=1:8) to afford the title compound (110 mg, 59% yield) as white solid.

$^1$H NMR (400 MHz, DMSO-d$_6$) δ 8.34 (s, 1H), 8.16, (s, 1H), 7.46 (s, 2H) and 3.14 (s, 6H).
LCMS: m/z 203 (M+H)$^+$(ES$^+$).

Intermediate P10:
6-Morpholinopyrazine-2-sulfonamide

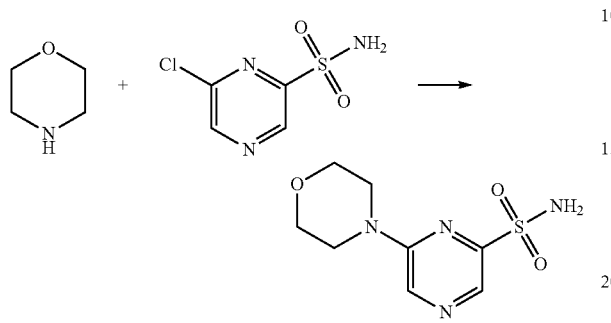

To a solution of 6-chloropyrazine-2-sulfonamide (0.25 g, 1.29 mmol) in acetonitrile (5 mL) was added morpholine (225 mg, 2.58 mmol, 227 μL) under an atmosphere of dry nitrogen. The reaction was stirred at 40° C. for 6 hours and then poured into ice water (10 mL) causing a white solid to precipitate. After stirring for 0.5 hours the mixture was filtrated and the residue was washed with petroleum ether, followed by methyl tert-butyl methylether. The residual solid was dried in vacuo to afford the title compound (0.12 g, 38%) as light yellow solid.

$^1$H NMR (DMSO-d$_6$) δ 8.51 (s, 1H), 8.23 (s, 1H), 7.48 (s, 2H), 3.72 (t, 4H) and 3.65 (t,H).
LCMS: m/z 245.0 (M+H)$^+$(ES$^+$).

Intermediate P11:
6-(Dimethylamino)pyrazine-2-sulfonamide

Step A: 2-(Benzylthio)-6-chloropyrazine

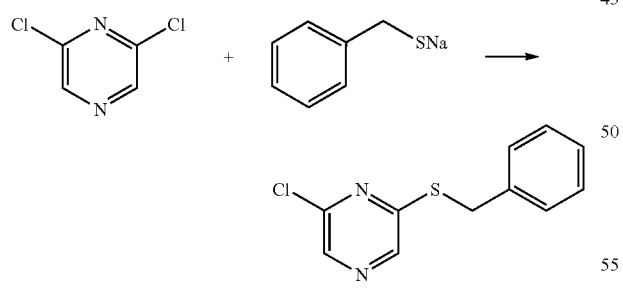

A solution of 2,6-dichloropyrazine (5 g, 33.56 mmol, 1.1 eq) and sodium phenylmethanethiolate (4.46 g, 3.51 mmol, 1 eq) in DMF (50 mL) was stirred at 25° C. for 16 hours. The reaction mixture was diluted with EtOAc (100 mL) and washed with saturated aqueous NH$_4$Cl solution (3×50 mL) and brine (3×50 mL). The organic layers were dried over anhydrous Na$_2$SO$_4$, filtered and concentrated in vacuo. The residue was purified by silica gel column chromatography (SiO$_2$, petroleum ether:ethyl acetate, 1:0 to 50:1) to give the title compound (2 g, 28%) as a colourless oil.

$^1$H NMR (CDCl$_3$): δ 8.33 (d, 1H), 8.23 (s, 1H), 7.46-7.42 (m, 2H), 7.37-7.29 (m, 3H) and 4.43 (s, 2H).
LCMS: m/z 237.0 (M+H)$^+$(ES$^+$).

Step B: 6-Chloropyrazine-2-sulfonyl chloride

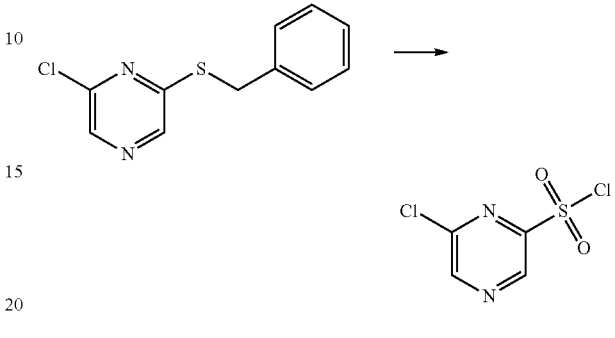

A solution of 2-(benzylthio)-6-chloropyrazine (2 g, 8.45 mmol, 1 eq) in CCl$_4$ (80 mL) and H$_2$O (20 mL) was bubbled with Cl2 at 0° C. for to minutes. The reaction mixture was filtered and the filtrate was concentrated in vacua to give the title compound (1.8 g, crude), which was used directly in the next step.

Step C: 6-Chloropyrazine-2-sulfonamide

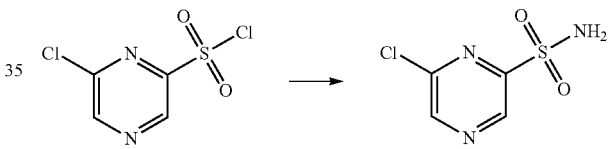

A solution of 6-chloropyrazine-2-sulfonyl chloride (1.8 g, crude) in THF (so mL) was bubbled with NH$_3$ at 0° C. for to minutes. The reaction mixture was filtered and the filtrate was concentrated in vacua. The residue was triturated with a mixture of petroleum ether and ethyl acetate (21 mL, v:v=20:1) to give the title compound (1.2 g, 73%) as a yellow solid.

$^1$H NMR (DMSO-d$_6$): δ 9.09 (d, 2H) and 7.96 (s, 2H).

Step D: 6-(Dimethylamino)pyrazine-2-sulfonamide

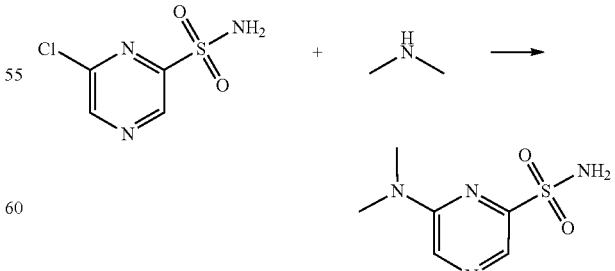

To a solution of 6-chloropyrazine-2-sulfonamide (1 g, 5.16 mmol, 1 eq) in MeCN (10 mL) was added with dimethylamine (2 M in THF, 3.23 mL, 1.25 eq). The mixture was stirred at 25° C. for 3 hours. The reaction mixture was concentrated in vacuo. The residue was purified by silica gel column chromatography (SiO$_2$, petroleum ether:ethyl acetate, 1:1 to 1:10) to give the title compound (210 mg, 20%) as a yellow solid.

$^1$H NMR (CD$_3$OD): δ 8.26 (s, 1H), 8.22 (s, 1H) and 3.22 (s, 6H).

LCMS: m/z 203.1 (M+H)$^+$(ES$^+$).

Intermediate P12:
5-(Dimethylamino)pyrazine-2-sulfonamide

Step A: 2-(Benzylthio)-5-chloropyrazine

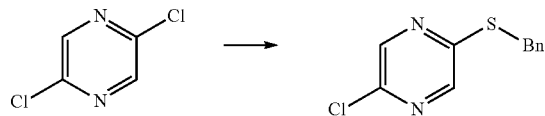 [SMILES: Clc1cnc(Cl)cn1 ; Clc1cnc(SCc2ccccc2)cn1]

To a solution of 2,5-dichloropyrazine (3 g, 20.14 mmol, 1 eq) in MeCN (30 mL) was added phenylmethanethiol (2.25 g, 18.12 mmol, 0.9 eq) and K$_2$CO$_3$ (5.57 g, 40.27 mmol, 2 eq). The reaction mixture was stirred at 25° C. for 12 hours. The reaction mixture was poured into water (100 mL) and extracted with EtOAc (2×100 mL). The combined organic layers were dried over Na$_2$SO$_4$, filtered and concentrated in vacua. The residue was purified by silica gel column chromatography (SiO$_2$, petroleum ether:ethyl acetate, 10:1 to 0:1) to give the title compound (4.5 g, 94%) as a yellow oil.

$^1$H NMR (CDCl$_3$): δ 8.43 (s, 1H), 8.19 (s, 1H), 7.42-7.38 (m, 2H), 7.35-7.28 (m, 3H) and 4.42 (s, 2H).

Step B: 5-Chloropyrazine-2-sulfonyl chloride

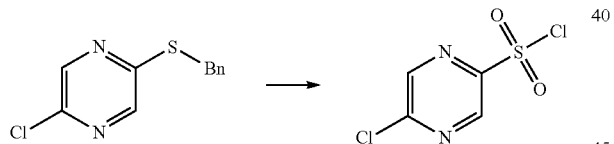

Cl$_2$ (15 psi) was bubbled into a solution of 2-(benzylthio)-5-chloropyrazine (4.5 g, 19.01 mmol, 1 eq) in CCl$_4$ (50 mL) and H$_2$O (10 mL) at −10° C. for 15 minutes. The reaction mixture was used directly in the next step without further work-up and purification.

Step C: 5-Chloropyrazine-2-sulfonamide

A saturated solution of NH$_3$ in THF (20 mL) was added into a solution of 5-chloropyrazine-2-sulfonyl chloride (theoretical amount: 4 g, crude) in CCl$_4$ (50 mL) and H$_2$O (10 mL) at −10° C. for 10 minutes. Then the reaction mixture was warmed to 25° C. and stirred at 25° C. for 50 minutes. The reaction mixture was concentrated in vacua.

The residue was purified by silica gel column chromatography (SiO$_2$, petroleum ether:ethyl acetate, 3:1 to 1:1) to give the title compound (1.6 g, 44%) as a yellow oil.

$^1$H NMR (CDCl$_3$): δ 8.98 (dd, 1H) and 7.88 (s, 1H).

Step D: 5-(Dimethylamino)pyrazine-2-sulfonamide

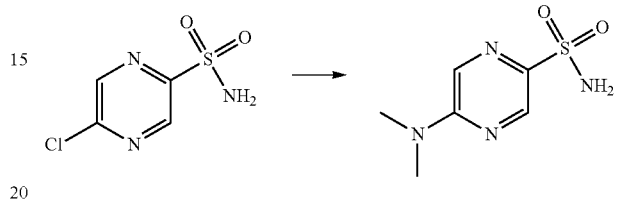

5-Chloropyrazine-2-sulfonamide (800 mg, 4.13 mmol, 1 eq) was added into a solution of dimethylamine in water (2 M, 10.00 mL, 33 wt % in H$_2$O, 4.84 eq). Then the mixture was stirred at 25° C. for 30 minutes. The reaction mixture was concentrated under reduced pressure. The residue was triturated with EtOAc (30 mL) to give the title compound (800 mg, 96%) as a white solid.

$^1$H NMR (DMSO-d$_6$): δ 8.46 (s, 1H), 8.20 (s, 1H), 7.28 (s, 2H) and 3.17 (s, 6H).

Intermediate P13:
3-(Difluoromethyl)pyrazine-2-sulfonamide

Step A: 3-Chloropyrazine-2-carbaldehyde

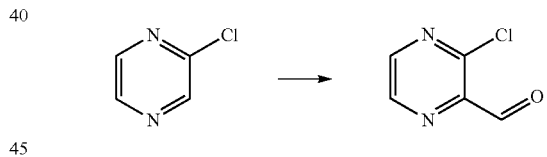

To a solution of 2,2,6,6-tetramethylpiperidine (27.13 g, 192.08 mmol, 2.2 eq) in THF (200 mL) was added n-BuLi (2.5 M, 73.34 mL, 2.1 eq) at −78° C. The reaction mixture was warmed to 0° C. and stirred for 15 minutes. Then the reaction mixture was cooled down to −78° C. and 2-chloropyrazine (10 g, 87.31 mmol, 1 eq) was added. The resulting mixture was stirred at −78° C. for 30 minutes. To the reaction mixture was added DMF (12.76 g, 174.62 mmol, 2 eq) at −78° C. The mixture was stirred at −78° C. for 30 minutes and then stirred at 0° C. for another 15 minutes. The reaction mixture was quenched with a solution of AcOH (50 mL) in THF (50 mL) at −78° C. Then the reaction mixture was poured into water (300 mL) and extracted with EtOAc (3×300 mL). The combined organic layers were washed with brine, dried over Na$_2$SO$_4$, filtered and concentrated in vacua. The residue was purified by silica gel column chromatography (SiO$_2$, petroleum ether:ethyl acetate, 10:1 to 5:1) to give the title compound (2.4 g, 19%) as a yellow oil.

$^1$H NMR (CDCl$_3$): δ 10.35 (s, 1H), 8.78-8.72 (m, 1H) and 8.62-8.58 (m, 1H).

Step B: 2-Chloro-3-(difluoromethyl)pyrazine

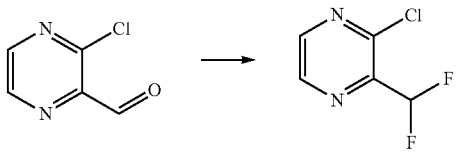 [SMILES: O=Cc1nccnc1Cl ; FC(F)c1nccnc1Cl]

To a solution of 3-chloropyrazine-2-carbaldehyde (1.2 g, 8.42 mmol, 1 eq) in DCM (50 mL) was added bis(2-methoxyethyl)aminosulfur trifluoride (2.79 g, 12.63 mmol, 1.5 eq) at −78° C. The mixture was warmed to 25° C. and stirred for 2 hours. The reaction mixture was quenched with water (50 mL) and extracted with DCM (3×80 mL). The combined organic layers were dried over $Na_2SO_4$, filtered and concentrated in vacua. The residue was purified by silica gel column chromatography ($SiO_2$, petroleum ether:ethyl acetate, 1:0 to 10:1) to give the title compound (800 mg, 58%) as a yellow oil.
$^1$H NMR ($CDCl_3$): δ 8.54 (d, 1H), 8.47 (d, 1H) and 6.85 (t, 1H).

Step C: 2-(Benzylthio)-3-(difluoromethyl)pyrazine

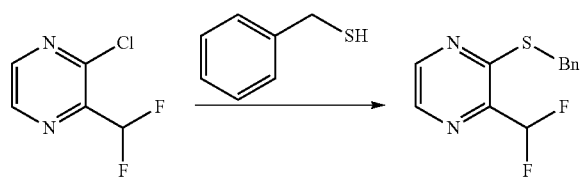

To a solution of 2-chloro-3-(difluoromethyl)pyrazine (800 mg, 4.86 mmol, 1 eq) in MeCN (15 mL) was added phenylmethanethiol (664 mg, 5.35 mmol, 1.1 eq) and $K_2CO_3$ (874 mg, 6.32 mmol, 1.3 eq). The mixture was stirred at 25° C. for 12 hours. Then the reaction mixture was poured into water (50 mL) and extracted with EtOAc (2×50 mL). The combined organic layers were dried over $Na_2SO_4$, filtered and concentrated in vacua. The residue was purified by silica gel column chromatography ($SiO_2$, petroleum ether:ethyl acetate, 1:0 to 10:1) to give the title compound (1.1 g, 90%) as a colourless oil.
$^1$H NMR ($CDCl_3$): δ 8.56-8.52 (m, 1H), 8.33 (d, 1H), 7.45-7.42 (m, 2H), 7.36-7.30 (m, 3H), 6.71 (t, 1H) and 4.51 (s, 2H).

Step D: 3-(Difluoromethyl)pyrazine-2-sulfonyl chloride

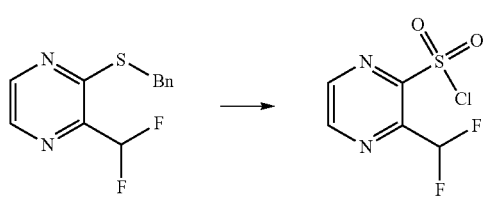 [SMILES: FC(F)c1nccnc1SCc1ccccc1 ; O=S(=O)(Cl)c1nccnc1C(F)F]

$Cl_2$ (15 psi) was bubbled into a solution of 2-(benzylthio)-3-(difluoromethyl)pyrazine (500 mg, 1.98 mmol, 1 eq) in DCM (20 mL) and $H_2O$ (2 mL) at −10° C. for 5 minutes. The reaction mixture was used directly in the next step without purification.

Step E: 3-(Difluoromethyl)pyrazine-2-sulfonamide

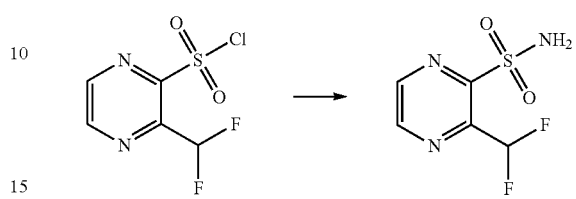

To a solution of 3-(difluoromethyl)pyrazine-2-sulfonyl chloride (theoretical amount: 453 mg, crude) in DCM (20 mL) and $H_2O$ (2 mL) was added $NH_3.H_2O$ (15 mL, 25 wt % in water) at 0° C. The reaction mixture was stirred at 0° C. for 5 minutes and then concentrated in vacua. The residue was treated with water (50 mL) and the mixture was washed with EtOAc (3×80 mL). The aqueous layer was concentrated in vacuo. The residue was treated with EtOAc (100 mL) and the mixture was stirred for 10 minutes. The mixture was filtered and the filtrate was concentrated in vacuo to give the title compound (260 mg, 63%) as a yellow oil.
$^1$H NMR (DMSO-$d_6$): δ 9.08 (d, 1H), 9.02 (s, 1H), 8.10 (br s, 2H) and 7.52 (t, 1H).
LCMS: m/z 210.1 $(M+H)^+(ES^+)$.

Intermediate P14:
4,6-Dimethylpyrimidine-2-sulfonamide

Step A: 4,6-Dimethylpyrimidine-2-thiol and 1,2-bis(4,6-dimethylpyrimidin-2-yl)disulfane

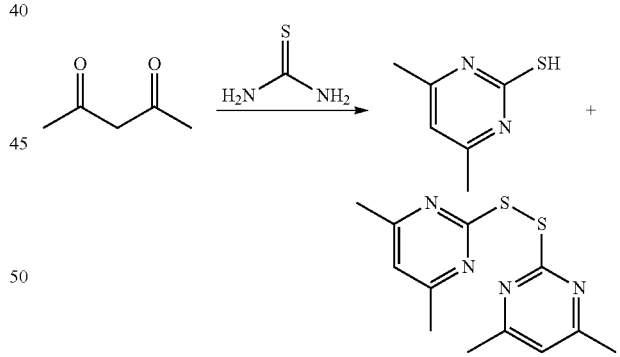

To a solution of pentane-2,4-dione (10.03 g, 100.17 mmol, 1.25 eq) in concentrated HCl solution (12 M, 20 mL, 2.99 eq) and EtOH (100 mL) was added thiourea (6.1 g, 80.14 mmol, 1 eq) at 10° C. The reaction mixture was stirred at 70° C. for 2 hours. The reaction mixture was cooled to 20° C. and a large amount of solid precipitated out. The mixture was filtered and the filter cake was treated with saturated aqueous $NaHCO_3$ solution (300 mL). The mixture was filtered again and the filter cake was triturated with MeOH (200 mL) to give the title compound (10.3 g, 44% yield, 97.2% purity on LCMS) as a yellow solid.
$^1$H NMR (DMSO-$d_6$): δ 6.39 (s, 2H) and 2.13 (s, 12H).
LCMS: m/z 279.1 $(M+H)^+(ES^+)$.

Step B: 4,6-Dimethylpyrimidine-2-sulfonyl chloride

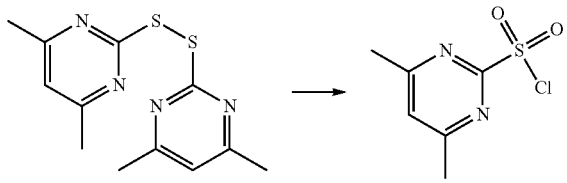

Cl$_2$ (15 psi) was bubbled into a solution of 1,2-bis(4,6-dimethylpyrimidin-2-yl)disulfane (1 g, 3.59 mmol, 1 eq) in DCM (40 mL) and H$_2$O (6 mL) at −10° C. for 10 minutes. The reaction mixture was quenched with water (20 mL) and extracted with DCM (2×40 mL). The solution of the title compound (crude) in DCM (80 mL) was used directly in the next step without further purification.

Step C: 4,6-Dimethylpyrimidine-2-sulfonamide

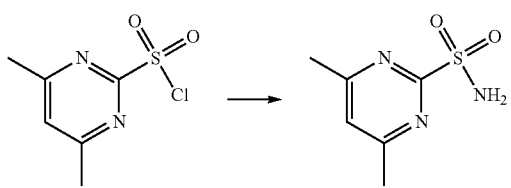

NH$_3$ (15 psi) was bubbled into a solution of 4,6-dimethylpyrimidine-2-sulfonyl chloride (theoretical amount: 0.74 g, crude) in DCM (80 mL) at 0° C. for 10 minutes. The reaction mixture was quenched with water (20 mL) and washed with DCM (40 mL). Then the aqueous phase was concentrated in vacuo. The residue was triturated with EtOAc (300 mL) to give the title compound (0.35 g, 52% yield, 100% purity on LCMS) as a yellow solid.

$^1$H NMR (DMSO-d$_6$): δ 7.49-7.47 (m, 3H) and 2.52 (s, 6H).

LCMS: m/z 188.1 (M+H)$^+$(ES$^+$).

Intermediate P15:
5-(Dimethylamino)pyridazine-3-sulfonamide

Step A: 6-Chloro-N,N-dimethylpyridazin-4-amine

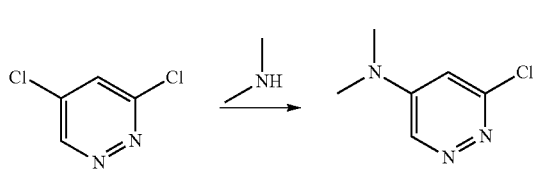

To a mixture of 3,5-dichloropyridazine (13.5 g, 90.62 mmol, 1 eq) in THF (100 mL) was added dimethylamine (270 mL, 543.70 mmol, in THF solution, 6 eq) in one portion at 25° C. Then the reaction mixture was stirred at 25° C. for 12 hours. The reaction mixture was concentrated in vacuo. The residue was purified by reversed phase flash chromatography (0.05% of NH$_3$.H$_2$O in water/MeCN) to give the title compound (7 g, 49% yield, 99.35% purity on LCMS) as a brown solid.

$^1$H NMR (CDCl$_3$): δ 8.63 (d, 1H), 6.53 (d, 1H) and 3.09 (s, 6H).

LCMS: m/z 158.1 (M+H)$^+$(ES$^+$).

Step B:
6-(Benzylthio)-N,N-dimethylpyridazin-4-amine

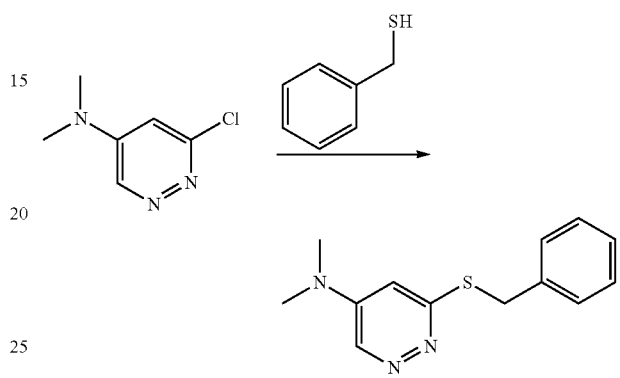

To a mixture of phenylmethanethiol (4.31 g, 34.70 mmol, 1.22 eq) in DMF (100 mL) was added NaH (1.37 g, 34.26 mmol, 60 wt % in mineral oil, 1.2 eq) at 0° C. in one portion under N$_2$. Then mixture was stirred at 0° C. for 0.5 hour. Then 6-chloro-N,N-dimethylpyridazin-4-amine (4.5 g, 28.55 mmol, 1 eq) was added. The reaction mixture was heated to 70° C. and stirred for 1 hour. Then the reaction mixture was quenched with water (200 mL) and extracted with EtOAc (3×200 mL). The combined organic phases were washed with brine (200 mL), dried over anhydrous Na$_2$SO$_4$, filtered and concentrated in vacua. The residue was purified by silica gel column chromatography (SiO$_2$, petroleum ether:ethyl acetate, 1:0 to 20:1, then flushed through with EtOAc:EtOH, 50:1 to 10:1) to give the title compound (5.2 g, 74%) as a brown solid.

$^1$H NMR (CDCl$_3$): δ 8.53 (d, 1H), 7.45-7.43 (m, 2H), 7.32-7.30 (m, 2H), 7.26-7.23 (m, 1H), 6.34 (d, 1H), 4.58 (s, 2H) and 3.09 (s, 6H).

Step C: 5-(Dimethylamino) pyridazine-3-sulfonyl chloride

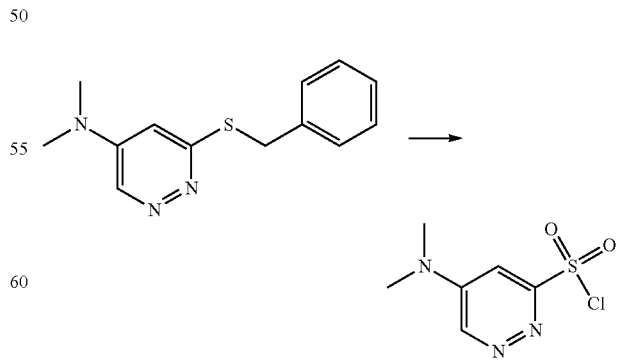

To a solution of 6-(benzylthio)-N,N-dimethylpyridazin-4-amine (1 g, 4.08 mmol, 1 eq) in DCM (50 mL) was added a solution of CaCl$_2$) (4.52 g, 40.76 mmol, 10 eq) in HCl (1

M, 20.38 mL, 5 eq) at −30° C. Then a solution of CaCl₂) (14.70 g, 132.47 mmol, 32.5 eq) in aqueous NaClO solution (19.22 g, 15.49 mmol, 6 wt % in water, 3.8 eq) was added dropwise at −30° C. The resulting mixture was stirred at −30° C. for 30 minutes. The reaction mixture was quenched with water (20 mL) and extracted with DCM (2×50 mL). The combined organic phases were dried over anhydrous Na₂SO₄, filtered and concentrated in vacua to give a solution of the title compound (theoretical amount: 0.9 g, crude) in DCM (100 mL), which was used directly in the next step without further purification.

Step D: 5-(Dimethylamino)pyridazine-3-sulfonamide

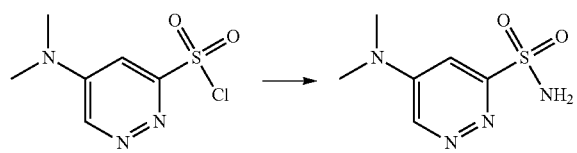

NH₃ (15 psi) was bubbled into a solution of 5-(dimethylamino)pyridazine-3-sulfonyl chloride (theoretical amount: 0.9 g, crude) in DCM (100 mL) at −20° C. for 10 minutes. The mixture was quenched with water (50 mL) and washed with DCM (30 mL). Then the aqueous phase (50 mL) was concentrated in vacua. The residue was purified by trituration with EtOAc (300 mL) to give the title compound (0.23 g, 28%) as a yellow solid.
¹H NMR (DMSO-d₆): δ 8.89 (d, 1H), 7.55 (s, 2H), 7.05 (d, 1H) and 3.09 (s, 6H).
LCMS: m/z 203.1 (M+H)⁺(ES⁺).

Intermediate P16:
4-(Dimethylamino)-6-methylpyrimidine-2-sulfonamide

Step A:
2-(Benzylthio)-N,N,6-trimethylpyrimidin-4-amine

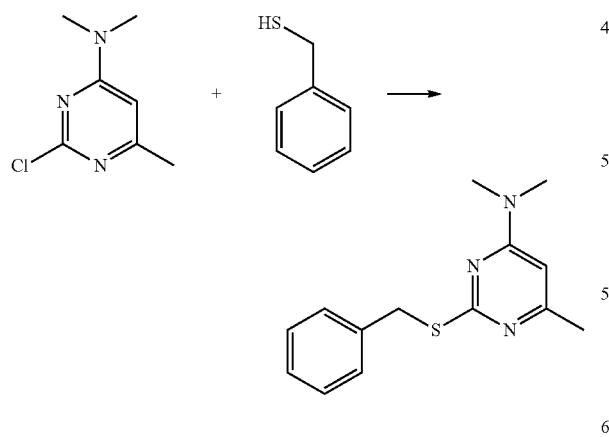

To a solution of 2-chloro-N,N,6-trimethylpyrimidin-4-amine (250 mg, 1.46 mmol) in dioxane (12 mL) was added diisopropylethylamine (383 mg, 2.90 mmol) and Xantphos (90 mg, 0.16 mmol). The solution was purged with N₂ for 10 minutes. Then Pd(dba)₃ (70 mg, 0.08 mol) was added, followed by benzylmercaptane (300 mg, 2.65 mmol). The mixture was refluxed under nitrogen for 30 hours. The solvents were evaporated and the residue was purified over silica using dichloromethane/methanol/ammonia as the eluent to afford the title compound (300 mg, 77%) as an oil, still containing 30% starting material.
¹H NMR (CDCl₃): δ7.4 (m, 2H), 7.25 (m, 3H), 5.97 (s, 1H), 4.39 (s, 2H), 3.07 (s, 6H), 2.3 (s, 3H).

Step B:
4-(Dimethylamino)-6-methylpyrimidine-2-sulfonamide

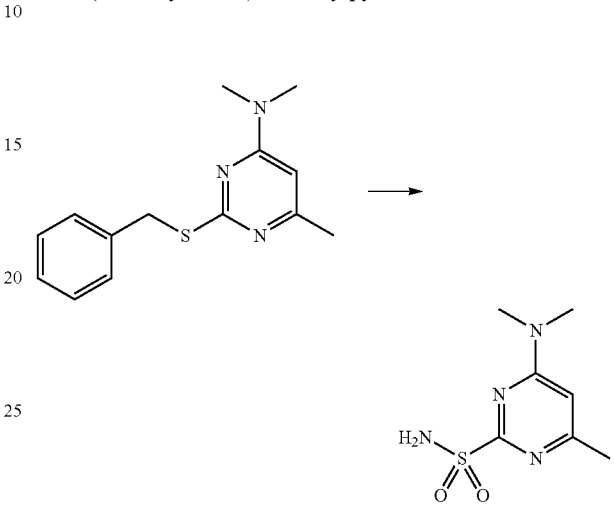

2-(Benzylthio)-N,N6-trimethylpyrimidin-4-amine (200 mg, 0.77 mmol) was dissolved in dichloromethane (10 ml) and 1 N HCl (5 mL) was added. The mixture was cooled to −10° C. Then sodium hypochlorite (1.6 mL, 2.54 mmol) was added dropwise over 15 minutes, during which the temperature was allowed to reach 0° C. The mixture was poured into ammonia in methanol (50 mL, 7N). After 1 hour stirring at room temperature, the solvents were evaporated. The residue was triturated in THF (15 mL) containing Et₃N (1 mL). The mixture was filtered and the solvents were evaporated. The residue was purified over silica using dichloromethane/methanol/ammonia as the eluent to afford the title compound as an oil (20 mg, 17%).
¹H NMR (CD₃OD): δ 6.43 (s, 1H), 3.3 (s, 6H), 2.5 (s, 3H).

Intermediate P17:
2-Isopropylpyridine-4-sulfonamide

Step A: 2-Chloropyridine-4-sulfonyl chloride

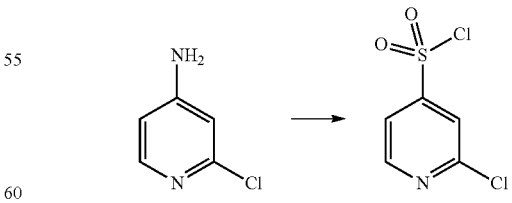

2-Chloropyridin-4-amine (1.29 g, 10.0 mmol) was added portionwise to a mixture of TFA (10 mL) and conc. HCl (5 mL) at 0° C. The resultant solution was treated with a solution of sodium nitrite (2.07 g, 29.1 mmol) in water (7.5 mL) and stirred at 0° C. for 1 hour. The reaction mixture was filtered into a pre-cooled (0° C.) flask and then added via cannula to a suspension of CuCl (0.1 g, 1.0 mmol) and CuCl$_2$ (0.67 g, 4.83 mmol) in acetic acid containing dissolved SO$_2$ (60 mL) (prepared by bubbling SO$_2$ through acetic acid for 45 minutes at room temperature). The reaction mixture was stirred at 0° C. for 1 hour, diluted with DCM (50 mL) and the organic layer was washed with ice-water (2×50 mL), sat aq NaHCO$_3$ (2×50 mL), brine (50 mL), dried (MgSO$_4$) and concentrated in vacua to afford the title compound as a pale yellow oil. The crude was used in the next step without further purification.

$^1$H NMR (Chloroform-d) δ 8.77 (d, J=5.2 Hz, 1H), 7.91 (d, J=1.1 Hz, 1H), 7.81 (dd, J=5.2, 1.7 Hz, 1H).

Step B: 2-Chloro-N,N-bis(4-methoxybenzyl)pyridine-4-sulfonamide

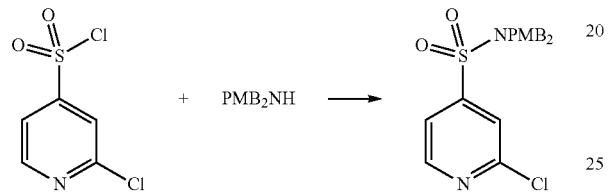

A solution of bis(4-methoxybenzyl)amine (1.788 g, 6.95 mmol) and Et$_3$N (1.15 mL, 8.25 mmol) in DCM (50 mL) at 0° C. was treated dropwise with a solution of 2-chloropyridine-4-sulfonyl chloride (1.46 g, 4.13 mmol) in DCM (6 mL). The resultant solution was stirred at 0° C. for 1 hour. Sat aq NH$_4$Cl (50 mL) was added and the organic layer was collected. The aqueous was extracted with DCM (50 mL) and the combined organic extracts were washed with sat aq NH$_4$Cl (2×50 mL), dried (MgSO$_4$) and concentrated in vacua. The residue was triturated with TBME (1×30 mL) and the resultant solid was filtered, rinsing with TBME, and dried in vacuo to afford the title compound (1.04 g, 24% over 2 steps) as a tan solid.

$^1$H NMR (Chloroform-d) δ 8.52-8.48 (m, 1H), 7.48-7.44 (m, 2H), 7.07-7.02 (m, 4H), 6.84-6.77 (m, 4H), 4.31 (s, 4H), 3.80 (s, 6H).

Step C: 2-Isopropyl-N,N-bis(4-methoxybenzyl)pyridine-4-sulfonamide

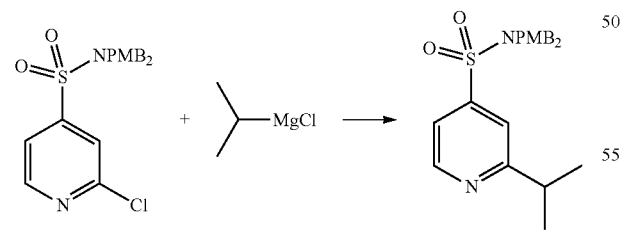

A suspension of 2-chloro-N,N-bis(4-methoxybenzyl) pyridine-4-sulfonamide (0.30 g, 0.69 mmol) and Ni(dppp) Cl2 (96 mg, 0.177 mmol) in dry THF (7 mL) was stirred for 10 minutes and then treated dropwise with $^i$PrMgCl (2 M in THF, 0.7 mL, 1.40 mmol). The resultant suspension was stirred at room temperature for 16 hours. HCl (1 M, 5 mL) and EtOAc (20 mL) were added and the organic layer was collected. The aqueous was extracted with EtOAc (2×20 mL). The combined organic extracts were washed with brine (20 mL), dried (MgSO$_4$) and concentrated in vacuo. The crude product was purified by chromatography on silica gel (12 g column, 0-2.5% MeOH/DCM) to afford the title compound (0.268 g, 83%) as a yellow solid.

$^1$H NMR (Chloroform-d) δ 8.71-8.67 (m, 1H), 7.45-7.41 (m, 2H), 7.03-6.96 (m, 4H), 6.80-6.75 (m, 4H), 4.29 (s, 4H), 3.78 (s, 6H), 3.10 (sept, J=6.9 Hz, 1H), 1.30 (d, J=6.9 Hz, 6H).

LCMS; m/z 441.0 (M+H)$^+$(ES$^+$).

Step D: 2-Isopropylpyridine-4-sulfonamide

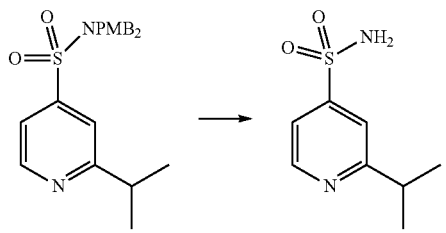

2-Isopropyl-N,N-bis(4-methoxybenzyl)pyridine-4-sulfonamide (260 mg, 0.555 mmol) was treated with TFA (3 mL, 38.9 mmol) and the resultant yellow solution was stirred at room temperature for 6$_3$ hours. TFA (3 mL, 38.9 mmol) was added and stirred for 5 hours. The reaction was concentrated in vacua and azeotroped with DCM (3×5 mL). The crude product was purified by chromatography on silica gel (4 g column, 0-10% MeOH/DCM) to afford the title compound (100 mg, 86%) as a sticky pale pink solid.

$^1$H NMR (DMSO-d$_6$) δ 8.74 (d, J=5.1 Hz, 1H), 7.65 (m, 3H), 7.60-7.56 (m, $^1$H), 3.14 (sept, J=6.8 Hz, 1H), 1.26 (d, J=6.9 Hz, 6H).

LCMS; m/z 201.1 (M+H)$^+$(ES$^+$); 199.1 (M–H)$^-$(ES$^-$).

SYNTHESIS OF EXAMPLES

Example 1: N-((1,2,3,5,6,7-Hexahydro-s-indacen-4-yl)carbamoyl)pyrazine-2-sulfonamide, potassium salt

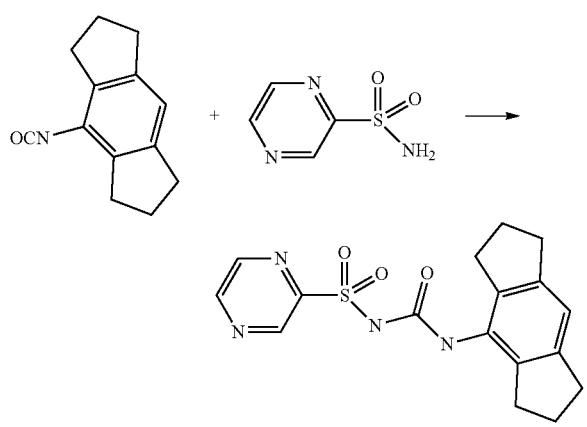

To a cooled (0° C.) solution of pyrazine-2-sulfonamide (55 mg, 0.35 mmol) in tetrahydrofuran (2 mL) was added potassium tert-butoxide (43 mg, 0.38 mmol). The ice bath was removed and the reaction mixture was stirred whilst being allowed to warm to room temperature over 40 minutes. A solution of 4-isocyanato-1,2,3,5,6,7-hexahydro-s-indacene (intermediate A1; 76 mg, 0.38 mmol) in THF (1 mL) was added followed by further THF (2 mL; to aid stirring) and the mixture was stirred overnight at room temperature. The resulting formed precipitate was collected by filtration and washed with THF (1 mL). The material was triturated with ethyl acetate (2 mL) for 1 hour, filtered and dried in vacuo to afford the title compound (84 mg; 67%) as a white solid.

$^1$H NMR (DMSO-$d_6$) δ 8.96 (d, 1H), 8.59 (m, 2H), 7.52 (s, 1H), 6.73 (s, 1H), 2.7 (t, 4H), 2.58 (t, 4H) and 1.85 (m, 4H).

LCMS: m/z 359 (M+H)$^+$(ES$^+$); 357 (M−H)$^-$(ES$^-$).

Example 2: N-((1,2,3,5,6,7-Hexahydro-s-indacen-4-yl)carbamoyl)pyridazine-3-sulfonamide, Potassium Salt

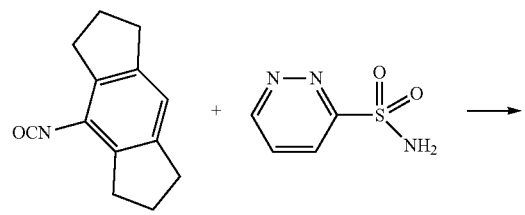

Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1) and pyridazine-3-sulfonamide except that the final reaction mixture was concentrated in vacua, water (2 mL) and TBME (2 mL) were added and the resulting suspension was filtered, but no solid was isolated. Therefore, the layers were separated and the product containing aqueous fraction was washed with TBME (2 mL) and ethyl acetate (2 mL) and subsequently submitted for purification by reversed phase column chromatography to afford the title compound (2.7%) as a white solid.

$^1$H NMR (DMSO-$d_6$) δ 9.16 (m, 1H), 7.99 (d, 1H), 7.71 (m, 1H), 7.53 (s, 1H), 6.73 (s, 1H), 2.7 (t, 4H), 2.58 (t, 4H) and 1.85 (m, 4H).

LCMS: m/z 359 (M+H)$^+$(ES$^+$); 357 (M−H)$^-$(ES$^-$).

Example 3: N-((1,2,3,5,6,7-Hexahydro-s-indacen-4-yl)carbamoyl) pyrimidine-2-sulfonamide, Potassium Salt

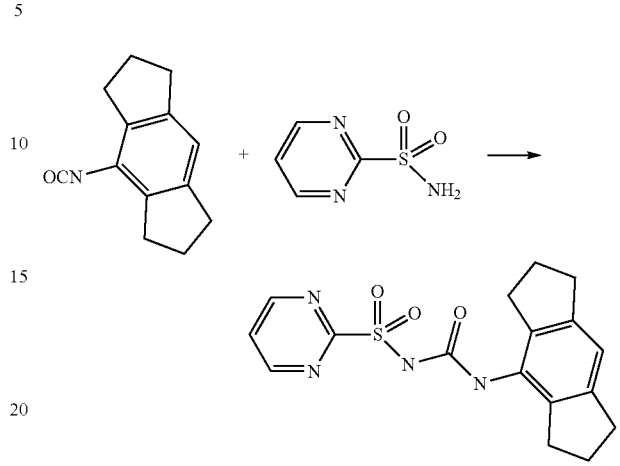

Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1) and pyrimidine-2-sulfonamide. The resulting mixture was concentrated in vacuo and submitted for purification by reversed phase column chromatography to afford the title compound (21% yield) as a white solid.

$^1$H NMR (DMSO-$d_6$) δ 8.8 (d, 2H), 7.54 (s, 1H), 7.48 (t, 1H), 6.73 (s, 1H), 2.7 (t, 4H), 2.58 (t, 4H) and 1.85 (m, 4H).

LCMS: m/z 359 (M+H)$^+$(ES$^+$); 357 (M−H)$^-$(ES$^-$).

Example 4: N-((1,2,3,5,6,7-Hexahydro-s-indacen-4-yl)carbamoyl)-6-methylpyridazine-3-sulfonamide, Sodium Salt

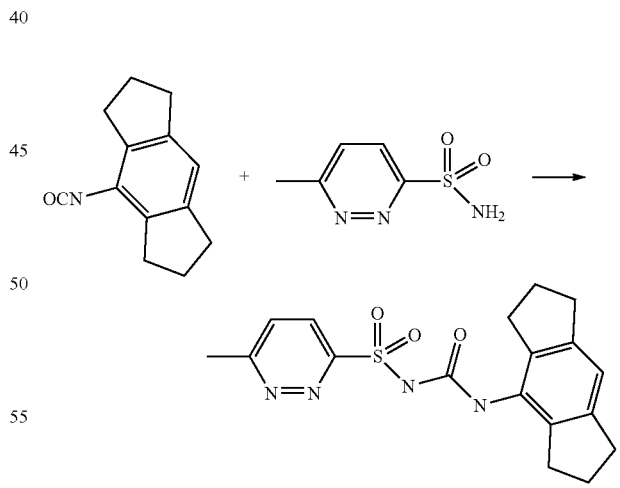

Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1) and 6-methylpyridazine-3-sulfonamide except that sodium tert-butoxide was used as the base. The final mixture was concentrated in vacua and submitted for purification by reversed phase column chromatography to afford the title compound (7% yield) as a white solid.

$^1$H NMR (CD$_3$OD) δ 8.14 (d, 1H), 7.7 (d, 1H), 6.83 (s, 1H), 2.79 (t, J=7.4 Hz, 4H), 2.72 (s, 3H), 2.68 (t, 4H) and 1.97 (m, 4H).

LCMS: m/z 373 (M+H)$^+$(ES$^+$).

Example 5: N-((2,6-Diisopropylphenyl)carbamoyl)-6-methylpyridazine-3-sulfonamide, Potassium Salt

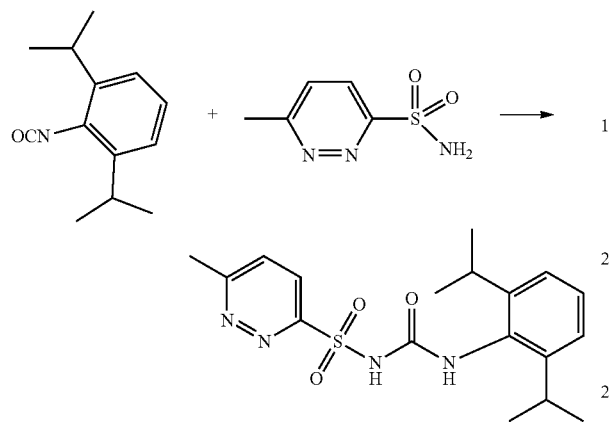

Prepared as described for N-((1,2,3,5,6,7-hexahydro-s-indacen-4-yl)carbamoyl)-pyrazine-2-sulfonamide (example 1) from 2-isocyanato-1,3-diisopropylbenzene (intermediate A2) and 6-methylpyridazine-3-sulfonamide. The mixture was concentrated in vacua and submitted for purification by reversed phase column chromatography which afforded the title compound (6$_9$% yield) as a white solid.

$^1$H NMR (CD$_3$OD) δ 8.17 (d, 1H), 7.68 (d, 1H), 7.02-7.17 (m, 3H), 3.08 (m, 2H), 2.71 (s, 3H) and 1.05 (d, 12H).

LCMS: m/z 377 (M+H)$^+$(ES$^+$); 375 (M−H)$^-$(ES$^-$).

Example 6: N-((2,6-Diisopropylphenyl)carbamoyl)pyrazine-2-sulfonamide, Sodium Salt

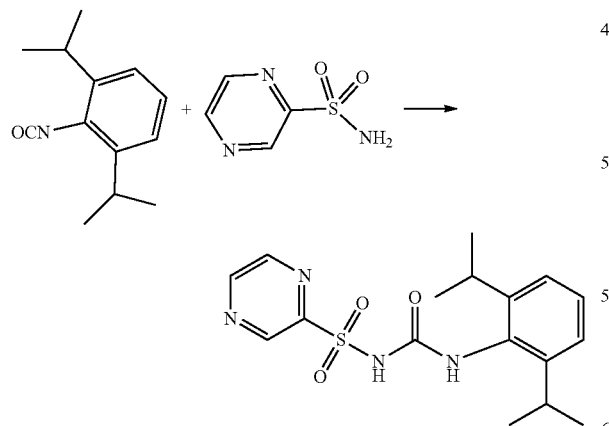

Prepared as described for N-((1,2,3,5,6,7-hexahydro-s-indacen-4-yl)carbamoyl)-pyrazine-2-sulfonamide (example 1) from 2-isocyanato-1,3-diisopropylbenzene (intermediate A2) and pyrazine-2-sulfonamide except that sodium tert-butoxide was used as the base. The residue was purified by means of reversed phase chromatography and the product containing fractions were lyophilized to afford the title compound (44% yield) as a white solid.

$^1$H NMR (D$_2$O): δ 9.0 (s, 1H), 8.7 (m, 2H), 7.3 (br s, 1H), 7.2 (m, 1H), 7.1 (d, 2H), 2.9 (m, 2H), 1.0 (d, 6H) and 0.9 (d, 6H).

LCMS: m/z 363 (M+H)$^+$(ES$^+$); 361 (M−H)$^-$(ES$^-$).

Example 7: N-((2,6-Diisopropylphenyl)carbamoyl)pyridazine-3-sulfonamide, Sodium Salt

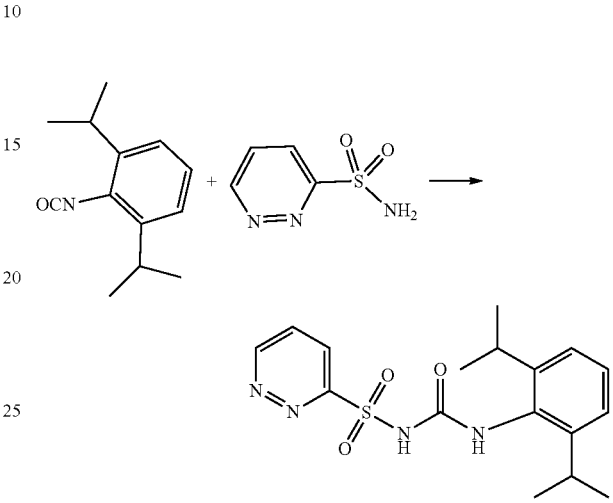

Prepared as described for N-((1,2,3,5,6,7-hexahydro-s-indacen-4-yl)carbamoyl)-pyrazine-2-sulfonamide (example 1) from 2-isocyanato-1,3-diisopropylbenzene (intermediate A2) and pyridazine-3-sulfonamide except that NaOtBu was used as the base. The residue was purified by means of reversed phase chromatography and the product containing fractions were lyophilized to afford the title compound (50% yield) as a white solid.

$^1$H NMR (D$_2$O): δ 9.2 (d, J=4.7 Hz, 1H), 8.0 (d, J=7.6 Hz, 1H), 7.7 (m, J=5.3 Hz, and 70.6 Hz, 1H), 7.3 (br s, 1H), 7.1 (m, J=7.0 Hz, 1H), 7.0 (d, J=7.6 Hz, 2H), 3.1 (m, 2H) and 1.0 (m, 12H).

LCMS: m/z 363 (M+H)$^+$(ES$^+$); 361 (M−H)$^-$(ES$^-$).

Example 8: N-((1,2,3,5,6,7-Hexahydro-s-indacen-4-yl)carbamoyl)-3-methoxypyrazine-2-sulfonamide, Potassium Salt

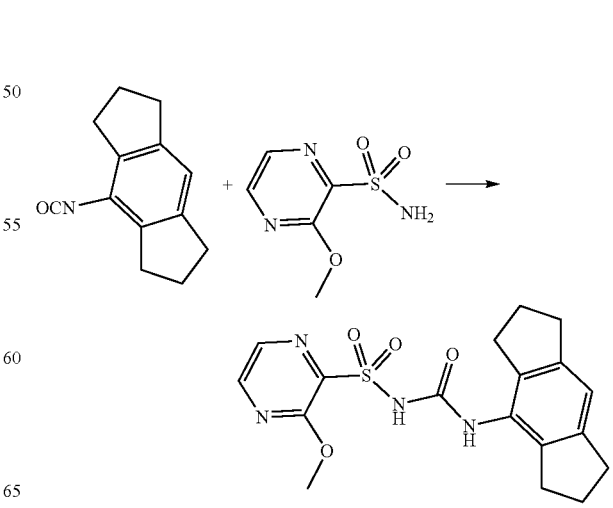

Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1) and 3-methoxypyrazine-2-sulfonamide, except that the reaction mixture was concentrated in vacuo and water (2 mL) was added. The suspension was filtered over cotton wool and subsequently submitted for purification by reversed phase column chromatography to afford the title compound (27%) as a white solid.

$^1$H NMR (D$_2$O) δ 8.22 (d, 1H), 8.07 (d, 1H), 6.92 (s, 1H), 3.97 (s, 3H), 2.7 (t, 4H), 2.55 (t, 4H) and 1.87 (m, 4H).

LCMS: m/z 389 (M+H)$^+$(ES$^+$); 387 (M–H)$^-$(ES$^-$).

Example 9: 2-Amino-N-((1,2,3,5,6,7-hexahydro-s-indacen-4-yl)carbamoyl) pyrimidine-5-sulfonamide, Potassium Salt

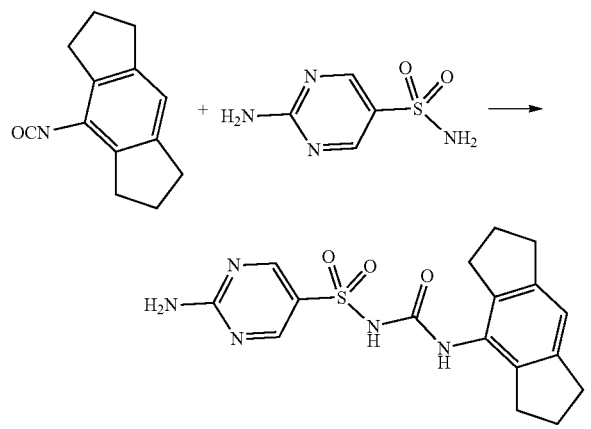

Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1; 1.5 equiv. compared to sulfonamide), 2-aminopyrimidine-5-sulfonamide and potassium tert-butoxide (2 mole equiv.) to afford the title compound (4%) as a white solid.

$^1$H NMR (CD$_3$OD) δ 8.68 (s, 2H), 6.83 (s, 1H), 2.8 (t, 4H), 2.7 (t, 4H) and 1.97 (m, 4H).

LCMS: m/z 374 (M+H)$^+$(ES$^+$); 372 (M–H)$^-$(ES$^-$).

Example 10: N-((1,2,3,5,6,7-Hexahydro-s-indacen-4-yl)carbamoyl) pyrimidine-5-sulfonamide, Potassium Salt

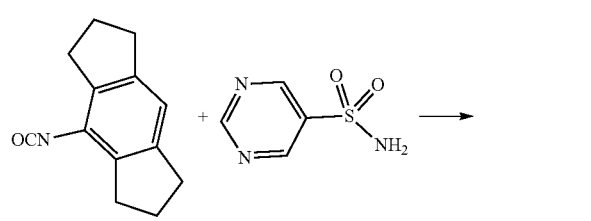

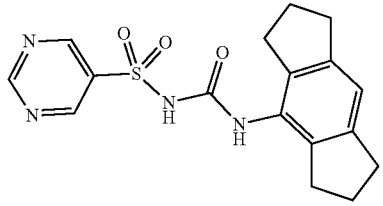

Prepared as described for N-((1,2,3,5,6,7-hexahydro-s-indacen-4-yl)carbamoyl)-3-methoxypyrazine-2-sulfonamide (example 8) from 4-isocyanato-1,2,3,5,6,7-hexahydro-s-indacene (intermediate A1) and pyrimidine-5-sulfonamide to afford the title compound (8%) as a white solid.

$^1$H NMR (CD$_3$OD) δ 9.19 (s, 1H), 9.18 (d, 2H), 6.83 (s, 1H), 2.8 (t, 4H), 2.7 (t, 4H) and 1.97 (m, 4H).

LCMS: m/z 359 (M+H)$^+$(ES$^+$); 357 (M–H)$^-$(ES$^-$).

Example 11: 6-Chloro-N-((1,2,3,5,6,7-hexahydro-s-indacen-4-yl)carbamoyl) pyridazine-3-sulfonamide, Potassium Salt

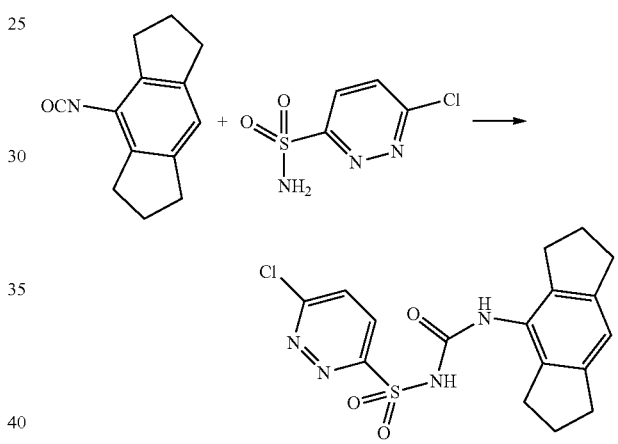

Prepared as described for N-((1,2,3,5,6,7-hexahydro-s-indacen-4-yl)carbamoyl)-pyrazine-2-sulfonamide (example 8) from 4-isocyanato-1,2,3,5,6,7-hexahydro-s-indacene (intermediate A1) and 6-chloropyridazine-3-sulfonamide (intermediate P3) to afford the title compound (48%) as a white solid.

$^1$H NMR (D$_2$O): δ 8.15 (d, J=8.8 Hz, 1H), 7.94 (d, 1H), 6.98 (s, 1H), 2.75 (t, 4H), 2.57 (t, 4H), 1.91 (m, 4H).

LCMS: m/z 393 (M+H)$^+$(ES$^+$); 391 (M–H)$^-$(ES$^-$).

Example 12: N-((1,2,3,5,6,7-Hexahydro-s-indacen-4-yl)carbamoyl)-3,6-di methoxypyridazine-4-sulfonamide, potassium salt

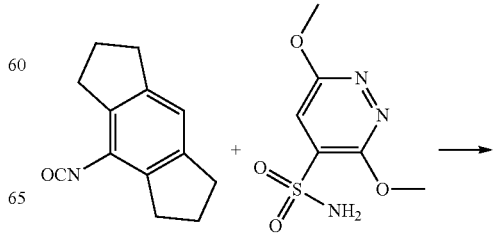

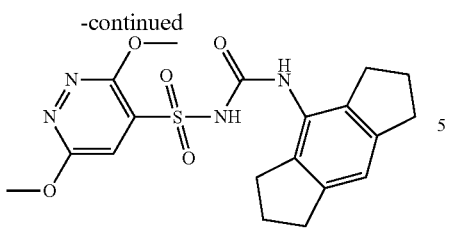

Prepared as described for N-((1,2,3,5,6,7-hexahydro-s-indacen-4-yl)carbamoyl)-pyrazine-2-sulfonamide (example 8) from (intermediate A1) and 3,6-dimethoxypyridazine-4-sulfonamide (intermediate P4) to afford the title compound (94%) as a white solid.

$^1$H NMR (D$_2$O): δ 7.47 (s, 1H), 6.98 (s, 1H), 4.02 (S, 3H), 3.95 (s, 3H), 2.75 (t, 4H), 2.59 (t, 4H) and 1.92 (m, 4H).
LCMS: m/z 419 (M+H)$^+$(ES$^+$); 417 (M−H)$^−$(ES$^−$).

Example 13: 6-(Dimethylamino)-N-((1,2,3,5,6,7-hexahydro-s-indacen-4-yl)carbamoyl)pyridazine-3-sulfonamide, potassium salt

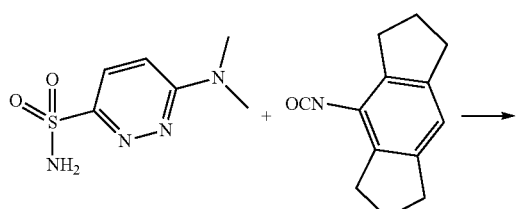

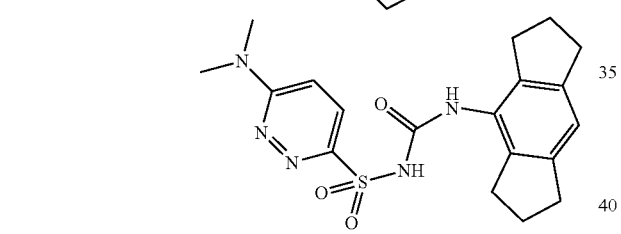

Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1) and 6-(dimethylamino)pyridazine-3-sulfonamide (intermediate P5) to afford the title compound (48%) as a white solid.

$^1$H NMR (D$_2$O): δ 7.73 (d, 1H), 7.10 (d, 1H), 6.97 (s, 1H), 3.05 (s, 6H), 2.75 (t, 4H), 2.57 (t, 4H) and 1.91 (m, 4H).
LCMS: m/z 402 (M+H)$^+$(ES$^+$).

Example 14: 3-(Difluoromethyl)-N-((1,2,3,5,6,7-hexahydro-s-indacen-4-yl)carbamoyl)pyrazine-2-sulfonamide, potassium salt

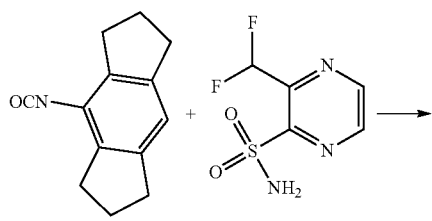

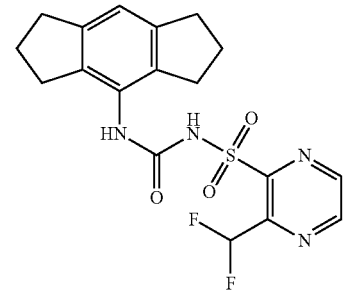

Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1) and 3-(difluoromethyl)-2-pyrazinesulfonamide to afford the title compound (34%) as a white solid.

$^1$H NMR (CD$_3$OD) δ 8.82 (d, 1H), 8.77 (d, 1H), 7.84 (t, 1H), 6.83 (s, 1H), 2.8 (t, 4H), 2.7 (t, 4H) and 1.97 (m, 4H).
LCMS: m/z 409 (M+H)$^+$(ES$^+$); 407 (M−H)$^−$(ES$^−$).

Example 15: N-((1,2,3,5,6,7-Hexahydro-s-indacen-4-yl)carbamoyl)-2-methoxypyridine-3-sulfonamide, Potassium Salt Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1) and 2-methoxypyridine-3-sulfonamide to afford the title compound (24%) as a white solid.

$^1$H NMR (CD$_3$OD) δ 8.22 (d, 2H), 7.01 (m, 1H), 6.83 (s, 1H), 4.03 (s, 3H), 2.8 (t, 4H), 2.7 (t, 4H) and 1.97 (m, 4H).
LCMS: m/z 388 (M+H)$^+$(ES$^+$); 386 (M−H)$^−$(ES$^−$).

Example 16: N-((1,2,3,5,6,7-Hexahydro-s-indacen-4-yl)carbamoyl)-5-(trifluoromethyl)pyridazine-3-sulfonamide, Potassium Salt

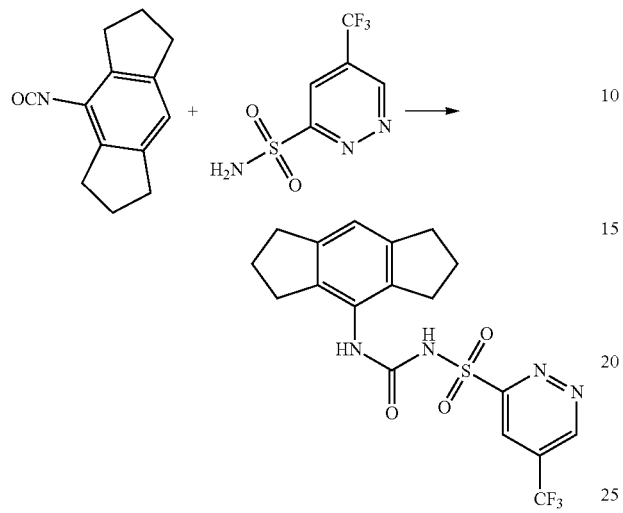

Prepared as described for N-((1,2,3,5,6,7-hexahydro-s-indacen-4-yl)carbamoyl)-pyrazine-2-sulfonamide (example 1) from 4-isocyanato-1,2,3,5,6,7-hexahydro-s-indacene (intermediate A1) and 5-(trifluoromethyl) pyridazine-3-sulfonamide to afford the title compound (54%) as a white solid.

¹H NMR (CD₃OD) δ 9.59 (s, 1H), 8.53 (s, 1H), 6.83 (s, 1H), 2.8 (t, 4H), 2.7 (t, 4H) and 1.97 (m, 4H).

LCMS: m/z 427 (M+H)⁺(ES⁺); 425 (M−H)⁻(ES⁻).

Example 17: N-((1,2,3,5,6,7-Hexahydro-s-indacen-4-yl)carbamoyl)-4-methyl pyrimidine-2-sulfonamide, Potassium Salt

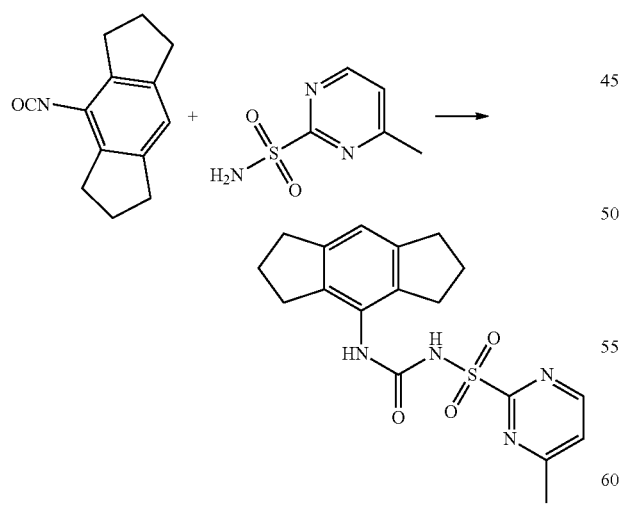

To a cooled (0° C.) solution of 4-methylpyrimidine-2-sulfonamide (68 mg, 0.39 mmol) in THF (2.5 mL) was added potassium tert-butoxide (44 mg, 0.39 mmol). The ice bath was removed and the reaction mixture was stirred whilst being allowed to warm to room temperature over 40 minutes. A solution of 4-isocyanato-1,2,3,5,6,7-hexahydro-s-indacene (intermediate A1; 78 mg, 0.39 mmol) in THF (1 mL) was added and the mixture was stirred overnight at room temperature. The reaction mixture was concentrated in vacuo and DMSO (1 mL) was added. The suspension was filtered over cotton wool and subsequently purified by reversed phase column chromatography (see General Methods, "Purification Method 1" above) to afford the title compound (39 mg; 27%) as a white solid.

¹H NMR (CD₃OD) δ 8.67 (d, 1H), 7.4 (d, 1H), 6.84 (s, 1H), 2.78 (m, 8H), 2.59 (s, 3H) and 1.98 (m, 4H).

LCMS: m/z 373 (M+H)⁺(ES⁺).

Example 18: N-((1,2,3,5,6,7-Hexahydro-s-indacen-4-yl)carbamoyl)-4,6-dimethyl pyrimidine-2-sulfonamide, Potassium Salt

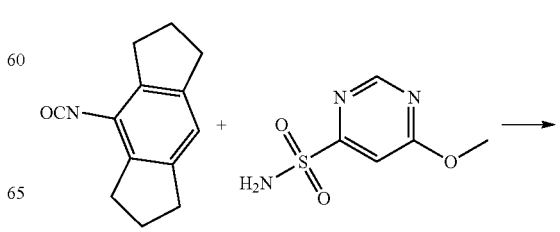

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 4,6-dimethylpyrimidine-2-sulfonamide to afford the title compound (38%) as a white solid.

¹H NMR (CD₃OD) δ 7.28 (s, 1H), 6.84 (s, 1H), 2.78 (m, 8H), 2.53 (s, 6H) and 1.98 (m, 4H).

LCMS: m/z 387 (M+H)⁺(ES⁺); 385 (M−H)⁻(ES⁻).

Example 19: N-((1,2,3,5,6,7-Hexahydro-s-indacen-4-yl)carbamoyl)-6-methoxypyrimidine-4-sulfonamide, Potassium Salt

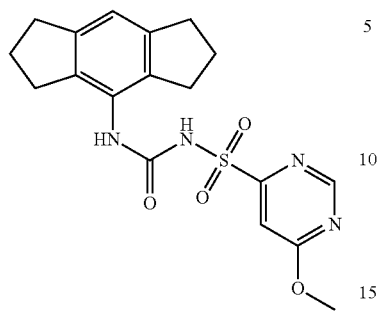

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 6-methoxypyrimidine-4-sulfonamide to afford the title compound (12%) as a white solid.

$^1$H NMR (CD$_3$OD) δ 8.76 (s, 1H), 7.36 (s, 1H), 6.85 (s, 1H), 4.03 (s, 3H), 2.76 (m, 8H), and 1.98 (m, 4H).

LCMS: m/z 389 (M+H)$^+$(ES$^+$); 387 (M−H)$^-$(ES$^-$).

Example 20: 6-(N-((1,2,3,5,6,7-Hexahydro-s-indacen-4-yl)carbamoyl)sulfamoyl) pyridazine-3-carboxamide, potassium salt

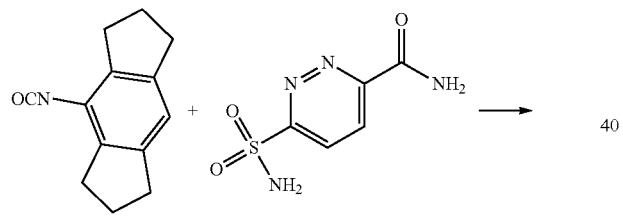

Prepared as described for N-((1,2,3,5,6,7-hexahydro-s-indacen-4-yl)carbamoyl)-4-methyl pyrimidine-2-sulfonamide, potassium salt (example 17), except that 2 eq of KO$^t$Bu were used, furthermore using 4-isocyanato-1,2,3,5,6,7-hexahydro-s-indacene (intermediate A1) and 6-sulfamoylpyridazine-3-carboxamide to afford the title compound (11%) as a white solid.

$^1$H NMR (CD$_3$OD) δ 8.38 (d, 2H), 6.83 (s, 1H), 2.82 (t, 4H), 2.72 (t, 4H) and 1.98 (m, 4H).

LCMS: m/z 402 (M+H)$^+$(ES$^+$).

Example 21: 5-(Dimethylamino)-N-((1,2,3,5,6,7-hexahydro-s-indacen-4-yl)carbamoyl)pyridazine-3-sulfonamide, Potassium Salt

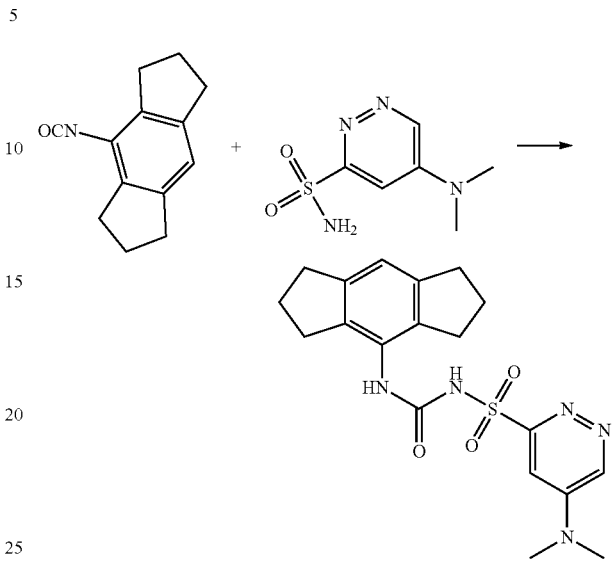

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 5-(dimethylamino)-pyridazine-3-sulfonamide (intermediate P6) to afford the title compound (31%) as a white solid.

$^1$H NMR (CD$_3$OD) δ 8.7 (s, 1H), 7.34 (s, 1H), 6.84 (s, 1H), 3.13 (s, 6H), 2.82 (t, 4H), 2.72 (t, 4H) and 1.98 (m, 4H).

LCMS: m/z 402 (M+H)$^+$(ES$^+$); 400 (M−H)$^-$(ES$^-$).

Example 22: N-((1,2,3,5,6,7-Hexahydro-s-indacen-4-yl)carbamoyl)-6-methoxy pyridazine-3-sulfonamide, Potassium Salt

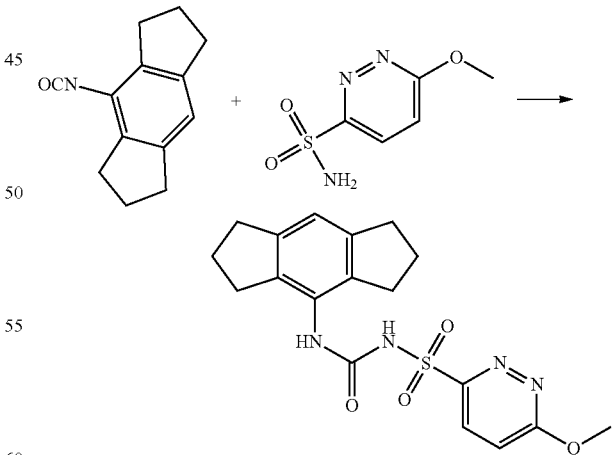

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 6-methoxypyridazine-3-sulfonamide to afford the title compound (56%) as a white solid.

$^1$H NMR (CD$_3$OD) δ 8.11 (d, 1H), 7.22 (d, 1H), 6.84 (s, 1H), 4.17 (s, 3H), 2.82 (t, 4H), 2.72 (t, 4H) and 1.98 (m, 4H).

LCMS: m/z 389 (M+H)$^+$(ES$^+$); 387 (M−H)$^−$(ES$^−$).

Example 23: N-((1,2,3,5,6,7-hexahydro-s-indacen-4-yl)carbamoyl)-6-oxo-1,6-dihydropyridine-3-sulfonamide, Potassium Salt

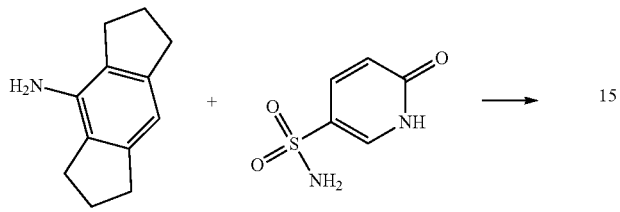

Diphenylcarbonate (107 mg, 0.5 mmol) was dissolved in acetonitrile (5 mL) and to this was added 4-dimethylaminopyridine (123 mg, 1 mmol) and 6-oxo-1,6-dihydropyridine-3-sulfonamide (90 mg, 0.5 mmol). The resultant mixture was heated to reflux for 4 hours and then 1,2,3,5,6,7-hexahydro-s-indacen-4-amine (85 mg, 0.5 mmol) was added and the mixture refluxed overnight. The mixture was cooled to room temperature and potassium tert-butoxide (56 mg, 0.5 mmol) and water (1 mL) were added, the mixture was filtered and the residue was purified by means of reversed phase chromatography and the product containing fractions were lyophilized to afford the title compound (28%) as a white solid.

$^1$H NMR (D$_2$O) δ 7.99 (s, 1H), 7.82 (d, 1H), 6.94 (s, 1H), 6.53 (d, 1H), 2.72 (m, 4H), 2.55 (m, 4H) and 1.87 (m, 4H).

LCMS: m/z 374 (M+H)$^+$(ES$^+$); 372 (M−H)$^−$(ES$^−$).

Example 24: 3-Cyano-N-((1,2,3,5,6,7-hexahydro-s-indacen-4-yl)carbamoyl)pyrazine-2-sulfonamide, Potassium Salt

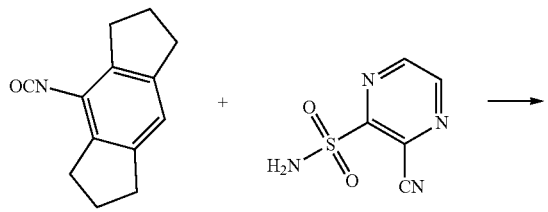

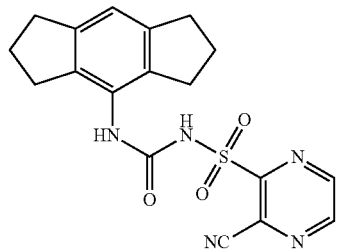

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 3-cyanopyrazine-2-sulfonamide to afford the title compound (2%) as a white solid.

LCMS: m/z 384 (M+H)$^+$(ES$^+$).

Example 25: 5-((2-(Dimethylamino)ethyl)amino)-N-((1,2,3,5,6,7-hexahydro-s-indacen-4-yl)carbamoyl)pyrazine-2-sulfonamide, potassium Salt

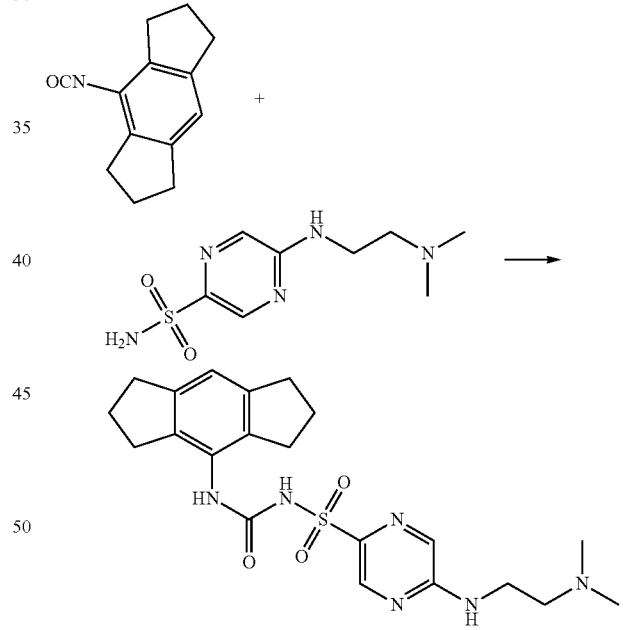

Prepared as described for N-((1,2,3,5,6,7-hexahydro-s-indacen-4-yl)carbamoyl)-4-methyl pyrimidine-2-sulfonamide, potassium salt (example 17) except that 2 eq of KO$^t$Bu were used, furthermore using 4-isocyanato-1,2,3,5,6,7-hexahydro-s-indacene (intermediate A1) and 5-((2-(dimethylamino)ethyl)amino)pyrazine-2-sulfonamide (intermediate P7) to afford the title compound (24%) as a white solid.

$^1$H NMR (CD$_3$OD) δ 8.46 (s, 1H), 7.89 (s, 1H), 6.84 (s, 1H), 3.55 (m, 2H), 2.82 (t, 4H), 2.72 (t, 4H), 2.57 (m, 2H), 2.29 (s, 6H) and 1.98 (m, 4H).

LCMS: m/z 445 (M+H)$^+$(ES$^+$); 443 (M−H)$^−$(ES$^−$).

Example 26: 5-(Dimethylamino)-N-((1,2,3,5,6,7-hexahydro-s-indacen-4-yl)carbamoyl)pyrazine-2-sulfonamide, Potassium Salt

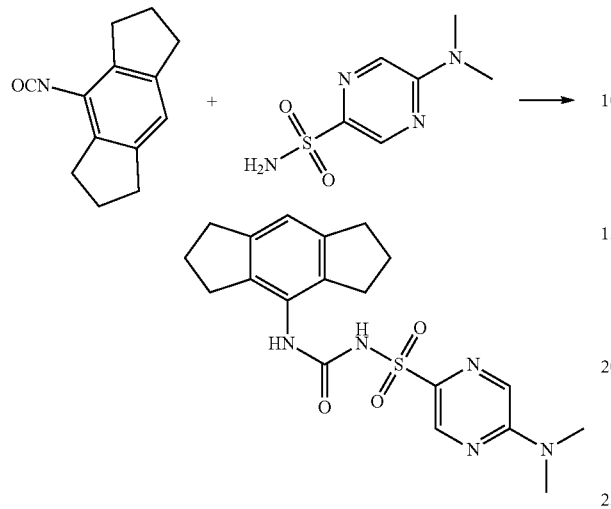

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 5-(dimethylamino)-pyrazine-2-sulfonamide (intermediate P8) to afford the title compound (34%) as a white solid.

$^1$H NMR (CD$_3$OD) δ 8.61 (s, 1H), 8.0 (s, 1H), 6.84 (s, 1H), 3.17 (s, 6H), 2.82 (t, 4H), 2.72 (t, 4H) and 1.98 (m, 4H).
LCMS: m/z 402 (M+H)$^+$(ES$^+$); 400 (M−H)$^−$(ES$^−$).

Example 27: 6-(Dimethylamino)-N-((1,2,3,5,6,7-hexahydro-s-indacen-4-yl)carbamoyl)pyrazine-2-sulfonamide, Potassium Salt

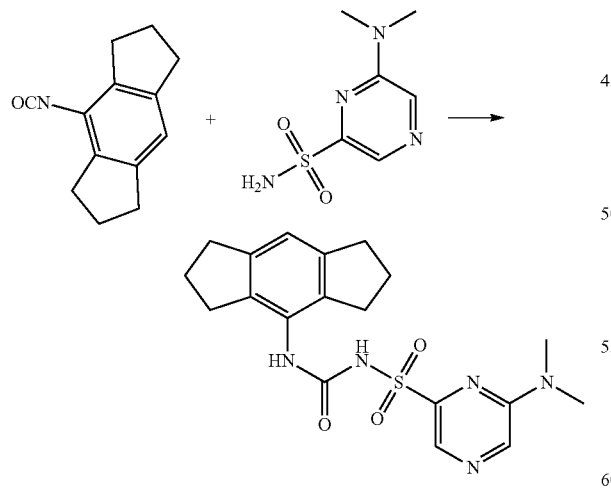

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 6-(dimethylamino)-pyrazine-2-sulfonamide (intermediate P9) to afford the title compound (53%) as a white solid.

$^1$H NMR (CD$_3$OD) δ 8.28 (s, 1H), 8.08 (s, 1H), 6.84 (s, 1H), 3.15 (s, 6H), 2.82 (t, 4H), 2.72 (t, 4H) and 1.98 (m, 4H).
LCMS: m/z 402 (M+H)$^+$(ES$^+$); 400 (M−H)$^−$(ES$^−$).

Example 28: N-((1,2,3,5,6,7-Hexahydro-s-indacen-4-yl)carbamoyl)-6-morpholinopyrazine-2-sulfonamide, Potassium Salt

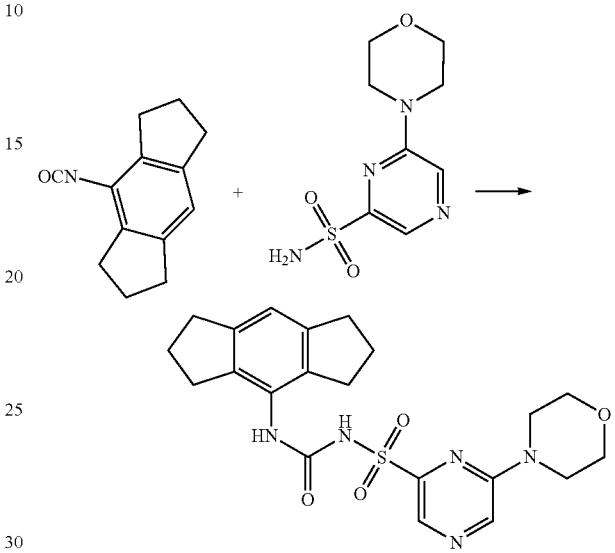

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 6-morpholinopyrazine-2-sulfonamide (intermediate P10) to afford the title compound (52%) as a white solid.

$^1$H NMR (CD$_3$OD) δ 8.36 (s, 1H), 8.23 (s, 1H), 6.84 (s, 1H), 3.74 (m, 4H), 3.63 (m, 4H), 2.82 (t, 4H), 2.72 (t, 4H) and 1.98 (m, 4H).
LCMS: m/z 444 (M+H)$^+$(ES$^+$); 442 (M−H)$^−$(ES$^−$).

Example 29: N-((1,2,3,5,6,7-Hexahydro-s-indacen-4-yl)carbamoyl)-3-methylpyrazine-2-sulfonamide, Potassium Salt

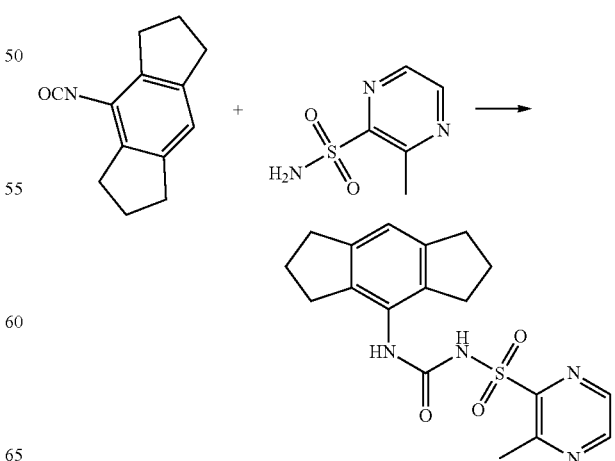

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 3-methylpyrazine-2-sulfonamide to afford the title compound (49%) as a white solid.

$^1$H NMR (CD$_3$OD) δ 8.53 (d, 1H), 8.42 (d, 1H), 6.84 (s, 1H), 2.95 (s, 3H), 2.76 (t, 4H), 2.68 (t, 4H) and 1.98 (m, 4H).

LCMS: m/z 373 (M+H)$^+$(ES$^+$); 371 (M−H)$^-$(ES$^-$).

Example 30: N-((1,2,3,5,6,7-Hexahydro-s-indacen-4-yl)carbamoyl)quinoxaline-2-sulfonamide, Potassium Salt

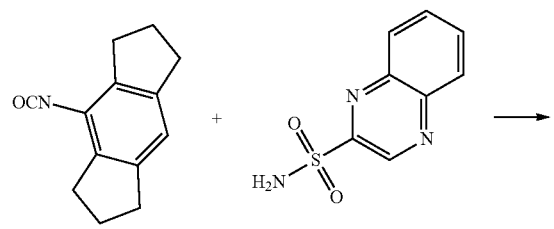

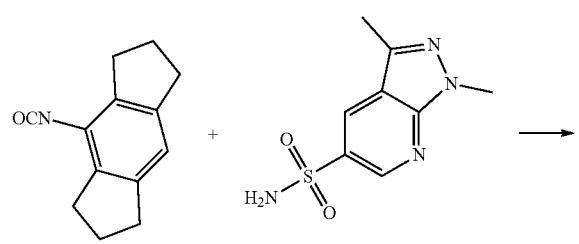

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and quinoxaline-2-sulfonamide to afford the title compound (28%) as a white solid.

$^1$H NMR (CD$_3$OD) δ 9.42 (s, 1H), 8.16 (m, 2H), 7.92 (m, 2H), 6.84 (s, 1H), 2.76 (t, 4H), 2.68 (t, 4H) and 1.9 (m, 4H).

LCMS: m/z 409 (M+H)$^+$(ES$^+$); 407 (M−H)$^-$(ES$^-$).

Example 31: N-((1,2,3,5,6,7-Hexahydro-s-indacen-4-yl)carbamoyl)-1,3-dimethyl-1H-pyrazolo[3,4-b]pyridine-5-sulfonamide, Potassium Salt

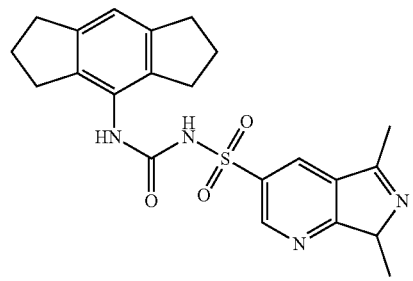

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 1,3-dimethyl-1H-pyrazolo[3,4-b]pyridine-5-sulfonamide to afford the title compound (9%) as a white solid.

$^1$H NMR (CD$_3$OD) δ 9.03 (s, 1H), 8.68 (d, 1H), 6.82 (s, 1H), 4.04 (s, 3H), 2.78 (m, 8H), 2.57 (s, 3H) and 1.98 (m, 4H).

LCMS: m/z 426 (M+H)$^+$(ES$^+$); 424 (M−H)$^-$(ES$^-$).

Example 32: 4-Ethoxy-N-((1,2,3,5,6,7-hexahydro-s-indacen-4-yl)carbamoyl)pyridine-3-sulfonamide, Potassium Salt

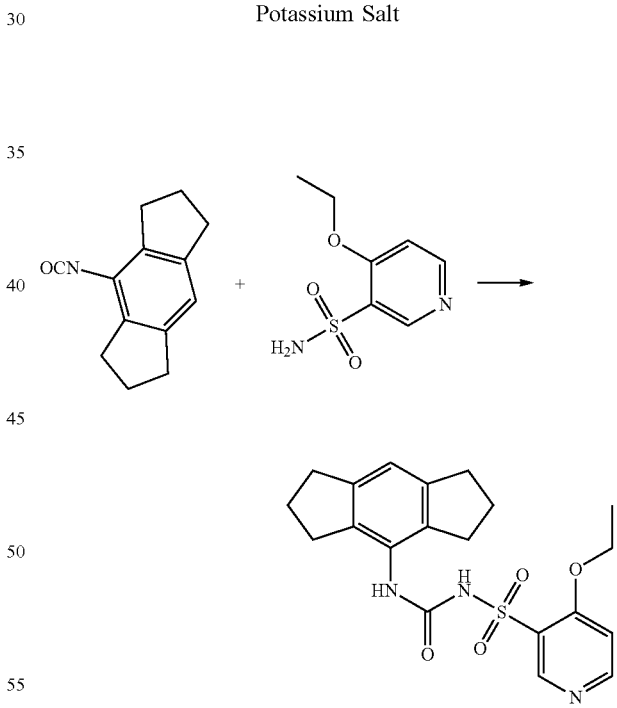

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 4-ethoxypyridine-3-sulfonamide to afford the title compound (26%) as a white solid.

$^1$H NMR (CD$_3$OD) δ 8.87 (s, 1H), 8.41 (d, 1H), 7.12 (d, 1H), 6.84 (s, 1H), 4.26 (q, 2H), 2.78 (m, 8H), 1.98 (m, 4H) and 1.48 (t, 3H).

LCMS: m/z 402 (M+H)$^+$(ES$^+$); 400 (M−H)$^-$(ES$^-$).

Example 33: N-((1,2,3,5,6,7-Hexahydro-s-indacen-4-yl)carbamoyl) pyridine-4-sulfonamide, potassium salt

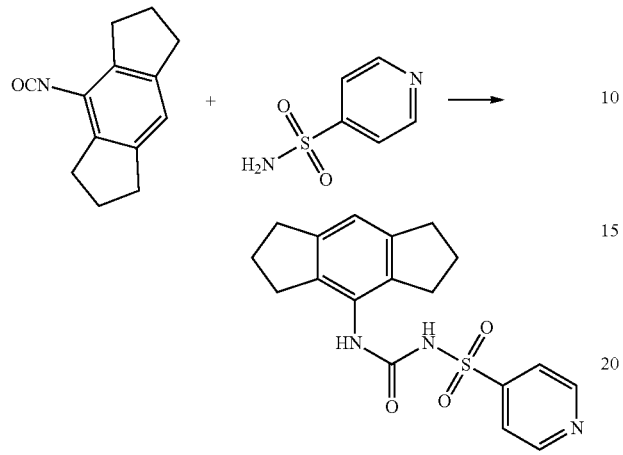

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and pyridine-4-sulfonamide to afford the title compound (50%) as a white solid.

$^1$H NMR (CD$_3$OD) δ 8.64 (d, 2H), 7.88 (d, 2H), 6.84 (s, 1H), 2.78 (m, 8H), and 1.98 (m, 4H).

LCMS: m/z 358 (M+H)$^+$(ES$^+$); 356 (M−H)$^-$(ES$^-$).

Example 34: N-((2-(2-Cyanopyridin-4-yl)-4-fluoro-6-isopropylphenyl)carbamoyl)-6-(dimethylamino) pyrazine-2-sulfonamide

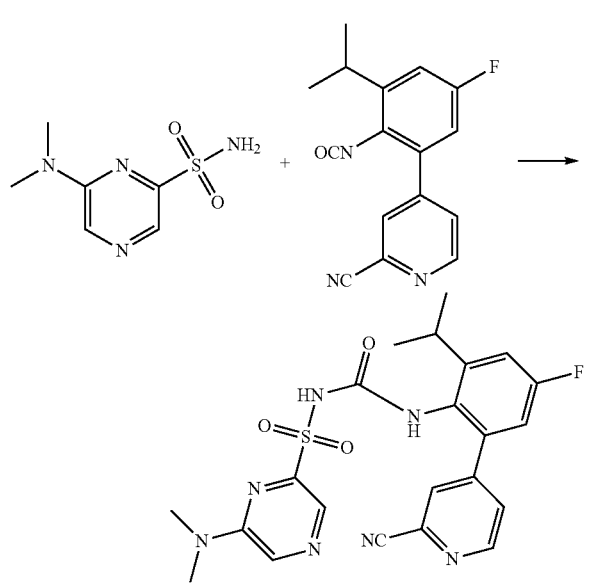

To a solution of 6-(dimethylamino)pyrazine-2-sulfonamide (intermediate P11) (65 mg, 321.41 μmol, 1 eq) in THF (2 mL) was added with t-BuONa (30 mg, 321.41 μmol, 1 eq). The mixture was stirred at 25° C. for 30 minutes. Then 4-(5-fluoro-2-isocyanato-3-isopropylphenyl)picolinonitrile (intermediate A3) (90 mg, 321.41 μmol, 1 eq) was added and the resulting mixture was stirred at 70° C. for 10 minutes. The reaction mixture was concentrated in vacuo. The residue was purified by prep-HPLC (column: Waters Xbridge C18, 150 mm*50 mm*10 μm; mobile phase: [A: water (0.05% ammonia hydroxide v/v); B: MeCN]; B %: 18%-48%, 11.5 min) to give the title compound (75.35 mg, 48% yield, 100% purity on LCMS) as a white solid.

$^1$H NMR (DMSO-d$_6$): δ 8.57 (d, 1H), 8.05 (s, 1H), 7.96 (s, 1H), 7.64 (br s, 1H), 7.20-7.14 (m, 4H), 3.19-3.15 (m, 1H), 3.07 (s, 6H) and 1.08 (d, 6H).

LCMS: m/z 484.2 (M+H)$^+$(ES$^+$).

Example 35: 6-(Dimethylamino)-N-((4-fluoro-2-isopropyl-6-(2-methoxypyridin-4-yl)phenyl)carbamoyl)pyrazine-2-sulfonamide

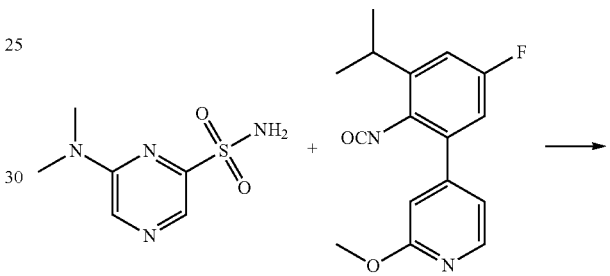

To a solution of 6-(dimethylamino) pyrazine-2-sulfonamide (intermediate P11) (65 mg, 321.41 μmol, 1 eq) in THF (2 mL) was added with t-BuONa (30 mg, 321.41 μmol, 1 eq). The mixture was stirred at 25° C. for 30 minutes. Then 4-(5-fluoro-2-isocyanato-3-isopropylphenyl)-2-methoxypyridine (intermediate A4) (92 mg, 321.41 μmol, 1 eq) was added. The mixture was stirred at 70° C. for 10 minutes and then concentrated in vacua. The residue was purified by prep-HPLC (column: Waters Xbridge C18, 150 mm*50 mm*10 μm; mobile phase: [A: water(10 mM NH$_4$HCO$_3$); B: MeCN]; B %: 20%-50%, 11.5 min) to give the title compound (41.48 mg, 26% yield, 100% purity on LCMS) as a white solid.

$^1$H NMR (DMSO-d$_6$): δ 8.27 (s, 1H), 8.10 (s, 1H), 8.05 (d, 1H), 7.74 (br s, 1H), 7.14 (d, 1H), 6.97 (d, 1H), 6.91 (s, 1H), 6.76 (s, 1H), 3.87 (s, 3H), 3.11 (s, 6H), 3.04-2.95 (m, 1H) and 1.25-1.02 (m, 6H).

LCMS: m/z 489.2 (M+H)$^+$(ES$^+$).

Example 36: 6-(Dimethylamino)-N-((5-(2-methoxy-pyridin-4-yl)-2,3-dihydro-1H-inden-4-yl)carbamoyl)pyrazine-2-sulfonamide

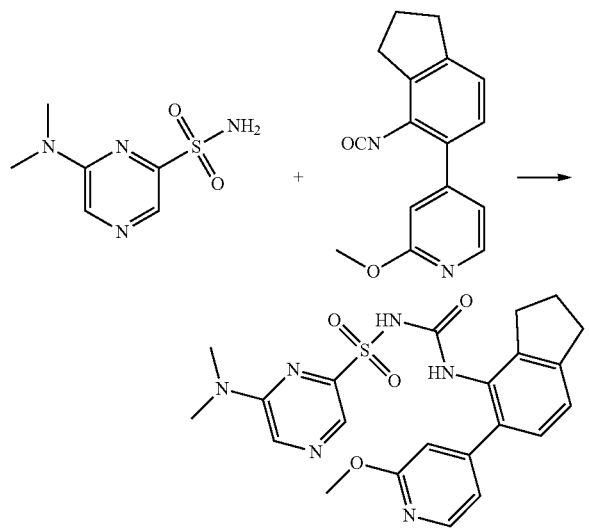

To a solution of 6-(dimethylamino) pyrazine-2-sulfonamide (intermediate P11) (65 mg, 321.41 μmol, 1 eq) in THF (2 mL) was added with t-BuONa (30 mg, 321.41 μmol, 1 eq). The mixture was stirred at 25° C. for 30 minutes. Then 4-(4-isocyanato-2,3-dihydro-1H-inden-5-yl)-2-methoxypyridine (intermediate A5) (85 mg, 321.41 μmol, 1 eq) was added. The mixture was stirred at 70° C. for 10 minutes and then concentrated in vacua. The residue was purified by prep-HPLC (column: Waters Xbridge C18, 150 mm*50 mm*10 μm; mobile phase: [A: water(10 mM NH$_4$HCO$_3$); B: MeCN]; B %: 18%-48%, 11.5 min) to give the title compound (96.47 mg, 64% yield, 100% purity on LCMS) as a white solid.

$^1$H NMR (DMSO-d$_6$): δ 8.23 (s, 1H), 8.14 (s, 1H), 8.06 (d, 1H), 7.65 (br s, 1H), 7.13 (d, 1H), 7.06 (d, 1H), 6.90 (d, 1H), 6.74 (s, 1H), 3.87 (s, 3H), 3.09 (s, 6H), 2.89 (t, 2H), 2.71-2.67 (m, 2H) and 2.00-1.91 (m, 2H).

LCMS: m/z 469.2 (M+H)$^+$(ES$^+$).

Example 37: 6-(Dimethylamino)-N-((7-fluoro-5-(pyridin-4-yl)-2,3-dihydro-1H-inden-4-yl)carbamoyl)pyrazine-2-sulfonamide

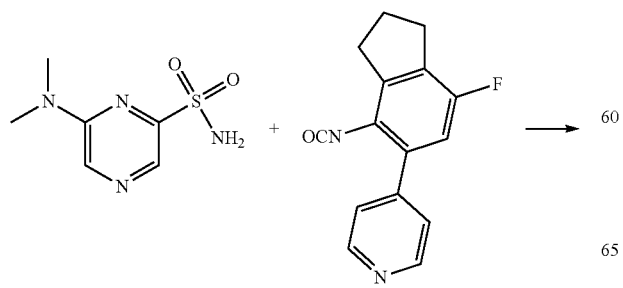

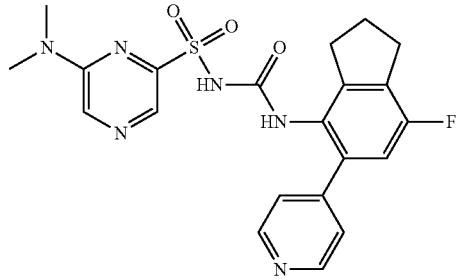

A mixture of 6-(dimethylamino)pyrazine-2-sulfonamide (intermediate P11) (60 mg, 296.69 μmol, 1 eq) and t-BuONa (29 mg, 296.69 μmol, 1 eq) in THF (2 mL) was stirred at 25° C. for 10 minutes. Then 4-(7-fluoro-4-isocyanato-2,3-dihydro-1H-inden-5-yl)pyridine (intermediate A6) (75 mg, 296.69 μmol, 1 eq) was added. The mixture was stirred at 25° C. for 10 minutes and then concentrated in vacua. The residue was purified by prep-HPLC (column: Waters Xbridge C18, 150 mm*25 mm*5 μm; mobile phase: [A: water (0.05% ammonia hydroxide v/v); B: MeCN]; B %: 5%-35%, 10 min) to give the title compound (10 mg, 7% yield, 100% purity on LCMS) as a white solid.

$^1$H NMR (DMSO-d$_6$): δ 11.13 (br s, 1H), 8.50 (d, 2H), 8.30 (s, 1H), 8.15 (s, 1H), 7.83 (br s, 1H), 7.30 (d, 2H), 6.98 (d, 1H), 3.11 (s, 6H), 2.94 (t, 2H), 2.73-2.69 (m, 2H) and 2.08-2.00 (m, 2H).

LCMS: m/z 457.2 (M+H)$^+$(ES$^+$).

Example 38: N-((2-(2-Cyanopyridin-4-yl)-4-fluoro-6-isopropylphenyl)carbamoyl)-5-(dimethylamino)pyrazine-2-sulfonamide

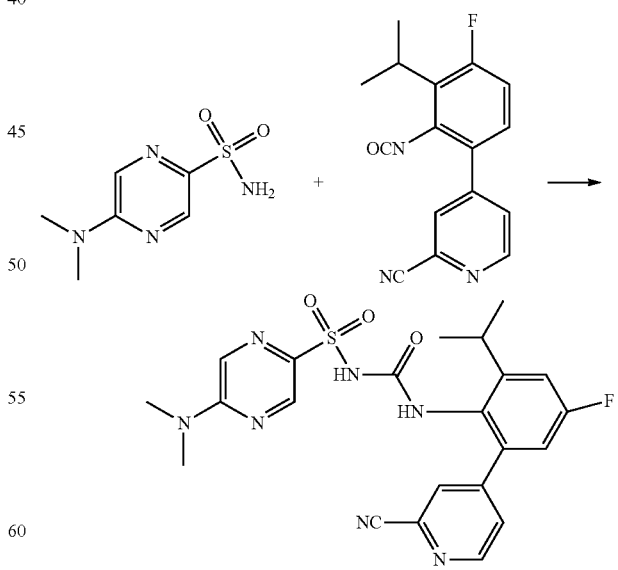

To a solution of 5-(dimethylamino)pyrazine-2-sulfonamide (intermediate P12) (60 mg, 296.69 μmol, 1 eq) in THF (4 mL) was added t-BuONa (29 mg, 296.69 μmol, 1 eq) and 4-(5-fluoro-2-isocyanato-3-isopropylphenyl)picolinonitrile (intermediate A3) (83 mg, 296.69 µmol, 1 eq). The mixture was stirred at 25° C. for 30 minutes and then concentrated under reduced pressure. The residue was purified by prep-HPLC (column: Phenomenex Gemini C18, 150 mm*25 mm*10 µm; mobile phase: [A: water (0.05% ammonia hydroxide v/v); B: MeCN]; B %: 5%-35%, 11.5 min) to give the title compound (49 mg, 34% yield, 100% purity on LCMS) as a white solid.

¹H NMR (DMSO-d₆): δ 8.58 (d, 1H), 8.24 (s, 1H), 7.99 (s, 1H), 7.9² (s, 1H), 7.78 (br s, 1H), 7.60 (s, 1H), 7.20 (dd, 1H), 7.06 (dd, 1H), 3.18 (s, 6H), 3.14-1.09 (m, 1H) and 1.10 (d, 6H).

LCMS: m/z 484.2 (M+H)⁺(ES⁺).

Example 39: 5-(Dimethylamino)-N-((4-fluoro-2-isopropyl-6-(2-methoxypyridin-4-yl)phenyl)carbamoyl)pyrazine-2-sulfonamide

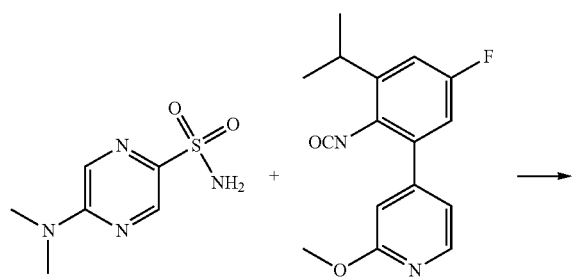

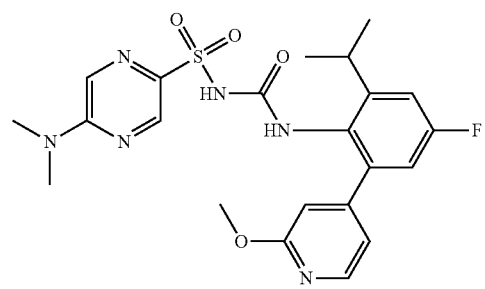

To a solution of 5-(dimethylamino)pyrazine-2-sulfonamide (intermediate P12) (71 mg, 349.28 µmol, 1 eq) in THF (5 mL) was added t-BuONa (34 mg, 349.28 µmol, 1 eq) and 4-(5-fluoro-2-isocyanato-3-isopropylphenyl)-2-methoxypyridine (intermediate A4) (100 mg, 349.28 µmol, 1 eq). The mixture was stirred at 25° C. for 30 minutes and then concentrated under reduced pressure. The residue was purified by prep-HPLC (column: Phenomenex Gemini C18, 150 mm*25 mm*5 µm; mobile phase: [A: water (0.05% ammonia hydroxide v/v); B: MeCN]; B %: 0%-30%, 10 min) to give the title compound (30 mg, 18% yield, 100% purity on LCMS) as a white solid.

¹H NMR (DMSO-d₆): δ 8.40 (s, 1H), 8.12 (s, 1H), 8.06 (d, 1H), 7.73 (br s, 1H), 7.16 (dd, 1H), 6.99-6.96 (m, 1H), 6.82 (d, 1H), 6.72 (s, 1H), 3.87 (s, 3H), 3.18 (s, 6H), 2.95-2.91 (m, 1H) and 1.12-0.95 (m, 6H).

LCMS: m/z 489.3 (M+H)⁺(ES⁺).

Example 40: 5-(Dimethylamino)-N-((5-(2-methoxypyridin-4-yl)-2,3-dihydro-1H-inden-4-yl)carbamoyl)pyrazine-2-sulfonamide

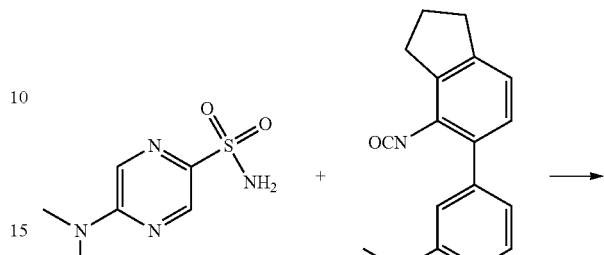

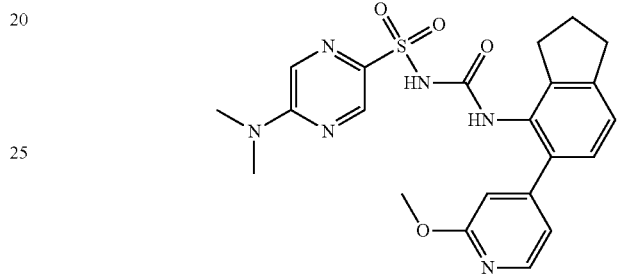

To a solution of 5-(dimethylamino)pyrazine-2-sulfonamide (intermediate P12) (70 mg, 346.13 µmol, 1 eq) in THF (5 mL) was added t-BuONa (33 mg, 346.13 µmol, 1 eq) and 4-(4-isocyanato-2,3-dihydro-1H-inden-5-yl)-2-methoxypyridine (intermediate A5) (92 mg, 346.13 µmol, 1 eq). The mixture was stirred at 25° C. for 30 minutes and then concentrated under reduced pressure. The residue was purified by prep-HPLC (column: Phenomenex Gemini C18, 150 mm*25 mm*10 µm; mobile phase: [A: water (0.05% ammonia hydroxide v/v); B: MeCN]; B %: 2%-32%, 11.5 min) to give the title compound (40 mg, 24% yield, 98.92% purity on LCMS) as a white solid.

¹H NMR (DMSO-d₆): δ 8.46-8.41 (m, 1H), 8.09-8.07 (t, 2H), 7.60 (br s, 1H), 7.13 (d, 1H), 7.05 (d, 1H), 6.82 (d, 1H), 6.68 (s, 1H), 3.86 (s, 3H), 3.16 (s, 6H), 2.88 (t, 2H), 2.65 (t, 2H) and 1.99-1.91 (m, 2H).

LCMS: m/z 469.3 (M+H)⁺(ES⁺).

Example 41: 5-(Dimethylamino)-N-((7-fluoro-5-(pyridin-4-yl)-2,3-dihydro-1H-inden-4-yl)carbamoyl)pyrazine-2-sulfonamide

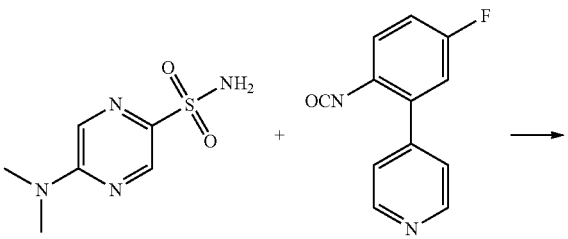

-continued

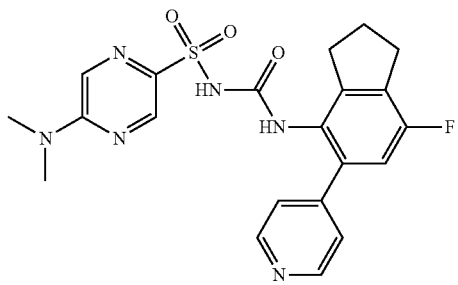

To a mixture of 5-(dimethylamino)pyrazine-2-sulfonamide (intermediate P12) (80 mg, 393.30 µmol, 1 eq) in THF (5 mL) was added t-BuONa (41 mg, 432.63 µmol, 1.1 eq) in one portion at 15° C. Then the reaction mixture was stirred for 15 minutes. Then a solution of 4-(7-fluoro-4-isocyanato-2,3-dihydro-1H-inden-5-yl)pyridine (intermediate A6) (100 mg, 393.3 µmol, 1 eq) in THF (2 mL) was added. The resulting mixture was stirred at 15° C. for 30 minutes and then concentrated under reduced pressure. The residue was purified by prep-HPLC (column: Waters Xbridge C18, 150 mm*25 mm*5 µm; mobile phase: [A: water (0.05% ammonia hydroxide v/v); B: MeCN]; B %: 5%-35%, 10 min) to give the title compound (72.57 mg, 40%) as an off-white solid.

$^1$H NMR (DMSO-d$_6$): δ 8.49 (d, 2H), 8.40 (s, 1H), 8.07 (s, 1H), 7.54 (br s, 1H), 7.28 (d, 2H), 6.93 (d, 1H), 3.16 (s, 6H), 2.93 (t, 2H), 2.74 (t, 2H) and 2.07-1.99 (m, 2H).

LCMS: m/z 457.2 (M+H)$^+$(ES$^+$).

Example 42: N-((2-(2-Cyanopyridin-4-yl)-4-fluoro-6-isopropylphenyl) carbamoyl)-3-(difluoromethyl)pyrazine-2-sulfonamide

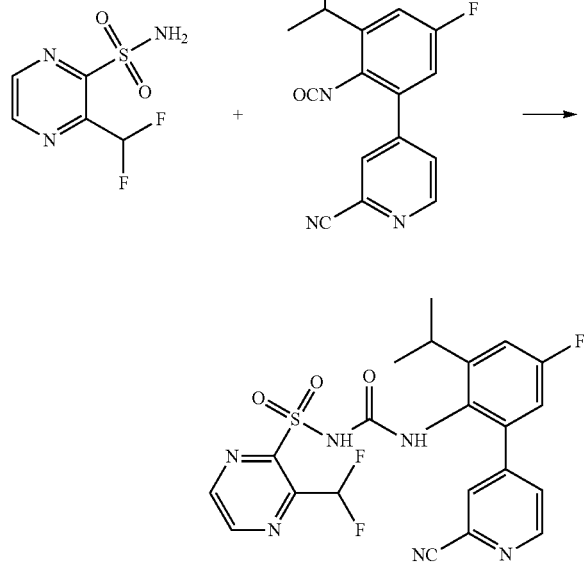

To a solution of 3-(difluoromethyl)pyrazine-2-sulfonamide (intermediate P13) (74 mg, 355.51 µmol, 1 eq) in THF (4 mL) was added t-BuONa (34 mg, 355.51 µmol, 1 eq) and 4-(5-fluoro-2-isocyanato-3-isopropylphenyl)picolinonitrile (intermediate A3) (0.1 g, 355.51 µmol, 1 eq). The mixture was stirred at 25° C. for 10 minutes and then concentrated in vacuo. The residue was purified by prep-HPLC (column: Phenomenex Gemini C18, 150 mm*25 mm*10 µm; mobile phase: [A: water (0.05% NH$_4$HCO$_3$); B: MeCN]; B %: 20%-50%, 12 min) to give the title compound (13.20 mg, 7% yield, 98.3% purity on LCMS) as a white solid.

$^1$H NMR (DMSO-d$_6$+D$_2$O): δ 8.75-8.61 (m, 2H), 8.45 (d, 1H), 7.95-7.59 (m, 2H), 7.48 (d, 1H), 7.19-7.13 (m, 1H), 7.12-6.95 (m, 1H), 3.20-3.04 (m, 1H) and 1.19-0.93 (m, 6H).

LCMS: m/z 491.2 (M+H)$^+$(ES$^+$).

Example 43: 3-(Difluoromethyl)-N-((4-fluoro-2-isopropyl-6-(2-methoxypyridin-4-yl)phenyl)carbamoyl)pyrazine-2-sulfonamide

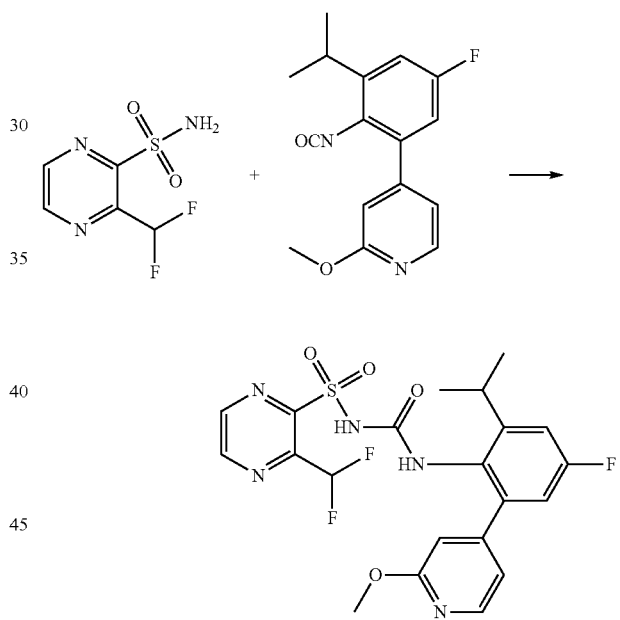

To a solution of 3-(difluoromethyl)pyrazine-2-sulfonamide (intermediate P13) (73 mg, 34928 µmol, 1 eq) in THF (4 mL) was added t-BuONa (34 mg, 349.28 µmol, 1 eq) and 4-(5-fluoro-2-isocyanato-3-isopropylphenyl)-2-methoxypyridine (intermediate A4) (100 mg, 349.28 µmol, 1 eq). The mixture was stirred at 25° C. for 10 minutes and then concentrated in vacuo. The residue was purified by prep-HPLC (column: Phenomenex Gemini C18, 150 mm*25 mm*10 µm; mobile phase: [A: water (0.05% NH$_4$HCO$_3$); B: MeCN]; B %: 17%-47%, 12 min) to give the title compound (14.57 mg, 8% yield, 98.6% purity on LCMS) as a white solid.

$^1$H NMR (DMSO-d$_6$+D$_2$O): δ 8.82-8.76 (m, 2H), 7.98-7.65 (m, 2H), 7.15-7.00 (m, 1H), 6.88-6.86 (m, 1H), 6.79 (d, 1H), 6.61 (s, 1H), 3.82-3.79 (m, 3H), 3.19-2.93 (m, 1H) and 1.21-0.97 (m, 6H).

LCMS: m/z 496.2 (M+H)$^+$(ES$^+$).

Example 44: 3-(Difluoromethyl)-N-((5-(2-methoxy-pyridin-4-yl)-2,3-dihydro-1H-inden-4-yl)carbamoyl)pyrazine-2-sulfonamide

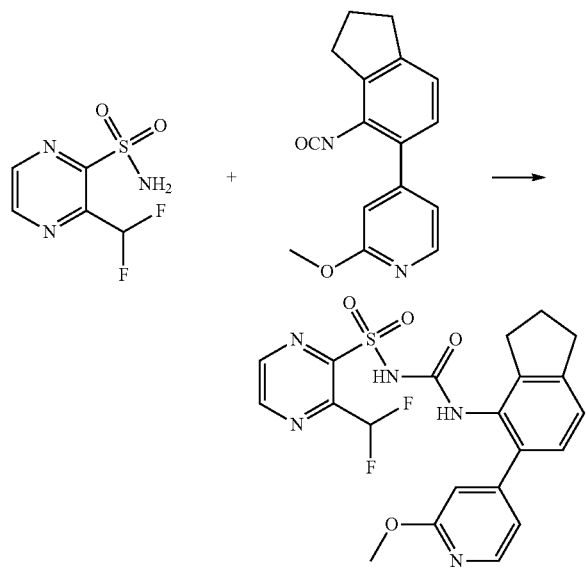

To a solution of 3-(difluoromethyl)pyrazine-2-sulfonamide (intermediate P13) (75 mg, 358.55 μmol, 1 eq) in THF (5 mL) was added t-BuONa (34 mg, 358.55 μmol, 1 eq) and 4-(4-isocyanato-2,3-dihydro-1H-inden-5-yl)-2-methoxypyridine (intermediate A5) (95 mg, 358.55 μmol, 1 eq). The mixture was stirred at 10° C. for 1 hour and then concentrated in vacua. The residue was purified by prep-HPLC (column: Phenomenex Gemini C18, 150 mm*25 mm*10 μm; mobile phase: [A: water(10 mM NH$_4$HCO$_3$); B: MeCN]; B %: 15%-45%, 12 min) to give the title compound (24.17 mg, 14% yield, 100% purity on LCMS) as a white solid.

$^1$H NMR (DMSO-d$_6$): δ 8.78 (s, 2H), 8.15-7.87 (m, 2H), 7.07 (d, 1H), 7.00 (d, 1H), 6.85-6.83 (m, 1H), 6.67 (s, 1H), 6.06 (br s, 1H), 3.85 (s, 3H), 2.88-2.84 (m, 2H), 2.68-2.63 (m, 2H) and 1.96-1.90 (m, 2H).

LCMS: m/z 476.2 (M+H)$^+$(ES$^+$).

Example 45: 3-(Difluoromethyl)-N-((7-fluoro-5-(pyridin-4-yl)-2,3-dihydro-1H-inden-4-yl)carbamoyl)pyrazine-2-sulfonamide

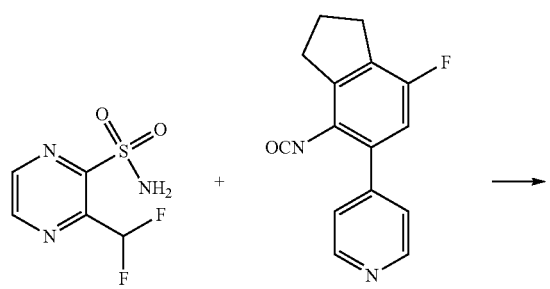

-continued

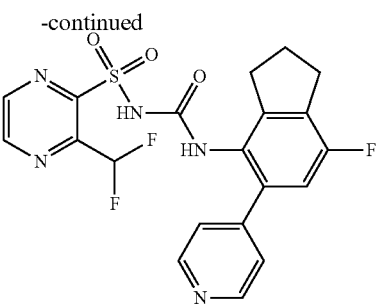

To a solution of 3-(difluoromethyl)pyrazine-2-sulfonamide (intermediate P13) (82.27 mg, 393.30 μmol, 1 eq) in THF (5 mL) was added t-BuONa (42 mg, 432.63 μmol, 1.1 eq) and a solution of 4-(7-fluoro-4-isocyanato-2,3-dihydro-1H-inden-5-yl)pyridine (intermediate A6) (100 mg, 393.30 μmol, 1 eq) in THF (5 mL) and DCM (5 mL). The reaction mixture was stirred at 16° C. for 0.5 hour and then concentrated in vacua. The residue was purified by prep-HPLC (column: Phenomenex Gemini C18, 150 mm*25 mm*10 μm; mobile phase: [A: water (0.05% NH$_4$HCO$_3$); B: MeCN]; B %: 15%-45%, 10 min) to give the title compound (25.31 mg, 14%) as a light yellow solid.

$^1$H NMR (DMSO-d$_6$+D$_2$O): δ 8.89 (s, 1H), 8.85 (d, 1H), 8.49 (d, 2H), 7.76 (t, 1H), 7.45-7.25 (m, 2H), 6.96 (d, 1H), 2.92 (t, 2H), 2.72-2.67 (m, 2H) and 2.05-2.01 (m, 2H).

LCMS: m/z 464.1 (M+H)$^+$(ES$^+$).

Example 46: N-((2-(2-Cyanopyridin-4-yl)-4-fluoro-6-isopropylphenyl)carbamoyl)-4,6-dimethylpyrimidine-2-sulfonamide

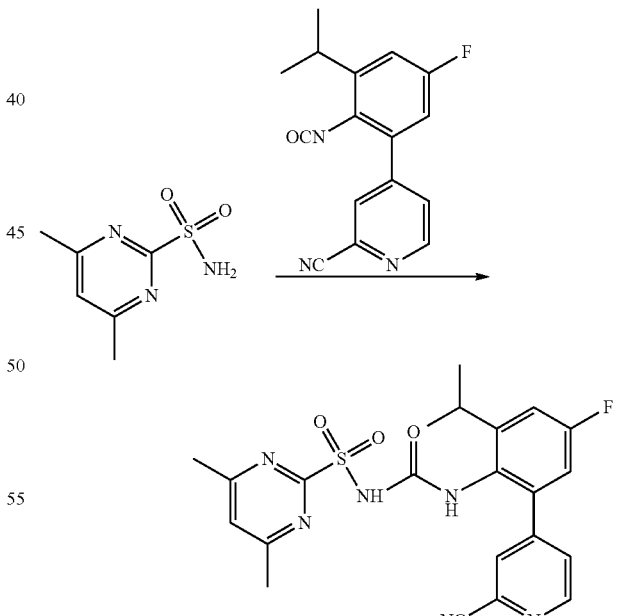

To a mixture of 4,6-dimethylpyrimidine-2-sulfonamide (intermediate P14) (65 mg, 347.19 μmol, 1 eq) in THF (5 mL) was added t-BuONa (33 mg, 347.19 μmol, 1 eq) in one portion at 25° C. under N$_2$. Then the reaction mixture was stirred for 10 minutes. Then 4-(5-fluoro-2-isocyanato-3-isopropylphenyl)picolinonitrile (intermediate A3) (98 mg, 347.19 μmol, 1 eq) was added. The resulting mixture was heated to 70° C. and stirred for 10 minutes. The reaction mixture was concentrated in vacua. The residue was purified by prep-HPLC (column: Phenomenex Gemini C18, 150 mm*25 mm*10 μm; mobile phase: [A: water (10 mM NH₄HCO₃); B: MeCN]; B %: 12%-42%, 10 min) to give the title compound (19.94 mg, 12% yield, 100% purity on LCMS) as a white solid.

¹H NMR (DMSO-d₆): δ 8.69-8.68 (m, 1H), 8.02 (s, 1H), 7.71-7.69 (m, 1H), 7.35-7.33 (m, 1H), 7.25-7.20 (m, 1H), 7.13-7.09 (m, 2H), 3.33-3.16 (m, 1H), 2.43 (s, 6H) and 1.10 (d, 6H).

LCMS: m/z 469.2 (M+H)⁺(ES⁺).

Example 47: N-((4-Fluoro-2-isopropyl-6-(2-methoxypyridin-4-yl)phenyl)carbamoyl)-4,6-dimethylpyrimidine-2-sulfonamide

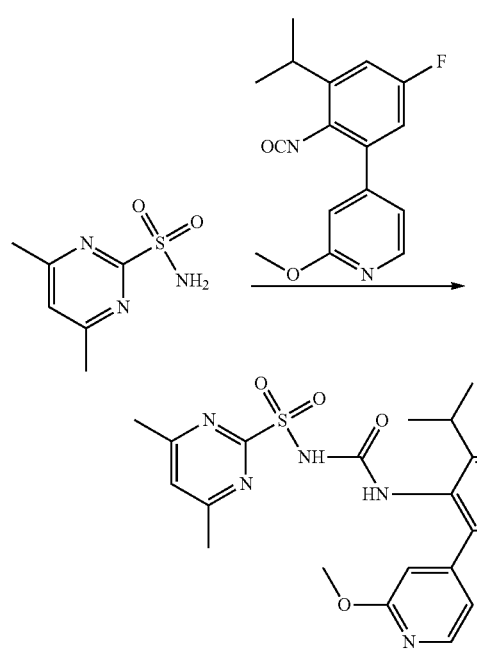

To a mixture of 4,6-dimethylpyrimidine-2-sulfonamide (intermediate P14) (65 mg, 349.28 μmol, 1 eq) in THF (5 mL) was added t-BuONa (34 mg, 349.28 μmol, 1 eq) in one portion at 25° C. under N₂. Then the reaction mixture was stirred for 10 minutes. Then 4-(5-fluoro-2-isocyanato-3-isopropylphenyl)-2-methoxypyridine (intermediate A4) (100 mg, 349.28 μmol, 1 eq) was added. The reaction mixture was heated to 70° C. and stirred for 10 minutes. The reaction mixture was concentrated in vacua. The residue was purified by prep-HPLC (column: Waters Xbridge C18, 150 mm*50 mm*10 μm; mobile phase: [A: water (0.05% ammonia hydroxide v/v); B: MeCN]; B %: 5%-35%, 11.5 min) to give the title compound (60.47 mg, 37% yield, 100% purity on LCMS) as a white solid.

¹H NMR (DMSO-d₆): δ 8.11-8.07 (m, 1H), 7.85 (br s, 1H), 7.42-7.39 (m, 1H), 7.18-7.12 (m, 1H), 7.05-6.94 (m, 2H), 6.76 (s, 1H), 3.90 (s, 3H), 3.12-3.08 (m, 1H), 2.46 (s, 6H) and 1.14-1.07 (m, 6H).

LCMS: m/z 474.2 (M+H)⁺(ES⁺).

Example 48: N-((5-(2-Methoxypyridin-4-yl)-2,3-dihydro-1H-inden-4-yl)carbamoyl)-4,6-dimethylpyrimidine-2-sulfonamide

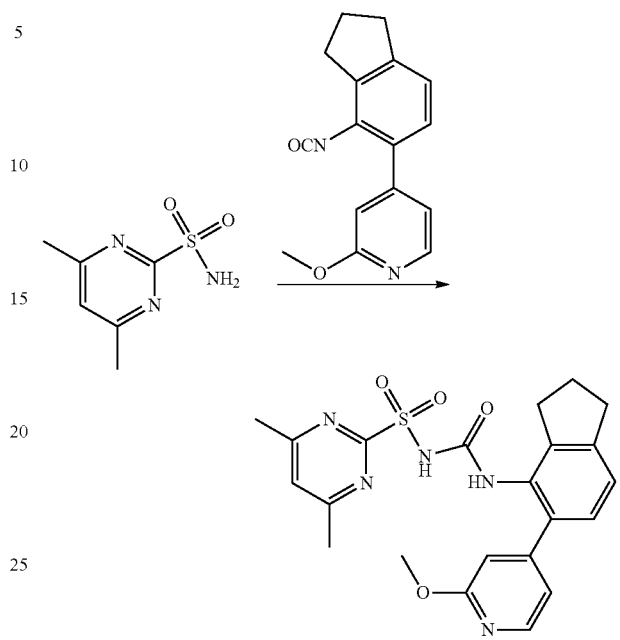

To a mixture of 4,6-dimethylpyrimidine-2-sulfonamide (intermediate P14) (70 mg, 375.52 μmol, 1 eq) in THF (5 mL) was added t-BuONa (36 mg, 375.52 μmol, 1 eq) in one portion at 25° C. under N₂. Then the reaction mixture was stirred for 10 minutes. Then 4-(4-isocyanato-2,3-dihydro-1H-inden-5-yl)-2-methoxypyridine (intermediate A5) (100 mg, 375.52 μmol, 1 eq) was added. The reaction mixture was heated to 70° C. and stirred for 10 minutes. The reaction mixture was concentrated in vacua. The residue was purified by prep-HPLC (column: Waters Xbridge C18, 150 mm*50 mm*10 μm; mobile phase: [A: water (0.05% ammonia hydroxide v/v); B: MeCN]; B %: 2%-32%, 11.5 min) to give the title compound (41.33 mg, 24% yield, 98.29% purity on LCMS) as a white solid.

¹H NMR (DMSO-d₆): δ 8.10 (d, 1H), 7.32-7.30 (m, 1H), 7.11 (d, 1H), 7.05 (d, 1H), 6.98 (d, 1H), 6.76 (s, 1H), 3.86 (s, 3H), 2.87 (t, 2H), 2.76-2.73 (m, 2H), 2.49 (s, 6H) and 1.98-1.93 (m, 2H).

LCMS: m/z 454.2 (M+H)⁺(ES⁺).

Example 49: N-((7-Fluoro-5-(pyridin-4-yl)-2,3-dihydro-1H-inden-4-yl)carbamoyl)-4,6-dimethylpyrimidine-2-sulfonamide

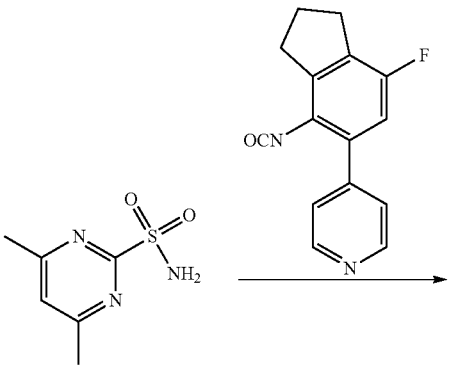

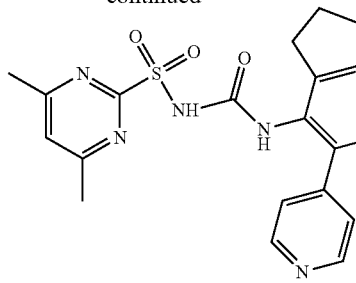

To a mixture of 4,6-dimethylpyrimidine-2-sulfonamide (intermediate P14) (50 mg, 267.07 μmol, 1 eq) in THF (3 mL) was added t-BuONa (26 mg, 267.07 μmol, 1 eq) in one portion at 25° C. under $N_2$. Then the reaction mixture was stirred for 10 minutes. Then 4-(7-fluoro-4-isocyanato-indan-5-yl) pyridine (intermediate A6) (68 mg, 267.07 μmol, 1 eq) was added. The reaction mixture was stirred at 25° C. for 10 minutes and then concentrated in vacua. The residue was purified by prep-HPLC (column: Waters Xbridge C18, 150 mm*25 mm*5 μm; mobile phase: [A: water (0.05% ammonia hydroxide v/v); B: MeCN]; B %: 5%-35%, 10 min) to give the title compound (22.84 mg, 19% yield, 97.11% purity on LCMS) as a white solid.

$^1$H NMR (DMSO-d$_6$): δ 8.56 (d, 2H), 7.75 (br s, 1H), 7.39-7.36 (m, 3H), 6.98 (d, 1H), 2.93 (t, 2H), 2.85-2.75 (m, 2H), 2.49 (s, 6H) and 2.06-2.02 (m, 2H).

LCMS: m/z 442.1 (M+H)$^+$(ES$^+$).

Example 50: N-((2-(2-Cyanopyridin-4-yl)-4-fluoro-6-isopropylphenyl)carbamoyl)-5-(dimethylamino) pyridazine-3-sulfonamide

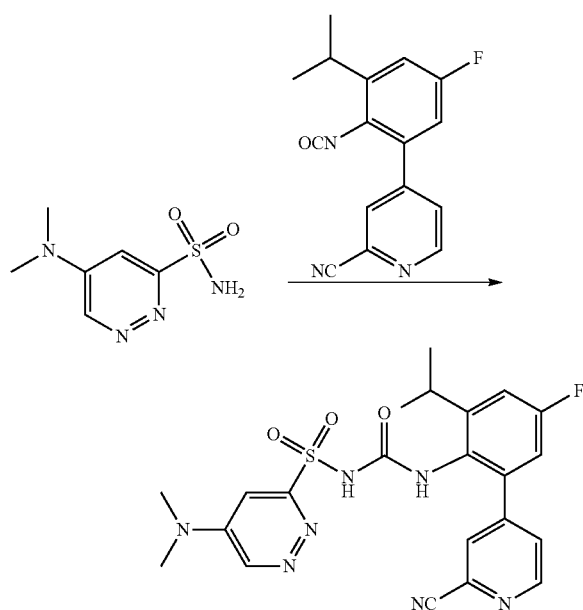

To a mixture of 5-(dimethylamino) pyridazine-3-sulfonamide (intermediate P15) (70 mg, 346.13 μmol, 1 eq) in THF (2 mL) was added t-BuONa (33 mg, 346.13 μmol, 1 eq) in one portion at 25° C. under $N_2$. Then the reaction mixture was stirred for 10 minutes. Then 4-(5-fluoro-2-isocyanato-3-isopropylphenyl)picolinonitrile (intermediate A3) (97 mg, 346.13 μmol, 1 eq) was added. The reaction mixture was stirred at 25° C. for 10 minutes and then concentrated in vacuo. The residue was purified by prep-HPLC (column: Waters Xbridge C18, 150 mm*25 mm*5 μm; mobile phase: [A: water (0.05% ammonia hydroxide v/v); B: MeCN]; B %: 5%-35%, 10 min) to give the title compound (65.88 mg, 39% yield, 99.38% purity on LCMS) as a white solid.

$^1$H NMR (DMSO-d$_6$): δ 8.77 (d, 1H), 8.61-8.59 (m, 1H), 7.94 (s, 1H), 7.87-7.84 (m, 1H), 7.59-7.58 (m, 1H), 7.20-7.17 (m, 1H), 7.07 (dd, 1H), 6.96 (s, 1H), 3.21-3.17 (m, 1H), 3.09 (s, 6H) and 1.15-1.08 (m, 6H).

LCMS: m/z 484.2 (M+H)$^+$(ES$^+$).

Example 51: 5-(Dimethylamino)-N-((4-fluoro-2-isopropyl-6-(2-methoxypyridin-4-yl)phenyl) carbamoyl) pyridazine-3-sulfonamide

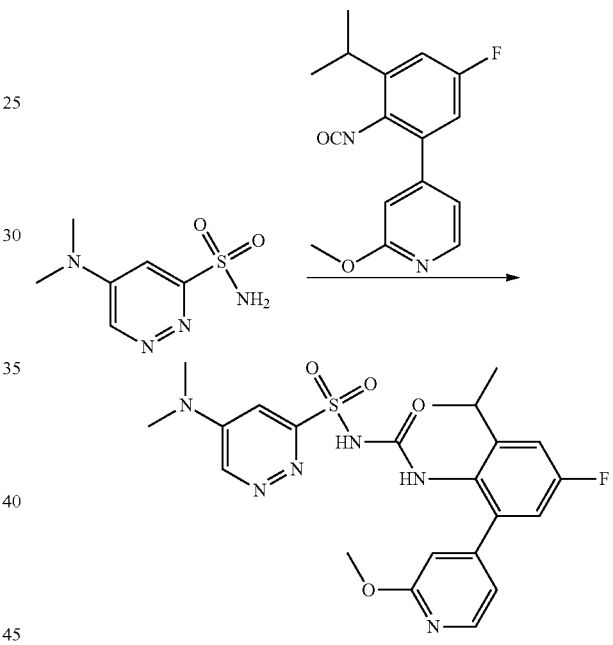

To a mixture of 5-(dimethylamino)pyridazine-3-sulfonamide (intermediate P15) (40 mg, 197.79 μmol, 1 eq) in THF (5 mL) was added t-BuONa (19 mg, 197.79 μmol, 1 eq) in one portion at 25° C. under $N_2$. Then the reaction mixture was stirred for 10 minutes. Then 4-(5-fluoro-2-isocyanato-3-isopropylphenyl)-2-methoxypyridine (intermediate A4) (57 mg, 197.79 μmol, 1 eq) was added. The resulting mixture was heated to 70° C. and stirred for 10 minutes. The reaction mixture was concentrated in vacua. The residue was purified by prep-HPLC (column: Phenomenex Gemini C18, 150 mm*25 mm*10 μm; mobile phase: [A: water (10 mM NH$_4$HCO$_3$); B: MeCN]; B %: 13%-43%, 10 min) to give the title compound (49.52 mg, 51% yield, 98.93% purity on LCMS) as a white solid.

$^1$H NMR (DMSO-d$_6$): δ 8.90-8.85 (m, 1H), 8.09-8.05 (m, 1H), 7.92-7.87 (m, 1H), 7.18-7.15 (m, 1H), 7.07 (d, 1H), 6.98 (d, 1H), 6.84 (d, 1H), 6.73 (s, 1H), 3.85 (s, 3H), 3.07 (s, 6H), 3.06-3.01 (m, 1H) and 1.09-0.94 (m, 6H).

LCMS: m/z 489.2 (M+H)$^+$(ES$^+$).

Example 52: 5-(Dimethylamino)-N-((5-(2-methoxy-pyridin-4-yl)-2,3-dihydro-1H-inden-4-yl) carbamoyl) pyridazine-3-sulfonamide

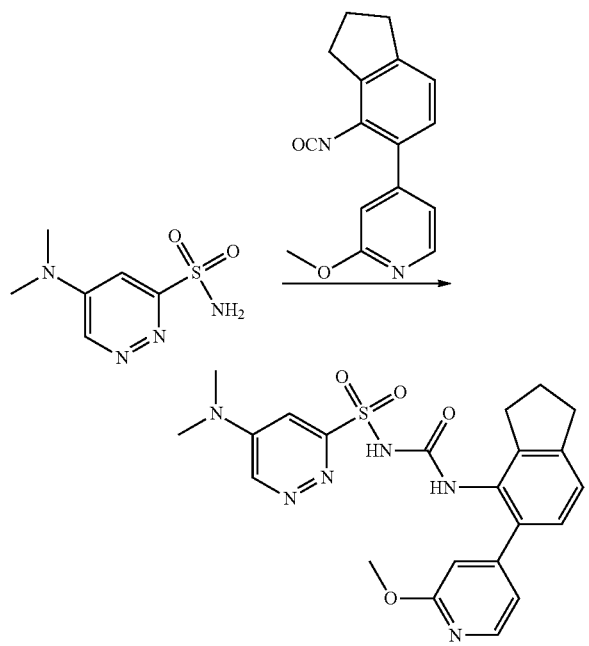

To a mixture of 5-(dimethylamino)pyridazine-3-sulfonamide (intermediate P15) (35 mg, 1₇3.07 µmol, 1 eq) in THF (2 mL) was added t-BuONa (17 mg, 173.07 µmol, 1 eq) in one portion at 25° C. under $N_2$. Then the reaction mixture was stirred for 10 minutes. Then 4-(4-isocyanato-2,3-dihydro-1H-inden-5-yl)-2-methoxypyridine (intermediate A5) (46 mg, 173.07 µmol, 1 eq) was added. The reaction mixture was heated to 25° C. and stirred for 20 minutes. The reaction mixture was concentrated in vacuo. The residue was purified by prep-HPLC (column: Waters Xbridge C18, 150 mm*25 mm*5 µm; mobile phase: [A: water (0.05% ammonia hydroxide v/v); B: MeCN]; B %: 5%-35%, 10 min) to give the title compound (21.73 mg, 27% yield, 99.14% purity on LCMS) as a white solid.

$^1$H NMR (DMSO-$d_6$): δ 8.83 (d, 1H), 8.06 (d, 1H), 7.75-7.74 (m, 1H), 7.13 (d, 1H), 7.07-7.05 (m, 2H), 6.86 (d, 1H), 6.71 (s, 1H), 3.88 (s, 3H), 3.06 (s, 6H), 2.86 (t, 2H), 2.68 (t, 2H) and 1.99-1.93 (m, 2H).

LCMS: m/z 469.2 (M+H)$^+$(ES$^+$).

Example 53: 5-(Dimethylamino)-N-((7-fluoro-5-(pyridin-4-yl)-2,3-dihydro-1H-inden-4-yl) carbamoyl) pyridazine-3-sulfonamide

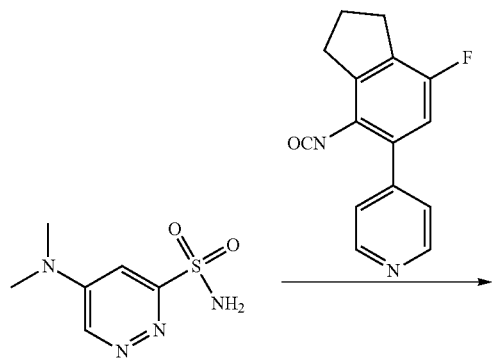

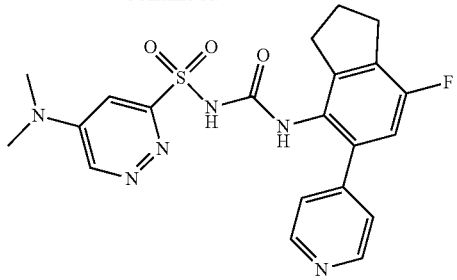

To a mixture of 5-(dimethylamino)pyridazine-3-sulfonamide (intermediate P15) (50 mg, 247.24 µmol, 1 eq) in THF (3 mL) was added t-BuONa (24 mg, 247.24 µmol, 1 eq) in one portion at 25° C. under $N_2$. Then the reaction mixture was stirred for 10 minutes. Then 4-(7-fluoro-4-isocyanato-2,3-dihydro-1H-inden-5-yl)pyridine (intermediate A6) (63 mg, 247.24 µmol, 1 eq) was added. The reaction mixture was stirred at 25° C. for 10 minutes. The reaction mixture was concentrated in vacua. The residue was purified by prep-HPLC (column: Phenomenex Gemini C18, 150 mm*25 mm*5 µm; mobile phase: [A: water (0.05% ammonia hydroxide v/v); B: MeCN]; B %: 5%-35%, 10 min) to give the title compound (22.81 mg, 20% yield, 98.41% purity on LCMS) as a white solid.

$^1$H NMR (DMSO-$d_6$): δ 8.83 (d, 1H), 8.51 (d, 2H), 7.71 (br s, 1H), 7.31-7.30 (m, 2H), 7.04 (d, 1H), 6.95 (d, 1H), 3.06 (s, 6H), 2.92 (t, 2H), 2.78-2.75 (m, 2H) and 2.05-2.00 (m, 2H).

LCMS: m/z 457.0 (M+H)$^+$(ES$^+$).

Example 54: N-((1,2,3,5,6,7-Hexahydro-s-indacen-4-yl)carbamoyl)-6-(4-methylpiperazin-1-yl)pyrazine-2-sulfonamide, Potassium Salt

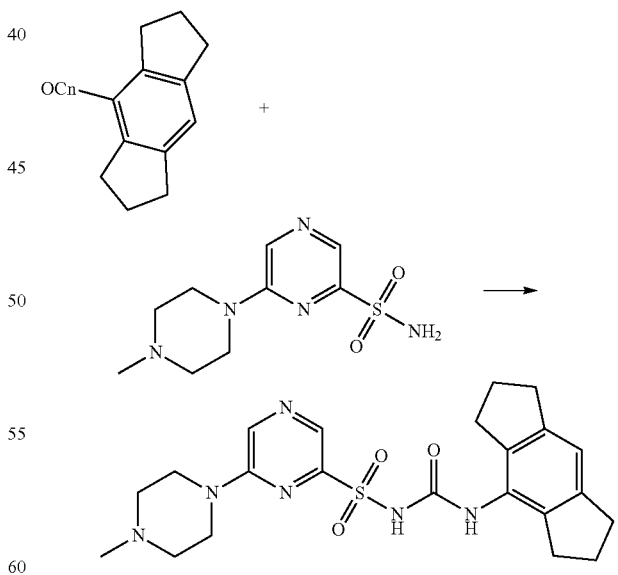

Prepared as described for N-((1,2,3,5,6,7-hexahydro-s-indacen-4-yl)carbamoyl)-4-methyl pyrimidine-2-sulfonamide, potassium salt (example 1) using 4-isocyanato-1,2,3,5,6,7-hexahydro-s-indacene (intermediate A1) and 6-(4-methylpiperazin-1-yl)pyrazine-2-sulfonamide to afford the title compound (30%) as a white solid.

¹H NMR (CD₃OD) δ: 8.34 (s, 1H), 8.24 (s, 1H), 6.85 (s, 1H), 3.72 (m, 4H), 2.82 (t, 4H), 2.72 (t, 4H), 2.52 (m, 4H), 2.33 (s, 3H) and 1.98 (m, 4H).

LCMS: m/z 457 (M+H)⁺(ES⁺); 455 (M–H)⁻(ES⁻).

Example 55: N-((1,2,3,5,6,7-Hexahydro-s-indacen-4-yl)carbamoyl)-2-methoxypyrimidine-5-sulfonamide, Potassium Salt

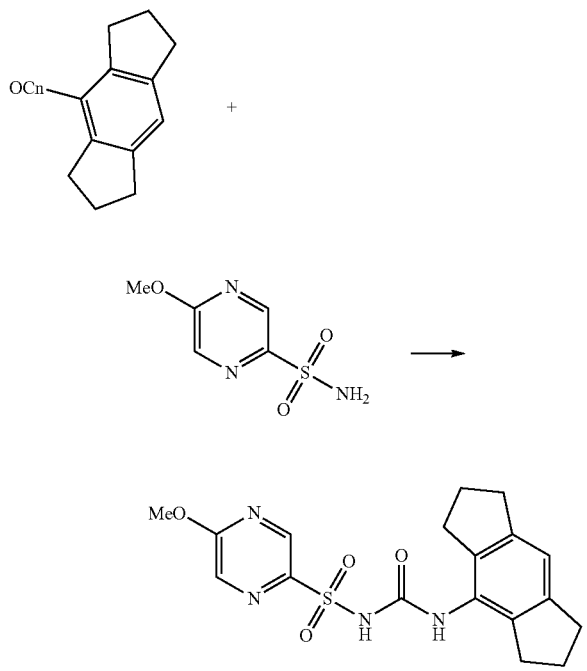

Prepared as described for N-((1,2,3,5,6,7-hexahydro-s-indacen-4-yl)carbamoyl)-4-methyl pyrimidine-2-sulfonamide, potassium salt (example 17) using 4-isocyanato-1,2,3,5,6,7-hexahydro-s-indacene (intermediate A1) and 2-methoxypyrimidine-5-sulfonamide to afford the title compound (25%) as a white solid.

¹H NMR (CD₃OD) δ: 8.95 (s, 2H), 6.84 (s, 1H), 4.04 (s, 3H), 2.78 (m, 8H), and 1.98 (m, 4H).

LCMS: m/z 389 (M+H)⁺(ES⁺); 387 (M–H)⁻(ES⁻).

Example 56: 4-(Dimethylamino)-N-((1,2,3,5,6,7-hexahydro-s-indacen-4-yl) carbamoyl)-6-methylpyrimidine-2-sulfonamide, potassium salt

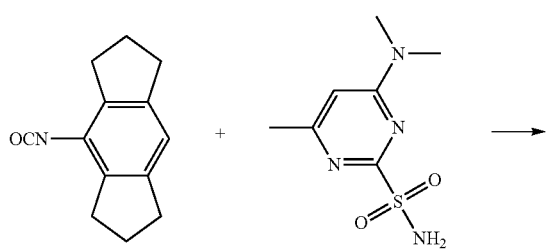

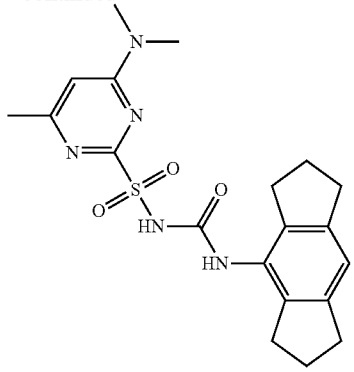

To a solution of 4-(dimethylamino)-6-methylpyrimidine-2-sulfonamide (intermediate P16) (20 mg, 0.092 mmol) in THF (5 mL) was added potassium tert-butoxide (16 mg, 0.14 mmol). The mixture was stirred at room temperature for 45 minutes. Then 4-isocyanato-1,2,3,5,6,7-hexahydro-s-indacene (intermediate A1) (23 mg, 0.092 mmol) was added and the mixture was stirred at room temperature overnight. The reaction mixture was concentrated in vacuo and DMSO (1 mL) was added. The mixture (filtered over cotton wool when solids were present) was submitted for purification by reversed phase column chromatography (see General Methods, "Purification Method 1" above) to afford the title compound (2 mg, 5%) as a white solid.

¹H NMR (Methanol-d₄): δ7.77 (s, 1H), 6.85 (s, 1H), 3.02 (s, 6H), 2.78 (m, 8H), 2.43 (d, 3H), 1.98 (m, 4H).

LCMS: m/z 416 (M+H)⁺(ES⁺); 414 (M–H)⁻(ES⁻).

Example 57: N-((1,2,3,5,6,7-Hexahydro-s-indacen-4-yl)carbamoyl)-2-isopropylpyridine-4-sulfonamide, Sodium Salt

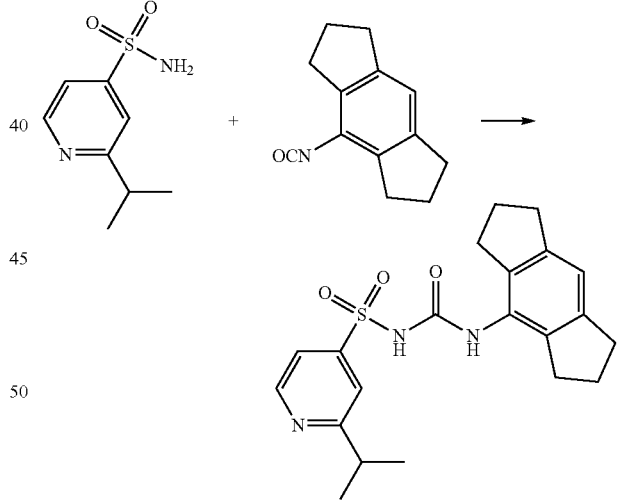

A solution of 2-isopropylpyridine-4-sulfonamide (intermediate P17) (51 mg, 0.242 mmol) in THF (2 mL) under nitrogen was treated with NaOtBu (2 M in THF, 0.13 mL, 0.260 mmol). The resultant solution was stirred at room temperature for 1 hour and then treated with a solution of 4-isocyanato-1,2,3,5,6,7-hexahydro-s-indacene (intermediate A1) (51 mg, 0.254 mmol) in THF (2 mL) and stirred for 17 hours. The reaction mixture was concentrated in vacua and purified by reversed phase prep-HPLC (General Methods, basic prep) to afford N-((1,2,3,5,6,7-hexahydro-s-indacen-4-yl)carbamoyl)-2-isopropylpyridine-4-sulfonamide (39 mg, 40%) as a flocculent white solid. The sodium salt was generated by dissolving N-((1,2,3,5,6,7-hexahydro-s- indacen-4-yl)carbamoyl)-2-isopropylpyridine-4-sulfonamide (32 mg, 0.079 mmol) in aq. NaOH (0.1M, 0.790 mL, 0.079 mmol). The mixture was freeze dried to afford the title compound (33 mg, 99%) as a white solid.

$^1$H NMR (DMSO-d$_6$) δ 8.50 (dd, J=5.0, 0.8 Hz, 1H), 7.53 (s, 1H), 7.50 (br s, 1H), 7.45 (dd, J=5.0, 1.6 Hz, 1H), 6.76 (s, 1H), 3.03 (sept, J=6.9 Hz, 1H), 2.74 (t, J=7.4 Hz, 4H), 2.62 (t, J=7.5 Hz, 4H), 1.88 (p, J=7.5 Hz, 4H), 1.23 (d, J=6.9 Hz, 6H).

LCMS; m/z 400.3 (M+H)$^+$(ES$^+$); 398.1 (M−H)$^−$(ES$^−$).

The compounds of examples 58-60 were synthesised by methods analogous to those outlined above.

| Ex | Structure and Name | 1H NMR spectrum | Mass spec | MW |
|---|---|---|---|---|
| 58 | 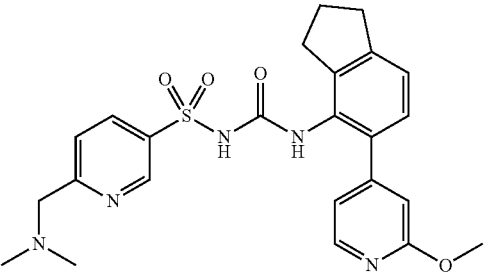<br>6-((Dimethylamino)methyl)-N-((5-(2-methoxypyridin-4-yl)-2,3-dihydro-1H-inden-4-yl)carbamoyl)pyridine-3-sulfonamide | 1H NMR (DMSO-d6) δ 10.25 (s broad, 1H), 8.88 (d, J = 2.1 Hz, 1H), 8.11-8.05 (m, 1H), 8.02 (d, J = 5.2 Hz, 1H), 7.52 (d, J = 8.1 Hz, 1H), 7.43 (s, 2H), 7.10 (d, J = 7.7 Hz, 1H), 7.03 (d, J = 7.6 Hz, 1H), 6.81 (d, J = 5.3 Hz, 2H), 6.69 (s, 2H), 4.21 (s, 2H), 3.86 (s, 3H), 2.88 (t, J = 7.4 Hz, 2H), 2.67 (t, J = 7.6 Hz, 2H), 2.62 (s, 6H), 1.94 (p, J = 7.5 Hz, 2H). | m/z 482.2 (M + H)$^+$ (ES$^+$). | 481.6 |
| 59 | 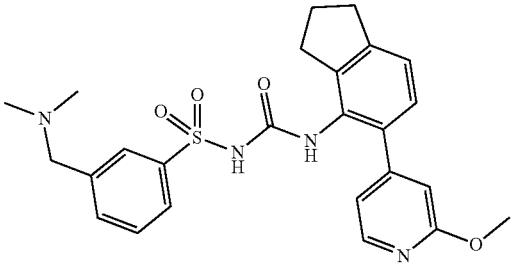<br>2-((Dimethylamino)methyl)-N-((5-(2-methoxypyridin-4-yl)-2,3-dihydro-1H-inden-4-yl)carbamoyl)pyridine-4-sulfonamide, sodium salt | 1H NMR (DMSO-d6) δ 8.46 (dd, J = 5.1, 0.8 Hz, 1H), 8.03 (dd, J = 5.3, 0.7 Hz, 1H), 7.69-7.66 (m, 1H), 7.41 (dd, J = 5.1, 1.6 Hz, 1H), 7.28 (br s, 1H), 7.06 (d, J = 7.7 Hz, 1H), 7.01 (d, J = 7.6 Hz, 1H), 6.89 (dd, J = 5.3, 1.5 Hz, 1H), 6.73 (d, J = 1.2 Hz, 1H), 3.85 (s, 3H), 3.52 (s, 2H), 2.86 (t, J = 7.4 Hz, 2H), 2.70 (t, J = 7.4 Hz, 2H), 2.19 (s, 6H), 1.93 (P, J = 7.5 Hz, 2H). | m/z 482.1 (M + H)$^+$ (ES$^+$); 480.1 (M − H)$^−$ (ES$^−$). | 481.6 |
| 60 | 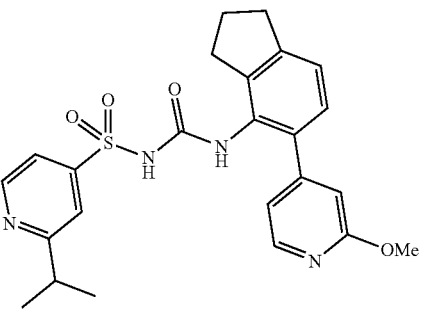 [SMILES: COc1cc(-c2ccc3c(c2NC(=O)NS(=O)(=O)c2ccnc(C(C)C)c2)CCC3)ccn1]<br>2-Isopropyl-N-((5-(2-methoxypyridin-4-yl)-2,3-dihydro-1H-inden-4-yl)carbamoyl)pyridine-4-sulfonamide, sodium salt | 1H NMR (DMSO-d6) δ 8.48 (dd, J = 5.0, 0.8 Hz, 1H), 8.02 (d, J = 5.4 Hz, 1H), 7.48 (s, 1H), 7.36 (dd, J = 5.0, 1.6 Hz, 1H), 7.31 (br s, 1H), 7.07 (d, J = 7.7 Hz, 1H), 7.02 (d, J = 7.6 Hz, 1H), 6.89 (dd, J = 5.3, 1.4 Hz, 1H), 6.74 (s, 1H), 3.86 (s, 3H), 3.03 (sept, J = 6.9 Hz, 1H), 2.87 (t, J = 7.4 Hz, 2H), 2.70 (t, J = 7.5 Hz, 2H), 1.93 (p, J = 7.5 Hz, 2H), 1.23 (d, J = 6.9 Hz, 6H). | m/z 467.3 (M + H)$^+$ (ES$^+$); 465.2 (M − H)$^−$ (ES$^−$). | 466.6 |

Other compounds listed in the Summary of the Invention may be synthesised by methods analogous to those outlined above.

Examples—Biological Studies

NLRP3 and Pyroptosis

It is well established that the activation of NLRP3 leads to cell pyroptosis and this feature plays an important part in the manifestation of the clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC # TIB-202) were grown in RPMI containing L-glutamine (Gibco #11835) supplemented with 1 mM sodium pyruvate (Sigma # S8636) and penicillin (100 units/ml)/streptomycin (0.1 mg/ml) (Sigma # P4333) in 10% Fetal Bovine Serum (FBS) (Sigma # F0804). The cells were routinely passaged and grown to confluency (~$10^6$ cells/ml). On the day of the experiment, THP-1 cells were harvested and resuspended into RPMI medium (without FBS). The cells were then counted and viability (>90%) checked by Trypan blue (Sigma # T8154). Appropriate dilutions were made to give a concentration of 625,000 cells/ml. To this diluted cell solution was added LPS (Sigma # L4524) to give a 1 μg/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.
1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C. in 5% $CO_2$
4. Add 5 μl nigericin (Sigma # N7143) (FAC 5 μM) to all wells
5. Incubate for 1 hr at 37° C. and 5% $CO_2$
6. At the end of the incubation period, spin plates at 300×g for 3 mins and remove supernatant
7. Then add 50 μl of resazurin (Sigma # R7017) (FAC 100 μM resazurin in RPMI medium without FBS) and incubate plates for a further 1-2 hrs at 37° C. and 5% $CO_2$
8. Plates were read in an Envision reader at Ex 560 nm and Em 590 nm
9. $IC_{50}$ data is fitted to a non-linear regression equation (log inhibitor vs response-variable slope 4-parameters)

|   | 1 | 2 | 3 | 4 | 5 | 6 | 7 | 8 | 9 | 10 | 11 | 12 |
|---|---|---|---|---|---|---|---|---|---|---|---|---|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Comp 8 | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |

High MCC950 (10 μM)  Compound 8-point half-log dilution
Low Drug free control

The results of the pyroptosis assays performed are summarised in Table 1 below as THP $IC_{50}$.

TABLE 1

NLRP3 inhibitory activity (≤10 μM = '+', ≤2000 nM = '++', ≤1600 nM = '+++', ≤1200 nM = '++++', ≤800 nM = '+++++').

| Example | THP $IC_{50}$ |
|---|---|
| 1 | ++++ |
| 2 | ++ |
| 3 | +++ |
| 4 | + |
| 5 | + |
| 6 | + |
| 7 | + |
| 8 | +++++ |
| 9 | ++ |
| 10 | + |
| 11 | + |
| 12 | ++++ |
| 13 | +++ |
| 14 | ++ |
| 15 | ++++ |
| 16 | + |
| 17 | ++++ |
| 18 | +++++ |
| 19 | +++++ |
| 20 | + |
| 21 | +++++ |
| 22 | +++ |
| 23 | + |
| 24 | + |
| 25 | +++++ |
| 26 | +++++ |
| 27 | +++++ |
| 28 | +++++ |
| 29 | + |
| 30 | + |
| 31 | + |
| 32 | + |
| 33 | +++ |
| 34 | +++++ |
| 35 | +++++ |
| 36 | +++++ |
| 37 | +++++ |
| 38 | +++++ |
| 39 | +++++ |
| 40 | +++++ |

TABLE 1-continued

NLRP3 inhibitory activity (≤10 μM = '+', ≤2000 nM = '++', ≤1600 nM = '+++', ≤1200 nM = '++++', ≤800 nM = '+++++').

| Example | THP IC$_{50}$ |
|---|---|
| 41 | +++++ |
| 42 | + |
| 43 | + |
| 44 | ++++ |
| 45 | + |
| 46 | +++++ |
| 47 | +++++ |
| 48 | +++++ |
| 49 | +++++ |
| 50 | +++++ |
| 51 | +++++ |
| 52 | +++++ |
| 53 | +++++ |
| 54 | ++ |
| 55 | + |
| 56 | +++++ |
| 57 | +++++ |
| 58 | +++++ |
| 59 | +++++ |
| 60 | +++++ |

As is evident from the above, surprisingly in spite of the structural differences versus the prior art compounds, the compounds of the invention show high levels of NLRP3 inhibitory activity. It is evident in particular that where $R^1$ is a 6-membered heteroaryl group containing at least two nitrogen atoms in the 6-membered ring structure, the compounds show high levels of NLRP3 inhibitory activity.

Moreover, further analysis of the data above reveals a number of surprising trends. For example, it has unexpectedly been found that where the 6-membered heteroaryl group of $R^1$ is substituted with at least one monovalent group that can mesomerically donate a lone pair of electrons from a nitrogen, oxygen or sulphur atom onto at least one nitrogen atom in the 6-membered ring structure, enhanced NLRP3 inhibitory activity results. This is demonstrated for instance by studying the pyrazine series, where Examples 8, 25, 26, 27, 28, 34, 35, 36, 37, 38, 39, 40 and 41, all of which are able to mesomerically donate a lone pair of electrons from a monovalent substituent onto a nitrogen atom in the pyrazine ring, all have greater activity than Examples 1, 14, 24, 29, 30, 4², 43, 44 and 45, none of which have such lone pair-donating capacity. Similarly, in the pyridazine series, Examples 13, 21, 22, 50, 51, 52 and 53 (with lone pair-donating ability) all have greater activity than Examples 2, 4, 11, 16 and 20 (without lone pair-donating ability). Likewise, in the pyrimidine series, Example 9 has a greater activity than Example to. This effect occurs even when considering compounds of equivalent steric profile.

A further unexpected trend may be observed where $R^1$ is a 6-membered heteroaryl group containing at least two nitrogen atoms in the 6-membered ring structure, including a first nitrogen atom at the 2-position and a second nitrogen atom at the 6-position. Comparing Examples 3, 17 and 18, it is evident that the level of activity increases with increasing substitution at the 3- and/or 5-position of the 6-membered ring structure. For instance, Example 3 with no substitution has an IC$_{50}$ value in excess of 1200 nM, a value which is reduced with the mono-alkylation of Example 17, and reduced still further with the 3,5-dialkylation to give the highly active compound of Example 18. Likewise, Examples 46, 47, 48, 49 and 56, all with 3,5-di-substitution are all highly active.

Human Whole Blood IL1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 μl of whole blood containing 1 μg/ml of LPS in 96-well, clear bottom cell culture plate (Corning #3585)
2. Add 10 μl compound (8 points half-log dilution with 10 μM top dose) or vehicle (DMSO 0.1% FAC) to the appropriate wells
3. Incubate for 3 hrs at 37° C., 5% CO$_2$
4. Add 10 μl Nigericin (Sigma # N7143) (10 μM FAC) to all wells
5. Incubate for 1 hr at 37° C., 5% CO$_2$
6. At the end of the incubation period, spin plates at 300×g for 5 mins to pellet cells and remove 20 μl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220E-5000)
8. IC$_{50}$ data is fitted to a non-linear regression equation (log inhibitor vs response-variable slope 4-parameters)

The results of the human whole blood assays are summarised in Table 2 below as HWB IC$_{50}$.

TABLE 2

NLRP3 inhibitory activity in HWB (≤10 μM = '+', ≤7.5 μM = '++', ≤5.0 μM = '+++', ≤2.5 μM = '++++').

| Example | HWB IC$_{50}$ |
|---|---|
| 7 | ++++ |
| 8 | +++ |
| 9 | ++++ |
| 10 | ++ |
| 17 | +++ |
| 18 | ++++ |
| 27 | ++ |
| 37 | ++++ |
| 38 | ++++ |
| 40 | ++++ |
| 41 | +++ |
| 46 | ++++ |
| 48 | ++++ |
| 49 | ++++ |
| 50 | ++++ |
| 51 | ++++ |
| 52 | ++++ |
| 53 | ++++ |
| 58 | ++++ |
| 59 | ++++ |
| 60 | ++++ |

Even in human whole blood, it has surprisingly been found that the compounds of the invention are highly effective inhibitors of NLRP3. Moreover, despite the complexities involved in the interaction with whole blood, the trends uncovered in the THP assays are repeated in the HWB assays. For instance, comparing Example 9 to Example to again reveals that the ability to mesomerically donate a lone pair of electrons from a monovalent substituent onto a nitrogen atom in the 6-membered heteroaryl ring enhances NLRP3 inhibitory activity. It can also be seen that the 3,5-dialkylated pyrimidine derivative of Example 18 possesses superior activity to the mono-alkylated derivative of Example 17.

PK protocol

Pharmacokinetic parameters were determined in male Sprague Dawley rats (Charles River, UK, 250-300 g; or Vital River Laboratory Animal Technology Co Ltd, Beijing, China, 7-9 weeks old). Animals were individually housed during the study and maintained under a 12 h light/dark cycle. Animals had free access to food and water.

For intravenous administration, compounds were formulated as a solution in water or DMSO:PBS [10:90] in 2 mL/kg dosing volume and administered via tail vein.

Serial blood samples (about 120-300 μL) were taken from each animal at each of 8 time-points post dose (0.083, 0.25, 0.5, 1, 2, 4, 8 and 24 h). Samples were held on ice for no longer than 30 minutes before centrifugation (10,000 rpm (8,385 g) for 3 minutes; or 5,696 rpm (3,000 g) for 15 minutes) for plasma generation. Plasma was frozen on dry ice prior to bioanalysis. PK parameters were generated from LC-MS/MS data using Dotmatics or Phoenix WinNonlin 6.3 software.

TABLE 3

| PK data (intravenous administration) | | | | | |
|---|---|---|---|---|---|
| Example No | Dose (mg/kg) | AUC (ng·hr/mL) | $T_{1/2}$ (hr) | $V_{dss}$ (L/kg) | Cl (mL/min·kg) |
| 35 | 1 | 346.3 | 2.2 | 1.77 | 48.1 |
| 36 | 1 | 841.0 | 1.2 | 1.04 | 19.8 |

As is evident from the results presented in Table 3, the compounds of the invention show advantageous pharmacokinetic properties, for example half-life $T_{1/2}$, area under the curve AUC, clearance Cl and/or bioavailability, compared to the prior art compounds.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (I):

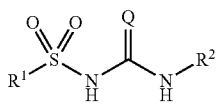

Formula (I)

or a pharmaceutically acceptable salt, solvate or prodrug thereof, wherein:

Q is O or S;

$R^1$ is a 6-membered heteroaryl group containing at least two nitrogen atoms in the 6-membered ring structure, wherein the 6-membered heteroaryl group of $R^1$ is substituted with at least one monovalent group X, wherein X is at each occurrence any group that can mesomerically donate a lone pair of electrons from a nitrogen, oxygen or sulphur atom onto at least one nitrogen atom in the 6-membered ring structure, and wherein the 6-membered heteroaryl group may optionally be further substituted; and $R^2$ is a cyclic group substituted at the α-position, wherein $R^2$ may optionally be further substituted, provided that the substituent at the a-position is not an optionally substituted monovalent heterocyclic group or an optionally substituted monovalent aromatic group, wherein a ring atom of the heterocyclic or aromatic group is directly attached to the α-ring atom of the cyclic group.

2. The compound or a pharmaceutically acceptable salt, solvate or prodrug thereof, as claimed in claim 1, wherein at least one of the two nitrogen atoms is located at the 3, 4 or 5-position of the 6-membered ring structure.

3. The compound or a pharmaceutically acceptable salt, solvate or prodrug thereof, as claimed in claim 1, wherein X is at each occurrence a monovalent group X', wherein:

each X' is attached at a position ortho- or para- to at least one nitrogen atom in the 6-membered ring structure;

the 6-membered heteroaryl group of R1 may optionally be further substituted;

X' is at each occurrence independently selected from a $-OR^3$, $-SR^3$, $-N(R^3)_2$, $-O-L-OR^3$, $-O-L-SR^3$, $-O-L-N(R^3)_2$, $-S-L-OR^3$, $-S-L-SR^3$, $-S-L-N(R^3)_2$, $-NR^3-L-OR^3$, $-NR^3-L-SR^3$ or $-NR^3-L-N(R^3)_2$ group;

each $R^3$ is independently selected from hydrogen or an alkyl, alkenyl, alkynyl or cyclic group, or any two $R^3$ in the same group X' may together with the atom or atoms to which they are attached form a heterocyclic group;

each L is independently selected from an alkylene, alkenylene or alkynylene group; and any L or $R^3$ may optionally be substituted.

4. The compound or a pharmaceutically acceptable salt, solvate or prodrug thereof, as claimed in claim 1, wherein at least one nitrogen atom is located at the 4-position of the 6-membered ring structure of $R^1$.

5. The compound or a pharmaceutically acceptable salt, solvate or prodrug thereof, as claimed in claim 1, wherein (i) the 6-membered heteroaryl group of $R^1$ is monocyclic; or (ii) the 6-membered heteroaryl group of $R^1$ is substituted with one or more fused cycloalkyl, cycloalkenyl, non-aromatic heterocyclic, aryl or heteroaryl rings such that the resultant group is bicyclic, tricyclic or polycyclic.

6. The compound or a pharmaceutically acceptable salt, solvate or prodrug thereof, as claimed in claim 1, wherein $R^2$ is an aryl or a heteroaryl group, wherein the aryl or the heteroaryl group is substituted at the a-position, and wherein $R^2$ may optionally be further substituted, and wherein optionally: (i) $R^2$ is an aryl or a heteroaryl group, wherein the aryl or the heteroaryl group is substituted at the α and α' positions, and wherein $R^2$ may optionally be further substituted; or (ii) $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein $R^2$ may optionally be further substituted.

7. The compound or a pharmaceutically acceptable salt, solvate or prodrug thereof, as claimed in claim 1, wherein $R^2$ is a cyclic group substituted at the α and α' positions, wherein $R^2$ may optionally be further substituted.

8. The compound or a pharmaceutically acceptable salt, solvate or prodrug thereof, as claimed claim 1, wherein Q is O.

9. The compound or a pharmaceutically acceptable salt, solvate or prodrug thereof, as claimed in claim 1, which is (a) a compound selected from the group consisting of:

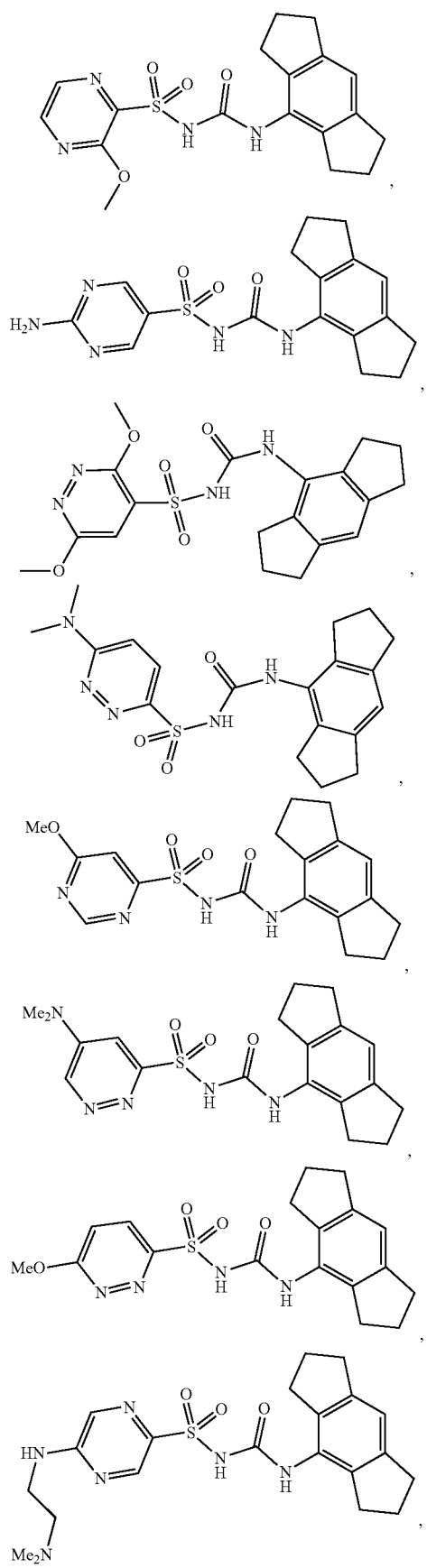

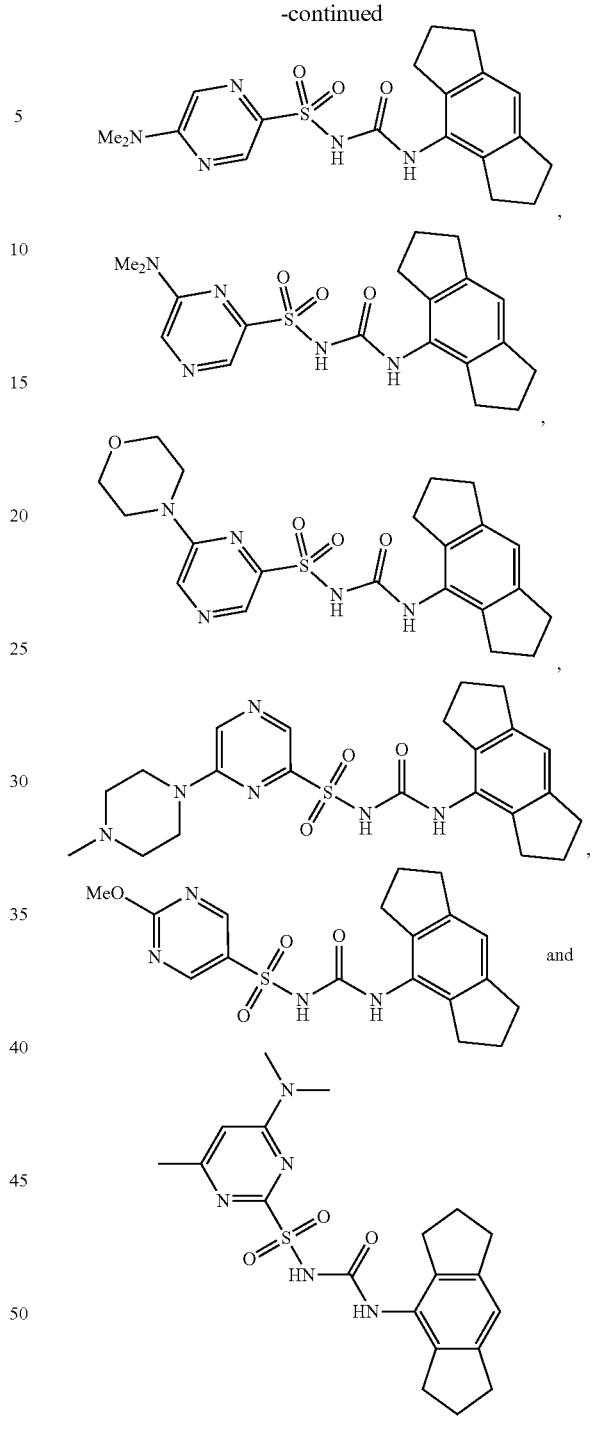

or (b) a pharmaceutically acceptable salt, solvate or prodrug of the selected compound.

10. A pharmaceutical composition comprising a compound or a pharmaceutically acceptable salt, solvate or prodrug as claimed in claim 1, and a pharmaceutically acceptable excipient.

11. A method of treating, reducing risk or delaying onset of a disease, disorder or condition in a subject, the method comprising the step of administering an effective amount of the compound or pharmaceutically acceptable salt, solvate or prodrug as claimed in claim 1 to the subject, thereby treating, reducing risk or delaying onset of the disease, disorder or condition, wherein the disease, disorder or condition is responsive to NLRP3 inhibition.

12. The method as claimed in claim 11, wherein the disease, disorder or condition is selected from:
   (i) inflammation;
   (ii) an auto-immune disease;
   (iii) cancer;
   (iv) an infection;
   (v) a central nervous system disease;
   (vi) a metabolic disease;
   (vii) a cardiovascular disease;
   (viii) a respiratory disease;
   (ix) a liver disease;
   (x) a renal disease;
   (xi) an ocular disease;
   (xii) a skin disease;
   (xiii) a lymphatic condition;
   (xiv) a psychological disorder;
   (xv) graft versus host disease;
   (xvi) allodynia; and
   (xvii) any disease where an individual has been determined to carry a germline or somatic non-silent mutation in NLRP3.

13. The method as claimed in claim 11, wherein the disease, disorder or condition is selected from:
   (i) cryopyrin-associated periodic syndromes (CAPS);
   (ii) Muckle-Wells syndrome (MWS);
   (iii) familial cold autoinflammatory syndrome (FCAS);
   (iv) neonatal onset multisystem inflammatory disease (NOMID);
   (v) familial Mediterranean fever (FMF);
   (vi) pyogenic arthritis, pyoderma gangrenosum and acne syndrome (PAPA);
   (vii) hyperimmunoglobulinemia D and periodic fever syndrome (HIDS);
   (viii) Tumour Necrosis Factor (TNF) Receptor-Associated Periodic Syndrome (TRAPS);
   (ix) systemic juvenile idiopathic arthritis;
   (x) adult-onset Still's disease (AOSD);
   (xi) relapsing polychondritis;
   (xii) Schnitzler's syndrome;
   (xiii) Sweet's syndrome;
   (xiv) Behcet's disease;
   (xv) anti-synthetase syndrome;
   (xvi) deficiency of interleukin 1 receptor antagonist (DIRA); and
   (xvii) haploinsufficiency of $A_{20}$ ($HA_{20}$).

14. The method as claimed in claim 11, wherein the compound is administered as a pharmaceutical composition further comprising a pharmaceutically acceptable excipient.

15. A method of inhibiting NLRP3 in a subject, comprising administering the compound or a pharmaceutically acceptable salt, solvate or prodrug thereof as claimed in claim 1 to the subject thereby inhibiting NLRP3.

16. A method of analysing inhibition of NLRP3 or an effect of inhibition of NLRP3 by a compound, comprising contacting a cell or non-human animal with the compound or a pharmaceutically acceptable salt, solvate or prodrug thereof as claimed in claim 1, and analysing inhibition of NLRP3 or an effect of inhibition of NLRP3 in the cell or non-human animal by the compound.

17. The compound or a pharmaceutically acceptable salt, solvate or prodrug thereof, as claimed in claim 1, wherein the 6-membered heteroaryl group of $R^1$ is a pyrazinyl or a pyridazinyl group.

18. The compound or pharmaceutically acceptable salt, solvate or prodrug as claimed in claim 1, which is the compound, pharmaceutically acceptable salt or solvate.

19. The compound or pharmaceutically acceptable salt, solvate or prodrug as claimed in claim 9, which is the compound, pharmaceutically acceptable salt or solvate.

* * * * *